United States Patent
Lavoie et al.

(10) Patent No.: US 9,464,313 B2
(45) Date of Patent: Oct. 11, 2016

(54) BIOSENSOR FOR DETECTING RAF/KSR FAMILY KINASE DIMERIZATION AND USES THEREOF

(71) Applicants: UNIVERSITE DE MONTREAL, Montreal, Quebec (CA); MOUNT SINAI HOSPITAL, Toronto, Ontario (CA)

(72) Inventors: Hugo Lavoie, Montreal (CA); Malha Sahmi, Ville Lemoyne (CA); Marc Therrien, Montreal West (CA); Thanashan Rajakulendran, Scarborough (CA); Frank Sicheri, Toronto (CA)

(73) Assignees: MOUNT SINAI HOSPITAL, Toronto (CA); UNIVERSITÉ DE MONTRÉAL, Montreal (CA)

( * ) Notice: Subject to any disclaimer, the term of this patent is extended or adjusted under 35 U.S.C. 154(b) by 0 days.

(21) Appl. No.: 14/135,934

(22) Filed: Dec. 20, 2013

(65) Prior Publication Data
US 2014/0378324 A1    Dec. 25, 2014

Related U.S. Application Data

(63) Continuation of application No. 13/356,059, filed on Jan. 23, 2012, now abandoned, which is a continuation of application No. PCT/CA2010/001164, filed on Jul. 23, 2010.

(60) Provisional application No. 61/228,273, filed on Jul. 24, 2009.

(51) Int. Cl.
| | | |
|---|---|---|
| G01N 33/53 | (2006.01) |
| C12Q 1/66 | (2006.01) |
| C07K 14/47 | (2006.01) |
| C12N 9/12 | (2006.01) |
| C12Q 1/48 | (2006.01) |
| G01N 33/58 | (2006.01) |
| A61K 38/00 | (2006.01) |

(52) U.S. Cl.
CPC .............. *C12Q 1/66* (2013.01); *C07K 14/47* (2013.01); *C12N 9/12* (2013.01); *C12Q 1/485* (2013.01); *G01N 33/581* (2013.01); *A61K 38/00* (2013.01); *G01N 2333/9121* (2013.01); *G01N 2333/91205* (2013.01); *G01N 2500/02* (2013.01)

(58) Field of Classification Search
CPC ....................................................... A61K 38/00
See application file for complete search history.

(56) References Cited

PUBLICATIONS

Weber et al, Active Ras Induces Heterodimerization of cRaf and BRaf. [Cancer Research vol. 61, 3595-3598, May 1, 2001].*
Xu et al, A bioluminescence resonance energy transfer (BRET) system: Application to interacting circadian clock proteins. Proc. Natl. Acad. Sci. USA vol. 96, pp. 151-156, Jan. 1999.*
Stokoe et al, Activation of Raf as a Result of Recruitment to the Plasma Membrane. Science vol. 264 Jun. 3, 1994 p. 1463-67.*
"Braf Transforming [Mus musculus]," GenBank Accession No. NP_647455.2, (gi:113199767), Jun. 26, 2007.

* cited by examiner

*Primary Examiner* — Sheridan Swope
(74) *Attorney, Agent, or Firm* — Darlene A. Vanstone, Esq.; Carolyn S. Elmore, Esq.; Elmore Patent Law Group, P.C.

(57) ABSTRACT

Disclosed herein are biosensors useful for detecting the dimerization of RAF and/or KSR polypeptides. These biosensors comprise fusion proteins comprising RAF and/or KSR proteins fused to bioluminescent or fluorescent proteins. Also disclosed are methods of using the biosensors to detect and measure the dimerization of RAF/RAF and RAF/KSR polypeptides by resonance energy transfer such as BRET or FRET, for example to screen for inhibitors of dimerization.

6 Claims, 54 Drawing Sheets

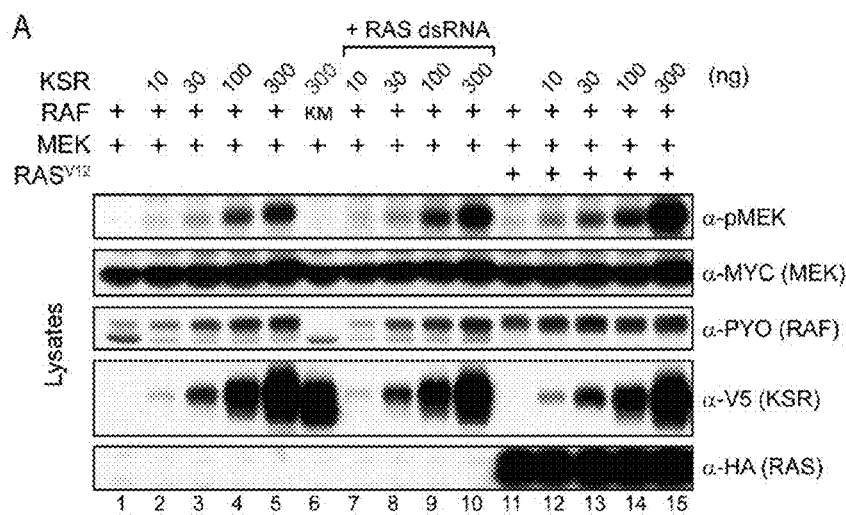
FIG. 1A
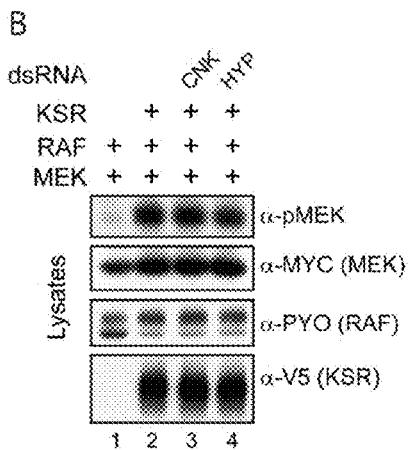 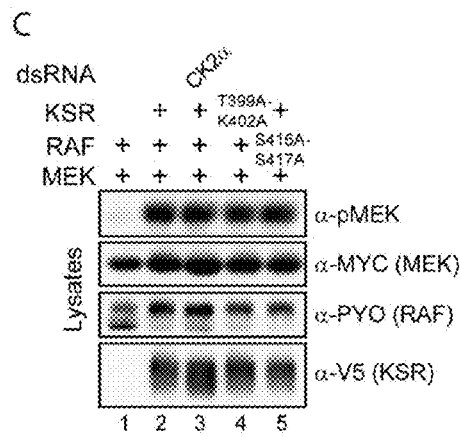
FIG. 1B          FIG. 1C

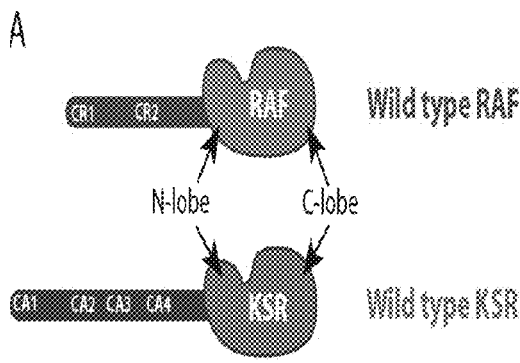
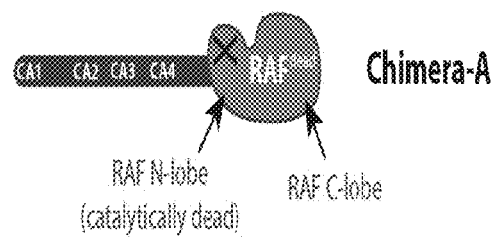
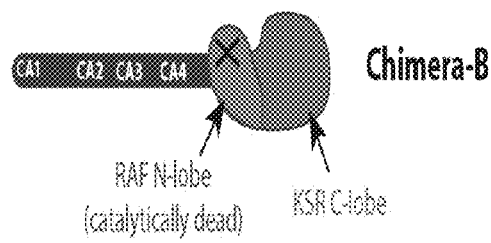
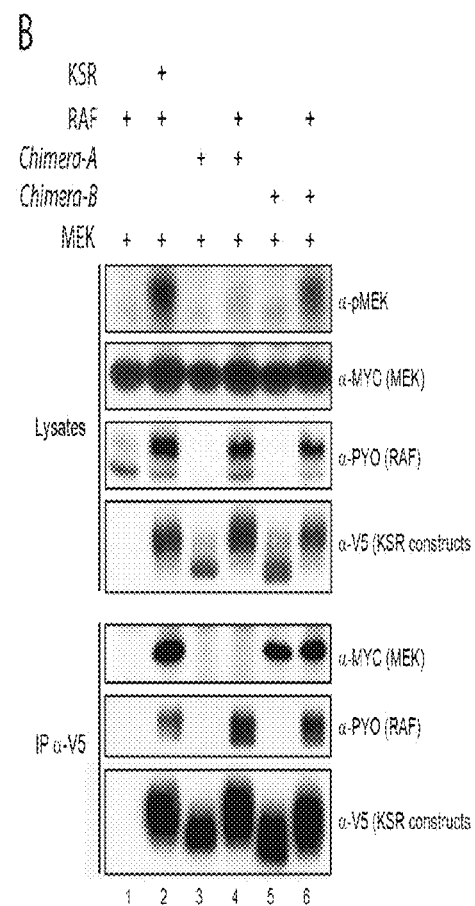
FIG. 7B
FIG. 7A

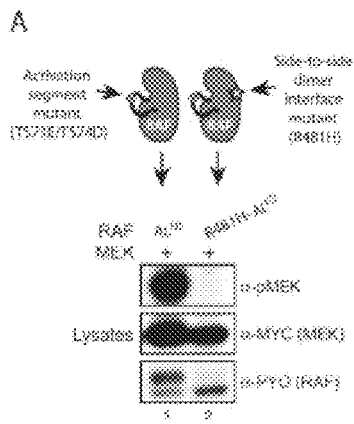
FIG. 11A
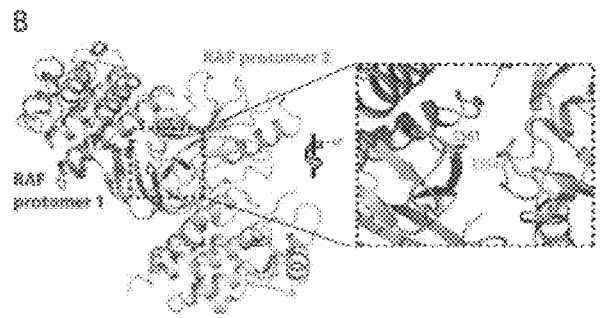
FIG. 11B
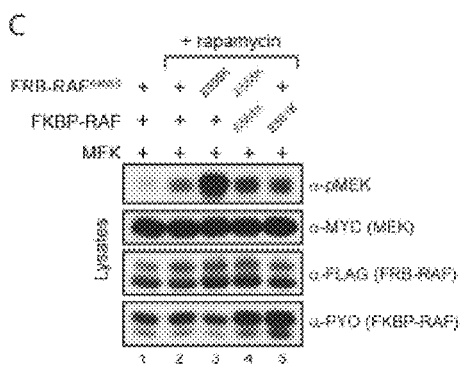
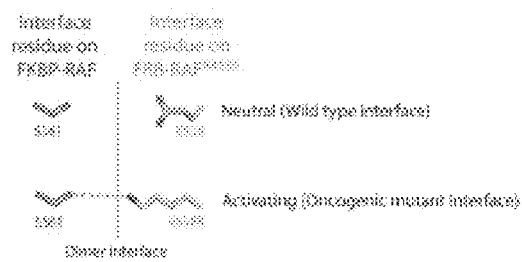
FIG. 11C
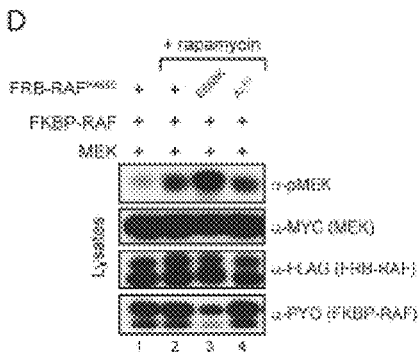
FIG. 11D

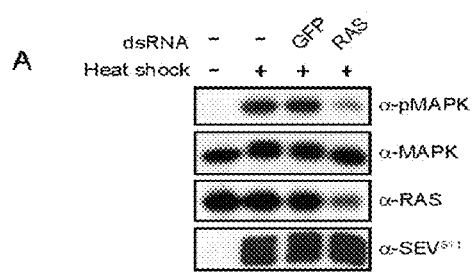
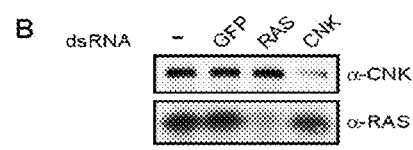
FIG. 13A
FIG. 13B
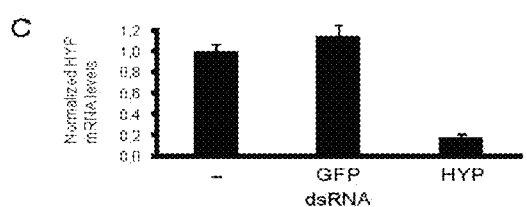
FIG. 13C
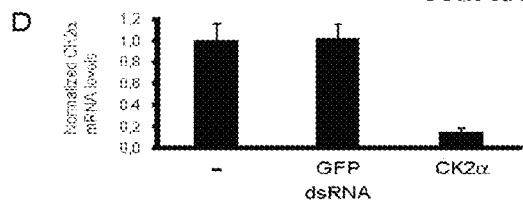
FIG. 13D
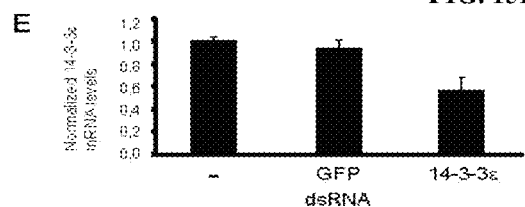
FIG. 13E
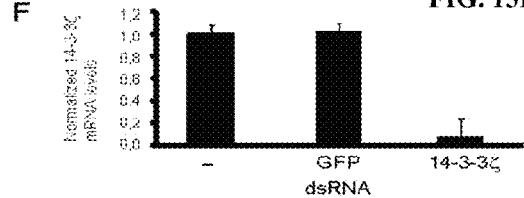
FIG.13F

Homo sapiens v-raf murine sarcoma viral oncogene homolog B1 (BRAF), mRNA

MAALSGGGGGGAEPGQALFNGDMEPEAGAGAGAAASSAADPAIP

EEVWNIKQMIKLTQEHIEALLDKFGGEHNPPSIYLEAYEEYTSKLDALQQREQQLLES

LGNGTDFSVSSSASMDTVTSSSSSSLSVLPSSLSVFQNPTDVARSNPKSPQKPIVRVF

LPNKQRTVVPARCGVTVRDSLKKALMMRGLIPECCAVYRIQDGEKKPIGWDTDISWLT

GEELHVEVLENVPLTTHNFVRKTFFTLAFCDFCRKLLFQGFRCQTCGYKFHQRCSTEV

PLMCVNYDQLDLLFVSKFFEHHPIPQEEASLAETALTSGSSPSAPASDSIGPQILTSP

SPSKSIPIPQPFRPADEDHRNQFGQRDRSSSAPNVHINTIEPVNIDDLIRDQGFRGDG

GSTTGLSATPPASLPGSLTNVKALQKSPGPQRERKSSSSSEDRNRMKTLGRRDSSDDW

EIPDGQITVGQRIGSGSFGTVYKGKWHGDVAVKMLNVTAPTPQQLQAFKNEVGVLRKT

RHVNILLFMGYSTKPQLAIVTQWCEGSSLYHHLHIIETKFEMIKLIDIARQTAQGMDY

LHAKSIIHRDLKSNNIFLHEDLTVKIGDFGLATVKSRWSGSHQFEQLSGSILWMAPEV

IRMQDKNPYSFQSDVYAFGIVLYELMTGQLPYSNINNRDQIIFMVGRGYLSPDLSKVR

SNCPKAMKRLMAECLKKKRDERPLFPQILASIELLARSLPKIHRSASEPSLNRAGFQT

EDFSLYACASPKTPIQAGGYGAFPVH (SEQ ID NO: 7)

FIG. 14A

```
ORIGIN
    1 cgcctccctt cccctcccc gcccgacagc ggccgctcgg gcccggctc tcggttataa
   61 gatggcggcg ctgagcggtg gcggtggtgg cggcgcggag ccgggccagg ctctgttcaa
  121 cgggacatg gagcccgagg ccggcgccgg cgccggcgcc gcggcctctt cggctgcgga
  181 ccctgccatt ccggaggagg tgtggaatat caaacaaatg attaagttga cacaggaaca
  241 tatagaggcc ctattggaca aatttggtgg ggagcataat ccaccatcaa tatatctgga
  301 ggcctatgaa gaatacacca gcaagctaga tgcactccaa caaagagaac aacagttatt
  361 ggaatctctg gggaacggaa ctgatttttc tgtttctagc tctgcatcaa tggataccgt
  421 tacatcttct tcctcttcta gcctttcagt gctaccttca tctctttcag ttttttcaaaa
  481 tcccacagat gtggcacgga gcaaccccaa gtcaccacaa aaacctatcg ttagagtctt
  541 cctgcccaac aaacagagga cagtggtacc tgcaaggtgt ggagttacag tccgagacag
  601 tctaaagaaa gcactgatga tgagaggtct aatcccagag tgctgtgctg tttacagaat
  661 tcaggatgga gagaagaaac caattggttg ggacactgat atttcctggc ttactggaga
  721 agaattgcat gtggaagtgt tggagaatgt tccacttaca acacacaact ttgtacgaaa
  781 aacgttttc accttagcat tttgtgactt ttgtcgaaag ctgcttttcc agggtttccg
  841 ctgtcaaaca tgtggttata aatttcacca gcgttgtagt acagaagttc cactgatgtg
  901 tgttaattat gaccaacttg atttgctgtt tgtctccaag ttctttgaac accacccaat
  961 accacaggaa gaggcgtcct tagcagagac tgccctaaca tctggatcat ccccttccgc
 1021 accgcctcg gactctattg ggcccaaat tctcaccagt ccgtctcctt caaaatccat
 1081 tccaattcca cagcccttcc gaccagcaga tgaagatcat cgaaatcaat ttgggcaacg
 1141 agaccgatcc tcatcagctc ccaatgtgca tataaacaca atagaacctg tcaatattga
 1201 tgacttgatt agagaccaag gatttcgtgg tgatggagga tcaaccacag gtttgtctgc
 1261 taccccccct gcctcattac ctggctcact aaagccttac agctttcagt cagatgtata
 1321 aggacctcag cgagaaagga agtcatcttc atcctcagaa gacaggaatc gaatgaaaac
 1381 acttggtaga cgggactcga gtgatgattg ggagattcct gatgggcaga ttacagtggg
 1441 acaaagaatt ggatctggat catttggaac agtctacaag ggaaagtggc atggtgatgt
 1501 ggcagtgaaa atgttgaatg tgacagcacc tacacctcag cagttacaag ccttcaaaaa
 1561 tgaagtagga gtactcagga aaacacgaca tgtgaatatc ctactcttca tgggctattc
 1621 cacaaagcca caactggcta ttgttaccca gtggtgtgag ggctccagct tgtatcacca
 1681 tctccatatc attgagacca aatttgagat gatcaaactt atagatattg cacgacagac
 1741 tgcacagggc atggattact tacacgccaa gtcaatcatc cacagagacc tcaagagtaa
 1801 taatatattt cttcatgaag acctcacagt aaaaataggt gattttggtc tagctacagt
 1861 gaaatctcga tggagtgggt cccatcagtt tgaacagttg tctggatcca ttttgtggat
 1921 ggcaccagaa gtcatcagaa tgcaagataa aaatccatac agctttcagt cagatgtata
 1981 tgcatttgga attgttctgt atgaattgat gactggacag ttaccttatt caaacatcaa
 2041 caacagggac cagataattt ttatggtggg acgaggatac ctgtctccag atctcagtaa
 2101 ggtacggagt aactgtccaa aagccatgaa gagattaatg gcagagtgcc tcaaaaagaa
 2161 aagagatgag agaccactct ttccccaaat tctcgcctct attgagctgc tggcccgctc
 2221 attgccaaaa attcaccgca gtgcatcaga ccctccttg aatcgggctg gtttccaaac
 2281 agaggatttt agtctatatg cttgtgcttc tccaaaaaca cccatccagg caggggata
 2341 tggtgcgttt cctgtccact gaaacaaatg agtgagagag ttcaggagag tagcaacaaa
 2401 aggaaaataa atgaacatat gtttgcttat atgttaaatt gaataaaata ctctctttt
 2461 ttttaaggtg aaccaaagaa cacttgtgtg gttaaagact agatataatt ttcccccaaa
 2521 ctaaaattta tacttaacat tggattttta acatccaagg gttaaaatac atagacattg
 2581 ctaaaaattg gcagagcctc ttctagagcc tttactttct gttccgggtt tgtatcattc
 2641 acttggttat tttaagtagt aaacttcagt ttctcatgca acttttgttg ccagctatca
 2701 catgtccact agggactcca gaagaagacc ctacctatgc ctgtgtttgc aggtgagaag
 2761 ttggcagtcg gttagcctgg gttagataag gcaaactgaa cagatctaat ttaggaagtc
 2821 agtagaattt aataattcta ttattattct taataatttt tctataacta tttctttta
 2881 taacaatttg gaaatgtgg atgtcttta tttccttgaa gcaataaact aagtttcttt
 2941 ttataaaaa (SEQ ID NO: 8)
```

FIG. 14B

Mus musculus Braf transforming gene (Braf), mRNA

MAALSGGGGSSSGGGGGGGGGGGGGDGGGGAEQGQALFNGDMEP

EAGAGAAASSAADPAIPEEVWNIKQMIKLTQEHIEALLDKFGGEHNPPSIYLEAYEEY

TSKLDALQQREQQLLESLVFQTPTDASRNNPKSPQKPIVRVFLPNKQRTVVPARCGVT

VRDSLKKALMMRGLIPECCAVYRIQDGEKKPIGWDTDISWLTGEELHVEVLENVPLTT

HNFVRKTFFTLAFCDFCRKLLFQGFRCQTCGYKFHQRCSTEVPLMCVNYDQLDLLFVS

KFFEHHPVPQEEASFPETALPSGSSSAPPSDSTGPQILTSPSPSKSIPIPQPFRPADE

DHRNQFGQRDRSSSAPNVHINTIEPVNIDEKFPEVELQDQRDLIRDQGFRGDGAPLNQ

LMRCLRKYQSRTPSPLLHSVPSEIVFDFEPGPVFRGSTTGLSATPPASLPGSLTNVKA

LQKSPGPQRERKSSSSSSSEDRSRMKTLGRRDSSDDWEIPDGQITVGQRIGSGSFGTV

YKGKWHGDVAVKMLNVTAPTPQQLQAFKNEVGVLRKTRHVNILLFMGYSTKPQLAIVT

QWCEGSSLYHHLHIIETKFEMIKLIDIARQTAQGMDYLHAKSIIHRDLKSNNIFLHED

LTVKIGDFGLATVKSRWSGSHQFEQLSGSILWMAPEVIRMQDKNPYSFQSDVYAFGIV

LYELMTGQLPYSNINNRDQIIFMVGRGYLSPDLSKVRSNCPKAMKRLMAECLKKKRDE

RPLFPQILASIELLARSLPKIHRSASEPSLNRAGFQTEDFSLYACASPKTPIQAGGYG

EFAAFK" (SEQ ID NO: 9)

FIG. 14C

```
ORIGIN
    1 ccctcaggct cggctgcgcc ggggccgccg gcgggttcca gaggtggcct ccgccccggc
   61 cgctccgccc acgcccccg cgcctccgcg cccgcctccg cccgccctgc gcctcccttc
  121 cccctccccg ccccgcggcg gccgctcggc ccggctcgcg cttcgaagat ggcggcgctg
  181 agtggcggcg gtggcagcag cagcggtggc ggcggcggcg gtggcggcgg cggtggcggt
  241 ggcgacggcg gcggcggcgc cgagcagggc caggctctgt tcaatggcga catggagccg
  301 gaggccgcg ctggcgccgc ggcctcttcg gctgcggacc cggccattcc tgaagaggta
  361 tggaatatca agcaaatgat taagttgaca caggaacata tagaggccct attggacaaa
  421 tttggtgtgag agcataaccc accatcaata tacctggagg cctatgaaga gtacaccagc
  481 aagctagatg cccttcagca aagagaacag cagcttttgg aatccctggt ttttcaaact
  541 cccacagatg catcacgaa caaccccaag tcaccacaga aacctatcgt tagagtcttc
  601 ctgcccaaca acagaggac agtggtaccc gcaagatgtg gtgttacagt tcgagacagt
  661 ctaaagaaag cactgatgat gagaggtctc atcccagaat gctgtgctgt ttacagaatt
  721 caggatggag agaagaaacc aattggctgg gacacggaca tttcctggct tactggagag
  781 gagttacatg ttgaagtact ggagaatgtc ccacttacaa cacacaactt gtacggaaa
  841 acttttttca ccttagcatt ttgtgacttt tgccgaaagc tgcttttcca gggtttccgt
  901 tgtcaaacat gtggttataa atttcaccag cgttgtagta cagaggttcc actgatgtgt
  961 gtaaattatg accaacttga tttgctgttt gtctccaagt tctttgagca tcacccagta
 1021 ccacaggagg aggcctcctt cccagagact gcccttccat ctggatcctc ttccgcaccc
 1081 ccctcagact ctactgggcc ccaaatcctc accagtccat ctccttcaaa atccattcca
```

FIG. 14D

```
1141 attccacagc ccttccgacc agcagatgaa gatcatcgca atcagtttgg gcaacgagac
1201 cggtcctcct cagctcccaa tgttcatata aacacaattg agcctgtgaa tatcgatgaa
1261 aaattcccag aagtggaatt acaggatcaa agggatttga ttagagacca ggggtttcgt
1321 ggtgatggag cccccttgaa ccaactgatg cgctgtcttc ggaaatacca atcccggact
1381 cccagccccc tcctccattc tgtccccagt gaaatagtgt ttgattttga gcctggccca
1441 gtgttcagag ggtcaaccac aggcttgtcc gccacccocgc ctgcctcatt acctggctca
1501 ctcactaacg tgaaagcctt acagaaatct ccaggtcctc agcgggaaag gaagtcatct
1561 tcttcctcat cctcggagga cagaagtcgg atgaaaacac ttggtagaag agattcaagt
1621 gatgactggg agattcctga tggacagatt acagtgggac agagaattgg atctgggtca
1681 tttggaactg tctacaaggg aaagtggcat ggtgatgtgg cagtgaaaat gttgaatgtg
1741 acagcaccca caccTcaaca gctacaggcc ttcaaaaatg aagtaggagt gctcaggaaa
1801 actcgacatg tgaatatcct cctttcatg ggctattcta caaagccaca actggcaatt
1861 gttacacagt ggtgtgaggg ctccagctta tatcaccatc tccacatcat tgagaccaaa
1921 tttgagatga tcaaacttat agatattgct cggcagactg cacagggcat ggattactta
1981 cacgccaagt caatcatcca cagagacctc aagagtaata atatatttct tcatgaagac
2041 ctcacggtaa aaataggtga cttTggtcta gccacagtga aatctcggtg gagtgggtcc
2101 catcagtttg aacagttgtc tggatctatt ttgtggatgg caccagaagt aatcagaatg
2161 caagataaaa acccgtatag cttTcagtca gacgtgtatg cgtttgggat tgttctgtac
2221 gaactgatga ccggccagct accttattca aacatcaaca acagggatca gataatttTt
2281 atggtgggac gaggatacct atctccagat ctcagtaagg tacggagtaa ctgtccaaaa
2341 gccatgaaga gattaatggc agagtgcctc aaaaagaaaa gagacgagag accactctt
2401 cccaaattc tcgcctccat tgagctgctg gcccgctcat tgccaaaaat tcaccgcagt
2461 gcatcagaac cttccttgaa tcgggctggt ttccaaacag aagattttag tctgtatgct
2521 tgtgcttctc cgaaaacacc catccaagca gggggatatg gagaatttgc agccttcaag
2581 tagccagtcc atcatggcag catctactct ttatttctta agtcttgtgt tcatacagtt
2641 tgttaacatc aaaacacagt tctgttcctc aaaaaatttt ttaaagatac aaaattttca
2701 atgcataagt tcatgtggaa cagaatggaa tttcctattc aacaaagag ggaagaatgt
2761 tttaggaacc agaattctct gctgccgtg tttcttcttc aacataacta tcacgtgcat
2821 acaagtctgc ccattcccaa gaagaaagag gagagaccct gaattctgcc cttttggtgg
2881 tcaggcatga tggaaagaat ttgctgctgc agcttgggaa aattgctatg gaaagtctgc
2941 cagtcgactt tgcccttcta accaccagat cagcctgtgg ctggtcatct gatgggcga
3001 tttccatcac caagcatcgt tcttgcctat tctgggatta tgttgtggag cactttccct
3061 gtccagcacc gttcatttct gagggatgga gtaaatgcag cattcccttg tgtagcgcct
3121 gttcagtcct cagcagctgc tgtcacagcg aagcttttta cagttaagtg gtgggggaga
3181 gttgaggaga gcctgcctcg gggcagagaa aaggggtgc tgcatcttct tcctcacctc
3241 cagctctctc acctcgggtt gccttgctca ctgggctccg cctaaccact caggctgctc
3301 agtgctggca cacattgcct tcttttctca ttgggtccag caattgagga gagggttggg
3361 ggattgtttc ctcctcaatg tagcaaattc tcaggaaaat acagtccata tcttcctctc
3421 agctcttcca gtcaccaaat acttacgtgg ctcctttgtc caggacataa aacaccgtgg
3481 acaacaccta attaaaagcc tacaaaactg cttactgaca gttttgaatg tgagacactt
3541 gtgtaattta aatgtaaggt acaggtttta atttctgagt ttcttctatt tttatttaaa
3601 agaagaaaat aattttcagt ttaattgga ataaatgagt acttcccaca agactatata
3661 ccctgaaaat tatattttg ttaattgtaa acaactttta aagataatt attatcctt
3721 tctctaccta aaaattatgg ggaatcttag cataatgaca attatttata ctttttaaat
3781 aaatggtact tgctggatcc acactaacat ctttgctaac aatcccattg ttTcttccaa
3841 cttaactcct acactacatc ctacatcctc ttTctagtct tttatctata atatgcaacc
3901 taaaataaac gtggtggcgt ctccattcat tctccctctt cctgttttcc ccaagcctgg
3961 tcttcaaaag gttgggtaat cggtccctga gctccctagc tggcaatgca actattaggg
```

FIG. 14E

```
4021 acattggagt tgcaggagag caggaagcct gtcccagct gttcttctag aaccctaaat
4081 cttatctttg cacagatcaa aagtatcacc tcgtcacagt tctccttagc ctttacttac
4141 aggtaatata aataaaaatc accatagtag taaagaaaac aactggatgg attgatgacc
4201 agtacctctc agagccagga atcttgaatc tccaggattt atacgtgcaa atttaaggag
4261 atgtacttag caacttcaag ccaagaactt ccaaaatact agcgaatcta aaataaaatg
4321 gaattttgag ttatttttaa agttcaaatt ataattgata ccactatgta tttaagccta
4381 ctcacagcaa gttagatgga ttttgctaaa ctcattgcca gactgtggtg gtggtggtgg
4441 tagtgtgcac ctttaatcca agcaactcag caatcagaat gaggtaaatc tctgtgaata
4501 caaggcctgc ctagtctgca gcgctagttc caggatagcc agggctacac acacaaaaac
4561 cctctctcaa aaaaacaaa attaattagt tgataataaa aaataactaa agtatcatca
4621 aaggaaggcc tactggaagt tttatatatt cccagtaaat tgaaaaatat tctgaagtta
4681 ttaaccagtt agcaacaatg tgtttttaag tcttacataa acagagcaaa gtcttcaaat
4741 gtttcagagc tgagaagata attgtgcttg atatgaaaaa tagcctctcc atatgatgtg
4801 ccacattgaa aggcgtcatt acccttttaa atacttctta atgtggcttt gttccttta
4861 cccaggatta gctagaaaga gctaggtagg cttcggccac agttgcacat tcgggcctg
4921 ctgaagaatg ggagctttga aggctggcct tggtggagga gccctcagt gtggagggt
4981 ggggcgtgta cgcagcatgg aagtggctca gacagagtgc aaaggacag acttctttct
5041 cattttagta tagggtgatg tctcacttga aatgagaaag tagagttgat attaaacgaa
5101 gctgtgccca gaaaccaggc tcagggtatt gtgagatttt ctttttaaat agagaatata
5161 aaagatagaa ataaatattt aaaccttcct tcttattttc tatcaaatag atttttttta
5221 tcatttgcaa acaacataaa aaaaggtttc ttttgtgggg ttttcttcc ttctttttt
5281 ttttttttt ttttaagac tgcagataat cttgttgagc tcctcggaaa atacaaggaa
5341 gtccgtgttt gtgcagagcg ctttatgagt aactgtatag acagtgtggc tgcttcactc
5401 atcccagagg gctgcagctg tcggcccatg aagtggctgc agtgcctgt gagatctgct
5461 ttgttttgtt tggagtgaag tctttgaaag gtttgagtgc aactatatag gactgttttt
5521 aaataagtag tattcctcat gaactttctc attgttaagc tacaggaccc aaactctacc
5581 actaagatat tattaacctc aaaatgtagt ttatagaagg aatttgcaaa tagaatatcc
5641 agttcgtact tatatgcatc ttcaacaaag attctctgtg acttgttgga tttggttcct
5701 gaacagccca tttctgtatt tgaggttagg agggcataat gaggcatcct aaaagacaat
5761 ctgatataaa ctgtatgcta gatgtatgct ggtaggggag aaagcattct gtaaagacat
5821 gatttaagac ttcagctctg tcaaccagaa accttgtaaa tacttcctgt cttggtgcag
5881 ccccgccct ttgatcacac gatgttgtct tgtgcttgtc agacactgtc agagctgctg
5941 ttcgtccctc tgcagatctc acctgtcccc actgcacacc cacctcctgc ctcttgcaga
6001 cctcagcatc tagctttagt tggaaacagt tcagggttca ggtgacttct taaaaaaaaa
6061 aaaaaccct acctcctcag aatgaggtaa tgaatagtta tttatttaaa gtatgaagag
6121 tcaggagcgc tgaacatga aggtgattta agatggttcc tttcgtgtgt attgtagctg
6181 agcacttgtt tttgtcctaa agggcattat acatttaagc agtgattctg tttaaagatg
6241 ttttttcttta aaggtgtagc tcagagtatc tgttgttgga attggtgcca gagtctgctt
6301 aatagatttc agaatcctaa gcttaagtca gtcgcatgaa gttaagtagt tatggtaaca
6361 ctttgctagc catgatataa ttctactttt taggagtagg tttggcaaaa ctgtatgcct
6421 tcaaagtgag ttggccacag ctttgtcaca tgcacagata ctcatctgaa gagactgccc
6481 agctaagagg gcggaaggat acccttttt cctacgattc gcttctttgt ccacgttggc
6541 attgttagta ctagtttatc agcaccttga ccagcagatg tcaaccaata agctattttt
6601 aaaaccatag ccagagatgg agaggtcact gtgagtagaa acagcaggac gcttacagga
6661 gtgaaatggt gtagggaggc tctagaaaaa tatcttgaca atttgccaaa tgatcttact
6721 gtgccttcat gatgcaataa aaaagctaac attttagcag aaatcagtga tttacgaaga
6781 gagtggccag tctggtttaa ctcagctggg ataatatttt tagagtgcaa tttagactgc
6841 gaagataaat gcactaaaga gtttatagcc aattcacatt tgaaaaataa gaaatggta
```

FIG. 14F

```
6901 aattttcagt gaaatatttt tttaaagcac ataatccota gtgtagccag aaatatttac
6961 cacatagagc agctaggctg agatacagtc cagtgacatt tctagagaaa cctttctac
7021 tcccacgggc tcctcaaagc atggaaattt tatacaaaat gtttgacatt ttaagatact
7081 gctgtagttt agttttgaaa tagtatgtgc tgagcagcaa tcatgtacta actcagagag
7141 agaaaacaac aacaaattgt gcatctgatt tgttttcaga gaaatgctgc caacttagat
7201 actgagttct cagagcttca agtgtaaact tgcctcccaa gtcctgtttg caaatgaagt
7261 tggctagtgc tactgactgc tccagcacat gatggaaggc aggggctgt ctctgaagtg
7321 tcttctataa agggacaata gaatagtgag agacctggtc agtgtgtgtc agctggacac
7381 tccatgctat gggacttgca tcttctgtcc tcaccatccc caagacattg tgctttcctc
7441 agttgtcctc tagctgtttc actcagacac caagatgaat tactgatgcc agaagggcc
7501 aaaatggcca gtgtgttttg ggggttgtat cagttgactg gacaataact ttaatagttt
7561 cagatcattt atttttactt ccattttgac agacatttaa atggaaattt agtcctaact
7621 tttgtcattt gaaaggaaaa attaacagtt cctataagat acttttgagg tggaatctga
7681 catcctaatt ttttttcttt tcagtgggtt tgcagcgagg gtcttgtatg cactaggcaa
7741 gggttctacc actaagccac attcccagg aaataaaatg ttaacagtta aaacatacac
7801 acaaatacac aaacacctta ttaccacttt agtaaagtga gagatgtgcg tcctttgtct
7861 cagtctccac gatttcagct gcccttgta tgaataactc agtctcgcta aactgtttac
7921 ttttatttac ctggtttgac tagttgcagc tatataacca gttgtgcatg aggacaacag
7981 ccagtgtgtt tgttttgttt ttggttttt gtggtacatt ttttgtaaag aattctgtag
8041 attgaagtgc tctttgaaaa cagaactgag atatatttat tcttgttagc atcaaaaaac
8101 attttgtgca aatgatttgc ttttcctggc aggctgagta ccatatccag cgcccacaat
8161 tgcgggttcc catctaccat gtccacaggg gagacagacg ggaagcacat gaggggtgtg
8221 tttacagagt tgtaggagtt atgtagttct cttgttgcct tggaaatcac tgttgtttta
8281 agactgttga acccgtgtgt ttggctgggc tgtgagttac atgaagaaac tgcaaactag
8341 catatgcaga caaagctcac agactaggcg taaatggagg aaaatggacc aaaataaggc
8401 agggtgacac ataaaccttg ggcttcggag aaaactaagg gtggagatga actataatca
8461 cctgaataca atgtaagagt gcaataagtg tgcttattct aagctgtgaa cttcttttaa
8521 atcattcctt tctaatacat ttatgtatgt tccattgctg actaaaacca gctatgagaa
8581 catatgcctt tttattcatg ttaactacca gtttaagtgg ctaaccttaa tgtcttattt
8641 atcttcattt tgtattagtt tacataccag gtatgtgtgt gtgctgtact cttcttcct
8701 ttatttgaaa acactttca ctgggtgcca ttccacaaca caactttggt
8761 ttggctttca atgtcacctt atttgatggc ctgtgtccca gtagcagaat ttatggtatt
8821 cccattgctg gctgctcttc cgacccttg cttctacagc acttgtctct cctaagatag
8881 tcagaaacta actgatcagg ggatggactt caccattcat cgtgtctctt caattctatt
8941 aaatagacca ctcttgggct ttagaccagg aaaaaggaga cagctctagc catctaccca
9001 gcctcaccct aaaaggtcac ccgtacttct tggtctgagg acaagtctcc actccagtaa
9061 gggagagggg aggaaatgct tcctgtttga aatgcagtga attcctatgg ctcctgtttc
9121 accacccgca cctatggcaa cccatataca ttcctcttgt ctgtaactgc caaaggttgg
9181 gtttatgtca cttcagttcc actcaagcat tgaaaaggtt ctcatggagt ctgggtgtg
9241 cccagtgaaa agatggggac tttttcatta tccacagacc tctctataec tgctttgcaa
9301 aaattataat ggagtaacta ttttttaaagc ttattttca attcataaga aaaagacatt
9361 tatttcaat caaatggatg atgtctctta tccctatcc ctcaatgttt gcttgaattt
9421 tgtttgttcc ctatacctac tccctaattc tttagttcct tcctgctcag gtcccttcat
9481 ttgtactttg gagtttttct catgtaaatt tgtataatgg aaaatattgt tcagtttgga
9541 tagaaagcat ggagaaataa ataaaaaag atagctgaaa atcaaattga agaaatttat
9601 ttctgtgtaa agttatttaa aaactctgta ttatatttaa agaaaaaagc ccaacccccc
9661 aaaagtgct atgtaattga tgtgaatatg cgaatactgc tataataaag attgactgca
9721 tggagaaa (SEQ ID NO: 10)
```

FIG. 14G

Homo sapiens kinase suppressor of ras 1 (KSR1), mRNA

MDRAALRAAAMGEKKEGGGGGDAAEGGAGAAASRALQQCGQLQKLIDISIGSLRGLRTKC

AVSNDLTQQEIRTLEAKLVRYICKQRQCKLSVAPGERTPELNSYPRFSDWLYTFNVRPEV

VQEIPRDLTLDALLEMNEAKVKETLRRCGASGDECGRLQYALTCLRKVTGLGGEHKEDS

SWSSLDARRESGSGPSTDTLSAASLPWPPGSSQLGRAGNSAQGPRSISVSALPASDSP

TPSFSEGLSDTCIPLHASGRLTPRALHSFITPPTTPQLRRHTKLKPPRTPPPPSRKVF

QLLPSFPTLTRSKSHESQLGNRIDDVSSMRFDLSHGSPQMVRRDIGLSVTHRFSTKSW

LSQVCHVCQKSMIFGVKCKHCRLKCHNKCTKEAPACRISFLPLTRLRRTESVPSDINN

PVDRAAEPHFGTLPKALTKKEHPPAMNHLDSSSNPSSTTSSTPSSPAPFPTSSNPSSA

TTPPNPSPGQRDSRFNFPAAYFIHHRQQFIFPVPSAGHCWKCLLIAESLKENAFNISA

FAHAAPLPEAADGTRLDDQPKADVLEAHEAEAEEPEAGKSEAEDDEDEVDDLPSSRRP

WRGPISRKASQTSVYLQEWDIPFEQVELGEPIGQGRWGRVHRGRWHGEVAIRLLEMDG

HNQDHLKLFKKEVMNYRQTRHENVVLFMGACMNPPHLAIITSFCKGRTLHSFVRDPKT

SLDINKTRQIAQEIIKGMGYLHAKGIVHKDLKSKNVFYDNGKVVITDFGLFGISGVVR

EGRRENQLKLSHDWLCYLAPEIVREMTPGKDEDQLPFSKAADVYAFGTVWYELQARDW

PLKNQAAEASIWQIGSGEGMKRVLTSVSLGKEVSEILSACWAFDLQERPSFSLLMDML

EKLPKLNRRLSHPGHFWKSAEL (SEQ ID NO: 11)

FIG. 14H

ORIGIN

```
    1 ctggacccct gccagggaag gggtcctcag acttgaggtt gccagctcag atgtggggct
   61 gctgatacta ggtgactgga ctgatgttct gttctagatg aaactccttg agggaccat
  121 ttgaaaaggc ttgatgtgct gcccaaagcc cccttcagag ctgacttctc caccccagc
  181 tgccgtgagc cttggctgct gacagctcat agctgagtcc ctcccgtgaa gtcaccttct
  241 gctgaagggt acatcctctc ccaaggcgaa gctggtccgt tacatttgta agcagaggca
  301 gtgcaagctg agcgtggctc ccgtgagag gaccccagag ctcaacagct accccccgtt
  361 cagcgactgg ctgtacactt tcaacgtgag gccggaggtg gtgcaggaga tccccgaga
  421 cctcacgctg gatgccctgc tggagatgaa tgaggccaag gtgaaggaga cgctgcggcg
  481 ctgtggggcc agcggggatg agtgtggccg tctgcagtat gccctcacct gcctgcgaa
  541 ggtgacaggc ctggaggggg agcacaagga ggactccagt tggagttcat ggatgcgcg
  601 gcgggaaagt ggctcaggc cttccacgga caccctctca gcagccagcc tgccctggcc
  661 cccagggagc tcccagctgg gcagagcagg caacagcgcc cagggccac gctccatctc
  721 cgtgtcagct ctgcccgcct cagactcccc caccccagc ttcagtgagg gcctctcaga
  781 cacctgtatt ccctgcacg ccagcggacg gctgaccccc cgtgccctgc acagcttcat
  841 caccccgccc accacccc agctgcgacg gcacaccaag ctgaagccac acggacgcc
  901 cccccaccc agccgcaagg tcttccagct gctgccagc ttcccacac tcacccggag
  961 caagtccat gagtctcagc tggggaaccg cattgatgac gtctcctcga tgaggtttga
```

FIG. 14I

```
1021 tctctcgcat ggatccccac agatggtacg gagggatatc gggctgtcgg tgacgcacag
1081 gttctccacc aagtcctggc tgtcgcaggt ctgccacgtg tgccagaaga gcatgatatt
1141 tggagtgaag tgcaagcatt gcaggttgaa gtgtcacaac aaatgtacca aagaagcccc
1201 tgcctgtaga atatccttcc tgccactaac tcggcttcgg aggacagaat ctgtcccctc
1261 ggacatcaac aacccggtgg acagagcagc cgaacccat tttggaaccc tccccaaagc
1321 actgacaaag aaggagcacc ctccggccat gaatcacctg gactccagca gcaaccctcc
1381 ctccaccacc tcctccacac cctcctcacc ggcgcccttc ccgacatcat ccaacccatc
1441 cagcgccacc acgccccca acccctcacc tggccagcgg gacagcaggt tcaacttccc
1501 agctgcctac ttcattcatc atagacagca gtttatcttt ccagtgccat ctgctggcca
1561 ttgctggaaa tgcctcctta ttgcagaaag tttaaggaa aacgctttca acatttcagc
1621 ctttgcacac gcagccccgc tccctgaagc tgccgacggt acccggctcg atgaccagcc
1681 gaaagcagat gtgttggaag ctcacgaagc ggaggctgag gagccagagg ctggcaagtc
1741 agaggcagaa gacgatgagg acgaggtgga cgacttgccg agctctcgcc ggccctggcg
1801 gggccccatc tctcgcaagg ccagccagac cagcgtgtac ctgcaggagt gggacatccc
1861 cttcgagcag gtagagctgg gcgagcccat cgggcaggc cgctggggcc gggtgcaccg
1921 cggccgctgg catggcgagg tggccattcg cctgctggag atggacggcc acaaccagga
1981 ccacctgaag ctcttcaaga aagaggtgat gaactaccgg cagacgcggc atgagaacgt
2041 ggtgctcttc atgggggcct gcatgaaccc gccccacctg gccattatca ccagcttctg
2101 caaggggcgg acgttgcact cgtttgtgag ggaccccaag acgtctctgg acatcaacaa
2161 gacgaggcaa atcgctcagg agatcatcaa gggcatggga tatcttcatg ccaagggcat
2221 cgtacacaaa gatctcaaat ctaagaacgt cttctatgac aacggcaagg tggtcatcac
2281 agacttcggg ctgtttggga tctcaggcgt ggtccgagag ggacggcgtg agaaccagct
2341 aaagctgtcc cacgactggc tgtgctatct ggccctgag attgtacgcg agatgacccc
2401 cgggaaggac gaggatcagc tgccattctc caaagctgct gatgtctatg catttgggac
2461 tgtttggtat gagctgcaag caagagactg gccttgaag aaccaggctg cagaggcatc
2521 catctggcag attggaagcg gggaaggaat gaagcgtgtc ctgacttctg tcagcttggg
2581 gaaggaagtc agtgagatcc tgtcggcctg ctgggctttc gacctgcagg agagacccag
2641 cttcagcctg ctgatggaca tgctggagaa acttcccaag ctgaaccggc ggctctccca
2701 ccctggacac ttctggaagt cagctgagtt gtaggcctgg ctgccttgca tgcaccaggg
2761 gctttcttcc tctaatcaa caactcagca ccgtgacttc tgctaaaatg caaaatgaga
2821 tgcgggcact aacccagggg atgccacctc tgctgctcca gtcgtctctc tcgaggctac
2881 ttcttttgct ttgttttaaa aactggccct ctgccctctc cacgtggcct gcatatgccc
2941 aagtaactgc tctcagagga tcccactaac tgagctccct ccaaggcagt ctgggcagct
3001 tctaactacc ttcctggaca tgactgattg ctcccgtgtt cttctgaggg ctggtcttgt
3061 ttttgtttgg gtggctctgt ctcactgcta acaccttagt gagatgcctt ccaccctcct
3121 gagcacacca gcctcccact gggtgtgtgc ctagtgcggg gcgggcggag gttgggaggg
3181 tgttggcttg gcttttaacc tgtgggatt ttgtccaaca aggagtggaa tgatttcaga
3241 gctgccctga ggctggcacc ctggtcacag gaaccctctg cgctggctcc tgtctcagtc
3301 ccctctgtag agttagatca gaagacacag aaagttctgt ggccatgaaa gataccagct
3361 tggaagggtt gtgtcttcag tggcaccctc agaaaaattg tcttaaagca aagaggtacc
3421 tggctccaga caattttcct gatgaaaaca aagtctctgc cccgtcccca ccctgccacc
3481 ctggcaaagt tacttccttt acagctgccc agtgtaccat agaccagacc ccaggtcagc
3541 atttgtcaag agcatggctg ctgagtcccc tgtggcagtc aatgcactgt ttaccaaatg
3601 caggtttctg ttctccctcc ccagcaagac ctgctgaacc cagatctctg gaatggggcc
3661 ctaggaattt gcatttcaac ctgcttccca ggtggcctg atgcaccca gtattagagt
3721 ttattgctaa aaggaacatg ccctgtcact cctggtatcc tgggagtcat gtttctcttc
3781 tctctcagtt ctacttggag caagagcttt cctgggctgc aaatgagaaa acaattccta
3841 ggaacccaca gcagtactga gcatgctggg agcttgggac ttggagatga atgagccacc
3901 gttgctgctc caagtaggac tacttggagt gtagctgagg ccttggacgc agtatgacca
```

FIG. 14J

```
3961  ggggcagctc tgccagggct gttggccaat cagtcatttt catttcttgt tggaggccag
4021  gtcctctgct gaactcattt cctagctagt gttaccctaa ttctgatgaa gatcaatggg
4081  gctataattc ttgtttttgt tcctctttgc agcattaaca gcagcaaagt tgtacccggg
4141  tttgaaaggt ttggcttggg cgtcctggag tccagtaatc caaagatgta gccagccata
4201  tggttttcg  ctgctgatct ctttcttttt aaatgtgtt  tctgaaacat cccaacaacc
4261  accacgacaa aaaaacactg cctgcccagc gctgcaaacc aggagcacac gtcctagatt
4321  cagactgttg gccataaacc ccactcggga gatggagctg cacctgctat ttcttaaaat
4381  gacaccacca acaaccaaac ctgtcatgac agacagcaaa tgtttacacg tatatttctc
4441  ctgagtgaac ctgatgtttt acaataggta ataataaaaa cagtctgtgc aaaaaaaaaa
4501  aaaaaaaaaa aaaaaaaaaa aaaaaaaaaa aaaaaaaaaa aaaaaaaaa aa
(SEQ ID NO: 12)
```

FIG. 14K

Mus musculus kinase suppressor of ras 1 (Ksr1), mRNA

MDRAALRAAAMGEKKEGGGGGAAADGGAGAAVSRALQQCGQLQK

LIDISIGSLRGLRTKCSVSNDLTQQEIRTLEAKLVKYICKQQQSKLSVTPSDRTAELN

SYPRFSDWLYIFNVRPEVVQEIPQELTLDALLEMDEAKAKEMLRRWGASTEECSRLQQ

ALTCLRKVTGLGGEHKMDSGWSSTDARDSSLGPPMDMLSSLGRAGASTQGPRSISVSA

LPASDSPVPGLSEGLSDSCIPLHTSGRLTPRALHSFITPPTTPQLRRHAKLKPPRTPP

PPSRKVFQLLPSFPTLTRSKSHESQLGNRIDDVTPMKFELPHGSPQLVRRDIGLSVTH

RFSTKSWLSQVCNVCQKSMIFGVKCKHCRLKCHNKCTKEAPACRITFLPLARLRRTES

VPSDINNPVDRAAEPHFGTLPKALTKKEHPPAMNLDSSSNPSSTTSSTPSSPAPFLTS

SNPSSATTPPNPSPGQRDSRFSFPDISACSQAAPLSSTADSTRLDDQPKTDVLGVHEA

EAEEPEAGKSEAEDDEEDEVDDLPSSRRPWRGPISRKASQTSVYLQEWDIPFEQVELG

EPIGQGRWGRVHRGRW░EVAIRLLEMDGHNQDHLKLFKKEVMNYRQT░HENVV░░G

ACMNPPHLAIITSFCKGRTLHSFVRDPKTSLDINKTRQIAQEIIKGMG░LH░GIVHK

DLKSKNVFYDNGKVVITDFGLFGISGVVREERRENQLKLSHDWLCYLAPEIVREMIFG

RDEDQLPFSKAADVYAFGTVWYELQARDWPFKHQPAEALIWQIGSGEGVRRVLASVSL

GKEVGEILSACWAFDLQERPSFSLLMDMLERLPKLNRRLSHPGHFWKSADINSSKVMP

RFERFGLGTLESGNPKM (SEQ ID NO: 13)

FIG. 14L

```
ORIGIN
    1 ctcgggcttt tcctgccgag gcgcccgtgt cccgggctc ctcgcctcgg ccccagcgg
   61 ccccgatgcc gaggcatgga tagagcggcg ttgcgcgcgg cagccgatggg cgagaaaaag
  121 gagggcggcg gcggggcgc cgcggcggac ggggcgcag gggccgccgt cagccgggcg
  181 ctgcagcagt gcggccagct gcagaagctc atcgatatct ccatcggcag tctgcgcggg
  241 ctgcgcacca agtgctcagt gtctaacgac ctcacacagc aggagatccg gaccctagag
  301 gcaaagctgg tgaaatacat ttgcaagcag cagcagagca agcttagtgt gaccccaagc
  361 gacaggaccg ccgagctcaa cagctaccca cgcttcagtg actggctgta catcttcaac
  421 gtgaggcctg aggtggtgca ggagatcccc aagagctca cactggatgc tctgctggag
  481 atggacgagg ccaaagccaa ggagatgctc cggcgctggg gggcagcac ggaggagtgc
  541 agccgcctac agcaagccct tacctgcctt cggaaggtga ctggcctgga agggggagcac
  601 aaaatggact caggttggag ttcaacagat gctcgagaca gtagcttggg gcctcccatg
  661 gacatgcttt cctcgctggg cagagcgggt gccagcactc agggaccccg ttccatctcc
  721 gtgtccgccc tgcctgcctc agactctccg gtcccggcc tcagtgaggg cctctcggac
  781 tcctgtatcc ccttgcacac cagcggccgg ctgaccccc gggccctgca cagcttcatc
  841 acgcccccta ccacacccca gctacgacgg cacgccaagc tgaagccacc aaggacaccc
  901 ccaccgccaa gtcgcaaggt cttccagctg ctcccagct tcccacact cacacggagc
  961 aagtccacg agtcccagct gggaaaccga atcgacgacg tcacccgat gaagtttgaa
 1021 ctccctcatg gatccccaca gctggtacga agggatatcg gctctcggt gacgcacagg
 1081 ttctccacaa agtcatggtt gtcacaggtg tgcaacgtgt gcagaagag catgattttt
 1141 ggcgtgaagt gcaaacactg caggttaaaa tgccataaca agtgcacaaa ggaagctccc
```

FIG. 14M

```
1201 gcctgcagga tcaccttcct cccactggcc aggcttcgga ggacagagtc tgtcccgtca
1261 gatatcaaca acccagtgga cagagcagca gagcccatt ttggaaccct tcccaaggcc
1321 ctgacaaaga aggagcaccc tccagccatg aacctggact ccagcagcaa cccatcctcc
1381 accacgtcct ccacacccte atcgccggca cctttcctga cctcatctaa tccctccagt
1441 gccaccacgc ctcccaaccc gtcacctggc cagcgggaca gcaggttcag cttcccagac
1501 atttcagcct gttctcaggc agcccgctg tccagcacag ccgacagtac acggctcgac
1561 gaccagccca aaacagatgt gctaggtgtt cacgaagcag aggctgagga gcctgaggct
1621 ggcaagtcag aggcagagga tgacgaggag gatgaggtgg acgacctccc cagctcccgc
1681 cggccctgga ggggccccat ctctcgaaag gccagccaga ccagcgttta cctgcaagag
1741 tgggacatcc cctttgaaca ggtggaactg ggcgagccca ttggacaggg tgctggggc
1801 cgggtgcacc gaggccgttg catggcgag gtggccattc ggctgctgga gatggacggc
1861 cacaatcagg accacctgaa gctgttcaag aaagaggtga tgaactaccg gcagacgcgg
1921 catgagaacg tggtgctctt catggggcc tgcatgaacc cacctcacct ggccattatc
1981 accagcttct gcaaggggcg gacattgcat tcattcgtga gggaccccaa gacgtctctg
2041 gacatcaata agactaggca gatcgcccag gagatcatca agggcatggg ttatcttcat
2101 gcaaaaggca tcgtgcacaa ggacctcaag tccaagaatg tcttctatga caacggcaaa
2161 gtggtcatca cagacttcgg gctgtttggg atctcgggtg tggtccgaga ggaacggcgc
2221 gagaaccaac tgaaactgtc acatgactgg ctgtgctacc tggccccga gatcgtacga
2281 gaaatgatcc cggggcggga cgaggaccag ctgccctct ccaaagcagc cgatgtctat
2341 gcattcggga ctgtgtggta tgaactacag gcaagagact ggccctttaa gcaccagcct
2401 gctgaggcct tgatctggca gattggaagt ggggaaggag tacggcgcgt cctggcatcc
2461 gtcagcctgg ggaaggaagt cggcgagatc ctgtctgcct gctgggcttt cgatctgcag
2521 gagagaccca gcttcagcct gctgatggac atgctggaga ggctgcccaa gctgaaccgg
2581 cggctctccc accctgggca cttttggaag tcggctgaca ttaacagcag caaagtcatg
2641 cccgcttg aaaggtttgg cctggggacc ctggagtccg gtaatccaaa gatgtagcca
2701 gccctgcacg ttcatgcaga gagtgtcttc ctttcgaaaa catgatcacg aaacatgcag
2761 accaccacct caaggaatca gaagcattgc atcccaagct gcggactggg agcgtgtctc
2821 ctccctaaag gacgtgcgtg cgtgcgtgcg tgcgtgcgtg cgtgcgtgcg tcaccaaggt
2881 gtgtggagct caggatcgca gccatacacg caactccaga tgataccact accgccagtg
2941 tttacacaga ggtttctgcc tggcaagctt ggtattttac agtaggtgaa gatcattctg
3001 cagaaggggtg ctggcacagt ggagcagcac ggatgtcccc agccccgtt ctggaagacc
3061 ctacagctgt gagaggccca gggttgagcc agatgaaaga aaagctgcgt gggtgtgggc
3121 tgtacccgga aaagggcagg tggcaggagg tttgccttgg cctgtgcttg ggccgagaac
3181 cacactaagg agcagcagcc tgagttagga atctatctgg attacgggga tcagagttcc
3241 tggagagtgg actcagtttc tgctctgatc caggcctgtt gtgctttttt tttttcccc
3301 ttaaaaaaa aaaagtacag acagaatctc agcggcttct agactgatct gatggatctt
3361 agcccggctt ctactgcggg gggaggggg ggagggatag ccacatatct gtggagacac
3421 ccacttcttt atctgaggcc tccaggtagg cacaaaggct gtggaactca gcctctatca
3481 tcagacaccc cccccaatg cctcattgac cccttcccc cagagccaag ggctagccca
3541 tcgggtgtgt gtacagtaag ttcttggtga aggagaacag ggacgttggc agaagcagtt
3601 tgcagtggcc ctagcatctt aaaacccatt gtctgtcaca ccagaaggtt ctagacctac
3661 caccacttcc cttcccatc tcatggaaac cttttagccc attctgaccc ctgtgtgtgc
3721 tctgagctca gatcgggtta tgagaccgcc caggcacatc agtcaggag gctctgatgt
3781 gagccgcaga cctctgtgtt cattcctatg agctggaggg gctggactgg gtggggtcag
3841 atgtgcttgg caggaactgt cagctgctga gcagggtggt ccctgagcgg aggataagca
3901 gcatcagact ccacaaccag aggaagaaag aaatggggat ggagcggaga cccacgggct
3961 gagtcccgct gtggagtggc cttgcagctc cctctcagtt aaaactccca gtaaagccac
4021 agttctccga gcacccaagt ctgctccagc cgtctcttaa aacaggccac tctctgagaa
4081 ggaattc (SEQ ID NO: 14)
```

FIG. 14N

Drosophila melanogaster pole hole (phl), transcript variant A, mRNA

MSSESSTEGDSDLYDPLAEELHNVQLVKHVTRENIDALNAKFAN

LQEPPAMYLIEYQELTSKLHELEAKEQELMERLNSQDQQEDSSLVERFKEQPHYQNQT

QILQQQRQLARVHHGNDLTDSLGSQPGSQCGTLTRQPKILLRAHLPNQQRTSVEVISG

VRLCDALMKALKLRQLTPDMCEVSTTHSGRHIIPWHTDIGTLHVEEIFVRLLDKFPIR

THIKHQIIRKTFFSLVFCEGCRRLLFTGFYCSQCNFRFHQRCANRVPMLCQPFPMDSY

YQLLLAENPDNGVGFPGRGTAVRFNMSSRSRSPRCSSSGSSSSSKPPSSSSGNHRQGR

PPRISQDDRSNSAPNVCINNIRSVTSEVQRSLIMQARPPLPHPCTDHSNSTQASPTST

LKHNRPRARSADESNKNLLLRDAKSSEENWNILAEEILIGPRIGSGSFGTVYRAHWHG

PVAVKTLNVKTPSPAQLQAFKNEVAMLKKTRHCNILLFMGCVSKPSLAIVTQWCEGSS

LYKHVHVSETKFKLNTLIDIGRQVAQGMDYLHAKNIIHRDLKSNNIFLHEDLSVKIGD

FGLATAKTRWSGEKQANQPTGSILWMAPEVIRMQELNPYSFQSDVYAFGIVMYELLAE

CLPYGHISNKDQILFMVGRGLLRPDMSQVRSDAPQALKRLAEDCIKYTPKDRPLFRPL

LNMLENMLRTLPKIHRSASEPNLTQSQLQNDEFLYLPSPKTPVNFNNFQFFGSAGNI

SEQ ID NO: 15)

FIG. 14O

```
ORIGIN
    1 cacttgtata tggttagttg attaatagca cgtcagaaac taatttacct gttgccgctc
   61 gtaccagatc cagatttgta ctatcccgag aagttaaaag ctctaggcaa attaacaatt
  121 agccgcgaca caaaccccgt ttcgcagagc acctgatacc ctttatcgtt atcgattggt
  181 acagccgaat cacgcctcct gataacgatt aaacaaaaag tcgaaatgta gtaaaattcg
  241 cggaaagtaa ataaattgtt atagccaagg tgaacgaacg agcggccagc tagtggcgat
  301 actgatactg ttgcgaacgt tgggcagcca ccgacggtgc cggctggtca ggttgttatc
  361 gggtaattgg cagctccttt ggaaaatcct caagttcagc tgcttctgca cacactgacc
  421 ttcattatac atacataccg tatatacgag ctgtttgtgt gcgtgtgtgt gtgtgcgctt
  481 gcaagtgtgt gggtgcactg aaaaaggtt ggaaggata caagccagaa atcagtgaaa
  541 accgggaata ttgcatcccg gagacggcg aaaagccgaa aaagcccatt aaaagtcaag
  601 gacgacatgc tgccctccgc ccacagaagt ggatgtgggt ggctcaccca ttagaactcc
  661 accaaaacgc aagcgcagga gttttttcctt caagaagtca aggcttcttc gttttcgggg
  721 tcatggtcac agcgcatagt atataggata aagcaacacc atgtccagcg agtcctccac
  781 cgaaggcgac agcgatctat acgatccttt ggccgaggag ctgcacaacg tccagttggt
  841 caaacatgtg accgcgaga atattgatgc cctgaatgcc cggcttgcca acctgcagga
  901 gccaccagcc atgtacttaa tagaatacca ggagttgacc tccaagctcc acgaactgga
  961 ggccaaggag caggaactaa tggagcgact gaactcgcag gaccagcagg aggactcctc
 1021 cttggtcgag cggttcaagg agcagcccca ctatcaaaat caaactcaaa tcctgcagca
 1081 acaacggcaa ttggcgcgag tgcaccacgg caacgatcta accgatagct gggctctca
 1141 gccgggcagc caatgtggaa ctttgacccg tcagcccaag atccttttgc gagcccact
 1201 gcccaatcaa cagcgcactt cagtggaggt aatttcggga gtacgactat gtgatgccct
```

FIG. 14P

```
1261 catgaaggcc ctgaaactcc ggcaactaac gccggatatg tgcgaagtaa gcacaactca
1321 ttccggaaga catatcatac cctggcacac ggatatcggc actctgcatg tggaggagat
1381 ctttgtcagg ctgctggata agtttcccat taggacacac atcaagcacc agatcatacg
1441 gaagaccttc ttctcgttgg tattctgcga gggctgtcga aggcttctgt tcaccgggtt
1501 ctactgtagc cagtgtaatt ttcgattcca tcagaggtgt gccaatagag tgccgatgct
1561 gtgccagccc tttcccatgg atagctacta tcagctactg ctggccgaga atccggataa
1621 tggcgttggt ttcccggca gaggcactgc tgtccgcttc aatatgagca gccggagtcg
1681 cagtcgtcgt tgcagcagca gtggcagcag cagcagctcg aagccaccat cttcatcctc
1741 cggcaatcat cgacagggtc gtccgccgag gatcagccaa gacgatcgat ccaattccgc
1801 gccaaatgtg tgcatcaaca acattcgatc ggtcacaagc gaagtgcagc gcagtttgat
1861 aatgcaggcc agacctcctt tgccgcatcc gtgcacagat cactccaact ccacgcaagc
1921 gtcgcccacg agcaccttga acacaatcg tcccagggcc aggtccgccg atgagagcaa
1981 taaaaatctg cttttaagag acgccaaaag ttccgaggaa aactggaata ttctggcgga
2041 ggagatttta attgggccgg gcatcggatc gggttccttt ggaaccgttt atcgcgcca
2101 ttggcacggt cccgtggccg taaagacact caacgtgaag acaccgagtc ccgcccagtt
2161 gcaggcgttt aagaacgagg tggccatgct gaaaaagacg cgccactgca atatcctcct
2221 cttcatgggc tgtgtatcca accatctct agcgattgtg acccagtggt gcgagggcag
2281 cagtctctac aagcacgtcc atgtcagcga aaccaagttt aaattgaaca cgctcatcga
2341 tatcggacgt caggtggccc agggcatgga ttacctgcat gccaagaata tcattcatag
2401 agacctcaag tcaaacaaca tcttttttgca cgaggatctt tccgtgaaga taggcgactt
2461 cggattggc actgcgaaaa ctcgatggtc gggtgaaaag caagccaatc aacccacggg
2521 cagtatttta tggatggctc cagaggtgat tcgcatgcag gagctaaacc cctactcctt
2581 ccagtcggac gttatgcct ttggtatcgt gatgtacgaa ctgttggcgg agtgcttgcc
2641 ctacggtcat attgcaaca aggatcagat cctgtttatg gtggggcgag gactctgcg
2701 tccggacatg agtcaagtgc gctcggatgc gccgcaggca ttgaagcgct tggccgagga
2761 ttgcattaag tatacccca aggatcgacc gctctttagg ccgctgctca atatgctgga
2821 gaacatgctg cgcactttgc ccaaaattca tcgcagtgcc agtgaaccaa acttgacgca
2881 atcgcagctg cagaacgatg agtttctgta tctgcccagc ccgaaaacgc cggtgaactt
2941 caacaacttt cagttcttcg gcagcgctgg gaatatctag acagcgacct gtacctgtac
3001 ttacatatat cctgcgtgat caacgtgatc ctacatctat atacttttg ttcttgtccc
3061 tctgtacata agcgattcgc gaaggggacg gctttggttg tccaccaaag tgaaagagag
3121 agagagagag agaaagagag agatgggt tgcctgccga cccgggagcg aaacttgctt
3181 ctttccttgg aactgacaaa gtcatttct gttaccacac acaaacgac tacaaactgt
3241 aaactaaact gcaacgccca tgtgtacata actgcatcat aacttatata cgttaggcaa
3301 gactactgaa actaaactaa actaaactaa actagctgat cgcaattaca ttatacacat
3361 tatacttata ctacaagaga tggtgttgtt tctggagtcg agcacgatga agaacattta
(SEQ ID NO: 16)
```

FIG. 14Q

Drosophila melanogaster kinase suppressor of ras (ksr), mRNA

MSSNNNAPASAPDTGSTNANDPISGSLSVDSNLVIIQDMIDLSA

NHLEGLRTQCAISSTLTQQEIRCLESKLVRYFSELLLAKMRLNERIPANGLVPHTTGN

ELRQWLRVVGLSQGTLTACLAPLTTLEQSLRLSDEEIRQLLADSPSQREEEELRRLTR

AMQNLRKCMESLESGTAASNNDPEQWHWDSWDRPTHIHRGSVGNIGLGNNSTASPRTH

HRQHGVKGKNSALANSTNFKSGRQSPSATEELNSTQGSQLTLTLTPSPPNSPFTPSSG

LSSSLNGTPQRSRGTPPPARKHQTLLSQSHVQVDGEQLARNRLPTDPSPDSHSSTSSD

IFVDPNTNASSGGSSSNVLMVPCSPGVGHVGMGHAIKHRFTKALGFMATCTLCQKQVF

HRWMKCTDCKYICHKSCAPHVPPSCGLPREYVDEFRHIKEQGGYASLPHVHGAAKGSP

LVKKSTLGKPLHQQHGDSSSPSSSCTSSTPSSPALFQQRERELDQAGSSSSANLLPTP

SLGKHQPSQFNFPNVTVTSSGGSGGVSLISNEPVPEQFPTAPATANGGLDSLVSSSNG

HMSSLIGSQTSNASTAATLTGSLVNSTTTTSTCSFFPRKLSTAGVDKRTPFTSEYTDT

HKSNDSDKTVSLSGSASTDSDRTPVRVDSTEDGDSGQWRQNSISLKEWDIPYGDLLLL

ERIGQGRFGTVHRALWHGDVAVKLLNEDYLQDEHMLETFRSEVANFKNTRHENLVLFM

GACMNPPYLAIVTSLCKGNTLYTYIHQPREKFAMNRTLLIAQQIAQGMGYLHAREIIH

KDLRTKNIFIENGKVIITDFGLFSSTKLLYCDMGLGVPHNWLCYLAPELIRALQPEKP

RGECLEFTPYSDVYSFGTVWYELICGEFTFKDQPAESIIWQVGRGMKQSLANLQSGRD

VKDLLMLCWTYEKEHRPQFARLLSLLEHLPKKRLARSPSHPVNLSRSAESVF (SEQ ID NO: 17)

FIG. 14R

ORIGIN
```
  1 cttgggtgta gagaaatttc aacaacagcc gaggaacttg tacaaattat tgcttttcg
 61 cattgcctaa gccgtttaga gttgcgggcg ttagcgtgcg cgatagcggc agcaccgaac
121 gtcaaggtcg cttggcgagg gccacaatgc gggcgggagt ccagccatt ggtcccatcg
181 aatcgtcgag tccccgaggg ggcgtctgaa aaaatcaatc gggctccact ccgtcgcgaa
241 taagcaggat gagcagcaac aacaacgcac ccgcatcggc tccagacacg ggctccacca
301 atgccaacga gagccatctcc ggttcgctgt cgtagacag caacctggtt atcattcagg
361 acatgattga tctctcggcc aaccatctgg agggcctgcg aacgcagtgc gcgatcagct
421 ccacgctgac gcagcaggag attcgttgcc tggagtcgaa gctggtgcga tacttctcgg
481 agctgctgct ggcgaagatg cggctaaatg agcgcatccc ggccaacggg cttgtgcccc
541 acacaacggg caacgaactg aggcaatggc tgcgcgtagt gggccttagc caggggactc
601 ttaccgcctg ccttgctcgc ctgaccactc tagagcaaag cctgcgtctc agcgacgagg
661 agatccgtca actcctggct gacagcccca gccagcgaga ggaggaggaa ctgcgaccgcc
721 tgaccagggc catgcagaac ttaaggaagt gcatggagtc gctggagagc ggtactgcgg
781 ctagcaacaa cgatccagag cagtggcact ggactcctg gacaggccc acccacattc
841 atcgcggcag tgtgggaaac attggactgg gtaacaattc aaccgcctcc ccgagaaccc
901 atcatcgcca gcatggtgtc aagggaaaga attccgctct ggccaactcc accaacttca
961 aaagtggccg ccaatcgccc tcagcgacag aagagctgaa cagcacacag ggttccagc
```

FIG. 14S

```
1021  tgactttaac ccttacgccc tcgccaccca attcgccctt cacgccttcc agtgggctga
1081  gcagcagcct taatggaaca ccacagagga gtcgtggtac cccgccgcca gctagaaagc
1141  accagacctt gctgagccag agtcatgtgc aagtggacgg ggagcaatta gcccgcaacc
1201  gtttgcccac tgatcccagc ccgatagcc acagctccac cagctcggac atctttgtgg
1261  acccaaatac taatgccagc tccggaggaa gttcctcgaa cgtgcttatg gtgccatgct
1321  ctccggggcgt gggtcacgtg gcatgggtc atgcaatcaa gcatcgtttc accaaggccc
1381  tgggcttcat ggccacctgt accctgtgcc agaagcaggt ctttcaccgc tggatgaagt
1441  gcaccgactg caagtacatc tgccacaagt catgcgcacc gcacgtaccg ccctcctgtg
1501  gacttccacg agaatatgtg gacgagtttc ggcacataaa ggagcaggga ggatacgcca
1561  gtctgccgca tgtgcatggc gcggcgaaag gatccccttt ggtaaaaaag agcaccctgg
1621  gtaagcccctt gcatcagcag cacggcgata gcagttcgcc gagttccagc tgcactagtt
1681  ccacgcccag cagtccggcg ctgttccagc aaagggagcg cgagctggat caggcgggca
1741  gcagctctag cgccaatctg ttacctacgc cttcgcttgg caagcaccag ccgagtcaat
1801  tcaactttcc caacgtgacg gtgacgagca gtggcggaag cggtggtgta tcgctcatct
1861  ccaatgaacc agtgccagag caattcccca cggcgcctgc aacagccaac ggaggacttg
1921  atagtctggt gagcagctcc aacgggcaca tgagctcgct catcggtagc caaacttcaa
1981  acgcttctac tgcggccacc ttgacgggca gtctggtcaa tagcacaacc accaccagca
2041  cctgcagttt ctttccgcga aaattgagca cagccggtgt ggataagagg acgccgttca
2101  ccagcgagta cacggatacc cacaagtcaa atgacagcga caagacagtc tccttgtctg
2161  gaagtgccag cacggactcg gaccggacac ccgttcgtgt ggattcaacg gaagacggag
2221  actcgggaca atggcgccag aactcgatct cactcaagga atgggacatc ccgtatggtg
2281  atctgcttct gctcgagcgg ataggggcag gacgcttcgg caccgtgcat cgagcccttt
2341  ggcacggaga tgtggcggtt aagctgctca acgaggacta tctgcaagac gaacacatgc
2401  tggagacgtt tcgcagcgag gtagccaact tcaagaacac tcgacacgag aacctggtgc
2461  tgttcatggg agcctgcatg aacccaccat atttggccat tgtgacttca ttgtgcaagg
2521  gcaacaccctt gtatacgtat attcaccagc gtcgggagaa gtttgccatg aaccggactc
2581  tcctcattgc ccagcagatc gcccagggca tgggctacct gcacgcaagg gagatcatcc
2641  acaaagatct gcgcaccaag aacatcttca tcgagaacgg caaggtgatt atcacggact
2701  ttgggctgtt cagctccacc aagctgctct actgtgatat gggcctagga gtgcccccaca
2761  actggttgtg ctacctggcg ccggagctaa tccgagcatt gcagccggag aagccgcgtg
2821  gagagtgtct ggagttcacc ccatactccg atgtctactc tttcggaacc gtttggtacg
2881  agctaatctg cggcgagttc acattcaagg atcagccggc ggaatcgatc atctggcagg
2941  ttggccgtgg gatgaagcag tcgctggcca acctgcagtc tggacgggat gtcaaggact
3001  tgctgatgct gtgctggacc tacgagaagg agcaccggcc gcagttcgca cgcctgctct
3061  ccctgctgga gcatcttccc aagaagcgtc tggcgcgcag tccctcccac cccgtcaacc
3121  tttcccgttc cgccgagtcc gtgttctgag ggaactgcag catggccact gtcactgtct
3181  agtacaattt cgatctacca actaagctag ctcgctttgt gccctcgtcc actctacaca
3241  aactctctcc caaggcgaag ttctatcgag ccgagcgaag attgtaaata cataaacgta
3301  actaccaaat tatagcaatc catttttaaaa actacataca tatgtgtagg catgtatcgg
3361  gagcactcca gttgcagttg ttagcaaacg aaacaaaggc aaatcaaatg ttaactcgaa
3421  aaagacaaaa cgcttaaatg tttaagagca gaggcaaaca gagaaggcat agacatacat
3481  atacaaacaa acaaacaagc actgtggcaa acataaatgt aaacgttaat caggtgagca
3541  atttctaaat tgttaattat gtgtaagaga actatatata tatatatata tatatatata
3601  tatatatata tatatataca tgtatataca gcagcaatgt attgtatatg acggactagt
3661  gttaaattaa atatatattg tgaattatgt atggtcaagt gtatatagta aatggacttt
3721  aaatgcgaaa tcgaaac (SEQ ID NO: 18)
```

FIG. 14T

A)
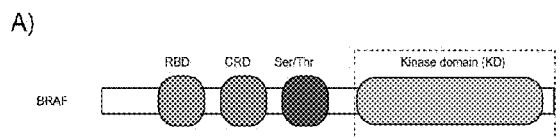
FIG. 15A
B)
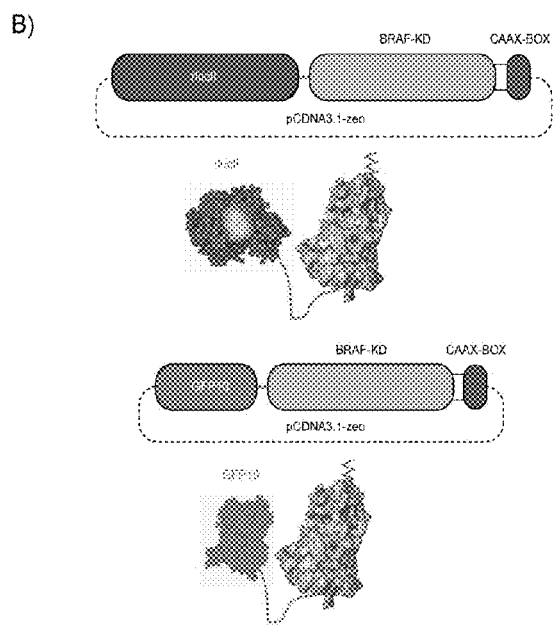
FIG. 15B
C)
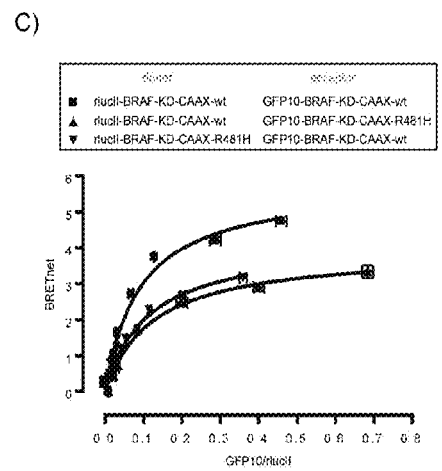
FIG. 15C
D)
FIG. 15D

CAAX-box and BRET donor and acceptor sequences

>human KRAS CAAX-box CDS
AAGATGAGCAAAGATGGTAAAAAGAAGAAAAAGAAGTCAAAGACAAAGTGTGTAATTA
TGTAA (SEQ ID NO: 19)

>human KRAS CAAX-box
KMSKDGKKKKKKSKTKCVIM (SEQ ID NO: 20)

>GFP10 CDS
ATGGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCCAC
CTACGGCAAGCTGACCCTGAAGTTCATCTGCACCACCGGCAAGCTGCCCGTGCCCTGG
CCCACCCTCGTGACCACCCTGAGCTACGGCGTGCAGTGCTTCAGCCGCTACCCCGACC
ACATGAAGCAGCACGACTTCTTCAAGTCCGCCATGCCCGAAGGCTACGTCCAGGAGCG
CACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCA
ACATCCTGGGGCACAAGCTGGAGTACAACTACAACCCCCACAACGTCTATATCATGGC
CGACAAGCAGAAGAACGGCATCAAGGTGAACTTCAAGATCCGCCACAACATCGAGGAC
GGCAGCGTGCAGCTCGCCGACCACTACCAGCAGAACACCCCCATCGGCGACGGCCCCG
TGCTGCTGCCCGACAACCACTACCTGTTCACCCAGTCCGCCCTGAGCAAAGACCCCAA
CGAGAAGCGCGATCACATGGTCCTGCTGGAGTTCGTGACCGCCGCCGGGATCACTCTC
GGCATGGACGAGCTGTACAAGGGATCCGCCTAG (SEQ ID NO:. 21)

>GFP10
MVSKGEELFTGVVPILVELDGDVNGHKFSVSGEGEGDATYGKLTLKFICTTGKLPVPW
PTLVTTLSYGVQCFSRYPDHMKQHDFFKSAMPEGYVQERTIFFKDDGNYKTRAEVKFE
GDTLVNRIELKGIDFKEDGNILGHKLEYNYNPHNVYIMADKQKNGIKVNFKIRHNIED
GSVQLADHYQQNTPIGDGPVLLPDNHYLFTQSALSKDPNEKRDHMVLLEFVTAAGITL
GMDELYKGSA (SEQ ID NO: 22)

FIG. 16A

```
>rlucII CDS
ATGACCAGCAAGGTGTACGACCCCGAGCAGAGGAAGAGGATGATCACCGGCCCCCAGT
GGTGGGCCAGGTGCAAGCAGATGAACGTGCTGGACAGCTTCATCAACTACTACGACAG
CGAGAAGCACGCCGAGAACGCCGTGATCTTCCTGCACGGCAACGCCACTAGCAGCTAC
CTGTGGAGGCACGTGGTGCCCCACATCGAGCCCGTGGCCAGGTGCATCATCCCCGATC
TGATCGGCATGGGCAAGAGCGGCAAGAGCGGCAACGGCAGCTACAGGCTGCTGGACCA
CTACAAGTACCTGACCGCCTGGTTCGAGCTCCTGAACCTGCCCAAGAAGATCATCTTC
GTGGGCCACGACTGGGGCGCCGCACTGGCCTTCCACTACAGCTACGAGCACCAGGACA
AGATCAAGGCCATCGTGCACGCCGAGAGCGTGGTTGACGTGATCGAGAGCTGGGACGA
GTGGCCAGACATCGAGGAGGACATCGCCCTGATCAAGAGCGAGGAGGGCGAGAAGATG
GTGCTGGAGAACAACTTCTTCGTGGAGACCGTTCTGCCCAGCAAGATCATGAGAAAGC
TGGAGCCCGAGGAGTTCGCCGCCTACCTGGAGCCCTTCAAGGAGAAGGGCGAGGTGAG
AAGACCCACCCTGAGCTGGCCCAGAGAGATCCCCCTGGTGAAGGGCGGCAAGCCCGAC
GTGGTGCAGATCGTGAGAAACTACAACGCCTACCTGAGAGCCAGCGACGACCTGCCCA
AGATGTTCATCGAGAGCGACCCCGGCTTCTTCAGCAACGCCATCGTGGAGGGCGCCAA
GAAGTTCCCCAACACCGAGTTCGTGAAGGTGAAGGGCCTGCACTTCAGCCAGGAGGAC
GCCCCCGACGAGATGGGCAAGTACATCAAGAGCTTCGTGGAGAGAGTGCTGAAGAACG
AGCAGggatccgcctag (SEQ ID NO: 23)

>rlucII
MTSKVYDPEQRKRMITGPQWWARCKQMNVLDSFINYYDSEKHAENAVIFLHGNATSSY
LWRHVVPHIEPVARCIIPDLIGMGKSGKSGNGSYRLLDHYKYLTAWFELLNLPKKIIF
VGHDWGAALAFHYSYEHQDKIKAIVHAESVVDVIESWDEWPDIEEDIALIKSEEGEKM
VLENNFFVETVLPSKIMRKLEPEEFAAYLEPFKEKGEVRRPTLSWPREIPLVKGGKPD
VVQIVRNYNAYLRASDDLPKMFIESDPGFFSNAIVEGAKKFPNTEFVKVKGLHFSQED
APDEMGKYIKSFVERVLKNEQGSA (SEQ ID NO: 24)
```

FIG. 16B

Human BRAF (hBRAF) sequences

>hBRAF-KD-wt CDS
ATGGATGATTGGGAGATTCCTGATGGGCAGATTACAGTGGGACAAAGAATTGGATCTG
GATCATTTGGAACAGTCTACAAGGGAAAGTGGCATGGTGATGTGGCAGTGAAAATGTT
GAATGTGACAGCACCTACACCTCAGCAGTTACAAGCCTTCAAAAATGAAGTAGGAGTA
CTCAGGAAAACACGACATGTGAATATCCTACTCTTCATGGGCTATTCCACAAAGCCAC
AACTGGCTATTGTTACCCAGTGGTGTGAGGGCTCCAGCTTGTATCACCATCTCCATAT
CATTGAGACCAAATTTGAGATGATCAAACTTATAGATATTGCACGACAGACTGCACAG
GGCATGGATTACTTACACGCCAAGTCAATCATCCACAGAGACCTCAAGAGTAATAATA
TATTTCTTCATGAAGACCTCACAGTAAAAATAGGTGATTTTGGTCTAGCTACAGTGAA
ATCTCGATGGAGTGGGTCCCATCAGTTTGAACAGTTGTCTGGATCCATTTGTGGATG
GCACCAGAAGTCATCAGAATGCAAGATAAAAATCCATACAGCTTTCAGTCAGATGTAT
ATGCATTTGGAATTGTTCTGTATGAATTGATGACTGGACAGTTACCTTATTCAAACAT
CAACAACAGGGACCAGATAATTTTTATGGTGGGACGAGGATACCTGTCTCCAGATCTC
AGTAAGGTACGGAGTAACTGTCCAAAAGCCATGAAGAGATTAATGGCAGAGTGCCTCA
AAAAGAAAAGAGATGAGAGACCACTCTTTCCCCAAATTCTCGCCTCTATTGAGCTGCT
GGCCCGCTCATTGCCAAAAATTCACCGCAGTGCATCAGAACCCTCCTTGAATCGGGCT
GGTTTCCAAACAGAGGATTTAGTCTATATGCTTGTGCTTCTCCAAAAACACCCATCC
AGGCAGGGGGATATGGTGCGTTTCCTGTCCAC (SEQ ID NO: 25)

>hBRAF-KD-wt
MDDWEIPDGQITVGQRIGSGSFGTVYKGKWHGDVAVKMLNVTAPTPQQLQAFKNEVGV
LRKTRHVNILLFMGYSTKPQLAIVTQWCEGSSLYHHLHIIETKFEMIKLIDIARQTAQ
GMDYLHAKSIIHRDLKSNNIFLHEDLTVKIGDFGLATVKSRWSGSHQFEQLSGSILWM
APEVIRMQDKNPYSFQSDVYAFGIVLYELMTGQLPYSNINNRDQIIFMVGRGYLSPDL
SKVRSNCPKAMKRLMAECLKKKRDERPLFPQILASIELLARSLPKIHRSASEPSLNRA
GFQTEDFSLYACASPKTPIQAGGYGAFPVH (SEQ ID NO: 26)

FIG. 17A

>hBRAF-KD-R481H CDS
ATGGATGATTGGGAGATTCCTGATGGGCAGATTACAGTGGGACAAAGAATTGGATCTG
GATCATTTGGAACAGTCTACAAGGGAAAGTGGCATGGTGATGTGGCAGTGAAAATGTT
GAATGTGACAGCACCTACACCTCAGCAGTTACAAGCCTTCAAAAATGAAGTAGGAGTA
CTCAGGAAAACACATCATGTGAATATCCTACTCTTCATGGGCTATTCCACAAAGCCAC
AACTGGCTATTGTTACCCAGTGGTGTGAGGGCTCCAGCTTGTATCACCATCTCCATAT
CATTGAGACCAAATTTGAGATGATCAAACTTATAGATATTGCACGACAGACTGCACAG
GGCATGGATTACTTACACGCCAAGTCAATCATCCACAGAGACCTCAAGAGTAATAATA
TATTTCTTCATGAAGACCTCACAGTAAAAATAGGTGATTTTGGTCTAGCTACAGTGAA
ATCTCGATGGAGTGGGTCCCATCAGTTTGAACAGTTGTCTGGATCCATTTTGTGGATG
GCACCAGAAGTCATCAGAATGCAAGATAAAAATCCATACAGCTTTCAGTCAGATGTAT
ATGCATTTGGAATTGTTCTGTATGAATTGATGACTGGACAGTTACCTTATTCAAACAT
CAACAACAGGGACCAGATAATTTTTATGGTGGGACGAGGATACCTGTCTCCAGATCTC
AGTAAGGTACGGAGTAACTGTCCAAAAGCCATGAAGAGATTAATGGCAGAGTGCCTCA
AAAAGAAAAGAGATGAGAGACCACTCTTTCCCCAAATTCTCGCCTCTATTGAGCTGCT
GGCCCGCTCATTGCCAAAAATTCACCGCAGTGCATCAGAACCCTCCTTGAATCGGGCT
GGTTTCCAAACAGAGGATTTTAGTCTATATGCTTGTGCTTCTCCAAAAACACCCATCC
AGGCAGGGGGATATGGTGCGTTTCCTGTCCAC (SEQ ID NO: 27)

>hBRAF-KD-R481H
MDDWEIPDGQITVGQRIGSGSFGTVYKGKWHGDVAVKMLNVTAPTPQQLQAFKNEVGV
LRKTHHVNILLFMGYSTKPQLAIVTQWCEGSSLYHHLHIIETKFEMIKLIDIARQTAQ
GMDYLHAKSIIHRDLKSNNIFLHEDLTVKIGDFGLATVKSRWSGSHQFEQLSGSILWM
APEVIRMQDKNPYSFQSDVYAFGIVLYELMTGQLPYSNINNRDQIIFMVGRGYLSPDL
SKVRSNCPKAMKRLMAECLKKKRDERPLFPQILASIELLARSLPKIHRSASEPSLNRA
GFQTEDFSLYACASPKTPIQAGGYGAFPVH (SEQ ID NO: 28)

FIG. 17B

All human BRAF-KD clones are between the NheI and XbaI sites in pCDNA3.1-zeo

>GFP10-hBRAF-KD-wt-CAAX CDS
ATGGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCCAC
CTACGGCAAGCTGACCCTGAAGTTCATCTGCACCACCGGCAAGCTGCCCGTGCCCTGG
CCCACCCTCGTGACCACCCTGAGCTACGGCGTGCAGTGCTTCAGCCGCTACCCCGACC
ACATGAAGCAGCACGACTTCTTCAAGTCCGCCATGCCCGAAGGCTACGTCCAGGAGCG
CACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCA
ACATCCTGGGGCACAAGCTGGAGTACAACTACAACCCCCACAACGTCTATATCATGGC
CGACAAGCAGAAGAACGGCATCAAGGTGAACTTCAAGATCCGCCACAACATCGAGGAC
GGCAGCGTGCAGCTCGCCGACCACTACCAGCAGAACACCCCCATCGGCGACGGCCCCG
TGCTGCTGCCCGACAACCACTACCTGTTCACCCAGTCCGCCCTGAGCAAAGACCCCAA
CGAGAAGCGCGATCACATGGTCCTGCTGGAGTTCGTGACCGCCGCCGGGATCACTCTC
GGCATGGACGAGCTGTACAAGGGATCCGCCGGTACCATGGATGATTGGGAGATTCCTG
ATGGGCAGATTACAGTGGGACAAAGAATTGGATCTGGATCATTTGGAACAGTCTACAA
GGGAAAGTGGCATGGTGATGTGGCAGTGAAAATGTTGAATGTGACAGCACCTACACCT
CAGCAGTTACAAGCCTTCAAAAATGAAGTAGGAGTACTCAGGAAAACACGACATGTGA
ATATCCTACTCTTCATGGGCTATTCCACAAAGCCACAACTGGCTATTGTTACCCAGTG
GTGTGAGGGCTCCAGCTTGTATCACCATCTCCATATCATTGAGACCAAATTTGAGATG
ATCAAACTTATAGATATTGCACGACAGACTGCACAGGGCATGGATTACTTACACGCCA
AGTCAATCATCCACAGAGACCTCAAGAGTAATAATATATTTCTTCATGAAGACCTCAC
AGTAAAAATAGGTGATTTTGGTCTAGCTACAGTGAAATCTCGATGGAGTGGGTCCCAT
CAGTTTGAACAGTTGTCTGGATCCATTTTGTGGATGGCACCAGAAGTCATCAGAATGC
AAGATAAAAATCCATACAGCTTTCAGTCAGATGTATATGCATTTGGAATTGTTCTGTA
TGAATTGATGACTGGACAGTTACCTTATTCAAACATCAACAACAGGGACCAGATAATT
TTTATGGTGGGACGAGGATACCTGTCTCCAGATCTCAGTAAGGTACGGAGTAACTGTC
CAAAAGCCATGAAGAGATTAATGGCAGAGTGCCTCAAAAAGAAAAGAGATGAGAGACC
ACTCTTTCCCCAAATTCTCGCCTCTATTGAGCTGCTGGCCCGCTCATTGCCAAAAATT
CACCGCAGTGCATCAGAACCCTCCTTGAATCGGGCTGGTTTCCAAACAGAGGATTTTA
GTCTATATGCTTGTGCTTCTCCAAAAACACCCATCCAGGCAGGGGATATGGTGCGTT
TCCTGTCCACAAGATGAGCAAAGATGGTAAAAGAAGAAAAAGAAGTCAAAGACAAAG
TGTGTAATTATGTAA (SEQ ID NO: 29)

FIG. 18A

>GFP10-hBRAF-KD-wt-CAAX
MVSKGEELFTGVVPILVELDGDVNGHKFSVSGEGEGDATYGKLTLKFICTTGKLPVPW
PTLVTTLSYGVQCFSRYPDHMKQHDFFKSAMPEGYVQERTIFFKDDGNYKTRAEVKFE
GDTLVNRIELKGIDFKEDGNILGHKLEYNYNPHNVYIMADKQKNGIKVNFKIRHNIED
GSVQLADHYQQNTPIGDGPVLLPDNHYLFTQSALSKDPNEKRDHMVLLEFVTAAGITL
GMDELYKGSAGTMDDWEIPDGQITVGQRIGSGSFGTVYKGKWHGDVAVKMLNVTAPTP
QQLQAFKNEVGVLRKTRHVNILLFMGYSTKPQLAIVTQWCEGSSLYHHLHIIETKFEM
IKLIDIARQTAQGMDYLHAKSIIHRDLKSNNIFLHEDLTVKIGDFGLATVKSRWSGSH
QFEQLSGSILWMAPEVIRMQDKNPYSFQSDVYAFGIVLYELMTGQLPYSNINNRDQII
FMVGRGYLSPDLSKVRSNCPKAMKRLMAECLKKKRDERPLFPQILASIELLARSLPKI
HRSASEPSLNRAGFQTEDFSLYACASPKTPIQAGGYGAFPVHKMSKDGKKKKKKSKTK
CVIM (SEQ ID NO: 30)

FIG. 18B

>GFP10-hBRAF-KD-R481H-CAAX CDS
ATGGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCCAC
CTACGGCAAGCTGACCCTGAAGTTCATCTGCACCACCGGCAAGCTGCCCGTGCCCTGG
CCCACCCTCGTGACCACCCTGAGCTACGGCGTGCAGTGCTTCAGCCGCTACCCCGACC
ACATGAAGCAGCACGACTTCTTCAAGTCCGCCATGCCCGAAGGCTACGTCCAGGAGCG
CACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCA
ACATCCTGGGGCACAAGCTGGAGTACAACTACAACCCCCACAACGTCTATATCATGGC
CGACAAGCAGAAGAACGGCATCAAGGTGAACTTCAAGATCCGCCACAACATCGAGGAC
GGCAGCGTGCAGCTCGCCGACCACTACCAGCAGAACACCCCCATCGGCGACGGCCCCG
TGCTGCTGCCCGACAACCACTACCTGTTCACCCAGTCCGCCCTGAGCAAAGACCCCAA
CGAGAAGCGCGATCACATGGTCCTGCTGGAGTTCGTGACCGCCGCCGGATCACTCTC
GGCATGGACGAGCTGTACAAGGGATCCGCCGGTACCATGGATGATTGGGAGATTCCTG
ATGGGCAGATTACAGTGGGACAAAGAATTGGATCTGGATCATTTGGAACAGTCTACAA
GGGAAAGTGGCATGGTGATGTGGCAGTGAAAATGTTGAATGTGACAGCACCTACACCT
CAGCAGTTACAAGCCTTCAAAAATGAAGTAGGAGTACTCAGGAAAACACATCATGTGA
ATATCCTACTCTTCATGGGCTATTCCACAAAGCCACAACTGGCTATTGTTACCCAGTG
GTGTGAGGGCTCCAGCTTGTATCACCATCTCCATATCATTGAGACCAAATTTGAGATG
ATCAAACTTATAGATATTGCACGACAGACTGCACAGGGCATGGATTACTTACACGCCA
AGTCAATCATCCACAGAGACCTCAAGAGTAATAATATATTTCTTCATGAAGACCTCAC
AGTAAAAATAGGTGATTTTGGTCTAGCTACAGTGAAATCTCGATGGAGTGGGTCCCAT
CAGTTTGAACAGTTGTCTGGATCCATTTTGTGGATGGCACCAGAAGTCATCAGAATGC
AAGATAAAAATCCATACAGCTTTCAGTCAGATGTATATGCATTTGGAATTGTTCTGTA
TGAATTGATGACTGGACAGTTACCTTATTCAAACATCAACAACAGGGACCAGATAATT
TTTATGGTGGGACGAGGATACCTGTCTCCAGATCTCAGTAAGGTACGGAGTAACTGTC
CAAAAGCCATGAAGAGATTAATGGCAGAGTGCCTCAAAAAGAAAAGAGATGAGAGACC
ACTCTTTCCCCAAATTCTCGCCTCTATTGAGCTGCTGGCCCGCTCATTGCCAAAAATT
CACCGCAGTGCATCAGAACCCTCCTTGAATCGGGCTGGTTTCCAAACAGAGGATTTTA
GTCTATATGCTTGTGCTTCTCCAAAAACACCCATCCAGGCAGGGGATATGGTGCGTT
TCCTGTCCACAAGATGAGCAAAGATGGTAAAAGAAGAAAAAGAAGTCAAAGACAAAG
TGTGTAATTATGTAA (SEQ ID NO: 31)

FIG. 18C

>GFP10-hBRAF-KD-R481H-CAAX
MVSKGEELFTGVVPILVELDGDVNGHKFSVSGEGEGDATYGKLTLKFICTTGKLPVPW
PTLVTTLSYGVQCFSRYPDHMKQHDFFKSAMPEGYVQERTIFFKDDGNYKTRAEVKFE
GDTLVNRIELKGIDFKEDGNILGHKLEYNYNPHNVYIMADKQKNGIKVNFKIRHNIED
GSVQLADHYQQNTPIGDGPVLLPDNHYLFTQSALSKDPNEKRDHMVLLEFVTAAGITL
GMDELYKGSAGTMDDWEIPDGQITVGQRIGSGSFGTVYKGKWHGDVAVKMLNVTAPTP
QQLQAFKNEVGVLRKTHHVNILLFMGYSTKPQLAIVTQWCEGSSLYHHLHIIETKFEM
IKLIDIARQTAQGMDYLHAKSIIHRDLKSNNIFLHEDLTVKIGDFGLATVKSRWSGSH
QFEQLSGSILWMAPEVIRMQDKNPYSFQSDVYAFGIVLYELMTGQLPYSNINNRDQII
FMVGRGYLSPDLSKVRSNCPKAMKRLMAECLKKKRDERPLFPQILASIELLARSLPKI
HRSASEPSLNRAGFQTEDFSLYACASPKTPIQAGGYGAFPVHKMSKDGKKKKKKSKTK
CVIM (SEQ ID NO: 32)

FIG. 18D

>rlucII-hBRAF-KD-wt-CAAX CDS
ATGACCAGCAAGGTGTACGACCCCGAGCAGAGGAAGAGGATGATCACCGGCCCCCAGT
GGTGGGCCAGGTGCAAGCAGATGAACGTGCTGGACAGCTTCATCAACTACTACGACAG
CGAGAAGCACGCCGAGAACGCCGTGATCTTCCTGCACGGCAACGCCACTAGCAGCTAC
CTGTGGAGGCACGTGGTGCCCCACATCGAGCCCGTGGCCAGGTGCATCATCCCCGATC
TGATCGGCATGGGCAAGAGCGGCAAGAGCGGCAACGGCAGCTACAGGCTGCTGGACCA
CTACAAGTACCTGACCGCCTGGTTCGAGCTCCTGAACCTGCCCAAGAAGATCATCTTC
GTGGGCCACGACTGGGGCGCCGCACTGGCCTTCCACTACAGCTACGAGCACCAGGACA
AGATCAAGGCCATCGTGCACGCCGAGAGCGTGGTTGACGTGATCGAGAGCTGGGACGA
GTGGCCAGACATCGAGGAGGACATCGCCCTGATCAAGAGCGAGGAGGGCGAGAAGATG
GTGCTGGAGAACAACTTCTTCGTGGAGACCGTTCTGCCCAGCAAGATCATGAGAAAGC
TGGAGCCCGAGGAGTTCGCCGCCTACCTGGAGCCCTTCAAGGAGAAGGGCGAGGTGAG
AAGACCCACCCTGAGCTGGCCCAGAGAGATCCCCCTGGTGAAGGGCGGCAAGCCCGAC
GTGGTGCAGATCGTGAGAAACTACAACGCCTACCTGAGAGCCAGCGACGACCTGCCCA
AGATGTTCATCGAGAGCGACCCCGGCTTCTTCAGCAACGCCATCGTGGAGGGCGCCAA
GAAGTTCCCCAACACCGAGTTCGTGAAGGTGAAGGGCCTGCACTTCAGCCAGGAGGAC
GCCCCCGACGAGATGGGCAAGTACATCAAGAGCTTCGTGGAGAGAGTGCTGAAGAACG
AGCAGggatccgccGGTACCATGGATGATTGGGAGATTCCTGATGGGCAGATTACAGT
GGGACAAAGAATTGGATCTGGATCATTTGGAACAGTCTACAAGGGAAAGTGGCATGGT
GATGTGGCAGTGAAAATGTTAATGTGACAGCACCTACACCTCAGCAGTTACAAGCCT
TCAAAAATGAAGTAGGAGTACTCAGGAAAACACGACATGTGAATATCCTACTCTTCAT
GGGCTATTCCACAAAGCCACAACTGGCTATTGTTACCCAGTGGTGTGAGGGCTCCAGC
TTGTATCACCATCTCCATATCATTGAGACCAAATTTGAGATGATCAAACTTATAGATA
TTGCACGACAGACTGCACAGGGCATGGATTACTTACACGCCAAGTCAATCATCCACAG
AGACCTCAAGAGTAATAATATATTTCTTCATGAAGACCTCACAGTAAAAATAGGTGAT
TTTGGTCTAGCTACAGTGAAATCTCGATGGAGTGGGTCCCATCAGTTTGAACAGTTGT
CTGGATCCATTTTGTGGATGGCACCAGAAGTCATCAGAATGCAAGATAAAAATCCATA
CAGCTTTCAGTCAGATGTATATGCATTTGGAATTGTTCTGTATGAATTGATGACTGGA
CAGTTACCTTATTCAAACATCAACAACAGGGACCAGATAATTTTTATGGTGGGACGAG
GATACCTGTCTCCAGATCTCAGTAAGGTACGGAGTAACTGTCCAAAAGCCATGAAGAG
ATTAATGGCAGAGTGCCTCAAAAAGAAAAGAGATGAGAGACCACTCTTTCCCCAAATT
CTCGCCTCTATTGAGCTGCTGGCCCGCTCATTGCCAAAAATTCACCGCAGTGCATCAG
AACCCTCCTTGAATCGGGCTGGTTTCCAAACAGAGGATTTTAGTCTATATGCTTGTGC
TTCTCCAAAAACACCCATCCAGGCAGGGGATATGGTGCGTTTCCTGTCCACAAGATG
AGCAAAGATGGTAAAAAGAAGAAAAAGAAGTCAAAGACAAAGTGTGTAATTATGTAA
(SEQ ID NO: 33)

FIG. 18E

\>rlucII-hBRAF-KD-wt-CAAX
MTSKVYDPEQRKRMITGPQWWARCKQMNVLDSFINYYDSEKHAENAVIFLHGNATSSY
LWRHVVPHIEPVARCIIPDLIGMGKSGKSGNGSYRLLDHYKYLTAWFELLNLPKKIIF
VGHDWGAALAFHYSYEHQDKIKAIVHAESVVDVIESWDEWPDIEEDIALIKSEEGEKM
VLENNFFVETVLPSKIMRKLEPEEFAAYLEPFKEKGEVRRPTLSWPREIPLVKGGKPD
VVQIVRNYNAYLRASDDLPKMFIESDPGFFSNAIVEGAKKFPNTEFVKVKGLHFSQED
APDEMGKYIKSFVERVLKNEQGSAGTMDDWEIPDGQITVGQRIGSGSFGTVYKGKWHG
DVAVKMLNVTAPTPQQLQAFKNEVGVLRKTRHVNILLFMGYSTKPQLAIVTQWCEGSS
LYHHLHIIETKFEMIKLIDIARQTAQGMDYLHAKSIIHRDLKSNNIFLHEDLTVKIGD
FGLATVKSRWSGSHQFEQLSGSILWMAPEVIRMQDKNPYSFQSDVYAFGIVLYELMTG
QLPYSNINNRDQIIFMVGRGYLSPDLSKVRSNCPKAMKRLMAECLKKKRDERPLFPQI
LASIELLARSLPKIHRSASEPSLNRAGFQTEDFSLYACASPKTPIQAGGYGAFPVHKM
SKDGKKKKKKSKTKCVIM (SEQ ID NO: 34)

FIG. 18F

>rlucII-hBRAF-KD-R481H-CAAX CDS
ATGACCAGCAAGGTGTACGACCCCGAGCAGAGGAAGAGGATGATCACCGGCCCCCAGT
GGTGGGCCAGGTGCAAGCAGATGAACGTGCTGGACAGCTTCATCAACTACTACGACAG
CGAGAAGCACGCCGAGAACGCCGTGATCTTCCTGCACGGCAACGCCACTAGCAGCTAC
CTGTGGAGGCACGTGGTGCCCCACATCGAGCCCGTGGCCAGGTGCATCATCCCCGATC
TGATCGGCATGGGCAAGAGCGGCAAGAGCGGCAACGGCAGCTACAGGCTGCTGGACCA
CTACAAGTACCTGACCGCCTGGTTCGAGCTCCTGAACCTGCCCAAGAAGATCATCTTC
GTGGGCCACGACTGGGGCGCCGCACTGGCCTTCCACTACAGCTACGAGCACCAGGACA
AGATCAAGGCCATCGTGCACGCCGAGAGCGTGGTTGACGTGATCGAGAGCTGGGACGA
GTGGCCAGACATCGAGGAGGACATCGCCCTGATCAAGAGCGAGGAGGGCGAGAAGATG
GTGCTGGAGAACAACTTCTTCGTGGAGACCGTTCTGCCCAGCAAGATCATGAGAAAGC
TGGAGCCCGAGGAGTTCGCCGCCTACCTGGAGCCCTTCAAGGAGAAGGGCGAGGTGAG
AAGACCCACCCTGAGCTGGCCCAGAGAGATCCCCCTGGTGAAGGGCGGCAAGCCCGAC
GTGGTGCAGATCGTGAGAAACTACAACGCCTACCTGAGAGCCAGCGACGACCTGCCCA
AGATGTTCATCGAGAGCGACCCCGGCTTCTTCAGCAACGCCATCGTGGAGGGCGCCAA
GAAGTTCCCCAACACCGAGTTCGTGAAGGTGAAGGGCCTGCACTTCAGCCAGGAGGAC
GCCCCCGACGAGATGGGCAAGTACATCAAGAGCTTCGTGGAGAGAGTGCTGAAGAACG
AGCAGggatccgccGGTACCATGGATGATTGGGAGATTCCTGATGGGCAGATTACAGT
GGGACAAAGAATTGGATCTGGATCATTTGGAACAGTCTACAAGGGAAAGTGGCATGGT
GATGTGGCAGTGAAAATGTTGAATGTGACAGCACCTACACCTCAGCAGTTACAAGCCT
TCAAAAATGAAGTAGGAGTACTCAGGAAAACACATCATGTGAATATCCTACTCTTCAT
GGGCTATTCCACAAAGCCACAACTGGCTATTGTTACCCAGTGGTGTGAGGGCTCCAGC
TTGTATCACCATCTCCATATCATTGAGACCAAATTTGAGATGATCAAACTTATAGATA
TTGCACGACAGACTGCACAGGGCATGGATTACTTACACGCCAAGTCAATCATCCACAG
AGACCTCAAGAGTAATAATATATTTCTTCATGAAGACCTCACAGTAAAAATAGGTGAT
TTTGGTCTAGCTACAGTGAAATCTCGATGGAGTGGGTCCCATCAGTTTGAACAGTTGT
CTGGATCCATTTTGTGGATGGCACCAGAAGTCATCAGAATGCAAGATAAAAATCCATA
CAGCTTTCAGTCAGATGTATATGCATTTGGAATTGTTCTGTATGAATTGATGACTGGA
CAGTTACCTTATTCAAACATCAACAACAGGGACCAGATAATTTTTATGGTGGGACGAG
GATACCTGTCTCCAGATCTCAGTAAGGTACGGAGTAACTGTCCAAAAGCCATGAAGAG
ATTAATGGCAGAGTGCCTCAAAAAGAAAAGAGATGAGAGACCACTCTTTCCCCAAATT
CTCGCCTCTATTGAGCTGCTGGCCCGCTCATTGCCAAAAATTCACCGCAGTGCATCAG
AACCCTCCTTGAATCGGGCTGGTTTCCAAACAGAGGATTTTAGTCTATATGCTTGTGC
TTCTCCAAAAACACCCATCCAGGCAGGGGATATGGTGCGTTTCCTGTCCACAAGATG
AGCAAAGATGGTAAAAAGAAGAAAAAGAAGTCAAAGACAAAGTGTGTAATTATGTAA
(SEQ ID NO: 35)

FIG. 18G

>rlucII-hBRAF-KD-R481H-CAAX
MTSKVYDPEQRKRMITGPQWWARCKQMNVLDSFINYYDSEKHAENAVIFLHGNATSSY
LWRHVVPHIEPVARCIIPDLIGMGKSGKSGNGSYRLLDHYKYLTAWFELLNLPKKIIF
VGHDWGAALAFHYSYEHQDKIKAIVHAESVVDVIESWDEWPDIEEDIALIKSEEGEKM
VLENNFFVETVLPSKIMRKLEPEEFAAYLEPFKEKGEVRRPTLSWPREIPLVKGGKPD
VVQIVRNYNAYLRASDDLPKMFIESDPGFFSNAIVEGAKKFPNTEFVKVKGLHFSQED
APDEMGKYIKSFVERVLKNEQGSAGTMDDWEIPDGQITVGQRIGSGSFGTVYKGKWHG
DVAVKMLNVTAPTPQQLQAFKNEVGVLRKTHHVNILLFMGYSTKPQLAIVTQWCEGSS
LYHHLHIIETKFEMIKLIDIARQTAQGMDYLHAKSIIHRDLKSNNIFLHEDLTVKIGD
FGLATVKSRWSGSHQFEQLSGSILWMAPEVIRMQDKNPYSFQSDVYAFGIVLYELMTG
QLPYSNINNRDQIIFMVGRGYLSPDLSKVRSNCPKAMKRLMAECLKKKRDERPLFPQI
LASIELLARSLPKIHRSASEPSLNRAGFQTEDFSLYACASPKTPIQAGGYGAFPVHKM
SKDGKKKKKKSKTKCVIM (SEQ ID NO: 36)

FIG. 18H

Human CRAF (hCRAF) sequences

>hCRAF-KD-wt CDS
ATGTATTATTGGGAAATAGAAGCCAGTGAAGTGATGCTGTCCACTCGGATTGGGTCAG
GCTCTTTTGGAACTGTTTATAAGGGTAAATGGCACGGAGATGTTGCAGTAAAGATCCT
AAAGGTTGTCGACCCAACCCCAGAGCAATTCCAGGCCTTCAGGAATGAGGTGGCTGTT
CTGCGCAAAACACGGCATGTGAACATTCTGCTTTTCATGGGGTACATGACAAAGGACA
ACCTGGCAATTGTGACCCAGTGGTGCGAGGGCAGCAGCCTCTACAAACACCTGCATGT
CCAGGAGACCAAGTTTCAGATGTTCCAGCTAATTGACATTGCCCGGCAGACGGCTCAG
GGAATGGACTATTTGCATGCAAAGAACATCATCCATAGAGACATGAAATCCAACAATA
TATTTCTCCATGAAGGCTTAACAGTGAAAATTGGAGATTTTGGTTTGGCAACAGTAAA
GTCACGCTGGAGTGGTTCTCAGCAGGTTGAACAACCTACTGGCTCTGTCCTCTGGATG
GCCCCAGAGGTGATCCGAATGCAGGATAACAACCCATTCAGTTTCCAGTCGGATGTCT
ACTCCTATGGCATCGTATTGTATGAACTGATGACGGGGGAGCTTCCTTATTCTCACAT
CAACAACCGAGATCAGATCATCTTCATGGTGGGCCGAGGATATGCCTCCCCAGATCTT
AGTAAGCTATATAAGAACTGCCCCAAAGCAATGAAGAGGCTGGTAGCTGACTGTGTGA
AGAAAGTAAAGGAAGAGAGGCCTCTTTTTCCCCAGATCCTGTCTTCCATTGAGCTGCT
CCAACACTCTCTACCGAAGATCAACCGGAGCGCTTCCGAGCCATCCTTGCATCGGGCA
GCCCACACTGAGGATATCAATGCTTGCACGCTGACCACGTCCCCGAGGCTGCCTGTCT
TCTAG (SEQ ID NO: 37)

>hCRAF-KD-wt
MYYWEIEASEVMLSTRIGSGSFGTVYKGKWHGDVAVKILKVVDPTPEQFQAFRNEVAV
LRKTRHVNILLFMGYMTKDNLAIVTQWCEGSSLYKHLHVQETKFQMFQLIDIARQTAQ
GMDYLHAKNIIHRDMKSNNIFLHEGLTVKIGDFGLATVKSRWSGSQQVEQPTGSVLWM
APEVIRMQDNNPFSFQSDVYSYGIVLYELMTGELPYSHINNRDQIIFMVGRGYASPDL
SKLYKNCPKAMKRLVADCVKKVKEERPLFPQILSSIELLQHSLPKINRSASEPSLHRA
AHTEDINACTLTTSPRLPVF (SEQ ID NO: 38)

FIG. 19

All hCRAF-KD fusions are cloned between NheI and XbaI in pCDNA3.1-zeo

>GFP10-hCRAF-KD-wt-CAAX CDS
ATGGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCCAC
CTACGGCAAGCTGACCCTGAAGTTCATCTGCACCACCGGCAAGCTGCCCGTGCCCTGG
CCCACCCTCGTGACCACCCTGAGCTACGGCGTGCAGTGCTTCAGCCGCTACCCCGACC
ACATGAAGCAGCACGACTTCTTCAAGTCCGCCATGCCCGAAGGCTACGTCCAGGAGCG
CACCATCTTCTTCAAGGACGACGGCAACTACAAGACCCGCGCCGAGGTGAAGTTCGAG
GGCGACACCCTGGTGAACCGCATCGAGCTGAAGGGCATCGACTTCAAGGAGGACGGCA
ACATCCTGGGGCACAAGCTGGAGTACAACTACAACCCCCACAACGTCTATATCATGGC
CGACAAGCAGAAGAACGGCATCAAGGTGAACTTCAAGATCCGCCACAACATCGAGGAC
GGCAGCGTGCAGCTCGCCGACCACTACCAGCAGAACACCCCCATCGGCGACGGCCCCG
TGCTGCTGCCCGACAACCACTACCTGTTCACCCAGTCCGCCCTGAGCAAAGACCCCAA
CGAGAAGCGCGATCACATGGTCCTGCTGGAGTTCGTGACCGCCGCCGGGATCACTCTC
GGCATGGACGAGCTGTACAAGGGATCCGCCGGTACCATGTATTATTGGGAAATAGAAG
CCAGTGAAGTGATGCTGTCCACTCGGATTGGGTCAGGCTCTTTTGGAACTGTTTATAA
GGGTAAATGGCACGGAGATGTTGCAGTAAAGATCCTAAAGGTTGTCGACCCAACCCCA
GAGCAATTCCAGGCCTTCAGGAATGAGGTGGCTGTTCTGCGCAAAACACGGCATGTGA
ACATTCTGCTTTTCATGGGGTACATGACAAAGGACAACCTGGCAATTGTGACCCAGTG
GTGCGAGGGCAGCAGCCTCTACAAACACCTGCATGTCCAGGAGACCAAGTTTCAGATG
TTCCAGCTAATTGACATTGCCCGGCAGACGGCTCAGGGAATGGACTATTTGCATGCAA
AGAACATCATCCATAGAGACATGAAATCCAACAATATATTTCTCCATGAAGGCTTAAC
AGTGAAAATTGGAGATTTTGGTTTGGCAACAGTAAAGTCACGCTGGAGTGGTTCTCAG
CAGGTTGAACAACCTACTGGCTCTGTCCTCTGGATGGCCCCAGAGGTGATCCGAATGC
AGGATAACAACCCATTCAGTTTCCAGTCGGATGTCTACTCCTATGGCATCGTATTGTA
TGAACTGATGACGGGGGAGCTTCCTTATTCTCACATCAACAACCGAGATCAGATCATC
TTCATGGTGGGCCGAGGATATGCCTCCCCAGATCTTAGTAAGCTATATAAGAACTGCC
CCAAAGCAATGAAGAGGCTGGTAGCTGACTGTGTGAAGAAAGTAAAGGAAGAGAGGCC
TCTTTTTCCCCAGATCCTGTCTTCCATTGAGCTGCTCCAACACTCTCTACCGAAGATC
AACCGGAGCGCTTCCGAGCCATCCTTGCATCGGGCAGCCCACACTGAGGATATCAATG
CTTGCACGCTGACCACGTCCCCGAGGCTGCCTGTCTTCAAGATGAGCAAAGATGGTAA
AAAGAAGAAAAAGAAGTCAAAGACAAAGTGTGTAATTATGTAA (SEQ ID NO: 39)

>GFP10-hCRAF-KD-wt-CAAX
MVSKGEELFTGVVPILVELDGDVNGHKFSVSGEGEGDATYGKLTLKFICTTGKLPVPW
PTLVTTLSYGVQCFSRYPDHMKQHDFFKSAMPEGYVQERTIFFKDDGNYKTRAEVKFE
GDTLVNRIELKGIDFKEDGNILGHKLEYNYNPHNVYIMADKQKNGIKVNFKIRHNIED
GSVQLADHYQQNTPIGDGPVLLPDNHYLFTQSALSKDPNEKRDHMVLLEFVTAAGITL
GMDELYKGSAGTMYYWEIEASEVMLSTRIGSGSFGTVYKGKWHGDVAVKILKVVDPTP
EQFQAFRNEVAVLRKTRHVNILLFMGYMTKDNLAIVTQWCEGSSLYKHLHVQETKFQM
FQLIDIARQTAQGMDYLHAKNIIHRDMKSNNIFLHEGLTVKIGDFGLATVKSRWSGSQ
QVEQPTGSVLWMAPEVIRMQDNNPFSFQSDVYSYGIVLYELMTGELPYSHINNRDQII
FMVGRGYASPDLSKLYKNCPKAMKRLVADCVKKVEERPLFPQILSSIELLQHSLPKI
NRSASEPSLHRAAHTEDINACTLTTSPRLPVFKMSKDGKKKKKKSKTKCVIM (SEQ
ID NO: 40)

FIG. 20A

>rlucII-hCRAF-KD-wt-CAAX CDS
ATGACCAGCAAGGTGTACGACCCCGAGCAGAGGAAGAGGATGATCACCGGCCCCCAGT
GGTGGGCCAGGTGCAAGCAGATGAACGTGCTGGACAGCTTCATCAACTACTACGACAG
CGAGAAGCACGCCGAGAACGCCGTGATCTTCCTGCACGGCAACGCCACTAGCAGCTAC
CTGTGGAGGCACGTGGTGCCCCACATCGAGCCCGTGGCCAGGTGCATCATCCCCGATC
TGATCGGCATGGGCAAGAGCGGCAAGAGCGGCAACGGCAGCTACAGGCTGCTGGACCA
CTACAAGTACCTGACCGCCTGGTTCGAGCTCCTGAACCTGCCCAAGAAGATCATCTTC
GTGGGCCACGACTGGGGCGCCGCACTGGCCTTCCACTACAGCTACGAGCACCAGGACA
AGATCAAGGCCATCGTGCACGCCGAGAGCGTGGTTGACGTGATCGAGAGCTGGGACGA
GTGGCCAGACATCGAGGAGGACATCGCCCTGATCAAGAGCGAGGAGGCGAGAAGATG
GTGCTGGAGAACAACTTCTTCGTGGAGACCGTTCTGCCCAGCAAGATCATGAGAAAGC
TGGAGCCCGAGGAGTTCGCCGCCTACCTGGAGCCCTTCAAGGAGAAGGGCGAGGTGAG
AAGACCCACCCTGAGCTGGCCCAGAGAGATCCCCTGGTGAAGGGCGGCAAGCCCGAC
GTGGTGCAGATCGTGAGAAACTACAACGCCTACCTGAGAGCCAGCGACGACCTGCCCA
AGATGTTCATCGAGAGCGACCCCGGCTTCTTCAGCAACGCCATCGTGGAGGGCGCCAA
GAAGTTCCCCAACACCGAGTTCGTGAAGGTGAAGGGCCTGCACTTCAGCCAGGAGGAC
GCCCCGACGAGATGGGCAAGTACATCAAGAGCTTCGTGGAGAGTGCTGAAGAACG
AGCAGggatccgccGGTACCATGTATTATTGGGAAATAGAAGCCAGTGAAGTGATGCT
GTCCACTCGGATTGGGTCAGGCTCTTTTGGAACTGTTTATAAGGGTAAATGGCACGGA
GATGTTGCAGTAAAGATCCTAAAGGTTGTCGACCCAACCCCAGAGCAATTCCAGGCCT
TCAGGAATGAGGTGGCTGTTCTGCGCAAAACACGGCATGTGAACATTCTGCTTTTCAT
GGGGTACATGACAAAGGACAACCTGGCAATTGTGACCCAGTGGTGCGAGGGCAGCAGC
CTCTACAAACACCTGCATGTCCAGGAGACCAAGTTTCAGATGTTCCAGCTAATTGACA
TTGCCCGGCAGACGGCTCAGGGAATGGACTATTTGCATGCAAAGAACATCATCCATAG
AGACATGAAATCCAACAATATATTTCTCCATGAAGGCTTAACAGTGAAAATTGGAGAT
TTTGGTTTGGCAACAGTAAAGTCACGCTGGAGTGGTTCTCAGCAGGTTGAACAACCTA
CTGGCTCTGTCCTCTGGATGGCCCCAGAGGTGATCCGAATGCAGGATAACAACCCATT
CAGTTTCCAGTCGGATGTCTACTCCTATGGCATCGTATTGTATGAACTGATGACGGGG
GAGCTTCCTTATTCTCACATCAACAACCGAGATCAGATCATCTTCATGGTGGGCCGAG
GATATGCCTCCCCAGATCTTAGTAAGCTATATAAGAACTGCCCCAAAGCAATGAAGAG
GCTGGTAGCTGACTGTGTGAAGAAAGTAAAGGAAGAGAGGCCTCTTTTTCCCCAGATC
CTGTCTTCCATTGAGCTGCTCCAACACTCTCTACCGAAGATCAACCGGAGCGCTTCCG
AGCCATCCTTGCATCGGGCAGCCCACACTGAGGATATCAATGCTTGCACGCTGACCAC
GTCCCCGAGGCTGCCTGTCTTCAAGATGAGCAAGATGGTAAAAGAAGAAAAAGAAG
TCAAAGACAAAGTGTGTAATTATGTAA (SEQ ID NO: 41)

FIG. 20B

```
>rlucII-hCRAF-KD-wt-CAAX
MTSKVYDPEQRKRMITGPQWWARCKQMNVLDSFINYYDSEKHAENAVIFLHGNATSSY
LWRHVVPHIEPVARCIIPDLIGMGKSGKSGNGSYRLLDHYKYLTAWFELLNLPKKIIF
VGHDWGAALAFHYSYEHQDKIKAIVHAESVVDVIESWDEWPDIEEDIALIKSEEGEKM
VLENNFFVETVLPSKIMRKLEPEEFAAYLEPFKEKGEVRRPTLSWPREIPLVKGGKPD
VVQIVRNYNAYLRASDDLPKMFIESDPGFFSNAIVEGAKKFPNTEFVKVKGLHFSQED
APDEMGKYIKSFVERVLKNEQGSAGTMYYWEIEASEVMLSTRIGSGSFGTVYKGKWHG
DVAVKILKVVDPTPEQFQAFRNEVAVLRKTRHVNILLFMGYMTKDNLAIVTQWCEGSS
LYKHLHVQETKFQMFQLIDIARQTAQGMDYLHAKNIIHRDMKSNNIFLHEGLTVKIGD
FGLATVKSRWSGSQQVEQPTGSVLWMAPEVIRMQDNNPFSFQSDVYSYGIVLYELMTG
ELPYSHINNRDQIIFMVGRGYASPDLSKLYKNCPKAMKRLVADCVKKVKEERPLFPQI
LSSIELLQHSLPKINRSASEPSLHRAAHTEDINACTLTTSPRLPVFKMSKDGKKKKKK
SKTKCVIM (SEQ ID NO: 42)
```

FIG. 20C

Human KSR1 (hKSR1) sequences

>hKSR1-KD-wt CDS
CCCATCTCTCGCAAGGCCAGCCAGACCAGCGTGTACCTGCAGGAGTGGGACATCCCCT
TCGAGCAGGTAGAGCTGGGCGAGCCCATCGGGCAGGGCCGCTGGGGCCGGGTGCACCG
CGGCCGCTGGCATGGCGAGGTGGCCATTCGCCTGCTGGAGATGGACGGCCACAACCAG
GACCACCTGAAGCTCTTCAAGAAAGAGGTGATGAACTACCGGCAGACGCGGCATGAGA
ACGTGGTGCTCTTCATGGGGGCCTGCATGAACCCGCCCCACCTGGCCATTATCACCAG
CTTCTGCAAGGGGCGGACGTTGCACTCGTTTGTGAGGGACCCCAAGACGTCTCTGGAC
ATCAACAAGACGAGGCAAATCGCTCAGGAGATCATCAAGGGCATGGGATATCTTCATG
CCAAGGGCATCGTACACAAAGATCTCAAATCTAAGAACGTCTTCTATGACAACGGCAA
GGTGGTCATCACAGACTTCGGGCTGTTTGGGATCTCAGGCGTGGTCCGAGAGGGACGG
CGTGAGAACCAGCTAAAGCTGTCCCACGACTGGCTGTGCTATCTGGCCCCTGAGATTG
TACGCGAGATGACCCCCGGGAAGGACGAGGATCAGCTGCCATTCTCCAAAGCTGCTGA
TGTCTATGCATTTGGGACTGTTTGGTATGAGCTGCAAGCAAGAGACTGGCCCTTGAAG
AACCAGGCTGCAGAGGCATCCATCTGGCAGATTGGAAGCGGGGAAGGAATGAAGCGTG
TCCTGACTTCTGTCAGCTTGGGGAAGGAAGTCAGTGAGATCCTGTCGGCCTGCTGGGC
TTTCGACCTGCAGGAGAGACCCAGCTTCAGCCTGCTGATGGACATGCTGGAGAAACTT
CCCAAGCTGAACCGGCGGCTCTCCCACCCTGGACACTTCTGGAAGTCAGCTGAGTTGT
AG (SEQ ID NO: 43)

>hKSR1-KD-wt
PISRKASQTSVYLQEWDIPFEQVELGEPIGQGRWGRVHRGRWHGEVAIRLLEMDGHNQ
DHLKLFKKEVMNYRQTRHENVVLFMGACMNPPHLAIITSFCKGRTLHSFVRDPKTSLD
INKTRQIAQEIIKGMGYLHAKGIVHKDLKSKNVFYDNGKVVITDFGLFGISGVVREGR
RENQLKLSHDWLCYLAPEIVREMTPGKDEDQLPFSKAADVYAFGTVWYELQARDWPLK
NQAAEASIWQIGSGEGMKRVLTSVSLGKEVSEILSACWAFDLQERPSFSLLMDMLEKL
PKLNRRLSHPGHFWKSAEL (SEQ ID NO: 44)

>hKSR1-KD-C922Y CDS
ATGCCCATCTCTCGCAAGGCCAGCCAGACCAGCGTGTACCTGCAGGAGTGGGACATCC
CCTTCGAGCAGGTAGAGCTGGGCGAGCCCATCGGGCAGGGCCGCTGGGGCCGGGTGCA
CCGCGGCCGCTGGCATGGCGAGGTGGCCATTCGCCTGCTGGAGATGGACGGCCACAAC
CAGGACCACCTGAAGCTCTTCAAGAAAGAGGTGATGAACTACCGGCAGACGCGGCATG
AGAACGTGGTGCTCTTCATGGGGGCCTGCATGAACCCGCCCCACCTGGCCATTATCAC
CAGCTTCTGCAAGGGGCGGACGTTGCACTCGTTTGTGAGGGACCCCAAGACGTCTCTG
GACATCAACAAGACGAGGCAAATCGCTCAGGAGATCATCAAGGGCATGGGATATCTTC
ATGCCAAGGGCATCGTACACAAAGATCTCAAATCTAAGAACGTCTTCTATGACAACGG
CAAGGTGGTCATCACAGACTTCGGGCTGTTTGGGATCTCAGGCGTGGTCCGAGAGGGA
CGGCGTGAGAACCAGCTAAAGCTGTCCCACGACTGGCTGTGCTATCTGGCCCCTGAGA
TTGTACGCGAGATGACCCCCGGGAAGGACGAGGATCAGCTGCCATTCTCCAAAGCTGC
TGATGTCTATGCATTTGGGACTGTTTGGTATGAGCTGCAAGCAAGAGACTGGCCCTTG
AAGAACCAGGCTGCAGAGGCATCCATCTGGCAGATTGGAAGCGGGGAAGGAATGAAGC
GTGTCCTGACTTCTGTCAGCTTGGGGAAGGAAGTCAGTGAGATCCTGTCGGCCTATTG
GGCTTTCGACCTGCAGGAGAGACCCAGCTTCAGCCTGCTGATGGACATGCTGGAGAAA
CTTCCCAAGCTGAACCGGCGGCTCTCCCACCCTGGACACTTCTGGAAGTCAGCTGAGT
TGTAG (SEQ ID NO: 45)

FIG. 21A

```
>hKSR1-KD-C922Y
MPISRKASQTSVYLQEWDIPFEQVELGEPIGQGRWGRVHRGRWHGEVAIRLLEMDGHN
QDHLKLFKKEVMNYRQTRHENVVLFMGACMNPPHLAIITSFCKGRTLHSFVRDPKTSL
DINKTRQIAQEIIKGMGYLHAKGIVHKDLKSKNVFYDNGKVVITDFGLFGISGVVREG
RRENQLKLSHDWLCYLAPEIVREMTPGKDEDQLPFSKAADVYAFGTVWYELQARDWPL
KNQAAEASIWQIGSGEGMKRVLTSVSLGKEVSEILSAYWAFDLQERPSFSLLMDMLEK
LPKLNRRLSHPGHFWKSAEL (SEQ ID NO: 46)
```

FIG. 21B

The human KSR1-KD-rlucII fusions are cloned between KpnI
and PmeI in pCDNA3.1-zeo >hKSR1-KD-wt-rlucII CDS
ATGCCCATCTCTCGCAAGGCCAGCCAGACCAGCGTGTACCTGCAGGAGTGGGACATCC
CCTTCGAGCAGGTAGAGCTGGGCGAGCCCATCGGGCAGGGCCGCTGGGGCCGGGTGCA
CCGCGGCCGCTGGCATGGCGAGGTGGCCATTCGCCTGCTGGAGATGGACGGCCACAAC
CAGGACCACCTGAAGCTCTTCAAGAAAGAGGTGATGAACTACCGGCAGACGCGGCATG
AGAACGTGGTGCTCTTCATGGGGGCCTGCATGAACCCGCCCCACCTGGCCATTATCAC
CAGCTTCTGCAAGGGGCGGACGTTGCACTCGTTTGTGAGGGACCCCAAGACGTCTCTG
GACATCAACAAGACGAGGCAAATCGCTCAGGAGATCATCAAGGGCATGGGATATCTTC
ATGCCAAGGGCATCGTACACAAGATCTCAAATCTAAGAACGTCTTCTATGACAACGG
CAAGGTGGTCATCACAGACTTCGGGCTGTTTGGGATCTCAGGCGTGGTCCGAGAGGGA
CGGCGTGAGAACCAGCTAAAGCTGTCCCACGACTGGCTGTGCTATCTGGCCCCTGAGA
TTGTACGCGAGATGACCCCCGGGAAGGACGAGGATCAGCTGCCATTCTCCAAAGCTGC
TGATGTCTATGCATTTGGGACTGTTTGGTATGAGCTGCAAGCAAGAGACTGGCCCTTG
AAGAACCAGGCTGCAGAGGCATCCATCTGGCAGATTGGAAGCGGGGAAGGAATGAAGC
GTGTCCTGACTTCTGTCAGCTTGGGGAAGGAAGTCAGTGAGATCCTGTCGGCCTGCTG
GGCTTTCGACCTGCAGGAGAGACCCAGCTTCAGCCTGCTGATGGACATGCTGGAGAAA
CTTCCCAAGCTGAACCGGCGGCTCTCCCACCCTGGACACTTCTGGAAGTCAGCTGAGT
TGTCTAGAGGAGGGGGGATGACCAGCAAGGTGTACGACCCCGAGCAGAGGAAGAGGAT
GATCACCGGCCCCCAGTGGTGGGCCAGGTGCAAGCAGATGAACGTGCTGGACAGCTTC
ATCAACTACTACGACAGCGAGAAGCACGCCGAGAACGCCGTGATCTTCCTGCACGGCA
ACGCCACTAGCAGCTACCTGTGGAGGCACGTGGTGCCCCACATCGAGCCCGTGGCCAG
GTGCATCATCCCCGATCTGATCGGCATGGGCAAGAGCGGCAAGAGCGGCAACGGCAGC
TACAGGCTGCTGGACCACTACAAGTACCTGACCGCCTGGTTCGAGCTCCTGAACCTGC
CCAAGAAGATCATCTTCGTGGGCCACGACTGGGGCGCCGCACTGGCCTTCCACTACAG
CTACGAGCACCAGGACAAGATCAAGGCCATCGTGCACGCCGAGAGCGTGGTTGACGTG
ATCGAGAGCTGGGACGAGTGGCCAGACATCGAGGAGGACATCGCCCTGATCAAGAGCG
AGGAGGGCGAGAAGATGGTGCTGGAGAACAACTTCTTCGTGGAGACCGTTCTGCCCAG
CAAGATCATGAGAAAGCTGGAGCCCGAGGAGTTCGCCGCCTACCTGGAGCCCTTCAAG
GAGAAGGGCGAGGTGAGAAGACCCACCCTGAGCTGGCCCAGAGAGATCCCCCTGGTGA
AGGGCGGCAAGCCCGACGTGGTGCAGATCGTGAGAAACTACAACGCCTACCTGAGAGC
CAGCGACGACCTGCCCAAGATGTTCATCGAGAGCGACCCCGGCTTCTTCAGCAACGCC
ATCGTGGAGGGCGCCAAGAAGTTCCCCAACACCGAGTTCGTGAAGGTGAAGGGCCTGC
ACTTCAGCCAGGAGGACGCCCCCGACGAGATGGGCAAGTACATCAAGAGCTTCGTGGA
GAGAGTGCTGAAGAACGAGCAGTAG (SEQ ID NO: 47)

FIG. 22A

>hKSR1-KD-wt-rlucII
MPISRKASQTSVYLQEWDIPFEQVELGEPIGQGRWGRVHRGRWHGEVAIRLLEMDGHN
QDHLKLFKKEVMNYRQTRHENVVLFMGACMNPPHLAIITSFCKGRTLHSFVRDPKTSL
DINKTRQIAQEIIKGMGYLHAKGIVHKDLKSKNVFYDNGKVVITDFGLFGISGVVREG
RRENQLKLSHDWLCYLAPEIVREMTPGKDEDQLPFSKAADVYAFGTVWYELQARDWPL
KNQAAEASIWQIGSGEGMKRVLTSVSLGKEVSEILSACWAFDLQERPSFSLLMDMLEK
LPKLNRRLSHPGHFWKSAELSRGGGMTSKVYDPEQRKRMITGPQWWARCKQMNVLDSF
INYYDSEKHAENAVIFLHGNATSSYLWRHVVPHIEPVARCIIPDLIGMGKSGKSGNGS
YRLLDHYKYLTAWFELLNLPKKIIFVGHDWGAALAFHYSYEHQDKIKAIVHAESVVDV
IESWDEWPDIEEDIALIKSEEGEKMVLENNFFVETVLPSKIMRKLEPEEFAAYLEPFK
EKGEVRRPTLSWPREIPLVKGGKPDVVQIVRNYNAYLRASDDLPKMFIESDPGFFSNA
IVEGAKKFPNTEFVKVKGLHFSQEDAPDEMGKYIKSFVERVLKNEQ- (SEQ ID NO:
48)

>hKSR1-KD-C922Y-rlucII CDS
ATGCCCATCTCTCGCAAGGCCAGCCAGACCAGCGTGTACCTGCAGGAGTGGGACATCC
CCTTCGAGCAGGTAGAGCTGGGCGAGCCCATCGGGCAGGGCCGCTGGGGCCGGGTGCA
CCGCGGCCGCTGGCATGGCGAGGTGGCCATTCGCCTGCTGGAGATGGACGGCCACAAC
CAGGACCACCTGAAGCTCTTCAAGAAAGAGGTGATGAACTACCGGCAGACGCGGCATG
AGAACGTGGTGCTCTTCATGGGGGCCTGCATGAACCCGCCCCACCTGGCCATTATCAC
CAGCTTCTGCAAGGGCGGACGTTGCACTCGTTTGTGAGGGACCCCAAGACGTCTCTG
GACATCAACAAGACGAGGCAAATCGCTCAGGAGATCATCAAGGGCATGGGATATCTTC
ATGCCAAGGGCATCGTACACAAAGATCTCAAATCTAAGAACGTCTTCTATGACAACGG
CAAGGTGGTCATCACAGACTTCGGGCTGTTTGGGATCTCAGGCGTGGTCCGAGAGGGA
CGGCGTGAGAACCAGCTAAAGCTGTCCCACGACTGGCTGTGCTATCTGGCCCCTGAGA
TTGTACGCGAGATGACCCCCGGGAAGGACGAGGATCAGCTGCCATTCTCCAAAGCTGC
TGATGTCTATGCATTTGGGACTGTTTGGTATGAGCTGCAAGCAAGAGACTGGCCCTTG
AAGAACCAGGCTGCAGAGGCATCCATCTGGCAGATTGGAAGCGGGAAGGAATGAAGC
GTGTCCTGACTTCTGTCAGCTTGGGAAGGAAGTCAGTGAGATCCTGTCGGCCTATTG
GGCTTTCGACCTGCAGGAGAGACCCAGCTTCAGCCTGCTGATGGACATGCTGGAGAAA
CTTCCCAAGCTGAACCGGCGGCTCTCCCACCCTGGACACTTCTGGAAGTCAGCTGAGT
TGTCTAGAGGAGGGGGGATGACCAGCAAGGTGTACGACCCCGAGCAGAGGAAGAGGAT
GATCACCGGCCCCAGTGGTGGGCCAGGTGCAAGCAGATGAACGTGCTGGACAGCTTC
ATCAACTACTACGACAGCGAGAAGCACGCCGAGAACGCCGTGATCTTCCTGCACGGCA
ACGCCACTAGCAGCTACCTGTGGAGGCACGTGGTGCCCACATCGAGCCCGTGGCCAG
GTGCATCATCCCCGATCTGATCGGCATGGGCAAGAGCGGCAAGAGCGGCAACGGCAGC
TACAGGCTGCTGGACCACTACAAGTACCTGACCGCCTGGTTCGAGCTCCTGAACCTGC
CCAAGAAGATCATCTTCGTGGGCCACGACTGGGCGCCGCACTGGCCTTCCACTACAG
CTACGAGCACCAGGACAAGATCAAGGCCATCGTGCACGCCGAGAGCGTGGTTGACGTG
ATCGAGAGCTGGGACGAGTGGCCAGACATCGAGGAGGACATCGCCCTGATCAAGAGCG
AGGAGGGCGAGAAGATGGTGCTGGAGAACAACTTCTTCGTGGAGACCGTTCTGCCCAG
CAAGATCATGAGAAAGCTGGAGCCCGAGGAGTTCGCCGCCTACCTGGAGCCCTTCAAG
GAGAAGGGCGAGGTGAGAAGACCCACCCTGAGCTGGCCCAGAGAGATCCCCCTGGTGA
AGGGCGGCAAGCCCGACGTGGTGCAGATCGTGAGAAACTACAACGCCTACCTGAGAGC
CAGCGACGACCTGCCCAAGATGTTCATCGAGAGCGACCCCGGCTTCTTCAGCAACGCC
ATCGTGGAGGGCGCCAAGAAGTTCCCCAACACCGAGTTCGTGAAGGTGAAGGGCCTGC
ACTTCAGCCAGGAGGACGCCCCCGACGAGATGGGCAAGTACATCAAGAGCTTCGTGGA
GAGAGTGCTGAAGAACGAGCAGTAG (SEQ ID NO: 49)

FIG. 22B

>hKSR1-KD-C922Y-rlucII
MPISRKASQTSVYLQEWDIPFEQVELGEPIGQGRWGRVHRGRWHGEVAIRLLEMDGHN
QDHLKLFKKEVMNYRQTRHENVVLFMGACMNPPHLAIITSFCKGRTLHSFVRDPKTSL
DINKTRQIAQEIIKGMGYLHAKGIVHKDLKSKNVFYDNGKVVITDFGLFGISGVVREG
RRENQLKLSHDWLCYLAPEIVREMTPGKDEDQLPFSKAADVYAFGTVWYELQARDWPL
KNQAAEASIWQIGSGEGMKRVLTSVSLGKEVSEILSAYWAFDLQERPSFSLLMDMLEK
LPKLNRRLSHPGHFWKSAELSRGGGMTSKVYDPEQRKRMITGPQWWARCKQMNVLDSF
INYYDSEKHAENAVIFLHGNATSSYLWRHVVPHIEPVARCIIPDLIGMKSGKSGNGS
YRLLDHYKYLTAWFELLNLPKKIIFVGHDWGAALAFHYSYEHQDKIKAIVHAESVVDV
IESWDEWPDIEEDIALIKSEEGEKMVLENNFFVETVLPSKIMRKLEPEEFAAYLEPFK
EKGEVRRPTLSWPREIPLVKGGKPDVVQIVRNYNAYLRASDDLPKMFIESDPGFFSNA
IVEGAKKFPNTEFVKVKGLHFSQEDAPDEMGKYIKSFVERVLKNEQ (SEQ ID NO:
50)

FIG. 22C

Human MEK1 (hMEK1)

>hMEK1 CDS
ATGCCCAAGAAGAAGCCGACGCCCATCCAGCTGAACCCGGCCCCCGACGGCTCTGCAG
TTAACGGGACCAGCTCTGCGGAGACCAACTTGGAGGCCTTGCAGAAGAAGCTGGAGGA
GCTAGAGCTTGATGAGCAGCAGCGAAAGCGCCTTGAGGCCTTTCTTACCCAGAAGCAG
AAGGTGGGAGAACTGAAGGATGACGACTTTGAGAAGATCAGTGAGCTGGGGGCTGGCA
ATGGCGGTGTGGTGTTCAAGGTCTCCCACAAGCCTTCTGGCCTGGTCATGGCCAGAAA
GCTAATTCATCTGGAGATCAAACCCGCAATCCGGAACCAGATCATAAGGGAGCTGCAG
GTTCTGCATGAGTGCAACTCTCCGTACATCGTGGGCTTCTATGGTGCGTTCTACAGCG
ATGGCGAGATCAGTATCTGCATGGAGCACATGGATGGAGGTTCTCTGGATCAAGTCCT
GAAGAAAGCTGGAAGAATTCCTGAACAAATTTTAGGAAAAGTTAGCATTGCTGTAATA
AAAGGCCTGACATATCTGAGGGAGAAGCACAAGATCATGCACAGAGATGTCAAGCCCT
CCAACATCCTAGTCAACTCCCGTGGGGAGATCAAGCTCTGTGACTTTGGGGTCAGCGG
GCAGCTCATCGACTCCATGGCCAACTCCTTCGTGGGCACAAGGTCCTACATGTCGCCA
GAAAGACTCCAGGGGACTCATTACTCTGTGCAGTCAGACATCTGGAGCATGGGACTGT
CTCTGGTAGAGATGGCGGTTGGGAGGTATCCCATCCCTCCTCCAGATGCCAAGGAGCT
GGAGCTGATGTTTGGGTGCCAGGTGGAAGGAGATGCGGCTGAGACCCCACCCAGGCCA
AGGACCCCCGGGAGGCCCCTTAGCTCATACGGAATGGACAGCCGACCTCCCATGGCAA
TTTTTGAGTTGTTGGATTACATAGTCAACGAGCCTCCTCCAAAACTGCCCAGTGGAGT
GTTCAGTCTGGAATTTCAAGATTTTGTGAATAAATGCTTAATAAAAAACCCCGCAGAG
AGAGCAGATTTGAAGCAACTCATGGTTCATGCTTTTATCAAGAGATCTGATGCTGAGG
AAGTGGATTTTGCAGGTTGGCTCTGCTCCACCATCGGCCTTAACCAGCCCAGCACACC
AACCCATGCTGCTGGCGTCTAA (SEQ ID NO: 51)

>hMEK1
MPKKKPTPIQLNPAPDGSAVNGTSSAETNLEALQKKLEELELDEQQRKRLEAFLTQKQ
KVGELKDDDFEKISELGAGNGGVVFKVSHKPSGLVMARKLIHLEIKPAIRNQIIRELQ
VLHECNSPYIVGFYGAFYSDGEISICMEHMDGGSLDQVLKKAGRIPEQILGKVSIAVI
KGLTYLREKHKIMHRDVKPSNILVNSRGEIKLCDFGVSGQLIDSMANSFVGTRSYMSP
ERLQGTHYSVQSDIWSMGLSLVEMAVGRYPIPPPDAKELELMFGCQVEGDAAETPPRP
RTPGRPLSSYGMDSRPPMAIFELLDYIVNEPPPKLPSGVFSLEFQDFVNKCLIKNPAE
RADLKQLMVHAFIKRSDAEEVDFAGWLCSTIGLNQPSTPTHAAGV (SEQ ID NO: 52)

FIG. 23

The human GFP10-MEK1 full length fusion is cloned between
NheI and XbaI in pCDNA3.1-zeo >GFP10-hMEK1 CDS
CACCATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGCGATG
CCACCTACGGCAAGCTGACCCTGAAGTTCATCTGCACCACCGGCAAGCTGCCCGTGCC
CTGGCCCACCCTCGTGACCACCCTGAGCTACGGCGTGCAGTGCTTCAGCCGCTACCCC
GACCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGAC
GGCAACATCCTGGGGCACAAGCTGGAGTACAACTACAACCCCCACAACGTCTATATCA
TGGCCGACAAGCAGAAGAACGGCATCAAGGTGAACTTCAAGATCCGCCACAACATCGA
GGACGGCAGCGTGCAGCTCGCCGACCACTACCAGCAGAACACCCCCATCGGCGACGGC
CCCGTGCTGCTGCCCGACAACCACTACCTGTTCACCCAGTCCGCCCTGAGCAAAGACC
CCAACGAGAAGCGCGATCACATGGTCCTGCTGGAGTTCGTGACCGCCGCCGGGATCAC
TCTCGGCATGGACGAGCTGTACAAGGGATCCGCCGGTACCCCCAAGAAGAAGCCGACG
CCCATCCAGCTGAACCCGGCCCCCGACGGCTCTGCAGTTAACGGGACCAGCTCTGCGG
AGACCAACTTGGAGGCCTTGCAGAAGAAGCTGGAGGAGCTAGAGCTTGATGAGCAGCA
GCGAAAGCGCCTTGAGGCCTTTCTTACCCAGAAGCAGAAGGTGGGAGAACTGAAGGAT
GACGACTTTGAGAAGATCAGTGAGCTGGGGGCTGGCAATGGCGGTGTGGTGTTCAAGG
TCTCCCACAAGCCTTCTGGCCTGGTCATGGCCAGAAAGCTAATTCATCTGGAGATCAA
ACCCGCAATCCGGAACCAGATCATAAGGGAGCTGCAGGTTCTGCATGAGTGCAACTCT
CCGTACATCGTGGGCTTCTATGGTGCGTTCTACAGCGATGGCGAGATCAGTATCTGCA
TGGAGCACATGGATGGAGGTTCTCTGGATCAAGTCCTGAAGAAAGCTGGAAGAATTCC
TGAACAAATTTTAGGAAAAGTTAGCATTGCTGTAATAAAAGGCCTGACATATCTGAGG
GAGAAGCACAAGATCATGCACAGAGATGTCAAGCCCTCCAACATCCTAGTCAACTCCC
GTGGGGAGATCAAGCTCTGTGACTTTGGGGTCAGCGGGCAGCTCATCGACTCCATGGC
CAACTCCTTCGTGGGCACAAGGTCCTACATGTCGCCAGAAAGACTCCAGGGGACTCAT
TACTCTGTGCAGTCAGACATCTGGAGCATGGGACTGTCTCTGGTAGAGATGGCGGTTG
GGAGGTATCCCATCCCTCCTCCAGATGCCAAGGAGCTGGAGCTGATGTTTGGGTGCCA
GGTGGAAGGAGATGCGGCTGAGACCCCACCCAGGCCAAGGACCCCGGGAGGCCCCTT
AGCTCATACGGAATGGACAGCCGACCTCCCATGGCAATTTTTGAGTTGTTGGATTACA
TAGTCAACGAGCCTCCTCCAAAACTGCCCAGTGGAGTGTTCAGTCTGGAATTTCAAGA
TTTTGTGAATAAATGCTTAATAAAAACCCCGCAGAGAGCAGATTTGAAGCAACTC
ATGGTTCATGCTTTTATCAAGAGATCTGATGCTGAGGAAGTGGATTTTGCAGGTTGGC
TCTGCTCCACCATCGGCCTTAACCAGCCCAGCACACCAACCCATGCTGCTGGCGTCTA
A (SEQ ID NO: 53)

FIG. 24A

```
>GFP10-hMEK1
MVSKGEELFTGVVPILVELDGDVNGHKFSVSGEGEGDATYGKLTLKFICTTGKLPVPW
PTLVTTLSYGVQCFSRYPDHMKQHDFFKSAMPEGYVQERTIFFKDDGNYKTRAEVKFE
GDTLVNRIELKGIDFKEDGNILGHKLEYNYNPHNVYIMADKQKNGIKVNFKIRHNIED
GSVQLADHYQQNTPIGDGPVLLPDNHYLFTQSALSKDPNEKRDHMVLLEFVTAAGITL
GMDELYKGSAGTPKKKPTPIQLNPAPDGSAVNGTSSAETNLEALQKKLEELELDEQQR
KRLEAFLTQKQKVGELKDDDFEKISELGAGNGGVVFKVSHKPSGLVMARKLIHLEIKP
AIRNQIIRELQVLHECNSPYIVGFYGAFYSDGEISICMEHMDGGSLDQVLKKAGRIPE
QILGKVSIAVIKGLTYLREKHKIMHRDVKPSNILVNSRGEIKLCDFGVSGQLIDSMAN
SFVGTRSYMSPERLQGTHYSVQSDIWSMGLSLVEMAVGRYPIPPPDAKELELMFGCQV
EGDAAETPPRPRTPGRPLSSYGMDSRPPMAIFELLDYIVNEPPPKLPSGVFSLEFQDF
VNKCLIKNPAERADLKQLMVHAFIKRSDAEEVDFAGWLCSTIGLNQPSTPTHAAGV-
(SEQ ID NO: 54)
```

FIG. 24B

CLONING OLIGONUCLEOTIDES:

Human BRAF
>OL5_hBRAF_KD_+start_F
GGGGTACCATGGATGATTGGGAGATTCCTGATGGGC (SEQ ID NO: 55)

>OL3_hBRAF_KD_+CAAX_+stop_R
GCTCTAGATTACATAATTACACACTTTGTCTTTGACTTCTTTTTCTTCTTTTTACCAT
CTTTGCTCATCTTGTGGACAGGAAACGCACCATA (SEQ ID NO: 56)

Human CRAF

>OL5_hCRAF_KD_+start_F
GGGGTACCATGTATTATTGGGAAATAGAAGCC (SEQ ID NO: 57)

>OL3_hCRAF_KD_+CAAX_+stop_R
GCTCTAGATTACATAATTACACACTTTGTCTTTGACTTCTTTTTCTTCTTTTTACCAT
CTTTGCTCATCTTGAAGACAGGCAGCCTCGGGGA (SEQ ID NO: 58)

Human KSR1
>OL5_hKSR1_KpnI_cloning_BRET
GGGGTACCCCATCTCTCGCAAGGCCAGCCAG (SEQ ID NO: 59)
>OL3_hKSR1_XbaI_cloning_BRET
GCTCTAGACTACAACTCAGCTGACTTCCAGAAG (SEQ ID NO: 60)
Human MEK
>OL5_hMEK1_KpnI_cloning_BRET
GGGGTACCCCAAGAAGAAGCCGACGCCCATC (SEQ ID NO: 61)
>OL3_hMEK1_XbaI_cloning_BRET
GCTCTAGATTAGACGCCAGCAGCATGGGTTGG (SEQ ID NO: 62)

FIG. 25

SEQUENCING OLIGONUCLEOTIDES:

>OL5_hBRAF_seq1_F
GGGTTTCCGCTGTCAAACATGTGG (SEQ ID NO: 63)

>OL5_hBRAF_seq2_F
TATTGTTACCCAGTGGTGTGAGGG (SEQ ID NO: 64)

>OL5_hCRAF_seq1_F
ACACCTAATGTCCACATGGTCAGC (SEQ ID NO: 65)

>OL5_hCRAF_seq2_F
TTTCCAGTCGGATGTCTACTCCTA (SEQ ID NO: 66)

FIG. 26

MUTAGENESIS OLIGONUCLEOTIDES:

The following primer pair was used to generate the side-to-side dimer interface mutant R481H in BRAF
>OL5_hBRAF_R481H_F
AATGAAGTAGGAGTACTCAGGAAAACACATCATGTGAATATCCTACTCTTCATGGGC
(SEQ ID NO: 67)
>OL3_hBRAF_R481H_R
GCCCATGAAGAGTAGGATATTCACATGATGTGTTTTCCTGAGTACTCCTACTTCATT
(SEQ ID NO: 68)

The following primer pair was used to introduce the C922Y hMEK1 interaction mutant in hKSR1

>OL5_hKSR1_C922Y_F
GAAGTCAGTGAGATCCTGTCGGCCTATGGGCTTTCGACCTGCAGGAGAGA
(SEQ ID NO: 69)
>OL3_hKSR1_C922Y_R
TCTCTCCTGCAGGTCGAAAGCCCAATAGGCCGACAGGATCTCACTGACTTC
(SEQ ID NO: 70)

BIOSENSOR FOR DETECTING RAF/KSR FAMILY KINASE DIMERIZATION AND USES THEREOF

RELATED APPLICATIONS

This application is a continuation application of U.S. application Ser. No. 13/356,059, filed Jan. 23, 2012, which is a continuation of International Application No. PCT/CA2010/001164, which designated the United States and was filed on Jul. 23, 2010, published in English, which claims the benefit of U.S. Provisional Application No. 61/228,273, filed on Jul. 24, 2009. The entire teachings of the above applications are incorporated herein by reference.

SEQUENCE LISTING

The instant application contains a Sequence Listing which has been electronically submitted in ASCII format and is hereby incorporated by reference in its entirety.

TECHNICAL FIELD

The present generally concerns mutated RAF and KSR isoforms, and more particularly to their inhibition of RAF/RAF and RAF/KSR dimer formation.

BACKGROUND

The ERK (extracellular signal-regulated kinase) pathway is an evolutionarily conserved signal transduction module that controls cellular growth, differentiation and survival (Wellbrock, C., Karasarides, M. & Marais, R. The RAF proteins take centre stage, Nat Rev Mol Cell Biol., 5, 875-85 (2004)). Activation of receptor tyrosine kinases (RTKs) by the binding of growth factors initiates GTP loading of RAS, which triggers the initial steps in the activation of the ERK pathway by modulating RAF family kinase function. Once activated, RAF participates in a sequential cascade of phosphorylation events that activate MEK, and in turn ERK. Unbridled signaling through the ERK pathway caused by activating mutations in RTKs, RAS or RAF, have been linked to a multitude of human cancers (Roberts, P. J. & Der, C. J., Targeting the Raf-MEK-ERK mitogen-activated protein kinase cascade for the treatment of cancer, Oncogene, 26, 3291-310 (2007)). Of note, one member of the RAF family, B-RAF, is the most frequently mutated oncogene within the kinase superfamily (Greenman, C. et al., Patterns of somatic mutation in human cancer genomes, Nature, 446, 153-8 (2007)).

Not surprisingly, there has been a colossal effort to understand the underlying regulation of this family of kinases. Despite intense scrutiny, the mechanisms governing RAF activation remain only partially understood. In particular, the process by which its kinase domain becomes catalytically activated towards its substrate MEK remains elusive.

A greater understanding of the mechanisms that govern RAF activation would be useful as a means to identify novel therapeutic intervention strategies for disease such as cancer.

BRIEF SUMMARY

The following addresses the shortcomings of the above.

In one aspect, there is provided a composition comprising: an aqueous solution of RAF/RAF homodimer. The composition includes equimolar amounts of RAF monomers. Each RAF monomer includes a RAF kinase domain having a dimerization interface. The RAF/RAF homodimer is a side-to-side dimer having a 2 fold axis of symmetry.

In one aspect, there is provided a composition comprising: an aqueous solution of RAF/KSR heterodimer. The composition includes equimolar amounts of KSR and RAF monomers. The KSR and the RAF monomer each include a kinase domain having a dimerization interface. The heterodimer has a 2-fold axis of symmetry.

In one aspect, there is provided a substantially pure nucleic acid encoding a mutated RAF polypeptide. The nucleic acid is DNA which contains the RAF gene. The DNA is genomic DNA or cDNA. The mutated RAF polypeptide is mutated A-RAF, mutated B-RAF or mutated C-RAF. The mutated RAF polypeptide includes at least one mutated residue located in a dimerization interface. The mutated residue is selected from the group consisting of: H449, G450, R481H, L487, F488, M489, Y538, A541 and K542. The mutation is selected from the group consisting of: H449E, G450W, R481H, L487R, F488A, F488L, M489W, Y538F, A541E and K542E. The mutated RAF polypeptide comprises a sequence of SEQ ID NO: 7, SEQ ID NO: 9, or SEQ ID NO: 15. The nucleic acid comprises a sequence of SEQ ID NO: 8, SEQ ID NO: 10 or SEQ ID NO: 16. The nucleic acid is DNA which is operably linked to regulatory sequences for expression of a mutated RAF polypeptide and wherein the regulatory sequences comprise a promoter. The promoter is a constitutive promoter, is inducible by one or more external agents, or is cell-type specific.

In another aspect, there is provided a method of producing a mutated RAF polypeptide, the method comprising:
 a) providing a cell transfected with a nucleic acid sequence encoding a mutated RAF polypeptide positioned for expression in the cell;
 b) culturing the transfected cells under conditions for expressing the nucleic acid; and
 c) producing the mutated RAF polypeptide.

In another aspect, there is provided a substantially pure mammalian mutated RAF polypeptide, or fragment thereof, the polypeptide being encoded by the nucleic acid, as described above. The polypeptide comprises an amino acid sequence substantially identical to an amino acid sequence of SEQ ID NO: 7 or SEQ ID NO: 9. The polypeptide includes at least one mutant selected from the group consisting of: H449E, G450W, R481H, L487R, F488A, F488L, M489W, Y538F, A541E and K542E.

In one aspect, there is provided a substantially pure nucleic acid encoding a mutated KSR polypeptide. The nucleic acid is DNA which contains the KSR gene. The DNA is genomic DNA or cDNA. The mutated KSR polypeptide is mutated KSR-1 or KSR-2. The mutated KSR polypeptide includes at least one mutated residue located in a dimerization interface. The mutated residue is selected from the group consisting of: H699, G700, R732, L738, F739, M740, Y790, A793 and R794. The mutation is selected from the group consisting of: H699E, G700W, R732H, L738R, F739A, F739L, M740W, Y790F, A793E and R794E. The mutated KSR polypeptide comprises a sequence of SEQ ID NO: 11, SEQ ID NO: 13, or SEQ ID NO: 17. The nucleic acid comprises a sequence of SEQ ID NO: 12, SEQ ID NO: 14 or SEQ ID NO: 18. The nucleic acid is DNA which is operably linked to regulatory sequences for expression of the polypeptide and wherein the regulatory sequences comprise a promoter. The promoter is a constitutive promoter, is inducible by one or more external agents, or is cell-type specific.

In another aspect, there is provided a method of producing a mutated KSR polypeptide, the method comprising:
a) providing a cell transfected with a nucleic acid sequence encoding a mutated KSR polypeptide positioned for expression in the cell;
b) culturing said transfected cells under conditions for expressing the nucleic acid; and
c) producing the mutated KSR polypeptide.

In another aspect, there is provided a substantially pure mammalian mutated KSR polypeptide, or fragment thereof, the polypeptide being encoded by the nucleic acid, as described above. The polypeptide comprises an amino acid sequence substantially identical to an amino acid sequence of SEQ ID NO: 11, SEQ ID NO: 13 or SEQ ID NO: 17. The polypeptide includes at least one mutant selected from the group consisting of: H699E, G700W, R732H, L738R, F739A, F739L, M740W, Y790F, A793E and R794E.

The polypeptide or the nucleic acid, as described above is mammalian. The mammal is murine or human.

The polypeptide or the nucleic acid, as described above, is non-mammalian. The non-mammal is *Drosophila melanogaster*.

In another aspect, there is provided a vector comprising the nucleic acid, as described above, the vector being capable of directing expression of the polypeptide encoded by the nucleic acid in a vector-containing cell.

In another aspect, there is provided a cell that contains the nucleic acid, as described above.

In another aspect, there is provided a transgenic cell that contains the nucleic acid, as described above, wherein the nucleic acid is expressed in the transgenic cell.

In another aspect, there is provided a transgenic non-human mammal generated from the cell, as described above, wherein the nucleic acid is expressed in the transgenic mammal. The transgenic non-human mammal is a mouse.

The cell, as described above, is a mammalian cell, a yeast cell, or a bacterial cell.

In one aspect, there is provided a method of detecting the presence of a mutation in a RAF kinase domain, the method comprising:
a) providing a WT RAF kinase domain and a suspected mutant RAF kinase domain, each domain having a cysteine residue located at its N-terminus;
b) incubating the WT RAF kinase domain and the suspected mutant RAF kinase domain with different cross-linking detectable labels;
c) incubating together equimolar amounts of the labeled WT RAF kinase domain and detecting a signal from the detectable label so as to provide a dimerization reference signal; and
d) incubating equimolar amounts of the labeled suspected mutant B-RAF kinase domain and detecting a signal from the detectable labels, an absent signal or a reduce signal compared to that of the dimerization reference signal being an indication that a mutant B-RAF kinase domain is present.

In one aspect, there is provided a method of monitoring the formation of RAF/RAF or RAF/KSR kinase domain dimers to detect mutations inhibiting dimerization or drug-like molecules interfering with dimerization, the method comprising:
a) fusing either (i) a RAF kinase domain or (ii) a KSR kinase domain at either of their N- or C-termini to a BRET donor or a BRET acceptor to produce donor labeled and acceptor labeled fusion proteins;
b) expressing the fusion proteins to identify combinations that provide specific BRET signals;
c) introducing dimer interface mutations into either of the labeled fusion proteins;
d) expressing the labeled mutated fusion proteins with WT RAF or KSR kinase domains;
e) measuring the BRET signals, a loss or significant reduction of the BRET signal using dimer interface mutations as opposed to mutations remote from the interface, being an indication that a specific BRET signal which depends on the RAF/RAF or RAF/KSR dimerization interface has been obtained.

The BRET donor is *renilla* luciferase variant II or rlucII. The BRET acceptor is GFP10. The acceptor label is Yellow Fluorescent Protein (YFP). The donor labeled fusion protein comprises a sequence selected from the group consisting of: SEQ ID NO: 24, SEQ ID NO: 34, SEQ ID NO: 42 and SEQ ID NO: 48. The acceptor labeled fusion protein comprises a sequence selected from the group consisting of: SEQ ID NO: 22, SEQ ID NO: 30, SEQ ID NO: 40 and SEQ ID NO: 54. The donor labeled mutated fusion proteins comprise sequences SEQ ID NO: 36 and SEQ ID NO: 50. The acceptor labeled mutated fusion proteins comprises a sequence of SEQ ID NO: 32.

In another aspect, there is provided a method of identifying a potential inhibitor of RAF/RAF homodimerization, the method comprising.
a) fusing a RAF kinase domain at either of its N- or C-termini to a BRET donor or a BRET acceptor to produce donor labeled and acceptor labeled fusion proteins;
b) expressing the fusion proteins to identify combinations that provide specific BRET signals;
c) introducing dimer interface mutations into either of the labeled fusion proteins;
d) expressing the labeled mutated fusion proteins with WT RAF kinase domains;
e) contacting the interface with the potential inhibitor; and
f) measuring the BRET signals, a loss or significant reduction of the BRET signal for the wild-type RAF/RAF BRET pair being an indication that the inhibitor is specifically bound to the interface.

In another aspect, there is provided a method of identifying a potential inhibitor of RAF/RAF homodimerization, the method comprising:
a) detectably labeling at least one of the dimerization interface residues to generate a detectably labeled RAF monomer;
b) incubating the detectably labeled RAF monomer with the potential inhibitor and a non-labeled RAF monomer;
c) measuring a signal from the detectable label;
d) contacting the RAF dimerization interface with the inhibitor to determine the ability of the potential inhibitor to inhibit RAF/RAF homodimerization.

The interface residues include H449, G450, R481, L487, F488, M489, Y538, A541 or K542.

In one aspect, there is provided a method of identifying a potential inhibitor of RAF/RAF homodimerization, the method comprising.
a) fusing a RAF kinase domain at either of its N- or C-termini to a BRET donor or a BRET acceptor to produce donor labeled and acceptor labeled fusion proteins;
b) expressing the fusion proteins to identify combinations that provide specific BRET signals;
c) introducing dimer interface mutations into either of the labeled fusion proteins;

d) expressing the labeled mutated fusion proteins with WT RAF kinase domains;
e) contacting the interface with the potential inhibitor; and
f) measuring the BRET signals, a loss or significant reduction of the BRET signal for the wild-type RAF/RAF BRET pair being an indication that the inhibitor is specifically bound to the interface.

In another aspect, there is provided a method of identifying compounds that bind to a RAF or a KSR dimerization interface, the method comprising:
a) contacting the interface with a probe to form a probe:interface complex, the probe being displaceable by a test compound;
b) measuring a signal from the probe so as to establish a reference level;
c) incubating the probe:interface complex with the test compound;
d) measuring the signal from the probe;
e) comparing the signal from step d) with the reference level, a modulation of the signal being an indication that the test compound binds to the BIR domain, wherein the probe is a compound labeled with a detectable label or an affinity label.

In another aspect, there is provided a method of identifying a potential inhibitor of RAF/RAF homodimerization, the method comprising:
a) using the atomic coordinates of at least one of the interface residues to generate a three dimensional structure of a RAF dimerization interface;
b) using the three-dimensional structure to design or select the potential inhibitor;
c) synthesizing the inhibitor; and
d) contacting the RAF dimerization interface with the inhibitor to determine the ability of the potential inhibitor to inhibit RAF/RAF homodimerization.

The interface residues are H449, G450, R481, L487, F488, M489, Y538, A541 or K542.

In one aspect, there is provided a method of identifying a potential inhibitor of RAF/KSR heterodimerization, the method comprising:
a) using the atomic coordinates of at least one of interface residues to generate a three dimensional structure of a KSR dimerization interface;
b) using the three-dimensional structure to design or select the potential inhibitor;
c) synthesizing the inhibitor; and
d) contacting the KSR dimerization interface with the inhibitor to determine the ability of the potential inhibitor to inhibit RAF/KSR heterodimerization.

The interface residues are H699, G700, R732, L738, F739, M740, Y790, A793 or R794.

In another aspect, there is provided a method of detecting in a subject the susceptibility to develop a condition or an increased likelihood of developing a condition characterized by impaired regulation of protein RAF or KSR dimerization, the method comprising:
a) obtaining from said subject a biological sample having DNA;
b) sequencing predetermined regions of said DNA encoding a RAF or KSR polypeptide; and
c) comparing the sequence obtained at (b) with a corresponding sequence from a non-susceptible control subject for identifying a RAF or KSR mutation known to be indicative of the susceptibility.

In another aspect, there is provided a human RAF or KSR polypeptide which comprises a mutation compared to wild type RAF or KSR, wherein said mutation produces a mutant version of human RAF or KSR polypeptide that includes at least one mutant H449, G450, R481, L487, F488, M489, Y538, A541 or K542 residue, and wherein the mutant version prevents the formation of a RAF/RAF homodimer.

In another aspect, there is provided a human RAF kinase domain which comprises a mutated dimerization interface having at least one mutant H449, G450, R481H, L487, F488, M489, Y538, A541 or K542 residue.

In another aspect, there is provided a human KSR kinase domain which comprises a mutated dimerization interface having at least one mutant H699, G700, R732, L738, F739, M740, Y790, A793 or R794 residue.

In another aspect, there is provided a substantially pure nucleic having the sequence of full length RAF and encoding the polypeptide sequences of SEQ ID NO: 7 and SEQ ID NO: 9.

In another aspect, there is provided a substantially pure nucleic acid having about 50% or greater nucleotide sequence identity to the sequences, as described above.

In another aspect, there is provided a substantially pure nucleic having the sequence of full length KSR and encoding the polypeptide sequences of SEQ ID NO: 11, SEQ ID NO: 13 and SEQ ID NO: 17.

In another aspect, there is provided a substantially pure nucleic acid having about 50% or greater nucleotide sequence identity to the sequences of SEQ ID NO: 12, SEQ ID NO: 14 and SEQ ID NO: 18.

In another aspect, there is provided a cell in vitro expressing a recombinant nucleic acid comprising a nucleic acid sequence encoding a mutated RAF polypeptide, as described above. In one example, the cell is a mammalian cell, a yeast cell, or a bacterial cell.

In one aspect, there is provided a method of producing a drug which inhibits RAF/RAF homodimerization, the method comprising: identifying a drug or designing a drug which interacts with at least one of the H449, G450, R481, L487, F488, M489, Y538, A541 and K542 residues; and synthesizing the drug.

In another aspect, there is provided a method of producing a drug which inhibits RAF/KSR heterodimerization, the method comprising: identifying a drug or designing a drug which interacts with at least one of the H699, G700, R732, L738, F739, M740, Y790, A793 and R794 residues; and synthesizing the drug.

In another aspect, there is provided a composition comprising: an inhibitor adapted to inhibit the formation of a RAF/RAF homodimer or a RAF/KSR heterodimer, in which the inhibitor binds to at least one of the H449, G450, R481, L487, F488, M489, Y538, A541 and K542 residues in a RAF monomer or at least one of the H699, G700, R732, L738, F739, M740, Y790, A793 and R794 residues in a KSR monomer.

In another aspect, there is provided a method of treating or preventing a disease in a subject, the disease being characterized by RAF/RAF homodimerization or RAF/KSR heterodimerization, the method comprising: administering to the subject in need thereof, an expression vector encoding mutated RAF or KSR polypeptide, the mutated RAF or KSR polypeptide being positioned in the vector for expression in a cell of the subject in which RAF/RAF homodimerization or RAF/KSR heterodimerization is taking place, so as to treat or prevent the disease.

In another aspect, there is provided a dominant negative mutant polypeptide of mammalian RAF or KSR, wherein the mutant polypeptide comprises a kinase domain having a dimerization interface and does not bind to a WT mammalian RAF or KSR dimerization interface.

In another aspect, there is provided a purified antibody which specifically binds to a mammalian mutated RAF or KSR polypeptide. The mammal is a human. The mammal is a mouse. The mutated RAF polypeptide is B-RAF. The KSR polypeptide is KSR-1. The antibody is a polyclonal antibody. The antibody is a monoclonal antibody.

BRIEF DESCRIPTION OF THE FIGURES

In order that the herein described may be readily understood, certain embodiments are illustrated by way of example in the accompanying drawings.

FIG. 1A to C—KSR possesses intrinsic RAF activating potential. FIG. 1A) Co-overexpression of KSR, RAF and its substrate MEK as indicated in S2 cells leads to activation of RAF in a KSR concentration-dependent manner in the presence or absence of RNAi-mediated knockdown of RAS or co-overexpression of a constitutively active $RAS^{V12}$ variant. RAF activation was assessed by immunoblotting for phospho-MEK. The catalytically-inactive RAF K455M (KM) mutant served as a negative control. FIGS. 1B and C) The RAF activation potential of overexpressed KSR is not affected by RNAi-mediated knockdown of CNK, HYP or CK2α or by mutation of the proposed CK2 α regulatory sites in KSR (T399A/K402A) and RAF (S416A/S417A). Assessment of the RNAi-mediated knock-downs for endogenous RAS, CNK, HYP and CK2 α is provided in FIG. 13.

FIG. 3A) Projection of highly conserved residues across both KSR and RAF orthologues onto the crystal structure (PDB ID=1UWH) (Wan, P. T. et al., Mechanism of activation of the RAF-ERK signaling pathway by oncogenic mutations of B-RAF, Cell, 116, 855-67 (2004)) of the B-RAF kinase domain (top panel) highlights common side-to-side dimer contact surfaces visualized originally in crystal structures of B-RAF (bottom panel). FIG. 3B) Crystal structure of B-RAF highlighting the position of Arg481 (equivalent to Arg732 in KSR) at the center of the side-to-side dimer interface (PDB ID=1UWH) (Wan, P. T. et al., Mechanism of activation of the RAF-ERK signaling pathway by oncogenic mutations of B-RAF, Cell, 116, 855-67 (2004)). Residue numbering scheme corresponds to Drosophila RAF. One protomer is displayed as a surface representation in orange and the other is shown as a ribbons representation in violet. Inset displays a close-up view of hydrogen bonding interactions involving Arg481, an ordered solute molecule, and main-chain carbonyl groups in the linker joining helix αC to strand β4. FIG. 3C) Analytical ultracentrifugation analysis reveals that mutation of Arg481 (R481H) in B-RAF transitions the protein from a dimer (left panel) to a monomer (right panel) in solution. The red line denotes a fitted curve to the self-association model. The residuals for the fit are shown in the upper panels.

FIG. 5A) Left panel: Model of a side-to-side heterodimer between KSR and RAF kinase domains. RAF is displayed as a surface representation in purple while KSR is shown in ribbons representations in green. Highlighted in red stick representation are the positions of residues selected for mutational analysis in KSR (G700W, R732H, F739A, M740W and Y790F). Position of analogous mutated sites in RAF (G450W, R481H, F488A, M489W and Y538F, respectively) are denoted by yellow surface; residue numbering scheme corresponds to Drosophila RAF. Right panel: The individual effect of KSR and RAF mutations on RAF activation was assessed by monitoring the levels of phosphorylated MEK in S2 cells as performed in FIG. 1. Control mutations outside the side-to-side dimer interface correspond to K460A, E601A and M640A in RAF, and D710A, E859A and V898A in KSR. FIG. 5B) Left panel: Schematic for induced side-to-side dimer formation using FRB/FKBP fusions to the kinase domains of KSR and RAF. Right panel: The RAF activation potential of the FRB/FKBP fused kinase domains of KSR and RAF were assessed by monitoring the levels of phosphorylated MEK in the presence or absence of rapamycin in S2 cells as performed in FIG. 1. FIG. 5C) Left panel: Schematic for induced side-to-side homodimer formation of RAF kinase domains. The catalytically-inactive (K455S) FRB-RAF fusion is indicated by an 'X' within the N-lobe. Right panel: Activation potential of FRB/FKBP RAF homodimers was assessed as in FIG. 3B.

FIG. 6A) The side-to-side dimer configuration of the kinase domain of B-RAF is shown viewed perpendicular to the 2-fold axis of symmetry (PDB ID=1UWH) (Wellbrock, C., Karasarides, M. & Marais, R., The RAF proteins take centre stage, Nat Rev Mol Cell Biol, 5, 875-85 (2004)). The N-lobes of the two kinase domains, which compose the majority of the dimer interaction surfaces, are colored in darker tint. FIG. 6B) Superposition of the six reported B-RAF kinase domain structures reveal an identical mode of side-to-side dimerization (PDB IDs: 1UWH (Wan, P. T. et al., Mechanism of activation of the RAF-ERK signaling pathway by oncogenic mutations of B-RAF, Cell, 116, 855-67 (2004)), 1UWJ (Wan, P. T. et al., Mechanism of activation of the RAF-ERK signaling pathway by oncogenic mutations of B-RAF, Cell, 116, 855-67 (2004)), 2FB8 (King, A. J. et al., Demonstration of a genetic therapeutic index for tumors expressing oncogenic BRAF by the kinase inhibitor SB-590885, Cancer Res, 66, 11100-5 (2006)), 3C4C (Tsai, J. et al., Discovery of a selective inhibitor of oncogenic B-Raf kinase with potent antimelanoma activity, Proc Natl Acad Sci, USA, 105, 3041-6 (2008)), 3C4D (Tsai, J. et al., Discovery of a selective inhibitor of oncogenic B-Raf kinase with potent antimelanoma activity. Proc Natl Acad. Sci., USA, 105, 3041-6 (2008)) and 3D4Q (Hansen, J. D. et al., Potent and selective pyrazole-based inhibitors of B-Raf kinase, Bioorg Med Chem Lett, 18, 4692-5 (2008)). FIG. 6C) Comparison of the B-RAF side-to-side mode of dimerization with the specific mode of dimerization of PKR (PDB ID=2A19 (Dar, A. C., Dever, T. E. & Sicheri, F., Higher-order substrate recognition of eIF2alpha by the RNA-dependent protein kinase PKR, Cell, 122, 887-900 (2005)) and EGFR (PDB ID=2GS2 (Zhang, X., Gureasko, J., Shen, K., Cole, P. A. & Kuriyan, J., An allosteric mechanism for activation of the kinase domain of epidermal growth factor receptor, Cell, 125, 1137-49 (2006)) kinase domains. Helix αC is a participant in all three modes of dimerization.

FIGS. 7A and B—An engineered KSR/RAF chimera can functionally mimic wildtype KSR. FIG. 7A) Schematics of wild type and chimeric KSR/RAF constructs involving either a full RAF kinase domain swap into KSR (Chimera-A) or just a RAF N-lobe swap into KSR (Chimera-B). FIG. 7B) The ability of wild type RAF, KSR, and KSR/RAF chimeric constructs to drive RAF activation in S2 cells was assessed by the levels of phosphorylated MEK.

FIG. 8A) Model of a side-to-side heterodimer between KSR and RAF kinase domains. RAF is displayed as a surface representation in purple while KSR is shown in ribbons representations in green. Highlighted in red stick representation are the positions of residues selected for mutational analysis in KSR (H699E, L738R, F739L, A793E, and R794E). Position of analogous mutated sites in RAF (H449E, L487R, F488L, A541E and K542E, respectively) are denoted by yellow surface; residue numbering scheme corresponds to *Drosophila* RAF. FIGS. 8B and C) The RAF activation potential of the FRB/FKBP fused kinase domains of KSR and RAF were assessed by monitoring the levels of phosphorylated MEK in the presence or absence of rapamycin in S2 cells as illustrated in the schematic.

FIG. 9A) Sequence alignment of the C-terminus of KSR reveals a highly conserved 14-3-3 recognition site common to that found in RAF (*Drosophila* RAF residue numbering is indicated above the alignment). Aligned sequences correspond to those from *Drosophila* (d), human (h), mouse (m), zebrafish (z), and chicken (c).

FIG. 11A to D—Side-to-side dimer formation underlies the aberrant signaling potential of oncogenic RAF mutants. FIG. 11A) RAF activation assay using overexpressed full-length RAF and MEK proteins in S2 cells. The dimer interface mutation (RAF_R481H) abrogates the pronounced activation potential of the activation segment mutation (analogous to oncogenic B-RAF mutation) RAF T571E/T574D (denoted RAF-AL$^{ED}$). FIG. 11B) Glu558 locates to the side-to-side dimer interface in RAF and is mutated to Lys in human cancers (E558K mutation; residue numbering scheme corresponds to *Drosophila* RAF). The longer Lys residue could potentially engage in hydrogen bonding interactions with Ser561 on the opposite protomer. FIG. 11C) Right panel: Schematic for induced side-to-side homodimer formation of RAF kinase domains as in FIG. 3C. Left panel and FIG. 11D: Catalytically inactive FRB-RAF harboring the E558K mutation was assessed for its activation potential towards FKBP-RAF in trans as in FIG. 3C.

FIG. 13A to F—Depletion of specific endogenous targets by RNAi. To ensure that dsRNAs directed against RAS (FIG. 13A), CNK (FIG. 13B), HYP (FIG. 13c), CK2α (FIG. 13D), 14-3-3ε (FIG. 13E) or 14-3-3ζ (FIG. 13F) worked as expected, we separately incubated S2 cells with specific dsRNAs (15 μg/ml) against these intended targets and monitored their respective protein or mRNA levels using either specific antibodies or qPCR. GFP dsRNA was used as negative control. In panel A, the effect of RAS depletion was also monitored by assessing phospho-MAPK (pMAPK) levels induced by the activated Sevenless (SEV$^{S11}$) RTK expressed under the control of the hsp70 promoter (Laberge, G., Douziech, M., & Therrien, M. Src42 binding activity regulates *Drosophila* RAF by a novel CNK-dependent derepression mechanism, EMBO J, 24, 487-98 (2005)).

FIGS. 14A and 14B show polypeptide and polynucleotide sequences (SEQ ID NO: 7 and 8), respectively, of *homo sapiens* v-raf murine sarcoma viral oncogene homolog B1 (BRAF) showing mutated residues as underlined and highlighted.

FIG. 14C shows polypeptide sequence (SEQ ID NO: 9) of *mus musculus* Braf transforming gene (Braf) showing mutated residues as underlined and highlighted.

FIG. 14D to G show nucleotide sequence (SEQ ID NO: 10) of *mus musculus* Braf transforming gene (Braf).

FIG. 14H shows polypeptide sequence (SEQ ID NO: 11) of *homo sapiens* kinase suppressor of ras 1 (KSR 1) showing mutated residues as underlined and highlighted.

FIG. 14I to K show nucleotide sequence (SEQ ID NO: 12) of *homo sapiens* kinase suppressor of ras 1 (KSR 1).

FIG. 14L shows polypeptide sequence (SEQ ID NO: 13) of *mus musculus* kinase suppressor of ras 1 (Ksr 1) showing mutated residues as underlined and highlighted.

FIGS. 14M and N show nucleotide sequence (SEQ ID NO: 14) of *mus musculus* kinase suppressor of ras 1 (Ksr 1).

FIG. 14O shows polypeptide sequence (SEQ ID NO: 15) of *Drosophila melanogaster* pole hole (phi) transcript variant A showing mutated residues as underlined and highlighted.

FIGS. 14P and Q show nucleotide sequence (SEQ ID NO: 16) of *Drosophila melanogaster* pole hole (phi) transcript variant A.

FIG. 14R shows polypeptide sequences (SEQ ID NO: 17) of *Drosophila melanogaster* kinase suppressor of ras (ksr) showing mutated residues as underlined and highlighted.

FIGS. 14S and T show nucleotide sequences (SEQ ID NO: 18) of *Drosophila melanogaster* kinase suppressor of ras (ksr).

FIG. 15A to D—Development of a Bioluminescence Resonance Energy Transfer (BRET) assay to monitor RAF/RAF homodimerization. (FIG. 15A) Structure of the human BRAF kinase. RBD, CRD and Ser/Thr stand for Ras-Binding Domain, Cysteine-Rich Domain and Ser/Thr-rich domains respectively. The Kinase domain (KD) and its C-terminal extension (dashed box) were used in all BRET constructs described here. (FIG. 15B) Structure of the BRAF-KD donor (rlucII) and acceptor (GFP10) expression constructs used in the BRET assay. (FIG. 15C) Saturation curve of the BRAF-KD-wt and BRAF-KD-R481H alleles showing a significant reduction in the $BRET_{max}$ and $BRET_{50}$ when a dimer interface mutation (R481H) is introduced in the BRAF-KD. (FIG. 15D) Parameters derived from fit of our data with a hyperbolic function. $R^2$ denotes the goodness of fit of our data to a hyperbolic function. $BRET_{max}$ and $BRET_{50}$ were interpolated using the hyperbolic function.

FIG. 16A shows CAAX-box and BRET donor and acceptor polypeptide sequences (human KRAS CAAX-box CDS: SEQ ID NO: 19; human KRAS CAAX-box: SEQ ID NO: 20; GFP10 CDS: SEQ ID NO: 21; GFP10: SEQ ID NO: 22).

FIG. 16B shows the nucleotide and polypeptide sequences of rlucII (CDS: SEQ ID NO: 23, amino acid: SEQ ID NO: 24)

FIG. 17A shows human BRAF (hBRAF) polypeptide sequences (hBRAF-KD-wt CDS: SEQ ID NO: 25; hBRAF-KD-wt: SEQ ID NO: 26).

FIG. 17B shows human hBRAF-KD-R481H CDS: SEQ ID NO: 27; hBRAF-KD-R481H: SEQ ID NO: 28). The bolded residues indicate linker and restriction sites. Mutated residues are shaded in black.

FIG. 18A to H show human BRAF-KD clones between the NheI and XbaI sites in pcDNA3.1-zeo (GFP10-hBRAF-KD-wt-CAAX CDS: SEQ ID NO: 29, FIG. 18A; GFP10-hBRAF-KD-wt-CAAX: SEQ ID NO:30, FIG. 18B; GFP10-hBRAF-KD-R481H-CAAX CDS: SEQ ID NO: 31, FIG. 18C; GFP10-hBRAF-KD-R481H-CAAX: SEQ ID NO: 32, FIG. 18D; rlucII-hBRAF-KD-wt-CAAX CDS: SEQ ID NO: 33, FIG. 18E: rlucII-hBRAF-KD-wt CAAX: SEQ ID NO: 34, FIG. 18F; rlucII-hBRAF-KD-R481H-CAAX CDS: SEQ ID NO: 35, FIG. 18G; and rlucII-hBRAF-KD-R481H-CAAX: SEQ ID NO: 36, FIG. 18H). The bolded residues indicate linker and restriction sites. Mutated residues are shaded in black.

FIG. 19 shows human CRAF (hCRAF) polypeptide sequences (hCRAF-KD-wt CDS: SEQ ID NO: 37: hCRAF-KD-wt: SEQ ID NO: 38).

FIG. 20A to C show hCRAF-KD fusions that are cloned between NheI and XbaI in pcDNA3.1-zeo (GFP10-hCRAF-KD-wt-CAAX CDA: SEQ ID NO: 39; GFP10-hCRAF-KD-wt-CAAX: SEQ ID NO: 40; rlucII-hCRAF-KD-wt-CAAX CDS: SEQ ID NO: 41; and rlucII-hCRAF-KD-wt-CAAX: SEQ ID NO: 42). The bolded residues indicate linker and restriction sites.

FIGS. 21A and B show human KSR1 (hKSR1) sequences (hKSR1-KD-wt-CDS: SEQ ID NO: 43; hKSR1-KD-wt: SEQ ID NO: 44; hKSR1-KD-C922Y CDS: SEQ ID NO: 45; and hKSR1-KD-C922Y: SEQ ID NO: 46). The bolded residues indicate linker and restriction sites. Mutated residues are shaded in black.

FIG. 22A to C show human KSR1-KD-rlucII fusions cloned between KpnI and PmeI in pcDNA3.1-zeo (hKSR1-KD-wt-rlucII CDS: SEQ ID NO: 47; hKSR1-KD-wt-rlucII: SEQ ID NO: 48; hKSR1-KD-C922Y-rlucII CDS: SEQ ID NO: 49; and hKSR1-KD-C922Y-rlucII: SEQ ID NO: 50). The bolded residues indicate linker and restriction sites.

FIG. 23 shows human MEK1 (hMEK1) sequences (hMEK1 CDS: SEQ ID NO: 51; and hMEK1: SEQ ID NO: 52).

FIGS. 24A and B show human GFP10-MEK1 full length fusion cloned between NheI and XbaI in pcDNA3.1-zeo (GFP10-hMEK1 CDS: SEQ ID NO: 53; and GFP10-hMEK1: SEQ ID NO: 54). The bolded residues indicate linker and restriction sites.

FIG. 25 shows the sequences of cloning oligonucleotides. Human BRAF (OL5_hBRAF_KD_+start_F: SEQ ID NO: 55; OL3_hBRAF_KD_+CAAX_+stop_R: SEQ ID NO: 56); human CRAF (OL5_hCRAF_KD_+start_F: SEQ ID NO: 57; OL5_hCRAF_KD_+CAAX_+stop_R: SEQ ID NO: 58); human KSR1 (OL5_hKSR1_KpnI_cloning_BRET: SEQ ID NO: 59; OL3_hKSR_XbaI_cloning_BRET: SEQ ID NO:60); and human MEK (OL5_hMEK1_KpnI_cloning_BRET: SEQ ID NO: 61; OL3_hMEK_XbaI_cloning_BRET: SEQ ID NO: 62). The bolded residues indicate linker and restriction sites.

FIG. 26 shows sequencing oligonucleotides (OL5_hBRAF_seq1_F: SEQ ID NO: 63; OL5_hBRAF_seq2_F: SEQ ID NO: 64; OL5_hCRAF_seq1_F: SEQ ID NO: 65; and OL5_hCRAF_seq2_F: SEQ ID NO: 66).

FIG. 27 shows mutagenesis oligonucleotides. The following primer pair were used to generate the side-to-side dimer interface mutant R481H in BRAF: OL5_hBRAF_R481H_F (SEQ ID NO: 67); and OL3_hBRAF_R481H_R (SEQ ID NO: 68). The following primer pair was used to introduce the C922Y hMEK1 interaction mutant in hKSR1: OL5_hKSR1_C922Y_F (SEQ ID NO: 69) and OL3_hKSR1_C922Y_R (SEQ ID NO: 70). The bolded residues indicate linker and restriction sites.

DETAILED DESCRIPTION

Figure 2:
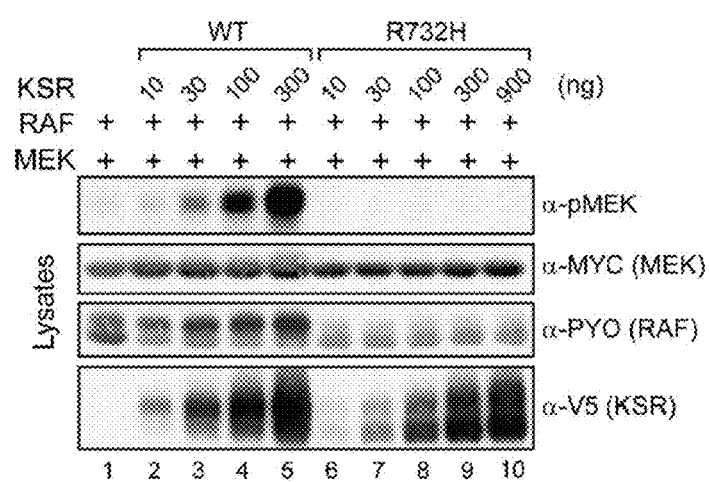
FIG. 2—KSR_R732H mutation abolishes its inherent RAF activating potential. Wild type KSR but not the KSR_R732H mutant is able to drive RAF activation in an S2 cell overexpression system. Experiments were performed as in FIG. 1.

In the following description of the embodiments, references to the accompanying Figures are by way of illustration of an example by which the embodiments described herein may be practiced. It will be understood that other embodiments may be made without departing from the scope of that disclosed herein.

DEFINITIONS

Unless otherwise specified, the following definitions apply throughout:

As used herein, the singular forms "a", "an", and "the" include plural referents unless the context clearly indicates otherwise. Thus, for example, reference to "a mutation" includes one or more of such mutations and reference to "the method" includes reference to equivalent steps and methods known to those of ordinary skill in the art that could be modified or substituted for the methods described herein.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "RAF" is intended to refer to a protein, a polypeptide or fragment thereof, encoded by a RAF gene. Examples of Wild-type (WT) human RAF proteins include the RAF protein isoforms known as A-RAF, B-RAF and C-RAF (e.g., genbank accession numbers P10398 for *Homo sapiens* A-RAF; P15056 for *Homo sapiens* B-RAF; and P04049 for *Homo sapiens* C-RAF). Examples of RAF xenologues are (e.g. genbank accession number P11346 for *Drosophila melanogaster* pole hole (phl;

RAF); P04627 for *Mus musculus* A-RAF; P28028 for *Mus musculus* B-RAF; and Q99N57 for *Mus musculus* C-RAF. Included in this definition are any functional RAF fragment, or any fusion of functional RAF fragments. Examples of these fragments include those that consist of, consist essentially of, or comprise the RAF kinase domain. Furthermore, the term also encompasses any fusion of full length RAF, or a functional fragment thereof, with another polypeptide. These fusions include, but are not limited to, GST-RAF, HA tagged RAF, or Flag tagged RAF. These additional polypeptides may be linked to the N-terminus and/or C-terminus of RAF. Chimeric RAF protein, including a protein comprising a fusion of a RAF domain or domains with a portion of another protein, wherein the chimeric RAF retains the properties of human RAF, are also included. Examples of chimeric RAF proteins include the fusion of any of the above RAF domains, or fragments thereof, to any domain or fragment of the following proteins such as, for example, GST, luciferase or GFP derivatives. RAF also includes any protein with at least 70% sequence identity with mammalian or non-mammalian RAF. The term also includes any conservative substitutions of amino-acid residues in RAF. The term "conservative substitution" refers to replacement of an amino acid residue by a chemically similar residue, e.g., a hydrophobic residue for a separate hydrophobic residue, a charged residue for a separate charged residue, etc. Examples of conserved substitutions for non-polar R groups are alanine, valine, leucine, isoleucine, proline, methionine, phenylalanine, and tryptophan. Examples of substitutions for polar, but uncharged R groups are glycine, serine, threonine, cysteine, asparagine, or glutamine. Examples of substitutions for negatively charged R groups are aspartic acid or glutamic acid. Examples of substitutions for positively charged R groups are lysine, arginine, or histidine. Furthermore, the term RAF includes conservative substitutions with non-natural amino-acids.

The following are Accession numbers for RAF cDNA and protein sequences for various species:

Accession Numbers for RAF cDNA Sequences
NM_080308: *Drosophila melanogaster* pole hole (phl; RAF)
NM_009703: *Mus musculus* A-RAF
NM_139294: *Mus musculus* B-RAF
AB057663: *Mus musculus* C-RAF
X04790: *Homo sapiens* A-RAF
NM_004333: *Homo sapiens* B-RAF
NM_002880: *Homo sapiens* C-RAF
Accession Numbers for RAF Protein Sequences
P11346: *Drosophila melanogaster* pole hole (phl; RAF)
P04627: *Mus musculus* A-RAF
P28028: *Mus musculus* B-RAF
Q99N57: *Mus musculus* C-RAF
P10398: *Homo sapiens* A-RAF
P15056: *Homo sapiens* B-RAF
P04049: *Homo sapiens* C-RAF As used herein, the terms "mutated RAF protein" and "mutated RAF polypeptide" are used interchangeably throughout and are intended to mean a WT RAF protein in which one or more amino acid residues have been changed. In certain examples described herein, the mutations include H449E, G450W, R481H, L487R, F488A, F488L, M489W, Y538F, A541E and K542E, which are located in the dimerization interface. Unless otherwise stated, amino acid residue positions in RAF proteins refer to those of the *Drosophila melanogaster* sequences.

As used herein, the term "KSR" is intended to refer to a Kinase Suppressor of Ras protein, a polypeptide or fragment thereof, encoded by a KSR gene. Examples of Wild type (WT) human KSR proteins include the KSR protein isoforms known as KSR1 and KSR2 (e.g. genbank accession number A8MY87 for *Homo sapiens* kinase suppressor of ras 1 (KSR1) and Q6VAB6: for *Homo sapiens* kinase suppressor of ras 2 (KSR2). Examples of KSR xenologues are (e.g. genbank accession numbers Q24171 for *Drosophila melanogaster* kinase suppressor of ras (KSR); Q61097 for *Mus musculus* kinase suppressor of ras 1 (KSR1); and Q3UVC0 for *Mus musculus* kinase suppressor of ras 2 (KSR2). The term "KSR" also means any functional KSR fragment, or any fusion of functional KSR fragments. Examples of these fragments include those that consist of, consist essentially of, or comprise the KSR kinase domain. Included in this definition are fusion of full length KSR, or a functional fragment thereof, with another polypeptide. These fusions include, but are not limited to, GST-KSR, HA tagged KSR, or Flag tagged KSR. These additional polypeptides may be linked to the N-terminus and/or C-terminus of KSR. Any chimeric KSR protein including a protein comprising a fusion of a KSR domain or domains with a portion of another protein, wherein the chimeric KSR retains the properties of human KSR, are also included. Examples of chimeric KSR proteins include the fusion of any of the above KSR domains, or fragments thereof, to any domain or fragment of the following proteins such as, for example, GST, luciferase or GFP derivatives. KSR also includes any protein with at least 70% sequence identity with mammalian or non-mammalian KSR. The term also includes any conservative substitutions of amino-acid residues in KSR. The term "conservative substitution" refers to replacement of an amino acid residue by a chemically similar residue, e.g., a hydrophobic residue for a separate hydrophobic residue, a charged residue for a separate charged residue, etc. Examples of conserved substitutions for non-polar R groups are alanine, valine, leucine, isoleucine, proline, methionine, phenylalanine, and tryptophan. Examples of substitutions for polar, but uncharged R groups are glycine, serine, threonine, cysteine, asparagine, or glutamine. Examples of substitutions for negatively charged R groups are aspartic acid or glutamic acid. Examples of substitutions for positively charged R groups are lysine, arginine, or histidine. Furthermore, the term KSR includes conservative substitutions with non-natural amino-acids.

The following are Accession numbers for KSR cDNA and protein sequences for various species:

Accession Numbers for KSR cDNA Sequences
NM_079512: *Drosophila melanogaster* kinase suppressor of ras (KSR)
NM_013571: *Mus musculus* kinase suppressor of ras 1 (KSR1)
DQ531035: *Mus musculus* kinase suppressor of ras 2 (KSR2)
NM_014238: *Homo sapiens* kinase suppressor of ras 1 (KSR1)
NM_173598: *Homo sapiens* kinase suppressor of ras 2 (KSR2)
Accession Numbers for KSR Protein Sequences
Q24171: *Drosophila melanogaster* kinase suppressor of ras (KSR)
Q61097: *Mus musculus* kinase suppressor of ras 1 (KSR1)
Q3UVC0: *Mus musculus* kinase suppressor of ras 2 (KSR2)
Q8IVT5: *Homo sapiens* kinase suppressor of ras 1 (KSR1)
Q6VAB6: *Homo sapiens* kinase suppressor of ras 2 (KSR2)

As used herein, the terms "mutated KSR protein" and "mutated KSR polypeptide" are used interchangeably throughout and are intended to mean a WT KSR protein in which one or more amino acid residues have been changed. In certain examples described herein, the mutations include H699E, G700W, R732H, L738R, F739A, F739L, M740W, Y790F, A793E and R794E, which are located in the dimerization interface. Unless otherwise stated, amino acid residue positions in KSR proteins refer to those of the *Drosophila melanogaster* sequences.

As used herein, the term "mutation" is intended to mean any alteration in a gene which alters function or expression of the gene products, such as mRNA and the encoded for protein. This includes, but is not limited to, altering mutation, point mutation, truncation mutation, deletion mutation, frameshift mutation, and null mutation.

As used herein, the term "RAF gene" is intended to mean a gene encoding a RAF polypeptide having a dimerization interface. The RAF gene is a gene having about 50% or greater nucleotide sequence identity to at least one of human RAF isoforms (e.g. genbank accession numbers X04790 for *Homo sapiens* A-RAF; NM_004333 for *Homo sapiens* B-RAF; and NM_002880 for *Homo sapiens* C-RAF. Examples of RAF xenologues are (e.g. genbank accession numbers NM_080308 for *Drosophila melanogaster* pole hole (phl; RAF); NM_009703 for *Mus musculus* A-RAF; NM_139294 for *Mus musculus* B-RAF; and AB057663 for *Mus musculus* C-RAF).

As used herein, the term "KSR gene" is intended to mean a gene encoding a KSR polypeptide having a dimerization interface. The KSR gene is a gene having about 50% or greater nucleotide sequence identity to at least one of human KSR isoforms (e.g. genbank accession numbers NM_014238 for *Homo sapiens* kinase suppressor of ras 1 (KSR1); and NM_173598 for *Homo sapiens* kinase suppressor of ras 2 (KSR2)). Examples of KSR xenologues are (e.g. genbank accession numbers NM_079512 for *Drosophila melanogaster* kinase suppressor of ras (KSR); NM_013571 for *Mus musculus* kinase suppressor of ras 1 (KSR1); and DQ531035 for *Mus musculus* kinase suppressor of ras 2 (KSR2).

As used herein, the term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

As used herein, the term "dimer interface" is intended to mean a site in the WT RAF or KSR polypeptide sequence or the mutated RAF or KSR polypeptide sequence, which reacts with a RAF or KSR substrate.

As used herein, the terms "RAF kinase domain" or "KSR kinase domain" are intended to mean the portion of the RAF or KSR proteins that are related in sequence to a generic protein kinase domain.

As used herein, the term "detectable label" is intended to mean a compound that may be linked to a RAF or KSR kinase domain, such that when the compound is associated with the domain, the label allows either direct or indirect recognition of the compound so that it may be detected, measured and quantified.

As used herein, the term "affinity tag" is intended to mean a ligand or group, which is linked to a RAF or KSR kinase domain to allow another compound to be extracted from a solution to which the ligand or group is attached.

As used herein, the term "nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids described herein, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Whenever applicable, the term "isolated nucleic acid" may also refer to a RNA molecule encoded by an isolated DNA molecule as defined above. Alternatively, the term may refer to an RNA molecule that has been sufficiently separated from other nucleic acids with which it would be associated in its natural state (i.e. in cells or tissues). An "isolated nucleic acid" (either DNA or RNA) may further represent a molecule produced directly by biological or synthetic means and separated from other components present during its production.

As used herein, the term "vector" is intended to mean a replicon, such as a plasmid, cosmid, bacmid, phage or virus, to which another genetic sequence or element (either DNA or RNA) may be attached so as to bring about the replication of the attached sequence or element.

As used herein, the terms "percent similarity", "percent identity" and "percent homology" when referring to a particular sequence are used as set forth in the University of Wisconsin GCG software program.

As used herein, the term "substantially pure" is intended to refer to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). Described herein are substantially pure mutated RAF or KSR isoforms (e.g., nucleic acids, oligonucleotides, proteins, fragments, mutants, etc.).

As used herein, the term "oligonucleotide" is intended to sequences, primers and probes as described herein, and is defined as a nucleic acid molecule comprised of two or more ribo- or deoxyribonucleotides, preferably more than three. The exact size of the oligonucleotide will depend on various factors and on the particular application and use of the oligonucleotide.

As used herein, the term "primer" is intended to refer to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 20-40, or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

As used herein, the term "probe" is intended to refer to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 20-40 or more nucleotides in length, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

With respect to single-stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule as described herein, to the substantial exclusion of hybridization of the oligonucleotide with single-stranded nucleic acids of non-complementary sequence. Appropriate conditions enabling specific hybridization of single-stranded nucleic acid molecules of varying complementarity are well known in the art. For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m = 81.5° C. + 16.6 \text{ Log } [Na+] + 0.41(\% \text{ G+C}) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5 with every 1% decrease in homology. Thus, targets with greater than about 75% sequence identity would be observed using a hybridization temperature of 42° C.

The stringency of the hybridization and wash depends primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. With regard to the nucleic acids as described herein, a moderate stringency hybridization is defined as hybridization in 6×SSC, 5×Denhardt's solution, 0.5% SDS and 100 µg/ml denatured salmon sperm DNA at 42° C. and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

Alternatively, as used herein, the term "probe" is intended to mean a compound which is labeled with either a detectable label or an affinity tag, and which is capable of binding, either covalently or non-covalently, to a RAF or KSR kinase domain. When, for example, the probe is non-covalently bound, it may be displaced by a test compound. When, for example, the probe is bound covalently, it may be used to form cross-linked adducts, which may be quantified and inhibited by a test compound.

As used herein, the term "isolated protein" or "isolated and purified protein" is intended to refer to a protein produced by expression of an isolated nucleic acid molecule as described herein. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

As used herein, the term "amino acid" is intended to mean a radical derived from the corresponding α-amino acid by eliminating the hydroxyl of the carboxy group and one hydrogen of the .alpha.-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively. Amino Acid residues are provided below:

Three and single letter abbreviations for α-amino acids used throughout are as follows:

| Amino acid. | Abbreviation | Abbreviation |
|---|---|---|
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Isoleucine | Ile | I |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "subject" is intended to mean humans and non-human mammals such as primates, cats, dogs, swine, cattle, sheep, goats, horses, rabbits, rats, mice and the like.

As used herein, the term "solid support" refers to any solid or stationary material to which reagents such as antibodies, antigens, and other test components can be attached. Examples of solid supports include, without limitation, microtiter plates (or dish), microscope (e.g. glass) slides, coverslips, beads, cell culture flasks, chips (for example, silica-based, glass, or gold chip), membranes, particles (typically solid; for example, agarose, sepharose, polystyrene or magnetic beads), columns (or column materials), and test tubes. Typically, the solid supports are water insoluble.

As used herein, the term "instructional material" or a "user manual" includes a publication, a recording, a diagram, or any other medium of expression which can be used to communicate the usefulness of reagents for performing a method as described herein.

As used herein, the term "biological sample" is intended to refer to a subset of the tissues of a biological organism, its cells or component parts (e.g. body fluids, including but not limited to, blood, mucus, lymphatic fluid, synovial fluid, cerebrospinal fluid, saliva, amniotic fluid, amniotic cord blood, urine, vaginal fluid and semen).

We have discovered, using a combination of structural analysis, site-directed mutagenesis and functional studies in vivo, a dimerization interface in RAF and KSR. We have identified a number of residues within the RAF and KSR kinase domains which, when mutated, prevent the formation of oncogenic dimers. Through this, we have discovered that RAF catalytic function is regulated in response to a specific mode of dimerization of its kinase domain (which we term the side-to-side dimer). Furthermore, we have discovered that the RAF-related pseudo-kinase KSR also participates in forming side-to-side heterodimers with RAF and thereby can trigger RAF activation. This mechanism provides an elegant explanation for the longstanding conundrum regarding RAF catalytic activation and provides an explanation for the capacity of KSR, despite lacking catalytic function, to directly mediate RAF activation. We have also demonstrated that RAF side-to-side dimer formation is essential for aberrant signaling by oncogenic B-RAF mutants and we have identified an oncogenic mutation that acts specifically by promoting side-to-side dimer formation. These discoveries allow us to identify the side-to-side dimer interface of RAF as a potential therapeutic target for intervention in B-RAF-dependent tumourigenesis.

I: Nucleic Acid Molecules, Vectors, Cells, Transgenes and Transgenic Non-Human Mammals Described herein are mutated isoforms of RAF and KSR proteins. Furthermore, we have discovered that single point mutations in the dimerization interface of RAF or KSR kinase domains prevents the formation of side-to-side dimers, when compared to wild type RAF or KSR. The single point mutations in the RAF kinase domain are at residues H449, G450, R481H, L487, F488, M489, Y538, A541 and K542 with the mutations being H449E, G450W, R481H, L487R, F488A, F488L, M489W, Y538F, A541E and K542E. The single point mutations in the KSR kinase domain are at residues H699, G700, R732, L738, F739, M740, Y790, A793 and R794 with the mutations being H699E, G700W, R732H, L738R, F739A, F739L, M740W, Y790F, A793E and R794E. We have also discovered that the isolated kinase domain of RAF forms homodimers in aqueous solution. Similar behavior is expected for the isolated KSR kinase domain as well as heterodimers should form in aqueous solution upon mixing equimolar amounts of RAF and KSR kinase domains.

Thus, a substantially pure DNA molecule, such as genomic, cDNA, or a synthetic DNA molecule, encodes one of the mammalian or non-mammalian RAF or KSR isoforms in which one or more nucleotide substitutions has/have been incorporated into the dimerization interface.

In certain embodiments, DNA sequences are substantially identical to the DNA sequences, or a fragment thereof, as illustrated in FIGS. 14A through 14F (SEQ ID NO's: 8, 10, 12, 14, 16, and 18). Another aspect features RNA, which is encoded by the DNA described herein. In one example, the RNA is mRNA. In another example, the RNA is antisense RNA.

Also contemplated are oligonucleotide probes, which specifically hybridize with the nucleic acid molecules as described herein. In certain examples, the probe specifically hybridizes with mutated RAF or KSR nucleic acid molecules (e.g. a nucleic acid having a sequence encoding a mutated RAF or KSR protein) while not hybridizing with the wild type or "normal" sequence under high or very high stringency conditions. Primers capable of specifically amplifying mutated RAF or KSR encoding nucleic acids described herein are also contemplated herein. As mentioned previously, such oligonucleotides are useful as probes and primers for detecting, isolating or amplifying mutated RAF or KSR genes.

Nucleic acid molecules encoding the mutated RAF or KSR proteins, as described herein, can be prepared by known general methods or isolated from appropriate biological sources using methods known in the art. Additionally, cDNA or genomic clones having homology with human and other known mammalian RAF or KSR, for example, mouse, rat, and the like, or non-mammalian RAF or KSR, such as *Drosophila*, may be isolated from other species using oligonucleotide probes corresponding to predetermined sequences within the human RAF or KSR encoding nucleic acids.

Nucleic acids described herein may be maintained as DNA in any convenient vector. Accordingly, vectors comprising a nucleic acid molecule as described herein and more particularly a plasmid expression vector are encompassed. Also encompassed are host cells transformed with such vectors and transgenic animals comprising such a nucleic acid molecule as described herein. Those cells and animals could serve as models of disease in order to study the mechanism of the function of the RAF or KSR gene and also allow for the screening of therapeutics.

In some embodiments, the vector, host cell or transgenic animal comprise a nucleic acid molecule (a transgene) encoding a mutated RAF or KSR protein that is expressed or delivered to tissues. The host cell is a transformed and stable cell line constitutively expressing the mutant RAF or KSR isoform.

Methods for producing host cells and transgenic animals are known in the art. Host cells include, but are not limited to mammalian, yeast or bacterial cells Transgenic animals can be selected from non-human mammals such as farm animals (such as pigs, goats, sheep, cows, horses, rabbits, and the like), rodents (such as rats, guinea pigs, mice, and the like), non-human primates (such as baboon, monkeys, chimpanzees, and the like), and domestic animals (such as dogs, cats, and the like) and wild and domestic (such as swans, ducks, fowl and the like). A transgenic animal is an animal having cells that contain a transgene which was introduced into the animal or an ancestor of the animal at a prenatal (embryonic) stage. The cells and transgenic animals can be useful to identify mutated RAF or KSR proteins specific to each organ, and monitoring dimerization of the RAF and KSR in response to therapeutic treatment.

II: Mutated RAF or KSR Polypeptides

A mutated RAF or KSR polypeptide sequence may have 80% homology or more with any of the amino acid sequences disclosed herein. A mutated RAF or KSR polypeptide sequence as described herein may also comprise at least 50 or more contiguous amino acids of any of sequences disclosed herein.

Mutated dimer interface residues in *Drosophila* RAF or *Drosophila* KSR and their equivalent positions in mammalian B-RAF or KSR1 are provided in the Tables below:

| Dmel KSR (Acc. # Q24171) | Hsap KSR1 (Acc. # Q8IVT5) | Mmus KSR1 (Acc. # Q61097) |
| --- | --- | --- |
| H699E | H631 | H583 |
| G700W | G632 | G584 |
| R732H | R663 | R615 |
| L738R | L669 | L621 |
| F739A | F670 | F622 |
| F739L | F670 | F622 |
| M740W | M671 | M623 |
| Y790F | Y721 | Y673 |
| A793E | A724 | A676 |
| R794E | K725 | K677 |

| Dmel RAF (Acc. # P11346) | Hsap BRAF (Acc. # P15056) | Mmus BRAF (Acc. # P28028) |
| --- | --- | --- |
| H449E | H477 | H514 |
| G450W | G478 | G515 |
| R481H | R509 | R546 |
| L487R | L515 | L552 |
| F488A | F516 | F553 |
| F488L | F516 | F553 |
| M489W | M517 | M554 |
| Y538F | Y566 | Y603 |
| A541E | A569 | A606 |
| K542E | K570 | K607 |

Other dimer interface residues in *Drosophila* RAF or *Drosophila* KSR and their equivalent positions in mammalian B-RAF or KSR1, and which are mutatable include those in the following Tables:

| Dmel RAF leap (Acc. # P11346) | Hsap BRAF (Acc. # P15056) | Mmus BRAF (Acc. # P28028) |
| --- | --- | --- |
| E420 | D448 | D485 |
| W422 | W450 | W487 |
| W448 | W476 | W513 |
| K478 | R506 | R543 |
| K479 | T507 | K544 |
| T480 | T508 | T545 |
| H482 | H510 | H547 |
| C483 | V511 | V548 |
| Q502 | Q530 | Q567 |
| D537 | D565 | D602 |
| L560 | L588 | L625 |
| S561 | T589 | T626 |
| E687 | E715 | E752 |

| Dmel KSR (Acc. # Q24171) | Hsap KSR1 (Acc. # Q8IVT5) | Mmus KSR1 (Acc. # Q61097) |
| --- | --- | --- |
| K670 | Q602 | Q554 |
| W672 | W604 | W556 |
| W698 | W630 | W582 |
| K729 | R660 | R612 |
| N730 | Q661 | Q613 |
| T731 | T662 | T614 |
| H733 | H664 | H616 |
| E734 | E665 | E617 |
| S754 | S685 | S637 |
| G789 | G720 | G672 |
| K812 | K743 | K695 |
| V813 | V744 | V696 |
| E941 | E876 | E828 |

SwissProt accession numbers are provided for reference

Referring to FIGS. 14A through 14T, specifically SEQ ID NO's: 7, 9, 11, 13, 15 and 17, the amino acid positions for the experimentally verified dimer interface residues are shaded in the protein sequences presented. In these Figures, predicted additional dimer interface residues are underlined.

In some embodiments, the mutated RAF or KSR polypeptide is an isolated mutated protein in which the mutations are located in the RAF or KSR kinase domain, specifically in the dimerization interface. In certain examples, the mutated RAF polypeptide comprises one or more mutations selected from H449E, G450W, R481H, L487R, F488A, F488L, M489W, Y538F, A541E and K542E. In certain examples, the mutated KSR polypeptide comprises one or more mutations selected from H699E, G700W, R732H, L738R, F739A, F739L, M740W, Y790F, A793E and R794E.

Mutated RAF or KSR proteins or polypeptides as described herein may be prepared in a variety of ways, according to known methods. The proteins may be purified from appropriate sources, e.g., transformed bacterial or animal cultured cells or tissues, by immunoaffinity purification. The availability of nucleic acid molecules encoding mutated RAF or KSR protein enables production of the protein using in vitro expression methods and cell-free expression systems known in the art. In vitro transcription and translation systems are commercially available, e.g., from Promega or Invitrogen.

Alternatively, larger quantities of mutated RAF or KSR proteins or polypeptides may be produced by expression in a suitable prokaryotic or eukaryotic system. For example, part or all of a DNA molecule encoding for mutated RAF or KSR may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences. Mutated RAF or KSR proteins or polypeptides produced by gene expression in a recombinant prokaryotic or eukaryotic system may be purified according to methods known in the art.

Thus, another embodiment includes a method of producing a mammalian mutated RAF or KSR polypeptide includes providing a cell transformed with a nucleic acid sequence encoding a mammalian mutated RAF or KSR polypeptide positioned for expression in the cell. The mutated RAF or KSR polypeptide has an amino acid change at one of the positions depicted in FIGS. 14A through 14T (SEQ ID NO's: 7, 9, 11, 13, 15 and 17) that correspond to specific dimerization interface residues. The transformed cell is cultured under conditions for expressing the nucleic acid; which then produces the mammalian mutated RAF or KSR polypeptide.

A dominant-negative protein is a protein that antagonizes the action of its normal counterpart. A dominant-negative RAF would be a mutant RAF that prevents endogenous RAF from performing its natural (or oncogenic) function. Such a dominant-negative RAF (or KSR) protein could do so by sequestering away key proteins that normally act in concert with endogenous RAF (or KSR). For example, overexpression of a kinase-defective RAF construct is known to act as a dominant-negative in part by its ability to out-compete for endogenous RAS, which is normally critical for RAF activation.

Thus a dominant negative mutant polypeptide of mammalian RAF or KSR, wherein the mutant polypeptide comprises a kinase domain having a disabled dimerization interface and therefore does not associate to a WT mammalian RAF or KSR dimerization interface.

The use of a dominant-negative polypeptide could be treating or preventing a disease in a subject, in which the disease being characterized by RAF/RAF homodimerization or RAF/KSR heterodimerization. This method comprises administering to the subject in need thereof, an expression vector encoding mutated RAF or KSR polypeptide, the mutated RAF or KSR polypeptide being positioned in the vector for expression in a cell of the subject in which RAF/RAF homodimerization or RAF/KSR heterodimerization is taking place, so as to treat or prevent the disease.

III: Detection Methods

Recombinant WT and mutated RAF or KSR polypeptides can be used during in vitro RAF or KSR dimerization experiments to follow the dimerization of RAF or KSR protomers. RAF or KSR polypeptides mutants can also be co-transfected in mammalian cells with target protein substrates, such as WT RAF or KSR.

Changes in WT and mutated RAF or KSR polypeptide dimerization in response to a potential therapeutic agent, and across cell phenotypes, can be monitored by measuring the variation of the levels of phosphorylated MEK in the presence or absence of rapamycin in animal cells such as S2 cells.

The RAF or KSR dimerization appears to be involved in many aspects of cancer from initiation to metastasis. One additional aspect includes a method of detecting in a subject susceptibility to express mutant RAF or KSR polypeptide. The method includes taking a biological sample from the subject that contains a sufficient amount of a nucleic acid, for example, DNA, and sequencing predetermined regions of the DNA, which encodes a RAF or KSR mutated polypeptide. By comparing this sequence with a corresponding sequence from a non-susceptible control subject, a RAF or KSR mutation known to be indicative of the susceptibility can be identified.

Thus, a method of detecting the presence of a mutation in a RAF kinase domain or a KSR kinase domain, comprises a) providing a WT RAF kinase domain or a WT KSR kinase domain and a suspected mutant RAF kinase domain or a mutant KSR kinase domain, each domain having a cysteine residue located at its N-terminus; b) incubating the WT RAF kinase domain or the WT KSR kinase domain and the suspected mutant RAF kinase domain or the suspected mutant KSR kinase domain with different cross-linking detectable labels; c) incubating together equimolar amounts of the labelled WT RAF kinase domain or the labeled WT KSR kinase domain and detecting a signal from the detectable label so as to provide a dimerization reference signal; and d) incubating equimolar amounts of the labeled suspected mutant B-RAF kinase domain or the suspected mutant KSR kinase domain and detecting a signal from the detectable labels, an absent signal or a reduce signal compared to that of the dimerization reference signal being an indication that a mutant B-RAF kinase domain or a mutatent KSR kinase domain is present.

Also included is a bioluminescence resonance energy transfer (BRET) fusion molecule, and method of use. The fusion molecule comprises three components: a bioluminescent donor protein (donor) and a fluorescent acceptor molecule (acceptor), wherein the acceptor can accept energy from the donor-generated luminescence when these components are in an appropriate spatial relationship and in the presence of an appropriate substrate. A modulator (a drug-like compound for example) can either influence the proximity/orientation of the donor and the acceptor and thereby the energy transfer between these components, or it can play a different role in affecting the energy transfer between the donor-generated activated product and the acceptor.

Thus, there is provided a method of monitoring the formation of RAF/RAF or RAF/KSR kinase domain dimers to detect mutations inhibiting dimerization or drug-like molecules interfering with dimerization. This method comprises a) fusing either (i) a RAF kinase domain or (ii) a KSR kinase domain at either of their N- or C-termini to a BRET donor or a BRET acceptor to produce donor labeled and acceptor labeled fusion proteins; b) expressing the fusion proteins to identify combinations that provide specific BRET signals; c) introducing dimer interface mutations into either of the labeled fusion proteins; d) expressing the labeled mutated fusion proteins with WT RAF or KSR kinase domains; e) measuring the BRET signals, a loss or significant reduction of the BRET signal using dimer interface mutations as opposed to mutations remote from the interface, being an indication that a specific BRET signal which depends on the RAF/RAF or RAF/KSR dimerization interface has been obtained.

In one example, the BRET donor is *renilla* luciferase variant II or rlucII and the BRET acceptor is GFP10. The acceptor label is Yellow Fluorescent Protein (YFP). The donor labeled fusion protein is SEQ ID NO's: 24, 34, 42 and 48, whereas the acceptor labeled fusion protein is SEQ ID NO's: 22, 30, 40 and 54. The donor labeled mutated fusion proteins are SEQ ID NO's: 36, 50 and the acceptor labeled mutated fusion proteins are SEQ ID NO: 32.

IV: Antibodies and Kits

Also provided are antibodies capable of immunospecifically binding to mutated RAF or KSR proteins and polypeptides as described herein. Such antibodies may include, but are not limited to, polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be may be used for immunoaffinity enrichment of the mutated RAF or KSR or they may be used in a kit for detecting in a subject the susceptibility to develop a condition or an increased likelihood of developing a condition characterized by dimerization of RAF and/or KSR.

Polyclonal antibodies directed toward mutated RAF or KSR protein, polypeptides or fragments thereof may be prepared according to standard methods. In one example, monoclonal antibodies are prepared, such that antibodies react immunospecifically with predetermined epitopes of the mutated RAF or KSR protein. In one example, the antibodies are immunogically specific to mutated RAF or KSR proteins and polypeptides. Monoclonal antibodies may be prepared according to general methods known in the art. Polyclonal or monoclonal antibodies that immunospecifically interact with mutant RAF or KSR proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

One advantageous use of antibodies as described herein is in the use of a kit for monitoring the RAF or KSR dimerization activity of a cell or the binding of RAF or KSR to specific protein substrates such as the 14-3-3 proteins. This information may be used for purposes of diagnosis, prognosis or for predicting the response to treatment. Examples of diseases include cancer. The kit comprises a substantially pure antibody that specifically binds to a mammalian mutated RAF or KSR polypeptide and a means for detecting the binding of the antibody to the mammalian RAF or KSR polypeptide.

V: Screening Methods

Because we have identified the amino acid residues involved in RAF/RAF homodimerization and RAF/KSR heterodimerization, we can use this knowledge to screen for potential therapeutic agents which interact, either covalently or non-covalently, with the WT amino residue counterparts. Thus, one additional aspect includes methods of identifying biological agents or small molecules that modulate or prevent RAF or KSR dimerization activity in the cell or modification of the regulation of protein RAF or KSR dimerization. This could also be exploited for example to screen for inhibitors, activators or modulators of RAF or KSR dimerization. The identified agents or molecules could be exploited as research reagents or for therapeutic purposes. The method could be used for in vitro screening assays using purified RAF or KSR WT polypeptides.

Generally speaking, there is provided a method of identifying inhibitors of RAF/RAF or RAF/KSR dimerization that bind to a RAF or KSR kinase domain, the RAF or KSR full protein or the kinase domain is bound to a support, and a potential inhibitor is added to the assay. Alternatively, the potential inhibitor may be bound to the support and the RAF or KSR full protein or the kinase domain is added.

Additionally, the above described BRET assay can be used as a method of identifying a potential inhibitor of RAF/RAF homodimerization. This method comprises a) fusing a RAF kinase domain at either of its N- or C-termini to a BRET donor or a BRET acceptor to produce donor labeled and acceptor labeled fusion proteins; b) expressing the fusion proteins to identify combinations that provide specific BRET signals; c) introducing dimer interface mutations into either of the labeled fusion proteins; d) expressing the labeled mutated fusion proteins with WT RAF kinase domains; e) contacting the interface with the potential inhibitor; and f) measuring the BRET signals, a loss or significant reduction of the BRET signal for the wild-type RAF/RAF BRET pair being an indication that the inhibitor is specifically bound to the interface.

There are a number of ways in which to determine the binding of a potential inhibitor to the RAF or KSR kinase domain. In one way, the potential inhibitor, for example, may be fluorescently or radioactively labeled and binding determined directly. For example, this may be done by attaching the RAF or KSR full protein or the kinase domain to a solid support, adding a detectably labeled potential inhibitor, washing off excess reagent, and determining whether the amount of the detectable label is present on the solid support. Numerous blocking and washing steps may be used, which are known to those skilled in the art.

In some cases, only one of the components is labeled. For example, specific residues, such as those identified as described herein, in the RAF or KSR kinase domain may be labeled. Alternatively, more than one component may be labeled with different labels; for example, using $I^{125}$ for the RAF or KSR domain, and a fluorescent label for the potential inhibitor.

As used herein, the terms "drug candidate", "test compounds" or "potential inhibitor" are used interchangeably and describe any molecule, for example, protein, oligopeptide, small organic molecule, polysaccharide, polynucleotide, and the like, to be tested for bioactivity. The compounds may be capable of inhibiting the formation of RAF/RAF homodimers or RAF/KSR heterodimers.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining a RAF or KSR kinase domain and a labeled probe to form a probe:RAF or KSR kinase domain complex in a first sample followed by adding a potential inhibitor from a second sample. The binding of the potential inhibitor is determined, and a change or difference in binding between the two samples indicates the presence of a test compound capable of binding to the RAF or KSR kinase domain and potentially modulating the RAF or KSR's dimerizing ability.

In one case, the binding of the potential inhibitor is determined through the use of competitive binding assays. In this embodiment, the probe is labeled with a fluorescent label. Under certain circumstances, there may be competitive binding between the potential inhibitor and the probe. Potential inhibitors which displace the probe, resulting in a change in fluorescence as compared to control, are considered to bind to the RAF or KSR kinase domain.

In one case, the potential inhibitor may be labeled. The potential inhibitor is added first to the RAF or KSR domain for a time sufficient to allow binding to form a complex.

Formation of the probe:RAF or KSR domain complex typically require incubations of between 4° C. and 40° C., for between 10 minutes to about 1 hour to allow for high-throughput screening. Any excess of reagents are generally removed or washed away. The potential inhibitor is then added, and the presence or absence of the labeled component is followed, to indicate binding to the RAF or KSR kinase domain.

In one case, the probe is added first, followed by the potential inhibitor. Displacement of the probe is an indication the potential inhibitor is binding to the RAF or KSR domain and thus is capable of binding to, and potentially modulating or inhibiting the dimerization of RAF and KSR. Either component can be labeled. For example, the presence of probe in the wash solution indicates displacement by the potential inhibitor. Alternatively, if the potential inhibitor is labeled, the presence of the probe on the support indicates displacement.

In one case, the potential inhibitor may be added first, with incubation and washing, followed by the probe. The absence of binding by the probe may indicate the potential inhibitor is bound to the RAF or KSR domain with a higher affinity. Thus, if the probe is detected on the support, coupled with a lack of potential inhibitor binding, may indicate the potential inhibitor is capable of binding to the RAF or KSR kinase domain.

Modulation is tested by screening for a potential inhibitor's ability to modulate the activity of RAF or KSR and includes combining a potential inhibitor with a RAF or KSR kinase domain, as described above, and determining an alteration in the biological activity of RAF or KSR. Therefore in this case, the potential inhibitor should both bind to the RAF or KSR kinase domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound potential inhibitor.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays as described herein include a fluorescent label such as Fluorescein, Oregon green, dansyl, rhodamine, tetramethyl rhodamine, texas red, $Eu^{3+}$; a chemiluminescent label such as luciferase; calorimetric labels; enzymatic markers; or radioisotopes such as tritium, $I^{125}$ and the like.

Affinity tags, which may be useful in performing the screening assays as described herein include biotin, polyhistidine and the like.

Examples

1. S2 Expression Plasmids

Copper-inducible pMet vectors were used for functional assays conducted in S2 cells as previously described (Douziech, M., Sahmi, M., Laberge, G. & Therrien, M. A KSR/CNK complex mediated by HYP, a novel SAM domain-containing protein, regulates RAS-dependent RAF activation in *Drosophila*. Genes Dev 20, 807-19 (2006)), Roy, F., Laberge, G., Douziech, M., Ferland-McCollough, D. & Therrien, M. KSR is a scaffold required for activation of the ERK/MAPK module. Genes Dev 16, 427-38 (2002)). The FRB-RAF$^{K455S}$ fusion construct was assembled by inserting an AseI/NotI PCR fragment encompassing residues 328-738 of RAF into the AseI/NotI site of FRB-KSR (Roy, F., Laberge, G., Douziech, M., Ferland-McCollough, D. & Therrien, M. KSR is a scaffold required for activation of the ERK/MAPK module. Genes Dev 16, 427-38 (2002)). The KSR-RAF chimera-A corresponds to KSR$^{1-665}$ fused to RAF$^{417-739}$, whereas chimera-B replaced the N-lobe of KSR (a.a. positions 666-757) with the one of RAF (a.a. positions 417-505). In both cases, the RAF N-lobe contained a K455M change to catalytically impair its kinase activity and thereby mimicked kinase-inert KSR. Variant full length *Drosophila* KSR, RAF or FRB/FKBP fusion mutants were generated by QuickChange mutagenesis (Stratagene). Mutagenized cDNAs were fully sequenced to verify that only the desired mutations had been introduced.

2. S2 Cell Assays

S2 cells were maintained in serum-free insect cell medium (Sigma) at 27° C. Cells were seeded at a density of $1.75 \times 10^6$ cells/ml 24 h prior to transfection. Between 10 to 300 ng (or up to 900 ng for KSR_R732H) of DNA was transfected per construct using Effectene (Qiagen). dsRNAs were produced and used in RNAi experiments as described (Roy, F., Laberge, G., Douziech, M., Ferland-McCollough, D. & Therrien, M. KSR is a scaffold required for activation of the ERK/MAPK module. Genes Dev 16, 427-38 (2002)). Protein expression was induced by adding $CuSO_4$ (0.7 mM) 36 h before harvesting the cells. For FRB/FKBP-mediated dimer formation, rapamycin (Sigma) was added (1 M) to the medium 2 h prior to harvesting the cells. Lysates, immunoprecipitations, western blot procedures and antibodies were essentially as previously described (Douziech, M., Sahmi, M., Laberge, G. & Therrien, M. A, KSR/CNK complex mediated by HYP, a novel SAM domain-containing protein, regulates RAS-dependent RAF activation in *Drosophila*, Genes Dev, 20, 807-19 (2006)).

3. Bacterial Protein Expression and Purification

B-RAF (residues 448-723) and mutant series (R481H, L487R and L487R/E558K) were recombinantly expressed from pProEx (Invitrogen) plasmid in *E. coli* BL21 cells as TEV protease-cleavable 6xHis-tagged fusions ("6xHis" disclosed as SEQ ID NO: 85). To increase the level of soluble protein expression in *E. coli*, 16 specific mutations (remote from the side-to-side dimer interface) were introduced in B-RAF as described Tsai, J. et al., Discovery of a selective inhibitor of oncogenic B-Raf kinase with potent antimelanoma activity, Proc Natl Acad Sci, USA, 105, 3041-6 (2008). Expressed proteins were bound to Ni-NTA and eluted with imidazole and subjected to TEV protease treatment. Further purification was performed by subtractive Ni-NTA and size exclusion (Superdex 200) chromatography.

4. Homology Modeling

A multiple sequence alignment of KSR and RAF kinase domains was used to build a structural model of the kinase domain of *Drosophila* KSR (residues 670-945) in SWISS-MODEL (Schwede, T., Kopp, J., Guex, N. & Peitsch, M. C. SWISS-MODEL: An automated protein homology-modeling server. Nucleic Acids Res 31, 3381-5 (2003)). An initial model with a total energy of −7474.3 KJ/mol was generated using the structure of the kinase domain of B-RAF as a template (chain A of PDB entry 1UWH) (Wan, P. T. et al., Mechanism of activation of the RAF-ERK signaling pathway by oncogenic mutations of B-RAF, Cell, 116, 855-67 (2004)). This model was manually edited in COOT (Emsley, P. & Cowtan, K., Coot: model-building tools for molecular graphics, Acta Crystallogr D Biol Crystallogr, 60, 2126-32 (2004)) and a poorly modelled loop spanning residues 821-838 was removed. To generate the KSR/RAF side-to-side heterodimer, the modelled structure of KSR was superimposed onto chain A of PDB entry 1UWH.

5. Analytical Ultracentrifugation

Equilibrium sedimentation was performed with a Beckman Optima XL-A ultracentrifuge and An60Ti rotor. B-RAF samples were prepared in 20 mM Tris (pH 7.5), 200 mM NaCl, 5% glycerol and 1.5 mM TCEP for analysis. Data was collected at 4° C. for three protein concentrations (25 µM, 12.5 µM, and 6.25 µM) at three rotor speeds (13,000 rpm, 18,000 rpm and 23,000 rpm for B-RAF_wt and B-RAF_R481H or 12,000 rpm, 17,000 rpm and 25,000 rpm for B-RAF_L487R and B-RAF-L487R/E558K). Model analysis of the data was performed simultaneously in a global curve-fitting procedure (Origin software, Beckman). For this, data collected at 13,000 rpm and 18,000 rpm for B-RAF_wt was analyzed at all three protein concentrations; data collected at 18,000 rpm and 23,000 rpm for B-RAF_R481H was analyzed at all three protein concentrations; data collected at 17,000 rpm and 25,000 rpm for B-RAF_L487R was analyzed at all three protein concentrations; data collected at 17,000 rpm and 25,000 rpm for B-RAF_L487R/E558K at 25 µM and 12.5 µM was analyzed. The term "global" refers to fits across all rotor speeds for a given concentration.

Figure 12:
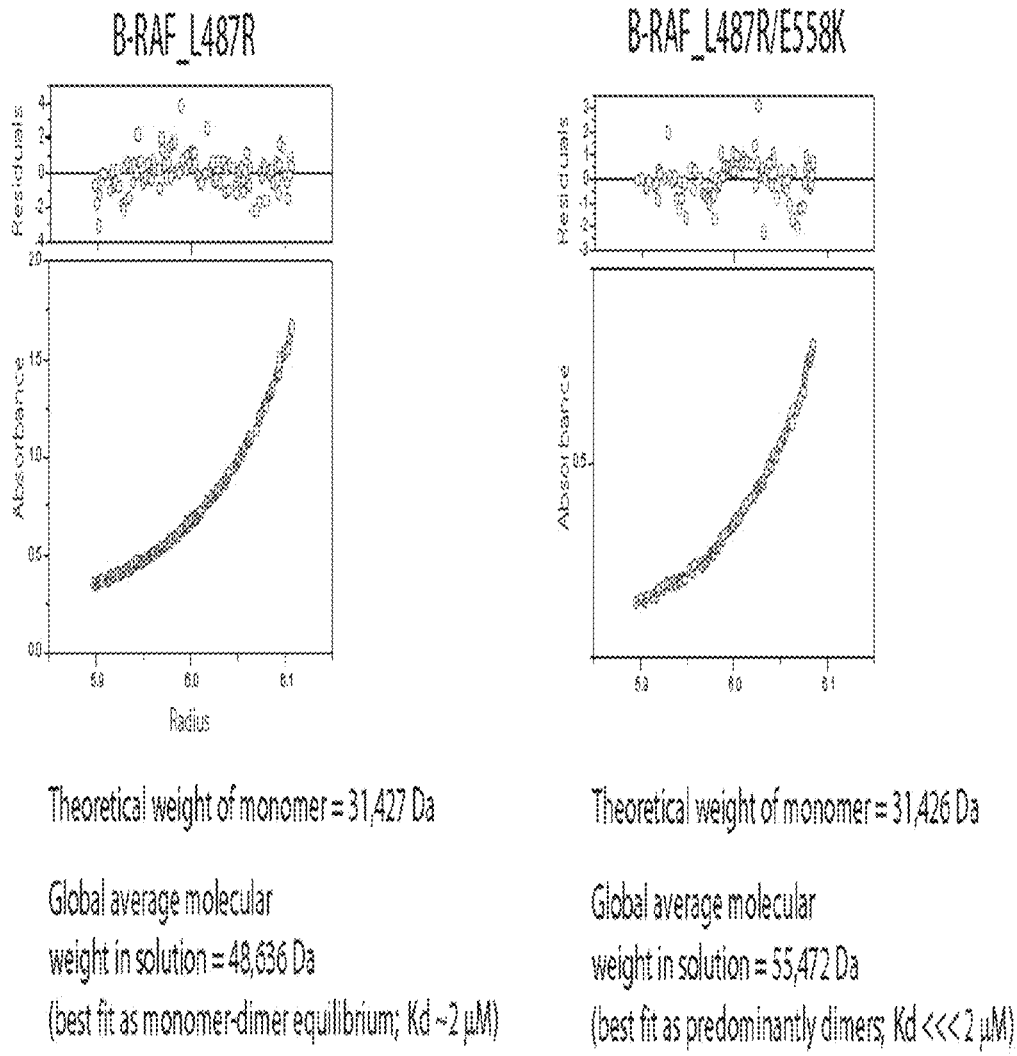
FIG. 12—Oncogenic B-RAF E558K mutation promotes kinase domain dimerization. Analytical ultracentrifugation analysis reveals that the oncogenic E558K mutation in B-RAF transitions the B-RAF_L487R dimer mutant from weak monomer-dimer equilibrium (left panel) to a dimer (right panel) in solution; residue numbering scheme corresponds to *Drosophila* RAF. The red line denotes a fitted curve to the self-association model. The residuals for the fit are shown in the upper panels.

The global self association fit yielded an average molecular weight (MW) of 57,978 Da for B-RAF_wt. The ratio of the observed average MW to the theoretical MW of the monomer is 1.9:1 suggesting that the sample contains mostly dimers. A single-species dimer model (shown by the red line; FIG. 3C) best fit the observed data (blue circles; FIG. 3C), indicated by the random distribution of the residuals—a measure of goodness of fit (the residual is the difference between the observed value and the predicted value). For B-RAF_R481H, the global self association fit yielded an average MW of 34,544 Da. The ratio of the observed average MW to the theoretical MW of the monomer is 1.1:1 suggesting that the sample contains mostly monomers. A single-species monomer model (red line; FIG. 3C) best fit the observed data (blue circles; FIG. 3C). For B-RAF_L487R, the global self association fit yielded an average MW of 48,636 Da. The ratio of the observed average MW to the theoretical MW of the monomer is 1.5:1 suggesting that the sample contains a mixture of monomers and dimers. Consistent with this, a monomer-dimer model (red line; FIG. 12) resulted in the best fit to the observed data (blue circles; FIG. 12) with a dissociation constant (Kd) of 2 M (Note: In order to reliably estimate Kd values from an AUC experiment, both species in a monomer-dimer equilibrium need to be sufficiently represented in solution; in our AUC analyses, we observed such a monomer-dimer equilibrium only for the B-RAF_L487R dimer mutant). For B-RAF_L487R/E558K, the global self association fit yielded an average MW of 55,472 Da. The ratio of the observed average MW to the theoretical MW of the monomer is 1.8:1 suggesting that the sample contains mostly dimers and the data (blue circles; FIG. 12) was best fit to a single-species dimer model (red line; FIG. 12).

6. RNA Preparation and Quantitative Real-Time PCR (qPCR)

S2 cells were treated with specific RNAi for four days and total RNA was extracted using Trizol reagent (Invitrogen) according to the manufacturer's instructions. qPCR analyses were performed as follows. A total of 2 µg of RNA was reverse transcribed using the High Capacity cDNA Archive Kit with random primers (Applied Biosystems, Foster City, Calif.) as described by the manufacturer. Primer and probe sets from Universal ProbeLibrary were used for quantitative real-time PCR. Primers were chosen so that the amplified regions did not overlap with the areas targeted by dsRNAs used for RNAi. PCR reactions for 384-well plate formats were performed using 2 µl of cDNA, 5 µl of the TaqMan fast Universal PCR Master Mix (Applied Biosystems, CA), 2 µM of each primer and 1 µM of the Universal TaqMan probe in a total volume of 10 µl. The ABI PRISM® 7900HT Sequence Detection System (Applied Biosystems) was used to detect the amplification level. The relative quantification of target genes was determined by using the CT method. Briefly, the Ct (threshold cycle) values of target genes were normalized to an endogenous control gene (Rp149) (CT=Ct target−Ct Rp149) and compared with a calibrator (wild type): CT=$Ct_{Sample}-Ct_{Calibrator}$. Relative expression (RQ) or fold change was calculated using the Sequence Detection System (SDS) 2.2.2 software (Applied Biosystems) and the formula RQ=$2^{-CT}$.

dsRNA Primers:

```
GFP amplicon
                                        (SEQ ID NO: 71)
top 5'-CGTAAACGGCCACAAGTTCAG (SEQ ID NO: 72)
bottom 5'-ACGAACTCCAGCAGGACCATG RAS amplicon
                                        (SEQ ID NO: 73)
top 5'-AATACAAACTGGTCGTCGTTG (SEQ ID NO: 74)
bottom 5'-AATCTACGATTCGGCTTGTTC
```

-continued

```
CNK amplicon
                                       (SEQ ID NO: 75)
top 5'-TTTGGACAGATCTATATGCAG (SEQ ID NO: 76)
bottom 5'-TCGGTTCAAAGGTCTCCAG HYP amplicon
                                       (SEQ ID NO: 77)
top 5'-CCGATTGTGTCACCCCTAAT (SEQ ID NO: 78)
bottom 5'-CCACTTGAGCACATCGCTAA CK2α amplicon
                                       (SEQ ID NO: 79)
top 5'-GACACTTCCTAGTGCGGCTCGCGTG (SEQ ID NO: 80)
bottom 5'-GTAATCATACATCTGGTAATCTACC 14-3-3ε amplicon
                                       (SEQ ID NO: 81)
top 5'-TGACTGAGCGCGAGAACAATG (SEQ ID NO: 82)
bottom 5'-TCTTCTGCCTGCATATCGGAC 14-3-3ζ amplicon
                                       (SEQ ID NO: 83)
top 5'-GACAGTCGATAAGGAAGAGCTGG (SEQ ID NO: 84)
bottom 5'-TCGTTCAGTGTGTCCAGCTC
```

7. Screening Assays

Two independent assays were developed to monitor RAF dimerization. The first is a FRET (fluorescence resonance energy transfer) assay. It is based on the observation that bacterially-expressed human B-RAF kinase domain form dimers in solution.

The second assay exploits the BRET (bioluminescence resonance energy transfer) technology to assess for RAF homodimerization or RAF-KSR heterodimerization using a cell-based system.

A. FRET Assay

A single cysteine residue is engineered at the N-terminus of the wild-type or mutant B-RAF kinase domain for cross-linking fluorescent probes. Following bacterial expression and purification, independent batch of proteins are labeled either with Alexa 555 (donor) or Alexa 647 (acceptor). Labeled proteins are re-purified and then combined in equimolar ratios. FRET detection is carried out using a Luminescence Spectrometer. Various controls are conducted in parallel. For instance, no FRET signal is detected when labeled proteins are tested alone. Similarly, no FRET signal or a significantly reduced one is detected when dimer interface mutants (e.g. R481H-like) are tested in combination with wild-type B-RAF.

B. BRET assay

The BRET assay can use either BRET1 or BRET2 as a means of measuring BRET signals. We used BRET2 donor (*renilla* luciferase variant II or rlucII) and acceptor (GFP10) fusions rather than BRET1 fusions (rluc and YFP) as well as the addition of a CAAX-box to target RAF to the plasma membrane, since the BRET2 system is more sensitive and has a higher signal to noise ratio (Kocan, See et al., 2008, *J Biomol Screen*. 13(9): 888-98), to independently fuse RAF and KSR kinase domains at either their N- or C-terminus. The addition of the CAAX-box is frequently used to generate BRAF gain of function alleles and is reported in the literature (Leevers, Paterson et al., 1994, *Nature*. 369(6479): 411-4). We focused on the human BRAF kinase domain (BRAF-KD) expressed from the pCDNA3.1 plasmid backbone (Invitrogen) in a HEK293 transfection setup.

The assay included co-transfection of rlucII fused to the N-terminus of the human BRAF-KD (referred to below as the donor) and of N-terminally GFP 10-tagged hBRAF-KD (referred to below as the acceptor) both targeted to the plasma membrane with a CAAX-box. Transfections were performed in HEK293T cells with PEI as a transfection reagent in a 6-well format with varying molar ratios of pcDNA3.1 donor:acceptor constructs (0:1, 0.25:1, 0.5:1, 1:1, 2:1, 5:1, 10:1 and 20:1). 48 hours post transfection, the cells were washed and resuspended in tyrode buffer and transferred to opaque microtiter plates. GFP10 raw signal was read on a FlexStation 3 plate reader (Molecular Devices) and BRET signals were read using a Mithras LB 940 plate reader following the addition of DeepBlue C (DBC) at a concentration of 10 μM. The data was then analysed using the GraphPad Prism software package.

The assay was highly reproducible and the BRET ratio obtained for the rlucII-BRAF-KD-CAAX versus GFP10-BRAF-KD-CAAX pair at saturating concentration of the acceptor construct was consistently between 4.7 and 4.9.

We also generated the dimer interface mutation R481H of the BRAF-KD and measured its impact on the affinity of the BRAF-BRAF interaction. The BRAF wt-wt pair yielded a significantly higher BRET ratio than when the R481H mutant was introduced as the donor or acceptor construct (FIG. 15). This reduction was reproducible and significant in terms of both the $BRET_{max}$ and $BRET_{50}$ ratios (FIG. 15). This was indicative of a significant decrease in BRAF-BRAF affinity when the dimer interface is perturbed.

Altogether, the BRET assay is specific for the BRAF-KD vs BRAF-KD interaction and is highly sensitive to the genetic alteration of the now well-characterized dimer interface (Hatzivassiliou, Song et al. 2010, *Nature* March 18; 464(7287): 431-5; Poulikakos, Zhang et al. 2010, *Nature* March 18; 464(7287): 427-30; Rajakulendran, Sahmi et al. 2009, *Nature* September 24; 461(7263): 542-5).

All BRET assays were developed with the human B-RAF (hBRAF), C-RAF (hCRAF), KSR1 (hKSR1) and MEK1 (hMEK1) isoforms (see FIGS. 16 through 27 and SEQ ID NO's: 19 through 70). In FIGS. 16 through 27, CDS stands for coding sequences. And KD stands for kinase domain.

The mutagenised residues are labeled according to their position in the *Drosophila* orthologous protein sequence. Thus, the R481H mutation of *Drosophila* RAF corresponds to the R509H mutation of human B-RAF, and the C922Y mutation of *Drosophila* KSR corresponds to the C722Y mutation of human KSR1.

Results and Discussion

In *Drosophila*, RAF activation is regulated by a core complex that notably includes the proteins RAS, CNK, HYP and KSR amongst others (Claperon, A. & Therrien, M. KSR and CNK: two scaffolds regulating RAS-mediated RAF activation, Oncogene, 26, 3143-58 (2007)). Of these proteins, the function of KSR (Kinase Suppressor of Ras) in RAF activation remains controversial. KSR contains a kinase domain of closest sequence similarity to RAF (Manning, G., Whyte, D. B., Martinez, R., Hunter, T. & Sudarsanam, S., The protein kinase complement of the human genome, Science, 298, 1912-34 (2002)) and was initially thought to drive RAF activation by virtue of its kinase activity. However, subsequent studies have been inconclusive in demonstrating this point and thus relegated KSR as a pseudo-kinase (Boudeau, J., Miranda-Saavedra, D., Barton, G. J. & Alessi, D. R., Emerging roles of pseudokinases, Trends Cell Biol, 16, 443-52 (2006)). Because of its capacity to bring MEK to RAF, the function of KSR is currently considered to be that of an organizing centre (or scaffold) in the ERK pathway (Kolch, W., Coordinating ERK/MAPK signalling through scaffolds and inhibitors, Nat Rev Mol Cell Biol, 6, 827-37 (2005)).

We previously showed in Drosophila S2 cells that co-overexpression of KSR with RAF and MEK stimulated RAF-dependent MEK phosphorylation (Douziech, M., Sahmi, M., Laberge, G. & Therrien, M., A KSR/CNK complex mediated by HYP, a novel SAM domain-containing protein, regulates RAS-dependent RAF activation in Drosophila, Genes Dev, 20, 807-19 (2006)). If KSR was solely acting as a scaffold, we reasoned that overexpression of KSR without co-overexpression of its scaffold partners would perturb the optimal stoichiometry of KSR containing complexes with the net effect of decreasing RAF activation. Since we observed increased RAF activation, this suggested that KSR might possess an inherent RAF activating capacity that becomes apparent upon overexpression. To investigate whether KSR can stimulate increasing RAF activation in a concentration dependent manner (as would be the case if KSR possessed an intrinsic RAF activating capacity), we titrated in increasing amounts of KSR in S2 cells and monitored the effect by assessing RAF-dependent MEK phosphorylation (Roy, F., Laberge, G., Douziech, M., Ferland-McCollough, D. & Therrien, M., KSR is a scaffold required for activation of the ERK/MAPK module, Genes Dev, 16, 427-38 (2002)). As shown in FIG. 1A, increasing levels of KSR correspondingly increased MEK phosphorylation. Surprisingly, this KSR-dependent RAF activation was unperturbed by RNAi-mediated knockdown of RAS (FIG. 1A; see FIG. 13A for a demonstration of the activity and specificity of the RAS dsRNA). Moreover, co-overexpression of a constitutively active RAS ($RAS^{V12}$) under these conditions did not considerably augment MEK phosphorylation, suggesting that KSR can drive RAF activation independently of RAS activity when overexpressed in S2 cells (FIG. 1A). These results suggest a role for KSR in RAF activation beyond a scaffold-only function.

To more rigorously rule out a scaffolding function as the origin of the observed stimulatory effect of overexpressed KSR on RAF, we used RNAi to knockdown a subset of known scaffold partners of KSR. Interestingly, in this context RAF activation was also unperturbed by RNAi-mediated knockdown of CNK or HYP (also known as AVE), which are normally required under physiological conditions (Douziech, M., Sahmi, M., Laberge, G. & Therrien, M., A KSR/CNK complex mediated by HYP, a novel SAM domain-containing protein, regulates RAS-dependent RAF activation in Drosophila, Genes Dev, 20, 807-19 (2006)), Douziech, M. et al., Bimodal regulation of RAF by CNK in Drosophila, Embo J, 22, 5068-78 (2003)) and Roignant, J. Y., Hamel, S., Janody, F. & Treisman, J. E., The novel SAM domain protein Aveugle is required for Raf activation in the Drosophila EGF receptor signaling pathway, Genes Dev, 20, 795-806 (2006) (FIG. 1B). Studies with mammalian cells recently suggested that CK2 (bound to KSR1) phosphorylates and activates B-RAF/C-RAF (Ritt, D. A. et al., CK2 is a component of the KSR1 scaffold complex that contributes to Raf kinase activation, Curr Biol, 17, 179-84 (2007)). We found that KSR not only potently stimulated RAF activation in the presence of RNAi-mediated knockdown of CK2 (FIG. 1C), but that mutating the proposed CK2 binding site on KSR or the sites of CK2-mediated phosphorylation on RAF (Rift, D. A. et al., CK2 Is a component of the KSR1 scaffold complex that contributes to Raf kinase activation, Curr Biol, 17, 179-84 (2007)) had no impact on the ability of KSR to drive RAF activation under our overexpression conditions (FIG. 1C). Taken together, these results suggest that the overexpression of KSR in S2 cells unmasks an inherent activation potential on RAF beyond its well established role as a scaffold.

We previously showed that the capacity of KSR to bind MEK was required for the ability of RAF to phosphorylate MEK (Roy, F., Laberge, G., Douziech, M., Ferland-McCollough, D. & Therrien, M., KSR is a scaffold required for activation of the ERK/MAPK module, Genes Dev, 16, 427-38 (2002)). This result supported a scaffolding role for KSR in RAF activation. More recently, we identified a mutation in KSR (R732H) within its kinase domain that completely abolished its RAF activating capacity yet fully retained its ability to bind MEK and RAF Douziech, M., Sahmi, M., Laberge, G. & Therrien, M, A KSR/CNK complex mediated by HYP, a novel SAM domain-containing protein, regulates RAS-dependent RAF activation in Drosophila, Genes Dev, 20, 807-19 (2006) (FIG. 2).

This mutant provided a starting point for unraveling the mechanism by which KSR directly activates the catalytic function of RAF.

Figure 4:
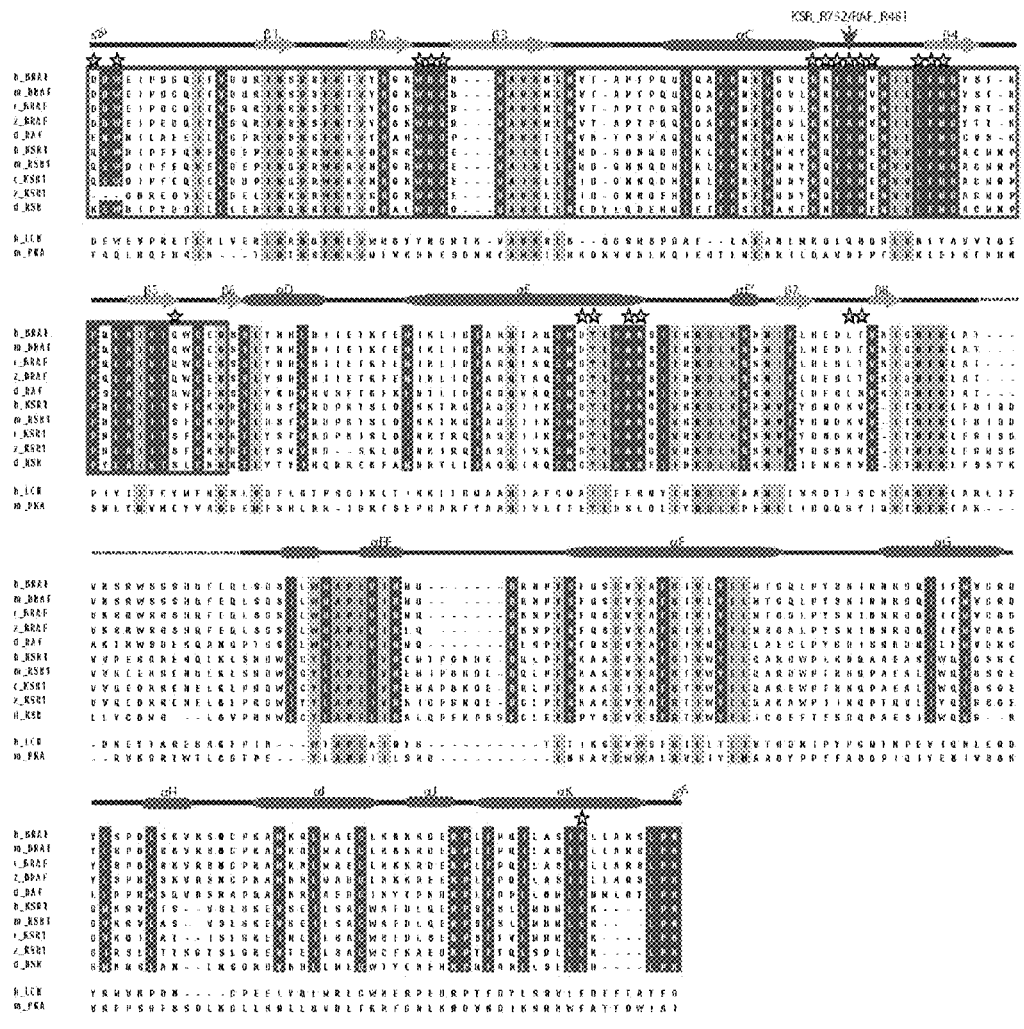
FIG. 4—Side-to-side dimer interface residues are conserved in all KSR and RAF proteins. Sequence alignment of the kinase domains of KSR and RAF from divergent organisms highlighting conserved residues. For comparison, the sequence of the kinase domains of LCK and PKA are co-aligned demonstrating that the side-to-side dimer contact residues are unique to the KSR/RAF family. The sequence of the kinase domain N-lobe is boxed in red and the secondary structural elements are indicated above the sequence. Aligned sequences correspond to those from Drosophila (d), human (h), mouse (m), zebrafish (z), and chicken (c). Only the B-RAF sequence is shown for species where multiple RAF isoforms exist. Figure discloses SEQ ID NOS 86-97, respectively, in order of appearance.
Figure 6A:
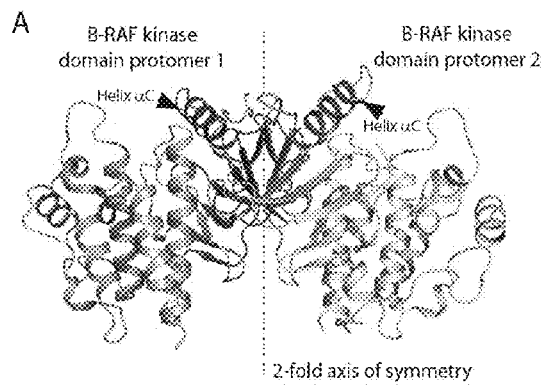
FIG. 6A to C—The kinase domain of RAF adopts a side-to-side dimeric configuration in the crystal structure.
Figure 6B:
Figure 6C:
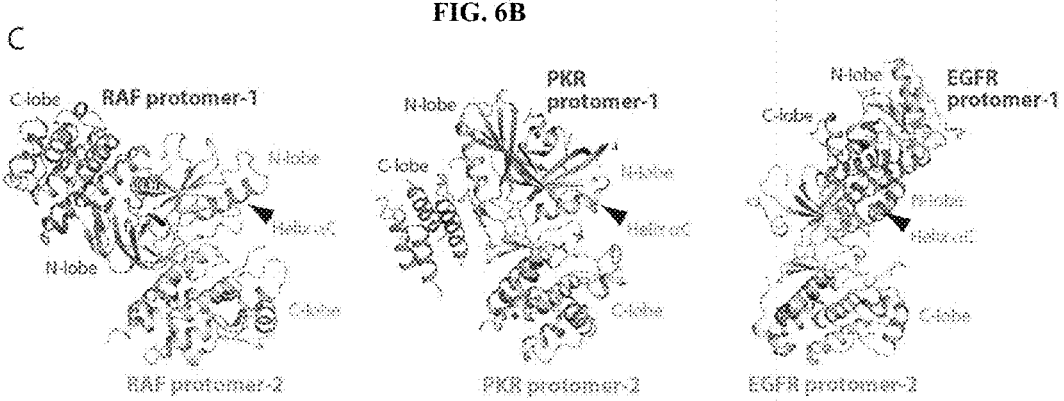

Since the kinase domain of KSR is most similar to that of RAF (Manning, G., Whyte, D. B., Martinez, R., Hunter, T. & Sudarsanam, S., The protein kinase complement of the human genome, Science, 298, 1912-34 (2002), we hypothesized that the previously determined crystal structure of the kinase domain of human B-RAF (the human orthologue of Drosophila RAF) might provide a good model to discern the mechanism of action of the KSR_R732H mutation. Indeed, Arg732 is not only invariant across all KSR proteins, it is invariant across the larger RAF/KSR family (but not in other closely related kinases; FIG. 4). Intriguingly, while the structure of the kinase domain of B-RAF was reported as a monomer (Wan, P. T. et al., Mechanism of activation of the RAF-ERK signaling pathway by oncogenic mutations of B-RAF, Cell, 116, 855-67 (2004)), the asymmetric unit of the crystal in fact contains two RAF kinase domains that interact in a unique side-to-side fashion involving the N-lobe of their kinase domains (FIG. 6A). This mode of dimerization, which was not appreciated to date, was observed in a total of five subsequent RAF structure analyses (Wan, P. T. et al., Mechanism of activation of the RAF-ERK signaling pathway by oncogenic mutations of B-RAF, Cell, 116, 855-67 (2004)), (Hansen, J. D. et al., Potent and selective pyrazole-based inhibitors of B-Raf kinase, Bioorg Med Chem Lett, 18, 4692-5 (2008)) (in distinct crystal lattices), suggesting that the mode of dimerization/oligomerization is functionally relevant rather than an artifact of crystal packing (FIG. 6B). Side-to-side dimerization of the RAF kinase domain buries a large surface area (~1280 Å$^2$) and provocatively involves helix αC, a key structural element whose conformation serves a regulatory function in numerous protein kinases (Huse, M. & Kuriyan, J. The conformational plasticity of protein kinases. Cell 109, 275-82 (2002)) (FIG. 6A). Most notably, a specific mode of dimerization involving helix αC underlies an allosteric mechanism for kinase activation for both PKR (Dar, A. C., Dever, T. E. & Sicheri, F. Higher-order substrate recognition of eIF2alpha by the RNA-dependent protein kinase PKR. Cell 122, 887-900 (2005)) and EGFR (Zhang, X., Gureasko, J., Shen, K., Cole, P. A. & Kuriyan, J. An allosteric mechanism for activation of the kinase domain of epidermal growth factor receptor. Cell 125, 1137-49 (2006)) kinase domains (FIG. 6C). As the structure of the RAF kinase domain adopts a productive conformation in the dimeric crystal configuration, we reasoned that side-to-side dimerization itself might directly modulate the attainment of an active kinase conformation of RAF.

Figure 3A:
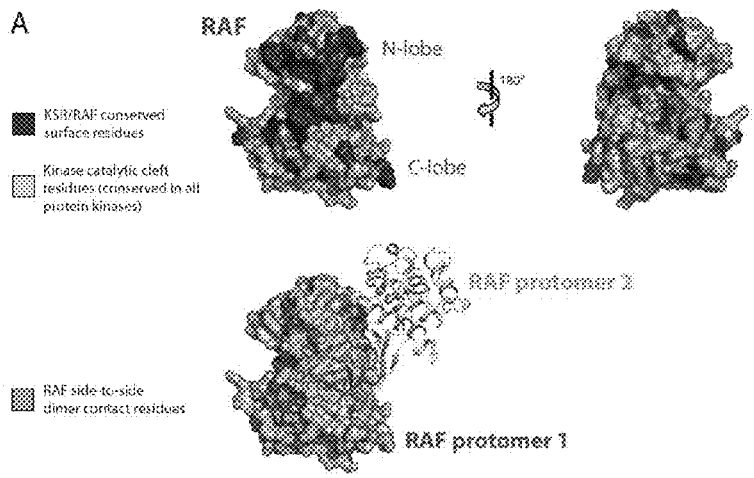
FIG. 3A to C—A side-to-side dimer configuration of RAF underlies an allosteric mode of regulation.
Figure 3B:
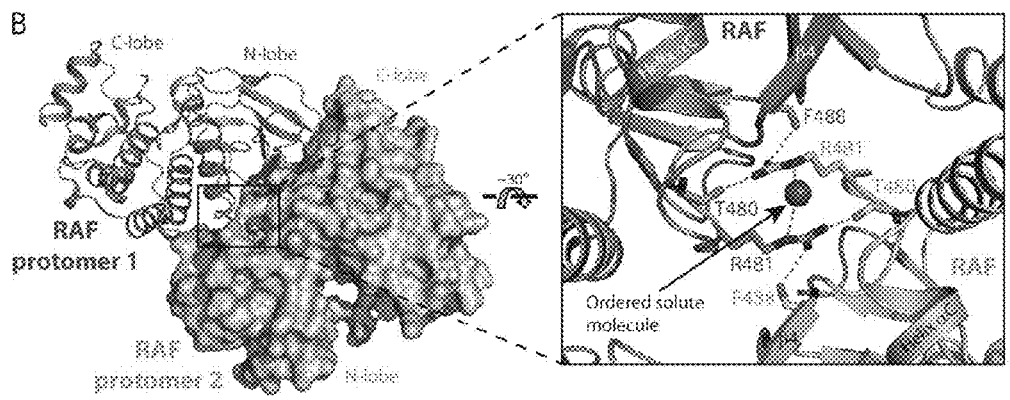
Figure 3C:
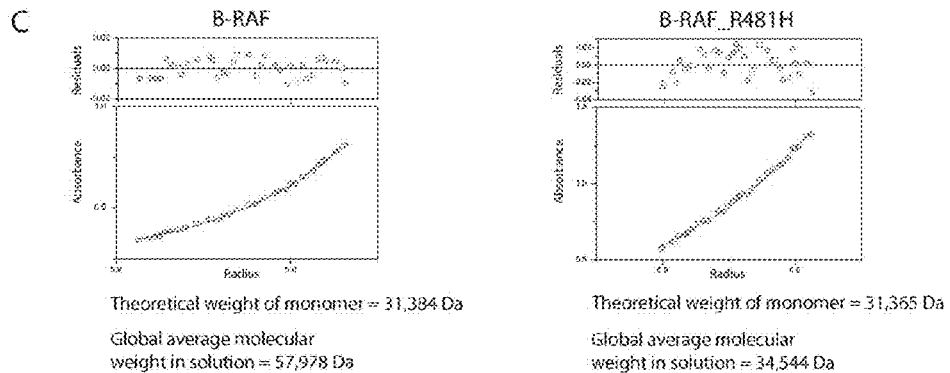

Projection of KSR/RAF conserved residues onto the RAF crystal structure revealed that nearly the entire side-to-side dimer contact surface of RAF, but no other surfaces, are conserved across the larger KSR/RAF family (FIG. 3A; FIG. 4). This suggested that KSR might form an analogous dimer structure. Moreover, the position of Arg481 (the equivalent of Arg732 in KSR; FIG. 4) at the center of the side-to-side dimer interface of the B-RAF crystal structure (FIG. 3B) hinted at the basis by which the mutation of Arg732 in KSR might exert a functional effect by perturbing dimerization (for simplicity, we used the *Drosophila* RAF numbering scheme for discussion of human B-RAF positions; see the Table below for list of residue equivalence between B-RAF and *Drosophila* RAF).

| *Drosophila* RAF | Human B-RAF |
|---|---|
| Trp422 | Trp450 |
| Trp448 | Trp476 |
| His449 | His477 |
| Gly450 | Gly478 |
| Lys478 | Arg506 |
| Lys479 | Lys507 |
| Thr480 | Thr508 |
| Arg481 | Arg509 |
| His482 | His510 |
| Cys483 | Val511 |
| Leu487 | Leu515 |
| Phe488 | Phe516 |
| Met489 | Met517 |
| Gln502 | Gln530 |
| Asp537 | Asp565 |
| Tyr538 | Tyr566 |
| Ala541 | Ala569 |
| Lys542 | Lys570 |
| Glu558 | Glu586 |
| Leu560 | Leu588 |
| Ser561 | Thr589 |
| Glu687 | Glu715 |

In order to investigate the potential of the RAF kinase domain to form dimers in solution, we performed analytical ultracentrifugation experiments (FIG. 3C). Equilibrium sedimentation analysis confirmed that RAF can form dimers under the conditions tested (i.e., micromolar concentrations). Consistent with the mode of dimerization seen in the crystal structure, mutation of Arg481 in B-RAF converted it to a predominant monomer in solution. This result shows that the side-to-side dimer configuration of RAF visualized in the crystal environments is also sampled in solution. Based on these findings, we reasoned that the R732H mutation in KSR most likely perturbs KSR's ability to form an analogous side-to-side homodimer or to form a side-to-side heterodimer with RAF. This in turn could explain the mechanism by which the KSR_R732H mutation abolishes RAF activation.

Figure 5A:
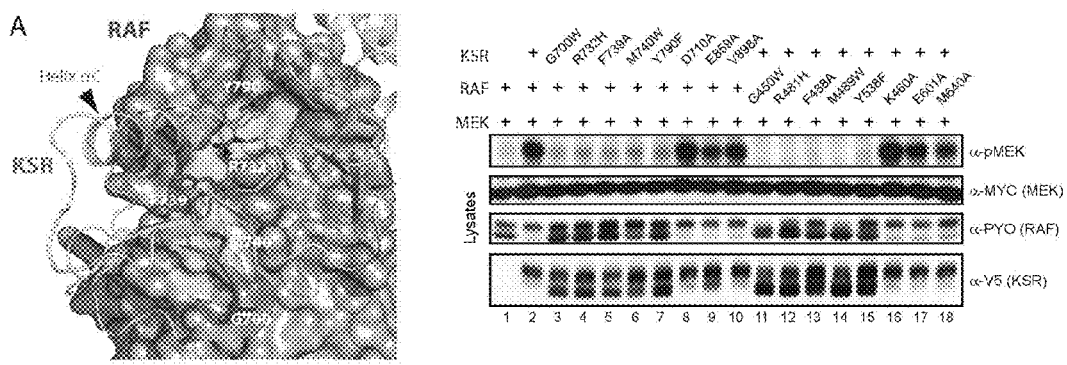
FIG. 5A to C—Perturbing the side-to-side dimer interface on RAF and KSR impairs RAF activation.

If KSR mediates RAF activation by a mechanism involving the formation of a specific side-to-side homodimer with itself (i.e. KSR/KSR side-to-side homodimer) or a heterodimer with the kinase domain of RAF (i.e. KSR/RAF side-to-side heterodimer), then mutation of other dimer interface residues on KSR in close vicinity to Arg732 might also impair RAF activation. Using our minimal KSR/RAF/MEK co-overexpression activation assay, we found this to be the case. Specifically, individual mutation of four additional residues (G700W, F739A, M740W and Y790F) on KSR severely impeded its ability to induce RAF activation (FIG. 5A). If KSR mediates RAF activation by forming a specific side-to-side heterodimer with the kinase domain of RAF, then mutations of the corresponding positions (residues) on RAF should also impair RAF activation. As shown in FIG. 5A, we also found this to be the case. In contrast, control mutations remote from the side-to-side dimer interface on the kinase domains of both KSR and RAF showed no significant effect on RAF activation (FIG. 5A). We note that none of the dimer interface mutations in KSR detectably affected the KSR/MEK interaction, indicating that the mutations did not simply destroy protein fold (data not shown). These results confirm that the integrity of the side-to-side dimer interface on KSR and on RAF is essential for RAF activation.

While our results above are consistent with the possibility that KSR and RAF heterodimerize through their kinase domains, it is equally possible that KSR/KSR side-to-side homodimers might instead contribute to RAF activation. To demonstrate that the formation of side-to-side kinase domain heterodimers by KSR and RAF per se leads to RAF activation, we employed the FRB/FKBP fusion protein system to inducibly promote KSR/RAF side-to-side heterodimer formation by the addition of rapamycin in vivo (Muthuswamy, S. K., Gilman, M. & Brugge, J. S. Controlled dimerization of ErbB receptors provides evidence for differential signaling by homo- and heterodimers, Mol Cell Biol, 19, 6845-57 (1999)).

Figure 5B:
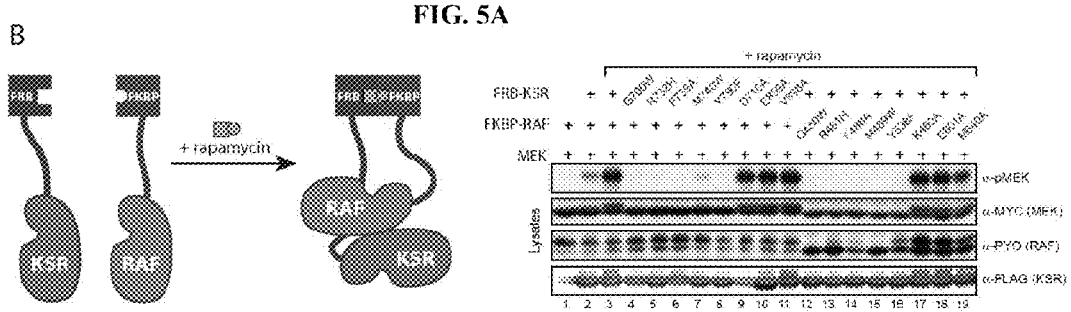
Figure 8A:
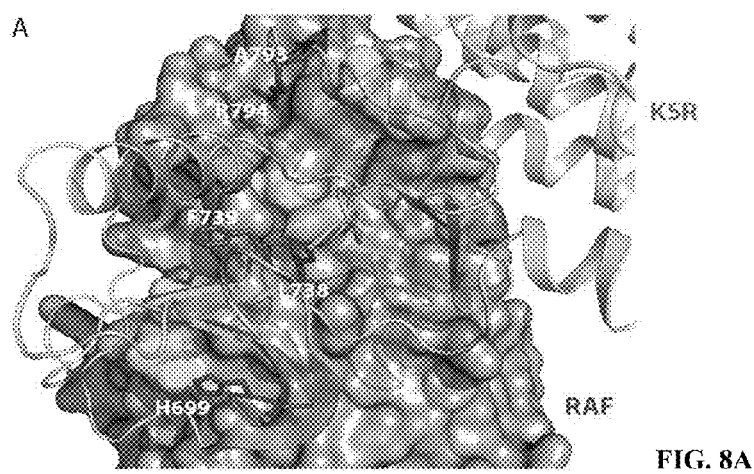
FIG. 8A to C—Perturbing the side-to-side dimer interface on RAF and KSR impairs RAF activation.
Figure 8C:
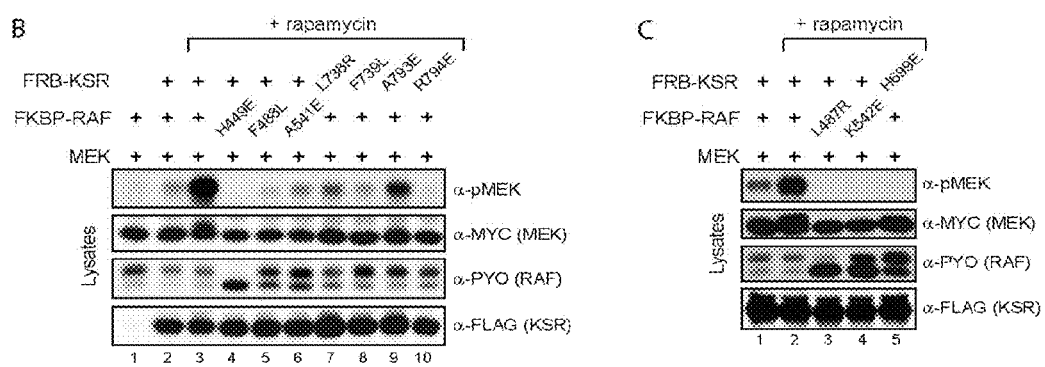
Figure 8B:
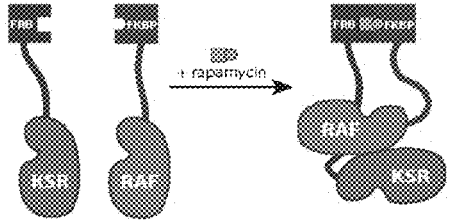

Towards this end, we fused a region encompassing the minimal kinase domains of KSR and RAF to the FRB and FKBP fragments, respectively (Roy, F., Laberge, G., Douziech, M., Ferland-McCollough, D. & Therrien, M., KSR is a scaffold required for activation of the ERK/MAPK module, Genes Dev, 16, 427-38 (2002)) (See FIG. 5B for schematic). The use of the FRB/FKBP fusion in conjunction with a myristoylation signal on the FKBP fusion construct (to localize it to the membrane) allowed us to tightly modulate heterodimerization of the kinase domains in a rapamycin-dependent manner (Roy, F., Laberge, G., Douziech, M., Ferland-McCollough, D. & Therrien, M., KSR is a scaffold required for activation of the ERK/MAPK module, Genes Dev, 16, 427-38 (2002)). In this setup, we observed that promoting the KSR/RAF heterodimer by addition of rapamycin was indeed sufficient to potently activate RAF as evidenced by the elevated levels of phosphorylated MEK (FIG. 5B). RAF activation was selectively perturbed by ten specific mutations at the side-to-side dimer interface on both KSR (H699E, G700W, R732H, L738R, F739A, F739L, M740W, Y790F, A793E and R794E) and on RAF (H449E, G450W, R481H, L487R, F488A, F488L, M489W, Y538F, A541E and K542E), but not by control mutations outside the side-to-side dimer interface of KSR or RAF (FIG. 5B; FIG. 8A to C). Taken together, these results indicate that formation of the side-to-side heterodimer between KSR and RAF kinase domains is both sufficient and necessary for RAF activation under the conditions tested.

Figure 5C:
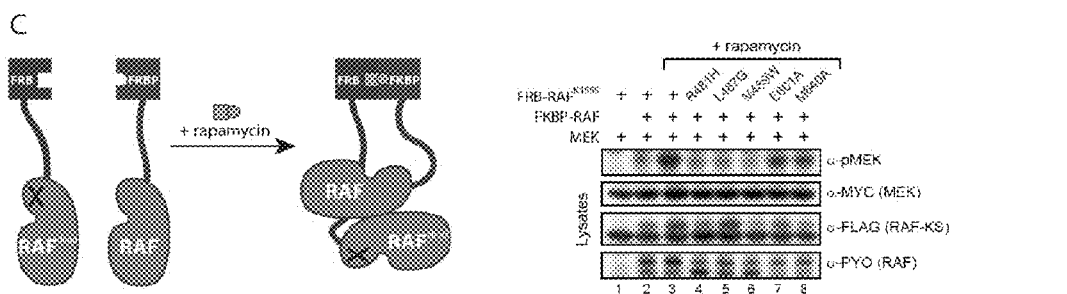

As both RAF and KSR likely form identical side-to-side dimers, by virtue of having near identical dimerization surfaces (FIG. 3A), it is conceivable that both KSR/RAF heterodimers and RAF/RAF homodimers might equally promote RAF activation, assuming RAF activation and downstream signaling is solely dependent on forming the kinase domain side-to-side dimer. To investigate whether the RAF/RAF homodimers can also lead to RAF activation, we used the FRB/FKBP/rapamycin system to drive side-to-side homodimer formation of RAF kinase domains in vivo (see FIG. 5C for schematic). To ensure our interpretation of side-to-side dimer formation induced activation is not confounded by trans autophosphorylation activity within the RAF/RAF homodimer, we introduced a mutation (K455S) in the FRB-RAF fusion to catalytically impair its kinase activity (i.e. to effectively mimic the kinase dead state of KSR). As shown in FIG. 5C, rapamycin induced formation of RAF/RAF homodimers can indeed drive RAF activation in a manner dependent on the ability to form the side-to-side dimers (FIG. 5C).

Although RAF/RAF homodimers are competent for activation, the level of activation is not as robust as that resulting from KSR/RAF heterodimers (based on quantification of induced MEK phosphorylation levels in the presence and absence of rapamycin; not shown). If the side-to-side dimer surfaces are in fact functionally equivalent on both KSR and RAF, this observation suggests that the KSR kinase domain may have a second function that is not shared with RAF. Based on the fact that KSR can stably bind MEK while RAF cannot (Roy, F., Laberge, G., Douziech, M., Ferland-McCollough, D. & Therrien, M. KSR is a scaffold required for activation of the ERK/MAPK module. Genes Dev 16, 427-38 (2002)), we reasoned that this may be the root of the difference. Since the side-to-side dimerization surface is comprised mainly by the N-lobe of KSR and RAF kinase domains, and MEK binding function is critically dependent on the C-lobe of KSR (Roy, F., Laberge, G., Douziech, M., Ferland-McCollough, D. & Therrien, M., KSR is a scaffold required for activation of the ERK/MAPK module, Genes Dev, 16, 427-38 (2002)), then a RAF N-lobe-KSR C-lobe chimera might possess both essential functions of the KSR kinase domain. If true, one would predict that substitution of the N-lobe of RAF into KSR, but not the whole kinase domain of RAF into KSR, would lead to the maintenance of KSR's ability to promote RAF mediated phosphorylation of MEK. This indeed proved to be the case. As shown in FIG. 7, overexpression of a form of KSR with a full kinase domain swap with RAF (FIG. 7A, Chimera-A) poorly activated RAF, while overexpression of a form with just an N-lobe swap (FIG. 7A, Chimera-B) was as potent as wild type KSR in promoting MEK phosphorylation by RAF (FIG. 7B). Confirming that MEK binding is indeed constrained to the C-lobe of KSR, Chimera-B but not Chimera-A bound to MEK as assessed by co-immunoprecipitation (FIG. 7B). Taken together, these results highlight two distinct functions for the kinase domain of KSR in RAF signaling. Firstly, the kinase domain of KSR functions as a scaffold whereby it binds to MEK and recruits it to RAF (i.e. KSR mediates RAF substrate targeting). Secondly, the kinase domain of KSR forms a side-to-side heterodimer with the kinase domain of RAF that underlies an allosteric mechanism for RAF catalytic activation.

Figure 10:
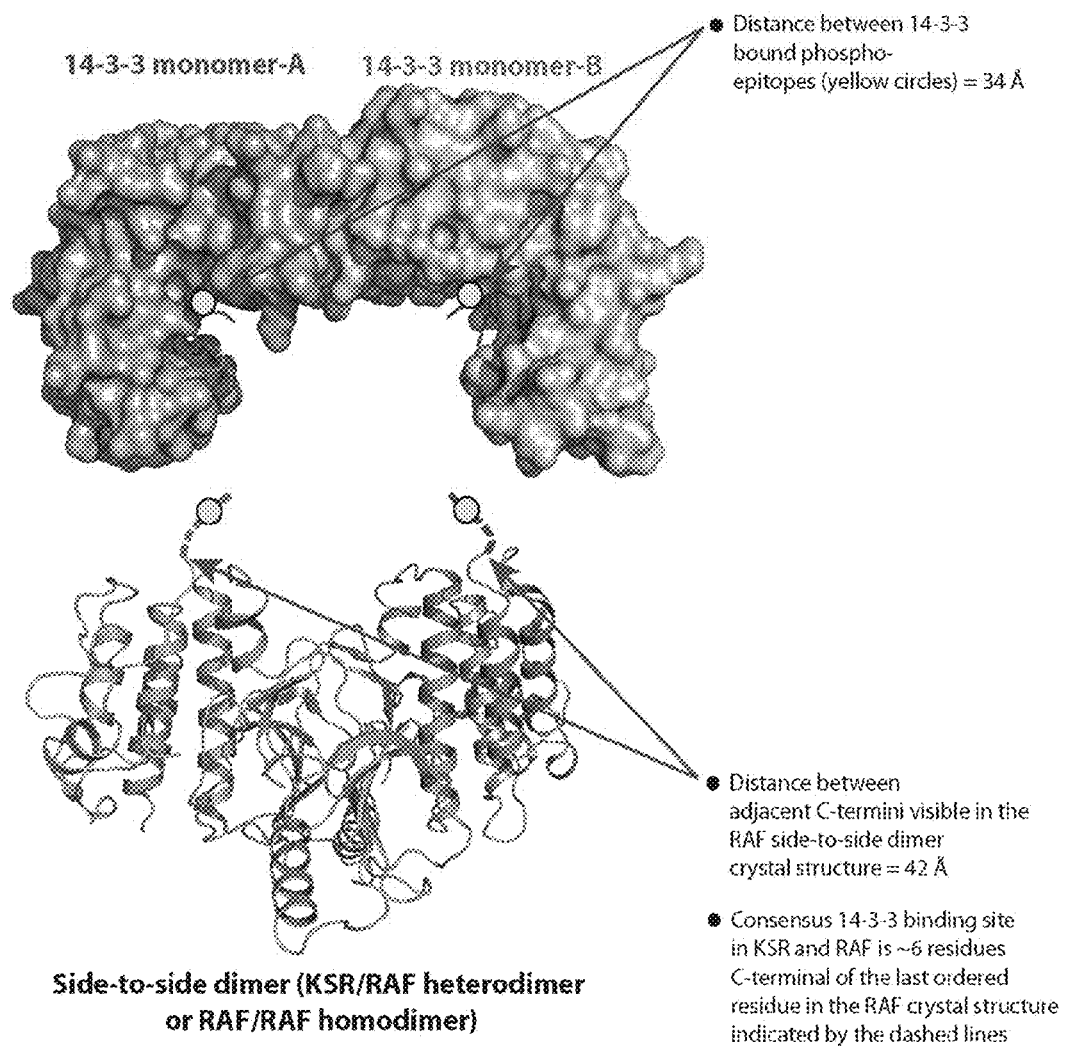
FIG. 10—Binding of 14-3-3 to KSR and RAF may promote the formation of hetero- and/or homotypic dimers by the kinase domain. Structural model showing that the geometry of the KSR/RAF (or RAF/RAF) side-to-side dimer is compatible with the spatial requirements for binding to dimeric 14-3-3 proteins. Surface representation of 14-3-3 bound to phospho-peptides is based on PDB ID 1YWT (Wilker, E. W., Grant, R. A., Artim, S. C. & Yaffe, M. B., A structural basis for 14-3-3sigma functional specificity, J Biol Chem, 280, 18891-8 (2005)).

Recent studies with mammalian cells, where multiple RAF isoforms exist, have found that RAF activation can also occur upon the physical juxtaposition of two isoforms of RAF mediated by 14-3-3 proteins (Weber, C. K., Slupsky, J. R., Kalmes, H. A. & Rapp, U. R., Active Ras induces heterodimerization of cRaf and Braf., Cancer Res, 61, 3595-8 (2001)), (Rushworth, L. K., Hindley, A. D., O'Neill, E. & Kolch, W., Regulation and role of Raf-1/B-Raf heterodimerization, Mol Cell Biol, 26, 2262-72 (2006)). Intriguingly, this activation route is independent of a phospho-transfer mechanism as reflected by the fact that in such RAF/RAF heterodimers, a kinase-dead isoform of RAF can activate a wild-type isoform of RAF (Chen, C., Lewis, R. E. & White, M. A., IMP modulates KSR1-dependent multivalent complex formation to specify ERK1/2 pathway activa-tion and response thresholds, J Biol Chem, 283, 12789-96 (2008)). This behaviour is highly reminiscent of how KSR activates RAF. We reasoned that 14-3-3 proteins, which are intrinsically dimeric, act to promote the specific side-to-side dimer conformation we see in the RAF crystal structure in a manner analogous to our forced FRB-RAF/FKBP-RAF system (FIG. 5C). Consistent with this possibility, our modeling studies showed that the binding of dimeric 14-3-3 proteins concurrently to the C-terminal extension of two RAF kinase domains is fully compatible with the adoption of a side-to-side dimer configuration (FIG. 10).

Figures 9A, 9B:
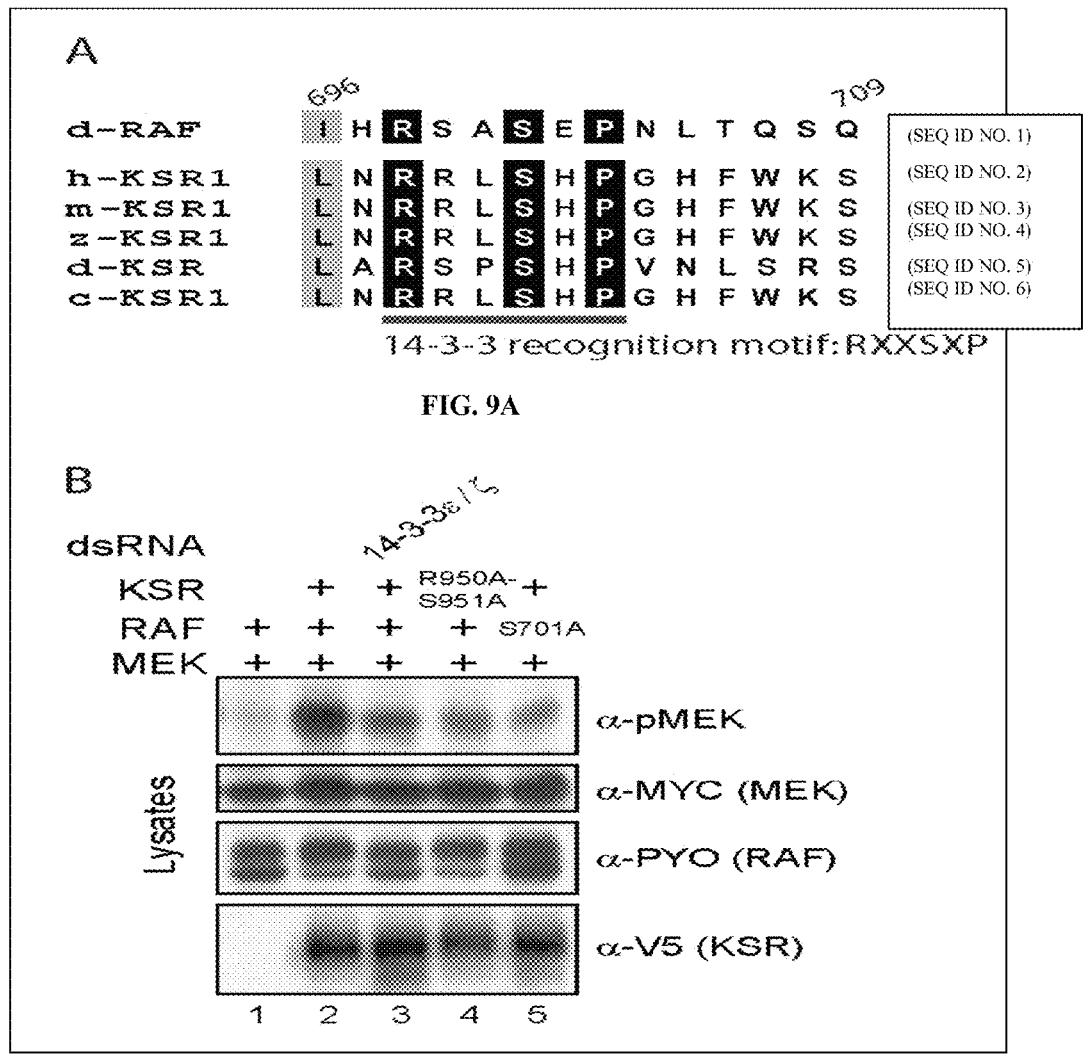
FIGS. 9A and B—KSR contains a putative 14-3-3 binding site C-terminal to its kinase domain.
FIG. 9B) S2 cell overexpression assay for RAF activation showing the effects of RNAi-mediated knockdown of 14-3-3 isoforms or mutation of putative 14-3-3 binding sites in KSR (R950A/S951A) and RAF (S701A). The effect of RNAi on endogenous 14-3-3 protein levels is shown in FIG. 13.

Interestingly, the 14-3-3 consensus binding site in human RAF is conserved in both RAF and KSR molecules in fly and in other organisms (FIG. 9A), suggesting that 14-3-3 could also act to promote RAF homodimers and more potent KSR/RAF heterodimers in flies. Demonstrating that 14-3-3 is indeed relevant for RAF activation in flies, we found that depletion of endogenous 14-3-3 proteins perturbed KSR-dependent RAF activation (FIG. 9B). Consistent with the notion that 14-3-3 mediates dimerization of KSR with RAF, mutation of the consensus 14-3-3 site in both KSR and RAF impaired RAF activation (FIG. 9B). These results suggest that 14-3-3 proteins might act to promote specific KSR/RAF and RAF/RAF side-to-side kinase domain dimers.

Together, our study indicates that dimerization of the RAF kinase domain with KSR or with other RAF molecules is central to its activation mechanism. We posit that other regulatory events that impinge on RAF activation may also act by modulating dimerization. In this regard, the large group of scaffolding proteins that act together with RAF and KSR, such as 14-3-3 proteins, may serve to spatially and temporally regulate the formation of side-to-side dimers (Douziech, M., Sahmi, M., Laberge, G. & Therrien, M. A, KSR/CNK complex mediated by HYP, a novel SAM domain-containing protein, regulates RAS-dependent RAF activation in *Drosophila, Genes Dev*, 20, 807-19 (2006)), Garnett, M. J., Rana, S., Paterson, H., Barford, D. & Marais, R., Wild-type and mutant B-RAF activate C-RAF through distinct mechanisms involving heterodimerization, Mol Cell, 20, 963-9 (2005)), Rushworth, L. K., Hindley, A. D., O'Neill, E. & Kolch, W., Regulation and role of Raf-1/B-Raf heterodimerization, Mol Cell Biol, 26, 2262-72 (2006)), Chen, C., Lewis, R. E. & White, M. A., IMP modulates KSR1-dependent multivalent complex formation to specify ERK1/2 pathway activation and response thresholds, J Biol Chem, 283, 12789-96 (2008)). Moreover, the fact that the formation of B-/C-RAF heterodimers appears to depend on RAS activity (Garnett, M. J., Rana, S., Paterson, H., Barford, D. & Marais, R., Wild-type and mutant B-RAF activate C-RAF through distinct mechanisms involving heterodimerization, Mol Cell, 20, 963-9 (2005)), strongly suggests that RAS may also play a role in forming side-to-side kinase domain dimers. In the absence of RTK/RAS activation, a regulatory element in the N-terminus of RAF engages the C-terminal kinase domain to inhibit catalytic activity by an unknown mechanism (Chong, H. & Guan, K. L., Regulation of Raf through phosphorylation and N terminus-C terminus interaction, J Biol Chem, 278, 36269-76 (2003)). We reason that this autoinhibitory interaction may interfere with the ability of the kinase domain to adopt a productive dimer configuration.

Although dependent on many more components, the activation mechanism of RAF appears analogous in principle, if not execution, to those employed by the PKR and EGFR protein kinases. In the case of the eIF2 protein kinase PKR, the attainment of a specific dimer configuration by the kinase domain is regulated by the binding of dsRNA viral by-products to regions N-terminal to the kinase domain (Dar, A. C., Dever, T. E. & Sicheri, F., Higher-order substrate recognition of eIF2alpha by the RNA-dependent protein kinase PKR, Cell, 122, 887-900 (2005)), Dey, M. et al., Mechanistic link between PKR dimerization, autophosphorylation, and eIF2alpha substrate recognition, Cel, 122, 901-13 (2005). In the case of EGFR kinase, adoption of a unique dimer/oligomer configuration by its kinase domain is regulated by the binding of growth factors to the extracellular ligand binding domain of the receptors (Zhang, X., Gureasko, J., Shen, K., Cole, P. A. & Kuriyan, J., An allosteric mechanism for activation of the kinase domain of epidermal growth factor receptor, Cell, 125, 1137-49 (2006)) (FIG. 6C). Reflecting the importance of self interaction in the function of all three protein kinase families, residues comprising the self interaction surfaces of the kinase domain in addition to the catalytic infrastructure are evolutionarily conserved within each kinase family. In this regard, KSR is essentially equivalent to a RAF molecule. In effect, we reason that RAF and KSR evolved from a single ancestral progenitor, one that possessed both protein kinase catalytic activity and stable substrate (MEK) binding function. Following a gene duplication event (Claperon, A. & Therrien, M., KSR and CNK: two scaffolds regulating RAS-mediated RAF activation, Oncogene, 26, 3143-58 (2007)), one gene dispensed with phospho-transfer function (i.e. KSR) and the other dispensed with the ability to stably bind MEK substrate (i.e. RAF). However, both maintained the ability to form allosteric dimers and this selective pressure maintained the side-to-side dimer interface and interdependence between KSR and RAF proteins in ERK signaling.

The mapping of human cancer causing mutations to the activation segment of B-RAF proved unequivocally that the activation segment of RAF is also a key modulator of its catalytic function (Wan, P. T. et al., Mechanism of activation of the RAF-ERK signaling pathway by oncogenic mutations of B-RAF, Cell, 116, 855-67 (2004)), (Davies, H. et al., Mutations of the BRAF gene in human cancer, Nature, 417, 949-54 (2002)). Consistent with this, we previously found that a mutation in the activation segment of Drosophila RAF (RAF-AL$^{ED}$) strongly hyperactivated its catalytic activity (Douziech, M., Sahmi, M., Laberge, G. & Therrien, M., A KSR/CNK complex mediated by HYP, a novel SAM domain-containing protein, regulates RAS-dependent RAF activation in Drosophila, Genes Dev, 20, 807-19 (2006)), suggesting that it likely acts via a similar mechanism as those identified in human cancers (Wan, P. T. et al., Mechanism of activation of the RAF-ERK signaling pathway by oncogenic mutations of B-RAF, Cell, 116, 855-67 (2004)). This raises the question of how kinase domain dimerization and the modulation of activation segment conformation are coordinated. Both events may be essential for the transmission of a downstream signal or each event may be sufficient on its own. If both are essential, then oncogenic activation segment mutants of RAF should still be sensitive to dimer interface mutations. Suggesting that this in fact is the case, introduction of a mutation (R481H) within the side-to-side dimer interface in Drosophila RAF effectively nullifies the aberrant signaling properties of RAF-AL$^{ED}$ (FIG. 11A).

Intriguingly, while most oncogenic RAF mutations act through modulation of the activation segment, one particular mutation, RAF_E558K (E586K in human B-RAF), is located on the opposite surface of the kinase domain from the activation segment (Wan, P. T. et al., Mechanism of activation of the RAF-ERK signaling pathway by oncogenic mutations of B-RAF, Cell, 116, 855-67 (2004)) and its mechanism of kinase activation remained enigmatic. Most conspicuously, Glu558 lies on the side-to-side dimer interface (FIG. 11B). If dimerization is indeed critical for RAF activation, we questioned whether RAF_E558K might promote kinase activity by promoting dimerization. We reasoned that mutation of Glu558 to the longer Lys (E558K) could potentially introduce a hydrogen bond with Ser561 (conservative Thr589 in B-RAF) on the second RAF protomer thereby promoting dimer formation (FIG. 11B). Indeed, as tested below we found that the RAF_E558K mutation promoted kinase domain dimerization in solution. Wild type RAF kinase domain is predominantly a dimer in solution (at the micromolar concentrations tested), which prevented a direct test of the RAF_E558K mutant for enhanced dimerization potential (FIG. 3C). To circumvent this problem, we employed the RAF_L487R dimer mutant which displayed a weak monomer-dimer binding equilibrium in solution (FIG. 12).

Thus, introduction of the E558K mutation (RAF_L487R/E558K double mutant) transitioned RAF_L487R back to a predominantly dimeric state (FIG. 6). To investigate how the RAF_E558K mutation functions to hyperactivate RAF in vivo, we used the FRB/FKBP/rapamycin system to assess RAF activation in S2 cells. When the E558K mutation was introduced in the kinase-dead (K455S) background (FRB-RAF_K455S/E558K double mutant), it displayed no activity when tested alone (not shown), but strongly hyperactivated the FKBP-RAF counterpart in a rapamycin dependent manner (FIG. 11C). Taken together, the ability of the E558K mutant to act in trans (i.e. in the context of a kinase dead mutant) in vivo, and the ability of the E558K mutation to promote kinase domain dimerization in vitro strongly suggests that the mechanism by which the oncogenic RAF_E558K mutation acts is by promoting side-to-side dimers. Given these results, it is now possible to develop small molecules strategies that are directed at preventing the formation of side-to-side dimers by RAF and which can serve as a therapeutic for RAF-dependent human tumors, one that would complement conventional strategies currently directed at inhibiting RAF enzymatic activity by blocking the catalytic cleft (Wu, S., Guo, W. & Fang, B., Development of small-molecule inhibitors of raf, Recent Patents Anti-Infect Drug Disc, 1, 241-6 (2006)).

It is understood that the examples and embodiments described herein are for illustrative purposes only and that various modifications or changes in light thereof will be suggested to persons skilled in the art and are to be included within the present discovery and scope of the appended claims.

While this invention has been particularly shown and described with references to preferred embodiments thereof, it will be understood by those skilled in the art that various changes in form and details may be made therein without departing from the scope of the invention encompassed by the appended claims.

What is claimed:

1. A biosensor comprising:
an isolated human embryonic kidney (HEK) cell expressing:
   (a) a first fusion molecule comprising the amino acid sequence of SEQ ID NO: 34: and
   (b) a second fusion molecule comprising the amino acid sequence of SEQ ID NO: 30.

2. The biosensor of claim 1, wherein said HEK cell is an HEK293T cell.

3. A method for determining whether a test agent modulates the dimerization of human BRAF with human CRAF, said method comprising:
   (a) providing the biosensor of claim 1 in the presence or absence of said test agent; and
   (b) measuring the fluorescence signal emitted by said second fusion molecule in said cell;
wherein a higher fluorescence signal measured in the presence of the test agent is indicative that said test agent increases the dimerization of human BRAF with human CRAF, and a lower fluorescence signal measured in the presence of the test agent is indicative that said test agent inhibits the dimerization of human BRAF with human CRAF.

4. The method of claim 3, wherein said method further comprises contacting the cell with a substrate for the donor bioluminescent protein present in said first fusion molecule.

5. The method of claim 4, wherein said substrate is Coelenterazine 400a (DeepBlue C™).

6. The method of claim 5, further comprising:
   (c) measuring the bioluminescent signal emitted by said first fusion molecule, and
   (d) determining the ratio;
wherein a higher ratio measured in the presence of the test agent is indicative that said test agent increases the dimerization of human BRAF with human CRAF, and a lower ratio measured in the presence of the test agent is indicative that said test agent inhibits the dimerization of human BRAF with human CRAF.

* * * * *

SEQUENCE LISTING

<160> NUMBER OF SEQ ID NOS: 97

<210> SEQ ID NO 1
<211> LENGTH: 14
<212> TYPE: PRT
<213> ORGANISM: Drosophila melanogaster

<400> SEQUENCE: 1

Ile His Arg Ser Ala Ser Glu Pro Asn Leu Thr Gln Ser Gln
1               5                   10

<210> SEQ ID NO 2
<211> LENGTH: 14
<212> TYPE: PRT
<213> ORGANISM: Homo sapiens

<400> SEQUENCE: 2

Leu Asn Arg Arg Leu Ser His Pro Gly His Phe Trp Lys Ser
1               5                   10

<210> SEQ ID NO 3
<211> LENGTH: 14
<212> TYPE: PRT
<213> ORGANISM: Mus musculus

<400> SEQUENCE: 3

Leu Asn Arg Arg Leu Ser His Pro Gly His Phe Trp Lys Ser
1               5                   10

<210> SEQ ID NO 4
<211> LENGTH: 14
<212> TYPE: PRT
<213> ORGANISM: Danio sp.

<400> SEQUENCE: 4

Leu Asn Arg Arg Leu Ser His Pro Gly His Phe Trp Lys Ser
1               5                   10

<210> SEQ ID NO 5
<211> LENGTH: 14
<212> TYPE: PRT
<213> ORGANISM: Drosophila melanogaster

<400> SEQUENCE: 5

Leu Ala Arg Ser Pro Ser His Pro Val Asn Leu Ser Arg Ser
1               5                   10

<210> SEQ ID NO 6
<211> LENGTH: 14
<212> TYPE: PRT
<213> ORGANISM: Gallus sp.

<400> SEQUENCE: 6

Leu Asn Arg Arg Leu Ser His Pro Gly His Phe Trp Lys Ser
1               5                   10

<210> SEQ ID NO 7
<211> LENGTH: 766
<212> TYPE: PRT
<213> ORGANISM: Homo sapiens

<400> SEQUENCE: 7

Met Ala Ala Leu Ser Gly Gly Gly Gly Gly Gly Ala Glu Pro Gly Gln
1               5                   10                  15

```
Ala Leu Phe Asn Gly Asp Met Glu Pro Glu Ala Gly Ala Gly
         20                  25                  30

Ala Ala Ala Ser Ser Ala Ala Asp Pro Ala Ile Pro Glu Glu Val Trp
             35                  40                  45

Asn Ile Lys Gln Met Ile Lys Leu Thr Gln Glu His Ile Glu Ala Leu
 50                  55                  60

Leu Asp Lys Phe Gly Gly Glu His Asn Pro Pro Ser Ile Tyr Leu Glu
 65                  70                  75                  80

Ala Tyr Glu Glu Tyr Thr Ser Lys Leu Asp Ala Leu Gln Gln Arg Glu
                 85                  90                  95

Gln Gln Leu Leu Glu Ser Leu Gly Asn Gly Thr Asp Phe Ser Val Ser
             100                 105                 110

Ser Ser Ala Ser Met Asp Thr Val Thr Ser Ser Ser Ser Ser Ser Leu
         115                 120                 125

Ser Val Leu Pro Ser Ser Leu Ser Val Phe Gln Asn Pro Thr Asp Val
     130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                 165                 170                 175

Val Arg Asp Ser Leu Lys Lys Ala Leu Met Met Arg Gly Leu Ile Pro
             180                 185                 190

Glu Cys Cys Ala Val Tyr Arg Ile Gln Asp Gly Glu Lys Lys Pro Ile
         195                 200                 205

Gly Trp Asp Thr Asp Ile Ser Trp Leu Thr Gly Glu Glu Leu His Val
     210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                 245                 250                 255

Gln Gly Phe Arg Cys Gln Thr Cys Gly Tyr Lys Phe His Gln Arg Cys
             260                 265                 270

Ser Thr Glu Val Pro Leu Met Cys Val Asn Tyr Asp Gln Leu Asp Leu
         275                 280                 285

Leu Phe Val Ser Lys Phe Phe Glu His His Pro Ile Pro Gln Glu Glu
     290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                 325                 330                 335

Ser Lys Ser Ile Pro Ile Pro Gln Pro Phe Arg Pro Ala Asp Glu Asp
             340                 345                 350

His Arg Asn Gln Phe Gly Gln Arg Asp Arg Ser Ser Ser Ala Pro Asn
         355                 360                 365

Val His Ile Asn Thr Ile Glu Pro Val Asn Ile Asp Asp Leu Ile Arg
     370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                 405                 410                 415

Gln Lys Ser Pro Gly Pro Gln Arg Glu Arg Lys Ser Ser Ser Ser Ser
             420                 425                 430

Glu Asp Arg Asn Arg Met Lys Thr Leu Gly Arg Arg Asp Ser Ser Asp
```

```
                435                 440                 445
Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 8
<211> LENGTH: 2949
<212> TYPE: DNA
<213> ORGANISM: Homo sapiens

<400> SEQUENCE: 8
cgcctccctt ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccgaggaggt gtggaatatc aaacaaatga ttaagttgac acaggaaca     240 tatagaggcc ctattggaca aatttggtgg ggagcataat ccaccatcaa tatatctgga     300
```

```
ggcctatgaa gaatacacca gcaagctaga tgcactccaa caaagagaac aacagttatt    360
ggaatctctg gggaacggaa ctgatttttc tgtttctagc tctgcatcaa tggataccgt    420
tacatcttct tcctcttcta gcctttcagt gctaccttca tctctttcag tttttcaaaa    480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg gacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
acccgcctcg gactctattg gccccaaat tctcaccagt ccgtctcctt caaaatccat    1080
tccaattcca cagcccttcc gaccagcaga tgaagatcat cgaaatcaat ttgggcaacg   1140
agaccgatcc tcatcagctc ccaatgtgca tataaacaca atagaacctg tcaatattga   1200
tgacttgatt agagaccaag gatttcgtgg tgatggagga tcaaccacag gtttgtctgc   1260 tacccccct gcctcattac ctggctcact aactaacgtg aaagccttac agaaatctcc    1320
aggacctcag cgagaaagga agtcatcttc atcctcagaa acaggaatc gaatgaaaac    1380 acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact acacgccaa gtcaatcatc cacagagacc tcaagagtaa   1800
taatatattt cttcatgaag acctcacagt aaaaataggt gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg tttccaaac    2280 agaggatttt agtctatatg cttgtgcttc tccaaaaaca cccatccagg caggggata    2340 tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggatttta acatccaagg gttaaaatac atagacattg    2580
ctaaaaattg gcagagcctc ttctagaggc tttactttct gttccgggtt tgtatcattc   2640
```

-continued

```
acttggttat tttaagtagt aaacttcagt ttctcatgca acttttgttg ccagctatca      2700
catgtccact agggactcca gaagaagacc ctacctatgc ctgtgtttgc aggtgagaag      2760
ttggcagtcg gttagcctgg gttagataag gcaaactgaa cagatctaat ttaggaagtc      2820
agtagaattt aataattcta ttattattct taataatttt tctataacta tttctttta       2880 taacaatttg gaaatgtggg atgtctttta tttccttgaa gcaataaact aagtttcttt      2940
ttataaaaa                                                             2949
```

<210> SEQ ID NO 9
<211> LENGTH: 804
<212> TYPE: PRT
<213> ORGANISM: Mus musculus

<400> SEQUENCE: 9

```
Met Ala Ala Leu Ser Gly Gly Gly Gly Ser Ser Gly Gly Gly Gly
1               5                   10                  15

Gly Gly Gly Gly Gly Gly Gly Gly Asp Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
            100                 105                 110

Glu Gln Gln Leu Leu Glu Ser Leu Val Phe Gln Thr Pro Thr Asp Ala
        115                 120                 125

Ser Arg Asn Asn Pro Lys Ser Pro Gln Lys Pro Ile Val Arg Val Phe
    130                 135                 140

Leu Pro Asn Lys Gln Arg Thr Val Val Pro Ala Arg Cys Gly Val Thr
145                 150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
        195                 200                 205

Glu Val Leu Glu Asn Val Pro Leu Thr Thr His Asn Phe Val Arg Lys
    210                 215                 220

Thr Phe Phe Thr Leu Ala Phe Cys Asp Phe Cys Arg Lys Leu Leu Phe
225                 230                 235                 240

Gln Gly Phe Arg Cys Gln Thr Cys Gly Tyr Lys Phe His Gln Arg Cys
                245                 250                 255

Ser Thr Glu Val Pro Leu Met Cys Val Asn Tyr Asp Gln Leu Asp Leu
            260                 265                 270

Leu Phe Val Ser Lys Phe Glu His His Pro Val Pro Gln Glu Glu
        275                 280                 285

Ala Ser Phe Pro Glu Thr Ala Leu Pro Ser Gly Ser Ser Ala Pro
    290                 295                 300

Pro Ser Asp Ser Thr Gly Pro Gln Ile Leu Thr Ser Pro Ser Pro Ser
305                 310                 315                 320
```

```
Lys Ser Ile Pro Ile Pro Gln Pro Phe Arg Pro Ala Asp Glu Asp His
            325                 330                 335

Arg Asn Gln Phe Gly Gln Arg Asp Arg Ser Ser Ala Pro Asn Val
        340                 345                 350

His Ile Asn Thr Ile Glu Pro Val Asn Ile Asp Glu Lys Phe Pro Glu
            355                 360                 365

Val Glu Leu Gln Asp Gln Arg Asp Leu Ile Arg Asp Gln Gly Phe Arg
    370                 375                 380

Gly Asp Gly Ala Pro Leu Asn Gln Leu Met Arg Cys Leu Arg Lys Tyr
385                 390                 395                 400

Gln Ser Arg Thr Pro Ser Pro Leu Leu His Ser Val Pro Ser Glu Ile
            405                 410                 415

Val Phe Asp Phe Glu Pro Gly Pro Val Phe Arg Gly Ser Thr Thr Gly
            420                 425                 430

Leu Ser Ala Thr Pro Pro Ala Ser Leu Pro Gly Ser Leu Thr Asn Val
        435                 440                 445

Lys Ala Leu Gln Lys Ser Pro Gly Pro Gln Arg Glu Arg Lys Ser Ser
    450                 455                 460

Ser Ser Ser Ser Ser Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
            485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
            565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
    595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
            645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
            725                 730                 735
```

```
Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
        770                 775                 780

Cys Ala Ser Pro Lys Thr Pro Ile Gln Ala Gly Gly Tyr Gly Glu Phe
785                 790                 795                 800

Ala Ala Phe Lys

<210> SEQ ID NO 10
<211> LENGTH: 9727
<212> TYPE: DNA
<213> ORGANISM: Mus musculus

<400> SEQUENCE: 10
```

| | | | | | |
|---|---|---|---|---|---|
| ccctcaggct | cggctgcgcc | ggggccgccg | gcgggttcca | gaggtggcct | ccgccccggc | 60 |
| cgctccgccc | acgcccccg | cgcctccgcg | cccgcctccg | cccgccctgc | gcctcccttc | 120 |
| ccctccccg | ccccgcggcg | gccgctcggc | ccggctcgcg | cttcgaagat | ggcggcgctg | 180 |
| agtggcggcg | gtggcagcag | cagcggtggc | ggcggcggcg | gtggcggcgg | cggtggcggt | 240 |
| ggcgacggcg | gcggcggcgc | cgagcagggc | caggctctgt | tcaatggcga | catggagccg | 300 |
| gaggccggc | ctggcgccgc | ggcctcttcg | gctgcggacc | cggccattcc | tgaagaggta | 360 |
| tggaatatca | agcaaatgat | taagttgaca | caggaacata | tagaggccct | attggacaaa | 420 |
| tttggtggag | agcataaccc | accatcaata | tacctggagg | cctatgaaga | gtacaccagc | 480 |
| aagctagatg | cccttcagca | aagagaacag | cagcttttgg | aatccctggt | ttttcaaact | 540 |
| cccacagatg | catcacggaa | caaccccaag | tcaccacaga | aacctatcgt | tagagtcttc | 600 |
| ctgcccaaca | acagaggac | agtggtaccc | gcaagatgtg | gtgttacagt | tcgagacagt | 660 |
| ctaaagaaag | cactgatgat | gagaggtctc | atcccagaat | gctgtgctgt | ttacagaatt | 720 |
| caggatggag | agaagaaacc | aattggctgg | gacacggaca | tttcctggct | tactggagag | 780 |
| gagttacatg | ttgaagtact | ggagaatgtc | ccacttacaa | cacacaactt | tgtacggaaa | 840 |
| acttttttca | ccttagcatt | ttgtgacttt | tgccgaaagc | tgcttttcca | gggtttccgt | 900 |
| tgtcaaacat | gtggttataa | atttcaccag | cgttgtagta | cagaggttcc | actgatgtgt | 960 |
| gtaaattatg | accaacttga | tttgctgttt | gtctccaagt | tctttgagca | tcacccagta | 1020 |
| ccacaggagg | aggcctcctt | cccagagact | gcccttccat | ctggatcctc | ttccgcaccc | 1080 |
| ccctcagact | ctactgggcc | ccaaatcctc | accagtccat | ctccttcaaa | atccattcca | 1140 |
| attccacagc | cctccgacc | agcagatgaa | gatcatcgca | atcagtttgg | gcaacgagac | 1200 |
| cggtcctcct | cagctcccaa | tgttcatata | aacacaattg | agcctgtgaa | tatcgatgaa | 1260 |
| aaattcccag | aagtggaatt | acaggatcaa | agggatttga | ttagagacca | ggggtttcgt | 1320 |
| ggtgatggag | ccccttgaa | ccaactgatg | cgctgtcttc | ggaaatacca | atcccggact | 1380 |
| cccagccccc | tcctccattc | tgtccccagt | gaaatagtgt | tgatttga | gcctggccca | 1440 |
| gtgttcagag | ggtcaaccac | aggcttgtcc | gccacccgc | ctgcctcatt | acctggctca | 1500 |
| ctcactaacg | tgaaagcctt | acagaaatct | ccaggtcctc | agcgggaaag | gaagtcatct | 1560 |
| tcttcctcat | cctcggagga | cagaagtcgg | atgaaaacac | ttggtagaag | agattcaagt | 1620 |
| gatgactggg | agattcctga | tggacagatt | acagtgggac | agagaattgg | atctgggtca | 1680 |
| tttggaactg | tctacaaggg | aaagtggcat | ggtgatgtgg | cagtgaaaat | gttgaatgtg | 1740 |

```
acagcaccca cacctcaaca gctacaggcc ttcaaaaatg aagtaggagt gctcaggaaa   1800
actcgacatg tgaatatcct cctttttcatg ggctattcta caaagccaca actggcaatt   1860
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatatttct tcatgaagac   2040
ctcacggtaa aaataggtga ctttggtcta gccacagtga atctcggtg gagtgggtcc    2100 catcagtttg aacagttgtc tggatctatt ttgtggatgg caccagaagt aatcagaatg   2160
caagataaaa acccgtatag ctttcagtca gacgtgtatg cgtttgggat tgttctgtac   2220
gaactgatga ccggccagct accttattca acatcaaca acagggatca gataattttt     2280
atggtgggac gaggatacct atctccagat ctcagtaagg tacggagtaa ctgtccaaaa   2340
gccatgaaga gattaatggc agagtgcctc aaaaagaaaa gagacgagag accactcttc   2400
cccaaattct cgcctccatt gagctgctgg cccgctcatt gccaaaaatt caccgcagtg   2460
catcagaacc ttccttgaat cgggctggtt tccaaacaga agattttagt ctgtatgctt   2520
gtgcttctcc gaaaacaccc atccaagcag ggggatatgg agaatttgca gccttcaagt   2580
agccagtcca tcatggcagc atctactctt tatttcttaa gtcttgtgtt catacagttt    2640
gttaacatca aaacacagtt ctgttcctca aaaaattttt taaagataca aaattttcaa   2700
tgcataagtt catgtggaac agaatggaat ttcctattca acaaaagagg gaagaatgtt   2760
ttaggaacca gaattctctg ctgcccgtgt ttcttcttca ataactat cacgtgcata      2820 caagtctgcc cattcccaag aagaaagagg agagaccctg aattctgccc ttttggtggt   2880
caggcatgat ggaaagaatt tgctgctgca gcttgggaaa attgctatgg aaagtctgcc   2940
agtcgacttt gcccttctaa ccaccagatc agcctgtggc tggtcatctg atggggcgat   3000
ttccatcacc aagcatcgtt cttgcctatt ctgggattat tgttgtggagc actttccctg   3060 tccagcaccg ttcatttctg agggatggag taaatgcagc attcccttgt gtagcgcctg   3120
ttcagtcctc agcagctgct gtcacagcga agcttttac agttaagtgg tgggggagag     3180
ttgaggagag cctgcctcgg ggcagagaaa aggggggtgct gcatcttctt cctcacctcc    3240
agctctctca cctcgggttg ccttgctcac tgggctccgc ctaaccactc aggctgctca     3300
gtgctggcac acattgcctt cttttctcat tgggtccagc aattgaggag agggttgggg    3360
gattgtttcc tcctcaatgt agcaaattct caggaaaata cagtccatat cttcctctca    3420
gctcttccag tcaccaaata cttacgtggc tcctttgtcc aggacataaa acaccgtgga   3480
caacacctaa ttaaaagcct acaaaactgc ttactgacag ttttgaatgt gagacacttg    3540
tgtaatttaa atgtaaggta caggttttaa tttctgagtt tcttctatt ttatttaaaa     3600 gaagaaaata attttcagtt ttaattggaa taaatgagta cttcccacaa gactatatac   3660
cctgaaaatt atatttttgt taattgtaaa caacttttaa agaataatta ttatcctttt    3720
ctctacctaa aaattatggg gaatcttagc ataatgacaa ttatttatac ttttaaata     3780 aatggtactt gctggatcca cactaacatc tttgctaaca atcccattgt ttcttccaac    3840
ttaactccta cactacatcc tacatcctct ttctagtctt ttatctataa tatgcaacct   3900
aaaataaacg tggtggcgtc tccattcatt ctccctcttc ctgtttttccc caagcctggt    3960 cttcaaaagg ttgggtaatc ggtccctgag ctccctagct ggcaatgcaa ctattaggga   4020
cattggagtt gcaggagagc aggaagcctg tccccagctg ttcttctaga accctaaatc   4080
```

```
ttatctttgc acagatcaaa agtatcacct cgtcacagtt ctccttagcc tttacttaca    4140
ggtaatataa ataaaaatca ccatagtagt aaagaaaaca actggatgga ttgatgacca    4200
gtacctctca gagccaggaa tcttgaatct ccaggattta tacgtgcaaa tttaaggaga    4260
tgtacttagc aacttcaagc caagaacttc caaaatacta gcgaatctaa aataaaatgg    4320
aattttgagt tattttttaaa gttcaaatta taattgatac cactatgtat ttaagcctac    4380
tcacagcaag ttagatggat tttgctaaac tcattgccag actgtggtgg tggtggtggt    4440
agtgtgcacc tttaatccaa gcaactcagc aatcagaatg aggtaaatct ctgtgaatac    4500
aaggcctgcc tagtctgcag cgctagttcc aggatagcca gggctacaca cacaaaaacc    4560
ctctctcaaa aaaacaaaa ttaattagtt gataataaaa ataactaaa gtatcatcaa    4620
aggaaggcct actggaagtt ttatatattc ccagtaaatt gaaaaatatt ctgaagttat    4680
taaccagtta gcaacaatgt gttttttaagt cttacataaa cagagcaaag tcttcaaatg    4740
tttcagagct gagaagataa ttgtgcttga tatgaaaaat agcctctcca tatgatgtgc    4800
cacattgaaa ggcgtcatta ccctttttaaa tacttcttaa tgtggctttg ttcccttttac    4860
ccaggattag ctagaaagag ctaggtaggc ttcggccaca gttgcacatt tcgggcctgc    4920
tgaagaatgg gagctttgaa ggctggcctt ggtggaggag cccctcagtg ctggagggtg    4980
gggcgtgtac gcagcatgga agtggtctag acagagtgca aagggacaga cttctttctc    5040
attttagtat agggtgatgt ctcacttgaa atgagaaagt agagttgata ttaaacgaag    5100
ctgtgcccag aaaccaggct cagggtattg tgagattttc ttttttaaata gagaatataa    5160
aagatagaaa taaatattta aaccttcctt cttattttct atcaaataga ttttttttat    5220
catttgcaaa caacataaaa aaaggtttct tttgtggggt tttctttcct tctttttttt    5280
ttttttttt ttttaagact gcagataatc ttgttgagct cctcggaaaa tacaaggaag    5340
tccgtgtttg tgcagagcgc tttatgagta actgtataga cagtgtggct gcttcactca    5400
tcccagaggg ctgcagctgt cggcccatga agtggctgca gtgcctcgtg agatctgctt    5460
tgttttgttt ggagtgaagt ctttgaaagg tttgagtgca actatatagg actgttttta    5520
aataagtagt attcctcatg aactttctca ttgttaagct acaggaccca aactctacca    5580
ctaagatatt attaacctca aaatgtagtt tatagaagga atttgcaaat agaatatcca    5640
gttcgtactt atatgcatct tcaacaaaga ttctctgtga cttgttggat ttggttcctg    5700
aacagcccat ttctgtattt gaggttagga gggcataatg aggcatccta aaagacaatc    5760
tgatataaac tgtatgctag atgtatgctg gtaggggaga aagcattctg taaagacatg    5820
atttaagact tcagctctgt caaccagaaa ccttgtaaat acttcctgtc ttggtgcagc    5880
cccgcccctt tgatcacacg atgttgtctt gtgcttgtca gacactgtca gagctgctgt    5940
tcgtccctct gcagatctca cctgtcccca ctgcacaccc acctcctgcc tcttgcagac    6000
ctcagcatct agctttagtt ggaaacagtt cagggttcag gtgacttctt aaaaaaaaaa    6060
aaaaaccta cctcctcaga atgaggtaat gaatagttat ttatttaaag tatgaagagt    6120
caggagcgct cgaacatgaa ggtgatttaa gatggttcct ttcgtgtgta ttgtagctga    6180
gcacttgttt ttgtcctaaa gggcattata catttaagca gtgattctgt ttaaagatgt    6240
ttttctttaa aggtgtagct cagagtatct gttgttggaa ttggtgccag agtctgctta    6300
atagatttca gaatcctaag cttaagtcag tcgcatgaag ttaagtagtt atggtaacac    6360
tttgctagcc atgatataat tctacttttt aggagtaggt ttggcaaaac tgtatgcctt    6420
caaagtgagt tggccacagc tttgtcacat gcacagatac tcatctgaag agactgccca    6480
```

```
gctaagaggg cggaaggata ccctttttc ctacgattcg cttctttgtc cacgttggca      6540
ttgttagtac tagtttatca gcaccttgac cagcagatgt caaccaataa gctattttta      6600
aaaccatagc cagagatgga gaggtcactg tgagtagaaa cagcaggacg cttacaggag      6660
tgaaatggtg tagggaggct ctagaaaaat atcttgacaa tttgccaaat gatcttactg      6720
tgccttcatg atgcaataaa aaagctaaca ttttagcaga aatcagtgat ttacgaagag      6780
agtggccagt ctggtttaac tcagctggga taatatttt agagtgcaat ttagactgcg       6840
aagataaatg cactaaagag tttatagcca attcacattt gaaaataag aaaatggtaa       6900 attttcagtg aaatatttt ttaaagcaca taatccctag tgtagccaga aatatttacc       6960
acatagagca gctaggctga gatacagtcc agtgacattt ctagagaaac cttttctact      7020
cccacgggct cctcaaagca tggaaatttt atacaaaatg tttgacattt taagatactg      7080
ctgtagttta gttttgaaat agtatgtgct gagcagcaat catgtactaa ctcagagaga      7140
gaaaacaaca acaaattgtg catctgattt gttttcagag aaatgctgcc aacttagata      7200
ctgagttctc agagcttcaa gtgtaaactt gcctcccaag tcctgtttgc aaatgaagtt      7260
ggctagtgct actgactgct ccagcacatg atggaaggca gggggctgtc tctgaagtgt      7320
cttctataaa gggacaatag aatagtgaga gacctggtca gtgtgtgtca gctggacact      7380
ccatgctatg ggacttgcat cttctgtcct caccatcccc aagacattgt gctttcctca      7440
gttgtcctct agctgtttca ctcagacacc aagatgaatt actgatgcca aaggggcca       7500 aaatggccag tgtgttttgg gggttgtatc agttgactgg acaataactt taatagtttc      7560
agatcattta ttttacttc cattttgaca gacatttaaa tggaaattta gtcctaactt       7620
ttgtcatttg aaaggaaaaa ttaacagttc ctataagata cttttgaggt ggaatctgac      7680
atcctaattt tttttctttt cagtgggttt gcagcgaggg tcttgtatgc actaggcaag      7740
ggttctacca ctaagccaca tttcccagga aataaaatgt taacagttaa acatacaca       7800 caaatacaca aacaccttat taccacttta gtaaagtgag agatgtgcgt cctttgtctc      7860
agtctccacg atttcagctg ccccttgtat gaataactca gtctcgctaa actgtttact      7920
tttatttacc tggtttgact agttgcagct atataaccag ttgtgcatga ggacaacagc      7980
cagtgtgttt gttttgtttt tggttttttg tggtacattt tttgtaaaga attctgtaga      8040
ttgaagtgct ctttgaaaac agaactgaga tatatttatt cttgttagca tcaaaaaaca      8100
ttttgtgcaa atgatttgct tttcctggca ggctgagtac catatccagc gcccacaatt      8160
gcgggttccc atctaccatg tccacagggg agacagacgg gaagcacatg agggggtgtgt     8220 ttacagagtt gtaggagtta tgtagttctc ttgttgcctt ggaaatcact gttgttttaa      8280
gactgttgaa cccgtgtgtt tggctgggct gtgagttaca tgaagaaact gcaaactagc      8340
atatgcagac aaagctcaca gactaggcgt aaatggagga aaatggacca aaataaggca      8400
gggtgacaca taaccttgg gcttcggaga aaactaaggg tggagatgaa ctataatcac       8460
ctgaatacaa tgtaagagtg caataagtgt gcttattcta agctgtgaac ttcttttaaa      8520
tcattccttt ctaatacatt tatgtatgtt ccattgctga ctaaaaccag ctatgagaac      8580
atatgccttt ttattcatgt taactaccag tttaagtggc taaccttaat gtcttattta      8640
tcttcatttt gtattagttt acataccagg tatgtgtgtg tgctgtactc ttcttccctt      8700
tatttgaaaa cacttttcac tgggtcatct ccttggccat tccacaacac aactttggtt      8760
tggctttcaa tgtcacctta tttgatggcc tgtgtcccag tagcagaatt tatggtattc      8820
```

```
ccattgctgg ctgctcttcc gacccttgc ttctacagca cttgtctctc ctaagatagt   8880
cagaaactaa ctgatcaggg gatggacttc accattcatc gtgtctcttc aattctatta   8940
aatagaccac tcttgggctt tagaccagga aaaggagac agctctagcc atctaccaag    9000
cctcacccta aaaggtcacc cgtacttctt ggtctgagga caagtctcca ctccagtaag   9060
ggagagggga ggaaatgctt cctgtttgaa atgcagtgaa ttcctatggc tcctgtttca   9120
ccacccgcac ctatgcaac ccatatacat tcctcttgtc tgtaactgcc aaaggttggg    9180
tttatgtcac ttcagttcca ctcaagcatt gaaaaggttc tcatggagtc tggggtgtgc   9240
ccagtgaaaa gatggggact ttttcattat ccacagacct ctctatacct gctttgcaaa   9300
aattataatg gagtaactat ttttaaagct tatttttcaa ttcataagaa aaagacattt   9360
attttcaatc aaatggatga tgtctcttat cccttatccc tcaatgtttg cttgaatttt   9420
gtttgttccc tatacctact ccctaattct ttagttcctt cctgctcagg tcccttcatt   9480
tgtactttgg agttttctc atgtaaattt gtataatgga aatattgtt cagtttggat     9540 agaaagcatg gagaaataa taaaaaaga tagctgaaaa tcaaattgaa gaaatttatt     9600
tctgtgtaaa gttatttaaa aactctgtat tatatttaaa gaaaaaagcc caacccccca   9660
aaaagtgcta tgtaattgat gtgaatatgc gaatactgct ataataaaga ttgactgcat   9720
ggagaaa                                                             9727

<210> SEQ ID NO 11
<211> LENGTH: 897
<212> TYPE: PRT
<213> ORGANISM: Homo sapiens

<400> SEQUENCE: 11

Met Asp Arg Ala Ala Leu Arg Ala Ala Ala Met Gly Glu Lys Lys Glu
1               5                   10                  15

Gly Gly Gly Gly Gly Asp Ala Ala Glu Gly Gly Ala Gly Ala Ala Ala
            20                  25                  30

Ser Arg Ala Leu Gln Gln Cys Gly Gln Leu Gln Lys Leu Ile Asp Ile
        35                  40                  45

Ser Ile Gly Ser Leu Arg Gly Leu Arg Thr Lys Cys Ala Val Ser Asn
    50                  55                  60

Asp Leu Thr Gln Gln Glu Ile Arg Thr Leu Glu Ala Lys Leu Val Arg
65                  70                  75                  80

Tyr Ile Cys Lys Gln Arg Gln Cys Lys Leu Ser Val Ala Pro Gly Glu
                85                  90                  95

Arg Thr Pro Glu Leu Asn Ser Tyr Pro Arg Phe Ser Asp Trp Leu Tyr
            100                 105                 110

Thr Phe Asn Val Arg Pro Glu Val Val Gln Glu Ile Pro Arg Asp Leu
        115                 120                 125

Thr Leu Asp Ala Leu Leu Glu Met Asn Glu Ala Lys Val Lys Glu Thr
    130                 135                 140

Leu Arg Arg Cys Gly Ala Ser Gly Asp Glu Cys Gly Arg Leu Gln Tyr
145                 150                 155                 160

Ala Leu Thr Cys Leu Arg Lys Val Thr Gly Leu Gly Gly Glu His Lys
                165                 170                 175

Glu Asp Ser Ser Trp Ser Ser Leu Asp Ala Arg Arg Glu Ser Gly Ser
            180                 185                 190

Gly Pro Ser Thr Asp Thr Leu Ser Ala Ala Ser Leu Pro Trp Pro Pro
        195                 200                 205
```

```
Gly Ser Ser Gln Leu Gly Arg Ala Gly Asn Ser Ala Gln Gly Pro Arg
210                 215                 220

Ser Ile Ser Val Ser Ala Leu Pro Ala Ser Asp Ser Pro Thr Pro Ser
225                 230                 235                 240

Phe Ser Glu Gly Leu Ser Asp Thr Cys Ile Pro Leu His Ala Ser Gly
            245                 250                 255

Arg Leu Thr Pro Arg Ala Leu His Ser Phe Ile Thr Pro Pro Thr Thr
            260                 265                 270

Pro Gln Leu Arg Arg His Thr Lys Leu Lys Pro Pro Arg Thr Pro Pro
            275                 280                 285

Pro Pro Ser Arg Lys Val Phe Gln Leu Pro Ser Phe Pro Thr Leu
290                 295                 300

Thr Arg Ser Lys Ser His Glu Ser Gln Leu Gly Asn Arg Ile Asp Asp
305                 310                 315                 320

Val Ser Ser Met Arg Phe Asp Leu Ser His Gly Ser Pro Gln Met Val
                325                 330                 335

Arg Arg Asp Ile Gly Leu Ser Val Thr His Arg Phe Ser Thr Lys Ser
            340                 345                 350

Trp Leu Ser Gln Val Cys His Val Cys Gln Lys Ser Met Ile Phe Gly
            355                 360                 365

Val Lys Cys Lys His Cys Arg Leu Lys Cys His Asn Lys Cys Thr Lys
370                 375                 380

Glu Ala Pro Ala Cys Arg Ile Ser Phe Leu Pro Leu Thr Arg Leu Arg
385                 390                 395                 400

Arg Thr Glu Ser Val Pro Ser Asp Ile Asn Asn Pro Val Asp Arg Ala
                405                 410                 415

Ala Glu Pro His Phe Gly Thr Leu Pro Lys Ala Leu Thr Lys Lys Glu
            420                 425                 430

His Pro Pro Ala Met Asn His Leu Asp Ser Ser Ser Asn Pro Ser Ser
            435                 440                 445

Thr Thr Ser Ser Thr Pro Ser Ser Pro Ala Pro Phe Pro Thr Ser Ser
        450                 455                 460

Asn Pro Ser Ser Ala Thr Thr Pro Pro Asn Pro Ser Pro Gly Gln Arg
465                 470                 475                 480

Asp Ser Arg Phe Asn Phe Pro Ala Ala Tyr Phe Ile His His Arg Gln
                485                 490                 495

Gln Phe Ile Phe Pro Val Pro Ser Ala Gly His Cys Trp Lys Cys Leu
            500                 505                 510

Leu Ile Ala Glu Ser Leu Lys Glu Asn Ala Phe Asn Ile Ser Ala Phe
            515                 520                 525

Ala His Ala Ala Pro Leu Pro Glu Ala Ala Asp Gly Thr Arg Leu Asp
        530                 535                 540

Asp Gln Pro Lys Ala Asp Val Leu Glu Ala His Glu Ala Glu Ala Glu
545                 550                 555                 560

Glu Pro Glu Ala Gly Lys Ser Glu Ala Glu Asp Asp Glu Asp Glu Val
                565                 570                 575

Asp Asp Leu Pro Ser Ser Arg Arg Pro Trp Arg Gly Pro Ile Ser Arg
            580                 585                 590

Lys Ala Ser Gln Thr Ser Val Tyr Leu Gln Glu Trp Asp Ile Pro Phe
            595                 600                 605

Glu Gln Val Glu Leu Gly Glu Pro Ile Gly Gln Gly Arg Trp Gly Arg
610                 615                 620

Val His Arg Gly Arg Trp His Gly Glu Val Ala Ile Arg Leu Leu Glu
```

```
                625                 630                 635                 640
Met Asp Gly His Asn Gln Asp His Leu Lys Leu Phe Lys Lys Glu Val
                    645                 650                 655

Met Asn Tyr Arg Gln Thr Arg His Glu Asn Val Val Leu Phe Met Gly
                    660                 665                 670

Ala Cys Met Asn Pro Pro His Leu Ala Ile Ile Thr Ser Phe Cys Lys
                    675                 680                 685

Gly Arg Thr Leu His Ser Phe Val Arg Asp Pro Lys Thr Ser Leu Asp
                    690                 695                 700

Ile Asn Lys Thr Arg Gln Ile Ala Gln Glu Ile Ile Lys Gly Met Gly
705                 710                 715                 720

Tyr Leu His Ala Lys Gly Ile Val His Lys Asp Leu Lys Ser Lys Asn
                    725                 730                 735

Val Phe Tyr Asp Asn Gly Lys Val Ile Thr Asp Phe Gly Leu Phe
                    740                 745                 750

Gly Ile Ser Gly Val Val Arg Glu Gly Arg Arg Glu Asn Gln Leu Lys
                    755                 760                 765

Leu Ser His Asp Trp Leu Cys Tyr Leu Ala Pro Glu Ile Val Arg Glu
                    770                 775                 780

Met Thr Pro Gly Lys Asp Glu Asp Gln Leu Pro Phe Ser Lys Ala Ala
785                 790                 795                 800

Asp Val Tyr Ala Phe Gly Thr Val Trp Tyr Glu Leu Gln Ala Arg Asp
                    805                 810                 815

Trp Pro Leu Lys Asn Gln Ala Ala Glu Ala Ser Ile Trp Gln Ile Gly
                    820                 825                 830

Ser Gly Glu Gly Met Lys Arg Val Leu Thr Ser Val Ser Leu Gly Lys
                    835                 840                 845

Glu Val Ser Glu Ile Leu Ser Ala Cys Trp Ala Phe Asp Leu Gln Glu
                    850                 855                 860

Arg Pro Ser Phe Ser Leu Leu Met Asp Met Leu Glu Lys Leu Pro Lys
865                 870                 875                 880

Leu Asn Arg Arg Leu Ser His Pro Gly His Phe Trp Lys Ser Ala Glu
                    885                 890                 895

Leu
```

<210> SEQ ID NO 12
<211> LENGTH: 4552
<212> TYPE: DNA
<213> ORGANISM: Homo sapiens

<400> SEQUENCE: 12

```
ctggacccct gccagggaag gggtcctcag acttgaggtt gccagctcag atgtggggct    60
gctgatacta ggtgactgga ctgatgttct gttctagatg aaactccttg aggggaccat   120
ttgaaaaggc ttgatgtgct gcccaaagcc cccttcagag ctgacttctc acccccagc    180 tgccgtgagc cttggctgct gacagctcat agctgagtcc ctcccgtgaa gtcaccttct   240
gctgaagggt acatcctctc ccaaggcgaa gctggtccgt acatttgta agcagaggca    300 gtgcaagctg agcgtggctc ccggtgagag accccagag ctcaacagct accccgctt     360 cagcgactgg ctgtacactt tcaacgtgag gccgaggtg gtgcaggaga tccccgaga    420 cctcacgctg gatgccctgc tggagatgaa tgaggccaag gtgaaggaga cgctgcggcg   480
ctgtggggcc agcggggatg agtgtggccg tctgcagtat gccctcacct gcctgcggaa   540
ggtgacaggc ctgggagggg agcacaagga ggactccagt tggagttcat ggatgcgcg    600
```

```
gcgggaaagt ggctcagggc cttccacgga caccctctca gcagccagcc tgccctggcc      660
cccagggagc tcccagctgg gcagagcagg caacagcgcc cagggcccac gctccatctc      720
cgtgtcagct ctgcccgcct cagactcccc accccccagc ttcagtgagg gcctctcaga      780
cacctgtatt cccctgcacg ccagcggccg gctgaccccc cgtgccctgc acagcttcat      840
caccccgccc accacacccc agctgcgacg gcacaccaag ctgaagccac cacggacgcc      900 cccccaccc agccgcaagg tcttccagct gctgcccagc ttccccacac tcacccggag       960
caagtcccat gagtctcagc tggggaaccg cattgatgac gtctcctcga tgaggtttga     1020
tctctcgcat ggatccccac agatggtacg gagggatatc gggctgtcgg tgacgcacag     1080
gttctccacc aagtcctggc tgtcgcaggt ctgccacgtg tgccagaaga gcatgatatt     1140
tggagtgaag tgcaagcatt gcaggttgaa gtgtcacaac aaatgtacca agaagcccc      1200 tgcctgtaga atatccttcc tgccactaac tcggcttcgg aggacagaat ctgtcccctc     1260
ggacatcaac aacccggtgg acagagcagc cgaaccccat tttggaaccc tccccaaagc     1320
actgacaaag aaggagcacc ctccggccat gaatcacctg gactccagca gcaacccttc     1380
ctccaccacc tcctccacac cctcctcacc ggcgcccttc ccgacatcat ccaacccatc     1440
cagcgccacc acgcccccca cccctcacc tggccagcgg gacagcaggt tcaacttccc     1500
agctgcctac ttcattcatc atagacagca gtttatcttt ccagtgccat ctgctggcca     1560
ttgctggaaa tgcctcctta ttgcagaaag tttaaaggaa aacgctttca acatttcagc     1620 cttttgcacac gcagccccgc tccctgaagc tgccgacggt acccggctcg atgaccagcc     1680
gaaagcagat gtgttggaag ctcacgaagc ggaggctgag gagccagagg ctggcaagtc     1740
agaggcagaa gacgatgagg acgaggtgga cgacttgccg agctctcgcc ggccctggcg     1800 gggcccatc tctcgcaagg ccagccagac cagcgtgtac ctgcaggagt gggacatccc     1860
cttcgagcag gtagagctgg gcgagcccat cgggcagggc cgctgggcc gggtgcaccg     1920 cggccgctgg catggcgagg tggccattcg cctgctggag atggacggcc acaaccagga     1980
ccacctgaag ctcttcaaga aagaggtgat gaactaccgg cagacgcggc atgagaacgt     2040
ggtgctcttc atgggggcct gcatgaaccc gccccacctg gccattatca ccagcttctg     2100
caaggggcgg acgttgcact cgtttgtgag ggaccccaag acgtctctgg acatcaacaa     2160
gacgaggcaa atcgctcagg agatcatcaa gggcatggga tatcttcatg ccaagggcat     2220
cgtacacaaa gatctcaaat ctaagaacgt cttctatgac aacggcaagg tggtcatcac     2280
agacttcggg ctgtttggga tctcaggcgt ggtccgagag ggacggcgtg agaaccagct     2340
aaagctgtcc cacgactggc tgtgctatct ggcccctgag attgtacgcg agatgacccc     2400
cgggaaggac gaggatcagc tgccattctc caaagctgct gatgtctatg catttgggac     2460
tgtttggtat gagctgcaag caagagactg gcccttgaag aaccaggctg cagaggcatc     2520
catctggcag attggaagcg gggaaggaat gaagcgtgtc ctgacttctg tcagcttggg     2580
gaaggaagtc agtgagatcc tgtcggcctg ctgggctttc gacctgcagg agagacccag     2640
cttcagcctg ctgatggaca tgctggagaa acttcccaag ctgaaccggc ggctctccca     2700
ccctggacac ttctggaagt cagctgagtt gtaggcctgg ctgccttgca tgcaccaggg     2760
gctttcttcc tcctaatcaa caactcagca ccgtgacttc tgctaaaatg caaaatgaga     2820
tgcgggcact aacccagggg atgccacctc tgctgctcca gtcgtctctc tcgaggctac     2880
ttcttttgct ttgtttttaaa aactggccct ctgccctctc cacgtggcct gcatatgccc     2940
```

-continued

| | |
|---|---|
| aagtaactgc tctcagagga tcccactaac tgagctccct ccaaggcagt ctgggcagct | 3000 |
| tctaactacc ttcctggaca tgactgattg ctcccgtgtt cttctgaggg ctggtcttgt | 3060 |
| ttttgtttgg gtggctctgt ctcactgcta acaccttagt gagatgcctt ccaccctcct | 3120 |
| gagcacacca gcctcccact gggtgtgtgc ctagtgcggg gcgggcggag gttgggaggg | 3180 |
| tgttggcttg gcttttaacc tgtggggatt ttgtccaaca aggagtggaa tgatttcaga | 3240 |
| gctgccctga ggctggcacc ctggtcacag gaaccctctg cgctggctcc tgtctcagtc | 3300 |
| ccctctgtag agttagatca gaagacacag aaagttctgt ggccatgaaa gataccagct | 3360 |
| tggaagggtt gtgtcttcag tggcaccctc agaaaaattg tcttaaagca aagaggtacc | 3420 |
| tggctccaga caattttttct gatgaaaaca aagtctctgc cccgtcccca ccctgccacc | 3480 |
| ctggcaaagt tacttccttt acagctgccc agtgtaccat agaccagacc ccaggtcagc | 3540 |
| atttgtcaag agcatggctg ctgagtcccc tgtggcagtc aatgcactgt ttaccaaatg | 3600 |
| caggtttctg ttctccctcc ccagcaagac ctgctgaacc cagatctctg gaatggggcc | 3660 |
| ctaggaatt gcatttcaac ctgcttccca ggtggccctg atgcaccca gtattagagt | 3720 |
| ttattgctaa aaggaacatg ccctgtcact cctggtatcc tgggagtcat gtttctcttc | 3780 |
| tctctcagtt ctacttggag caagagcttt cctgggctgc aaatgagaaa acaattccta | 3840 |
| ggaacccaca gcagtactga gcatgctggg agcttgggac ttggagatga atgagccacc | 3900 |
| gttgctgctc caagtaggac tacttggagt gtagctgagg ccttggacgc agtatgacca | 3960 |
| ggggcagctc tgccagggct gttggccaat cagtcatttt catttcttgt tggaggccag | 4020 |
| gtcctctgct gaactcattt cctagctagt gttaccctaa ttctgatgaa gatcaatggg | 4080 |
| gctataattc ttgtttttgt tcctctttgc agcattaaca gcagcaaagt tgtaccccgg | 4140 |
| tttgaaaggt ttggcttggg cgtcctggag tccagtaatc caaagatgta gccagccata | 4200 |
| tggttttcg ctgctgatct ctttcttttt aaaatgtgtt tctgaaacat cccaacaacc | 4260 |
| accacgacaa aaaacactg cctgcccagc gctgcaaacc aggagcacac gtcctagatt | 4320 |
| cagactgttg gccataaacc ccactcggga gatggagctg cacctgctat ttcttaaaat | 4380 |
| gacaccacca acaaccaaac ctgtcatgac agacagcaaa tgtttacacg tatatttctc | 4440 |
| ctgagtgaac ctgatgtttt acaataggta ataataaaaa cagtctgtgc aaaaaaaaaa | 4500 |
| aaaaaaaaaa aaaaaaaaaa aaaaaaaaaa aaaaaaaaaa aaaaaaaaaa aa | 4552 |

<210> SEQ ID NO 13
<211> LENGTH: 873
<212> TYPE: PRT
<213> ORGANISM: Mus musculus

<400> SEQUENCE: 13

Met Asp Arg Ala Ala Leu Arg Ala Ala Ala Met Gly Glu Lys Lys Glu
1               5                   10                  15

Gly Gly Gly Gly Gly Ala Ala Ala Asp Gly Gly Ala Gly Ala Ala Val
            20                  25                  30

Ser Arg Ala Leu Gln Gln Cys Gly Gln Leu Gln Lys Leu Ile Asp Ile
        35                  40                  45

Ser Ile Gly Ser Leu Arg Gly Leu Arg Thr Lys Cys Ser Val Ser Asn
    50                  55                  60

Asp Leu Thr Gln Gln Glu Ile Arg Thr Leu Glu Ala Lys Leu Val Lys
65                  70                  75                  80

Tyr Ile Cys Lys Gln Gln Gln Ser Lys Leu Ser Val Thr Pro Ser Asp
                85                  90                  95

-continued

```
Arg Thr Ala Glu Leu Asn Ser Tyr Pro Arg Phe Ser Asp Trp Leu Tyr
                100                 105                 110
Ile Phe Asn Val Arg Pro Glu Val Gln Glu Ile Pro Gln Glu Leu
        115                 120                 125
Thr Leu Asp Ala Leu Leu Glu Met Asp Glu Ala Lys Ala Lys Glu Met
    130                 135                 140
Leu Arg Arg Trp Gly Ala Ser Thr Glu Glu Cys Ser Arg Leu Gln Gln
145                 150                 155                 160
Ala Leu Thr Cys Leu Arg Lys Val Thr Gly Leu Gly Gly Glu His Lys
                165                 170                 175
Met Asp Ser Gly Trp Ser Ser Thr Asp Ala Arg Asp Ser Ser Leu Gly
            180                 185                 190
Pro Pro Met Asp Met Leu Ser Ser Leu Gly Arg Ala Gly Ala Ser Thr
            195                 200                 205
Gln Gly Pro Arg Ser Ile Ser Val Ser Ala Leu Pro Ala Ser Asp Ser
    210                 215                 220
Pro Val Pro Gly Leu Ser Glu Gly Leu Ser Asp Ser Cys Ile Pro Leu
225                 230                 235                 240
His Thr Ser Gly Arg Leu Thr Pro Arg Ala Leu His Ser Phe Ile Thr
                245                 250                 255
Pro Pro Thr Thr Pro Gln Leu Arg Arg His Ala Lys Leu Lys Pro Pro
            260                 265                 270
Arg Thr Pro Pro Pro Ser Arg Lys Val Phe Gln Leu Leu Pro Ser
        275                 280                 285
Phe Pro Thr Leu Thr Arg Ser Lys Ser His Glu Ser Gln Leu Gly Asn
    290                 295                 300
Arg Ile Asp Asp Val Thr Pro Met Lys Phe Glu Leu Pro His Gly Ser
305                 310                 315                 320
Pro Gln Leu Val Arg Arg Asp Ile Gly Leu Ser Val Thr His Arg Phe
                325                 330                 335
Ser Thr Lys Ser Trp Leu Ser Gln Val Cys Asn Val Cys Gln Lys Ser
            340                 345                 350
Met Ile Phe Gly Val Lys Cys Lys His Cys Arg Leu Lys Cys His Asn
            355                 360                 365
Lys Cys Thr Lys Glu Ala Pro Ala Cys Arg Ile Thr Phe Leu Pro Leu
    370                 375                 380
Ala Arg Leu Arg Arg Thr Glu Ser Val Pro Ser Asp Ile Asn Asn Pro
385                 390                 395                 400
Val Asp Arg Ala Ala Glu Pro His Phe Gly Thr Leu Pro Lys Ala Leu
                405                 410                 415
Thr Lys Lys Glu His Pro Pro Ala Met Asn Leu Asp Ser Ser Ser Asn
            420                 425                 430
Pro Ser Ser Thr Thr Ser Ser Thr Pro Ser Ser Pro Ala Pro Phe Leu
        435                 440                 445
Thr Ser Ser Asn Pro Ser Ser Ala Thr Thr Pro Pro Asn Pro Ser Pro
    450                 455                 460
Gly Gln Arg Asp Ser Arg Phe Ser Phe Pro Asp Ile Ser Ala Cys Ser
465                 470                 475                 480
Gln Ala Ala Pro Leu Ser Ser Thr Ala Asp Ser Thr Arg Leu Asp Asp
                485                 490                 495
Gln Pro Lys Thr Asp Val Leu Gly Val His Glu Ala Glu Ala Glu Glu
            500                 505                 510
```

Pro Glu Ala Gly Lys Ser Glu Ala Glu Asp Asp Glu Asp Glu Val
        515                 520                 525

Asp Asp Leu Pro Ser Ser Arg Arg Pro Trp Arg Gly Pro Ile Ser Arg
530                 535                 540

Lys Ala Ser Gln Thr Ser Val Tyr Leu Gln Glu Trp Asp Ile Pro Phe
545                 550                 555                 560

Glu Gln Val Glu Leu Gly Glu Pro Ile Gly Gln Gly Arg Trp Gly Arg
                565                 570                 575

Val His Arg Gly Arg Trp His Gly Glu Val Ala Ile Arg Leu Leu Glu
                580                 585                 590

Met Asp Gly His Asn Gln Asp His Leu Lys Leu Phe Lys Lys Glu Val
        595                 600                 605

Met Asn Tyr Arg Gln Thr Arg His Glu Asn Val Val Leu Phe Met Gly
        610                 615                 620

Ala Cys Met Asn Pro Pro His Leu Ala Ile Ile Thr Ser Phe Cys Lys
625                 630                 635                 640

Gly Arg Thr Leu His Ser Phe Val Arg Asp Pro Lys Thr Ser Leu Asp
                645                 650                 655

Ile Asn Lys Thr Arg Gln Ile Ala Gln Glu Ile Ile Lys Gly Met Gly
                660                 665                 670

Tyr Leu His Ala Lys Gly Ile Val His Lys Asp Leu Lys Ser Lys Asn
        675                 680                 685

Val Phe Tyr Asp Asn Gly Lys Val Val Ile Thr Asp Phe Gly Leu Phe
        690                 695                 700

Gly Ile Ser Gly Val Val Arg Glu Glu Arg Arg Glu Asn Gln Leu Lys
705                 710                 715                 720

Leu Ser His Asp Trp Leu Cys Tyr Leu Ala Pro Glu Ile Val Arg Glu
                725                 730                 735

Met Ile Pro Gly Arg Asp Glu Asp Gln Leu Pro Phe Ser Lys Ala Ala
                740                 745                 750

Asp Val Tyr Ala Phe Gly Thr Val Trp Tyr Glu Leu Gln Ala Arg Asp
        755                 760                 765

Trp Pro Phe Lys His Gln Pro Ala Glu Ala Leu Ile Trp Gln Ile Gly
770                 775                 780

Ser Gly Glu Gly Val Arg Arg Val Leu Ala Ser Val Ser Leu Gly Lys
785                 790                 795                 800

Glu Val Gly Glu Ile Leu Ser Ala Cys Trp Ala Phe Asp Leu Gln Glu
                805                 810                 815

Arg Pro Ser Phe Ser Leu Leu Met Asp Met Leu Glu Arg Leu Pro Lys
                820                 825                 830

Leu Asn Arg Arg Leu Ser His Pro Gly His Phe Trp Lys Ser Ala Asp
        835                 840                 845

Ile Asn Ser Ser Lys Val Met Pro Arg Phe Glu Arg Phe Gly Leu Gly
850                 855                 860

Thr Leu Glu Ser Gly Asn Pro Lys Met
865                 870

<210> SEQ ID NO 14
<211> LENGTH: 4087
<212> TYPE: DNA
<213> ORGANISM: Mus musculus

<400> SEQUENCE: 14
ctcggggctt tcctgccgag gcgcccgtgt ccccgggctc ctcgcctcgg ccccagcgg    60

-continued

| | |
|---|---|
| ccccgatgcc gaggcatgga tagagcggcg ttgcgcgcgg cagcgatggg cgagaaaaag | 120 |
| gagggcggcg gcggggcgc cgcggcggac ggggcgcag gggccgccgt cagccgggcg | 180 |
| ctgcagcagt gcggccagct gcagaagctc atcgatatct ccatcggcag tctgcgcggg | 240 |
| ctgcgcacca agtgctcagt gtctaacgac ctcacacagc aggagatccg gaccctagag | 300 |
| gcaaagctgg tgaaatacat ttgcaagcag cagcagagca agcttagtgt gaccccaagc | 360 |
| gacaggaccg ccgagctcaa cagctaccca cgcttcagtg actggctgta catcttcaac | 420 |
| gtgaggcctg aggtggtgca ggagatcccc caagagctca cactggatgc tctgctggag | 480 |
| atggacgagg ccaaagccaa ggagatgctg cggcgctggg gggccagcac ggaggagtgc | 540 |
| agccgcctac agcaagccct tacctgcctt cggaaggtga ctggcctggg aggggagcac | 600 |
| aaaatggact caggttggag ttcaacagat gctcgagaca gtagcttggg gcctcccatg | 660 |
| gacatgcttt cctcgctggg cagagcgggt gccagcactc agggaccccg ttccatctcc | 720 |
| gtgtccgccc tgcctgcctc agactctccg gtcccggcc tcagtgaggg cctctcggac | 780 |
| tcctgtatcc ccttgcacac cagcggccgg ctgacccccc gggccctgca cagcttcatc | 840 |
| acgccccta ccacacccca gctacgacgg cacgccaagc tgaagccacc aaggacaccc | 900 |
| ccaccgccaa gccgcaaggt cttccagctg ctccccagct tccccacact cacacggagc | 960 |
| aagtcccacg agtcccagct gggaaaccga atcgacgacg tcaccccgat gaagtttgaa | 1020 |
| ctccctcatg gatccccaca gctggtacga agggatatcg gctctcggt gacgcacagg | 1080 |
| ttctccacaa agtcatggtt gtcacaggtg tgcaacgtgt gccagaagag catgatttt | 1140 |
| ggcgtgaagt gcaaacactg caggttaaaa tgccataaca agtgcacaaa ggaagctccc | 1200 |
| gcctgcagga tcaccttcct cccactggcc aggcttcgga ggacagagtc tgtcccgtca | 1260 |
| gatatcaaca acccagtgga cagagcagca gagccccatt ttggaaccct tcccaaggcc | 1320 |
| ctgacaaaga aggagcaccc tccagccatg aacctggact ccagcagcaa cccatcctcc | 1380 |
| accacgtcct ccacacccct catcgccggca ccttttcctga cctcatctaa tccctccagt | 1440 |
| gccaccacgc ctcccaaccc gtcacctggc cagcgggaca gcaggttcag cttcccagac | 1500 |
| atttcagcct gttctcaggc agccccgctg tccagcacag ccgacagtac acggctcgac | 1560 |
| gaccagccca aaacagatgt gctaggtgtt cacgaagcag aggctgagga gcctgaggct | 1620 |
| ggcaagtcag aggcagagga tgacgaggag gatgaggtgg acgacctccc cagctcccgc | 1680 |
| cggccctgga ggggccccat ctctcgaaag gccagccaga ccagcgttta cctgcaagag | 1740 |
| tgggacatcc cctttgaaca ggtggaactg ggcgagccca ttggacaggg tcgctggggc | 1800 |
| cgggtgcacc gaggccgttg gcatggcgag gtggccattc ggctgctgga gatggacggc | 1860 |
| cacaatcagg accacctgaa gctgttcaag aaagaggtga tgaactaccg gcagacgcgg | 1920 |
| catgagaacg tggtgctctt catgggggcc tgcatgaacc cacctcacct ggccattatc | 1980 |
| accagcttct gcaaggggcg gacattgcat tcattcgtga gggacccaa gacgtctctg | 2040 |
| gacatcaata agactaggca gatcgcccag gagatcatca agggcatggg ttatcttcat | 2100 |
| gcaaaaggca tcgtgcacaa ggacctcaag tccaagaatg tcttctatga caacggcaaa | 2160 |
| gtggtcatca cagacttcgg gctgtttggg atctcgggtg tggtccgaga ggaacgcgc | 2220 |
| gagaaccaac tgaaactgtc acatgactgg ctgtgctacc tggccccga gatcgtacga | 2280 |
| gaaatgatcc cggggcggga cgaggaccag ctgcccttct ccaaagcagc cgatgtctat | 2340 |
| gcattcggga ctgtgtggta tgaactacag gcaagagact ggcccttaa gcaccagcct | 2400 |
| gctgaggcct tgatctggca gattggaagt ggggaaggag tacggcgcgt cctggcatcc | 2460 |

-continued

```
gtcagcctgg ggaaggaagt cggcgagatc ctgtctgcct gctgggcttt cgatctgcag      2520
gagagaccca gcttcagcct gctgatggac atgctggaga ggctgcccaa gctgaaccgg      2580
cggctctccc accctgggca cttttggaag tcggctgaca ttaacagcag caaagtcatg      2640
ccccgctttg aaaggtttgg cctggggacc ctggagtccg gtaatccaaa gatgtagcca      2700
gccctgcacg ttcatgcaga gagtgtcttc ctttcgaaaa catgatcacg aaacatgcag      2760
accaccacct caaggaatca gaagcattgc atcccaagct gcggactggg agcgtgtctc      2820
ctccctaaag gacgtgcgtg cgtgcgtgcg tgcgtgcgtg cgtgcgtgcg tcaccaaggt      2880
gtgtggagct caggatcgca gccatacacg caactccaga tgataccact accgccagtg      2940
tttacacaga ggtttctgcc tggcaagctt ggtattttac agtaggtgaa gatcattctg      3000
cagaagggtg ctggcacagt ggagcagcac ggatgtcccc agcccccgtt ctggaagacc      3060
ctacagctgt gagaggccca gggttgagcc agatgaaaga aaagctgcgt gggtgtgggc      3120
tgtacccgga aaagggcagg tggcaggagg tttgccttgg cctgtgcttg ggccgagaac      3180
cacactaagg agcagcagcc tgagttagga atctatctgg attacgggga tcagagttcc      3240
tggagagtgg actcagtttc tgctctgatc caggcctgtt gtgcttttt tttttccccc       3300 ttaaaaaaaa aaaagtacag acagaatctc agcggcttct agactgatct gatggatctt      3360
agcccggctt ctactgcggg gggagggggg ggagggatag ccacatatct gtggagacac      3420
ccacttcttt atctgaggcc tccaggtagg cacaaaggct gtggaactca gcctctatca      3480
tcagacaccc ccccccaatg cctcattgac ccccttcccc cagagccaag ggctagccca      3540
tcgggtgtgt gtacagtaag ttcttggtga aggagaacag ggacgttggc agaagcagtt      3600
tgcagtggcc ctagcatctt aaaacccatt gtctgtcaca ccagaaggtt ctagacctac      3660
caccacttcc cttccccatc tcatggaaac ctttttagcc cattctgaccc ctgtgtgtgc     3720 tctgagctca gatcgggtta tgagaccgcc caggcacatc agtcagggag gctctgatgt      3780
gagccgcaga cctctgtgtt cattcctatg agctggaggg gctggactgg gtggggtcag      3840
atgtgcttgg caggaactgt cagctgctga gcagggtggt ccctgagcgg aggataagca      3900
gcatcagact ccacaaccag aggaagaaag aaatggggat ggagcggaga cccacgggct      3960
gagtcccgct gtggagtggc cttgcagctc cctctcagtt aaaactccca gtaaagccac      4020
agttctccga gcacccaagt ctgctccagc cgtctcttaa acaggccac tctctgagaa       4080 ggaattc                                                               4087
```

<210> SEQ ID NO 15
<211> LENGTH: 739
<212> TYPE: PRT
<213> ORGANISM: Drosophila melanogaster

<400> SEQUENCE: 15

```
Met Ser Ser Glu Ser Ser Thr Glu Gly Asp Ser Asp Leu Tyr Asp Pro
1               5                   10                  15

Leu Ala Glu Glu Leu His Asn Val Gln Leu Val Lys His Val Thr Arg
                20                  25                  30

Glu Asn Ile Asp Ala Leu Asn Ala Lys Phe Ala Asn Leu Gln Glu Pro
            35                  40                  45

Pro Ala Met Tyr Leu Ile Glu Tyr Gln Glu Leu Thr Ser Lys Leu His
        50                  55                  60

Glu Leu Glu Ala Lys Glu Gln Glu Leu Met Glu Arg Leu Asn Ser Gln
65                  70                  75                  80
```

```
Asp Gln Gln Glu Asp Ser Ser Leu Val Glu Arg Phe Lys Glu Gln Pro
                85                  90                  95
His Tyr Gln Asn Gln Thr Gln Ile Leu Gln Gln Gln Arg Gln Leu Ala
            100                 105                 110
Arg Val His His Gly Asn Asp Leu Thr Asp Ser Leu Gly Ser Gln Pro
        115                 120                 125
Gly Ser Gln Cys Gly Thr Leu Thr Arg Gln Pro Lys Ile Leu Leu Arg
130                 135                 140
Ala His Leu Pro Asn Gln Gln Arg Thr Ser Val Glu Val Ile Ser Gly
145                 150                 155                 160
Val Arg Leu Cys Asp Ala Leu Met Lys Ala Leu Lys Leu Arg Gln Leu
                165                 170                 175
Thr Pro Asp Met Cys Glu Val Ser Thr Thr His Ser Gly Arg His Ile
            180                 185                 190
Ile Pro Trp His Thr Asp Ile Gly Thr Leu His Val Glu Glu Ile Phe
        195                 200                 205
Val Arg Leu Leu Asp Lys Phe Pro Ile Arg Thr His Ile Lys His Gln
    210                 215                 220
Ile Ile Arg Lys Thr Phe Phe Ser Leu Val Phe Cys Glu Gly Cys Arg
225                 230                 235                 240
Arg Leu Leu Phe Thr Gly Phe Tyr Cys Ser Gln Cys Asn Phe Arg Phe
                245                 250                 255
His Gln Arg Cys Ala Asn Arg Val Pro Met Leu Cys Gln Pro Phe Pro
            260                 265                 270
Met Asp Ser Tyr Tyr Gln Leu Leu Leu Ala Glu Asn Pro Asp Asn Gly
        275                 280                 285
Val Gly Phe Pro Gly Arg Gly Thr Ala Val Arg Phe Asn Met Ser Ser
    290                 295                 300
Arg Ser Arg Ser Arg Arg Cys Ser Ser Ser Gly Ser Ser Ser Ser Ser
305                 310                 315                 320
Lys Pro Pro Ser Ser Ser Gly Asn His Arg Gln Gly Arg Pro Pro Pro
                325                 330                 335
Arg Ile Ser Gln Asp Asp Arg Ser Asn Ser Ala Pro Asn Val Cys Ile
            340                 345                 350
Asn Asn Ile Arg Ser Val Thr Ser Glu Val Gln Arg Ser Leu Ile Met
        355                 360                 365
Gln Ala Arg Pro Pro Leu Pro His Pro Cys Thr Asp His Ser Asn Ser
    370                 375                 380
Thr Gln Ala Ser Pro Thr Ser Thr Leu Lys His Asn Arg Pro Arg Ala
385                 390                 395                 400
Arg Ser Ala Asp Glu Ser Asn Lys Asn Leu Leu Leu Arg Asp Ala Lys
                405                 410                 415
Ser Ser Glu Glu Asn Trp Asn Ile Leu Ala Glu Glu Ile Leu Ile Gly
            420                 425                 430
Pro Arg Ile Gly Ser Gly Ser Phe Gly Thr Val Tyr Arg Ala His Trp
        435                 440                 445
His Gly Pro Val Ala Val Lys Thr Leu Asn Val Lys Thr Pro Ser Pro
    450                 455                 460
Ala Gln Leu Gln Ala Phe Lys Asn Glu Val Ala Met Leu Lys Lys Thr
465                 470                 475                 480
Arg His Cys Asn Ile Leu Leu Phe Met Gly Cys Val Ser Lys Pro Ser
                485                 490                 495
```

-continued

```
Leu Ala Ile Val Thr Gln Trp Cys Glu Gly Ser Ser Leu Tyr Lys His
                500                 505                 510

Val His Val Ser Glu Thr Lys Phe Lys Leu Asn Thr Leu Ile Asp Ile
            515                 520                 525

Gly Arg Gln Val Ala Gln Gly Met Asp Tyr Leu His Ala Lys Asn Ile
        530                 535                 540

Ile His Arg Asp Leu Lys Ser Asn Asn Ile Phe Leu His Glu Asp Leu
545                 550                 555                 560

Ser Val Lys Ile Gly Asp Phe Gly Leu Ala Thr Ala Lys Thr Arg Trp
                565                 570                 575

Ser Gly Glu Lys Gln Ala Asn Gln Pro Thr Gly Ser Ile Leu Trp Met
            580                 585                 590

Ala Pro Glu Val Ile Arg Met Gln Glu Leu Asn Pro Tyr Ser Phe Gln
        595                 600                 605

Ser Asp Val Tyr Ala Phe Gly Ile Val Met Tyr Glu Leu Leu Ala Glu
610                 615                 620

Cys Leu Pro Tyr Gly His Ile Ser Asn Lys Asp Gln Ile Leu Phe Met
625                 630                 635                 640

Val Gly Arg Gly Leu Leu Arg Pro Asp Met Ser Gln Val Arg Ser Asp
                645                 650                 655

Ala Pro Gln Ala Leu Lys Arg Leu Ala Glu Asp Cys Ile Lys Tyr Thr
            660                 665                 670

Pro Lys Asp Arg Pro Leu Phe Arg Pro Leu Leu Asn Met Leu Glu Asn
        675                 680                 685

Met Leu Arg Thr Leu Pro Lys Ile His Arg Ser Ala Ser Glu Pro Asn
690                 695                 700

Leu Thr Gln Ser Gln Leu Gln Asn Asp Glu Phe Leu Tyr Leu Pro Ser
705                 710                 715                 720

Pro Lys Thr Pro Val Asn Phe Asn Asn Phe Gln Phe Phe Gly Ser Ala
                725                 730                 735

Gly Asn Ile

<210> SEQ ID NO 16
<211> LENGTH: 3420
<212> TYPE: DNA
<213> ORGANISM: Drosophila melanogaster

<400> SEQUENCE: 16
cacttgtata tggttagttg attaatagca cgtcagaaac taatttacct gttgccgctc      60
gtaccagatc cagatttgta ctatcccgag aagttaaaag ctctaggcaa attacaatt     120 agccgcgaca caaccccgt ttcgcagagc acctgatacc ctttatcgtt atcgattggt     180
acagccgaat cacgcctcct gataacgatt aaacaaaaag tcgaaatgta gtaaaattcg     240
cggaaagtaa ataaattgtt atagccaagg tgaaataacg agcggccagc tagtggcgat     300
actgatactg ttgcgaacgt tgggcagcca ccgacggtgc cggctggtca ggttgttatc     360
gggtaattgg cagctccttt ggaaaatcct caagttcagc tgcttctgca cacactgacc     420
ttcattatac atacataccg tatatacgag ctgtttgtgt gcgtgtgtgt gtgtgcgctt     480
gcaagtgtgt gggtgcactg aaaaaaggtt ggaaaggata caagccagaa atcagtgaaa     540
accgggaata ttgcatcccg agacggcgg aaaagccgaa aaagcccatt aaaagtcaag     600
gacgacatgc tgccctccgc ccacagaagt ggatgtgggt ggctcaccca ttagaactcc     660
accaaaacgc aagcgcagga gttttccctt caagaagtca aggcttcttc gttttcgggg     720
```

```
tcatggtcac agcgcatagt atataggata aagcaacacc atgtccagcg agtcctccac    780
cgaaggcgac agcgatctat acgatccttt ggccgaggag ctgcacaacg tccagttggt    840
caaacatgtg acccgcgaga atattgatgc cctgaatgcc aagttTgcca acctgcagga    900
gccaccagcc atgtacttaa tagaatacca ggagttgacc tccaagctcc acgaactgga    960
ggccaaggag caggaactaa tggagcgact gaactcgcag gaccagcagg aggactcctc   1020
cttggtcgag cggttcaagg agcagcccca ctatcaaaat caaactcaaa tcctgcagca   1080
acaacggcaa ttggcgcgag tgcaccacgg caacgatcta accgatagct tgggctctca   1140
gccgggcagc caatgtggaa ctttgacccg tcagcccaag atccttttgc gagcccacct   1200
gcccaatcaa cagcgcactt cagtggaggt aatttcggga gtacgactat gtgatgccct   1260
catgaaggcc ctgaaactcc ggcaactaac gccggatatg tgcgaagtaa gcacaactca   1320
ttccggaaga catatcatac cctggcacac ggatatcggc actctgcatg tggaggagat   1380
cttTgtcagg ctgctggata agtttcccat taggacacac atcaagcacc agatcatacg   1440
gaagaccttc ttctcgttgg tattctgcga gggctgtcga aggcttctgt tcaccgggtt   1500
ctactgtagc cagtgtaatt ttcgattcca tcagaggtgt gccaatagag tgccgatgct   1560
gtgccagccc tttcccatgg atagctacta tcagctactg ctggccgaga tccggataa   1620
tggcgttggt ttccccggca gaggcactgc tgtccgcttc aatatgagca gccggagtcg   1680
cagtcgtcgt tgcagcagca gtggcagcag cagcagctcg aagccaccat cttcatcctc   1740
cggcaatcat cgacagggtc gtccgccgag gatcagccaa gacgatcgat ccaattccgc   1800
gccaaatgtg tgcatcaaca acattcgatc ggtcacaagc gaagtgcagc gcagtttgat   1860
aatgcaggcc agacctcctt tgccgcatcc gtgcacagat cactccaact ccacgcaagc   1920
gtcgcccacg agcaccttga acacaatcg tcccagggcc aggtccgccg atgagagcaa   1980
taaaaatctg ctttTaagag acgccaaaag ttccgaggaa aactggaata ttctggcgga   2040
ggagatttta attgggccgc gcatcggatc gggttccttt ggaaccgttt atcgcgccca   2100
ttggcacggt cccgtggccg taaagacact caacgtgaag acaccgagtc ccgcccagtt   2160
gcaggcgttt aagaacgagg tggccatgct gaaaaagacg cgccactgca atatcctcct   2220
cttcatgggc tgtgtatcca aaccatctct agcgattgtg acccagtggt gcgagggcag   2280
cagtctctac aagcacgtcc atgtcagcga aaccaagttT aaattgaaca cgctcatcga   2340
tatcggacgt caggtggccc agggcatgga ttacctgcat gccaagaata tcattcatag   2400
agacctcaag tcaaacaaca tcttTTtgca cgaggatctt tccgtgaaga taggcgactt   2460
cggattggcc actgcgaaaa ctcgatggtc gggtgaaaag caagccaatc aacccacggg   2520
cagtatttta tggatggctc cagaggtgat tcgcatgcag gagctaaacc cctactcctt   2580
ccagtcggac gtttatgcct ttggtatcgt gatgtacgaa ctgttggcgg agtgcttgcc   2640
ctacggtcat attagcaaca aggatcagat cctgtttatg gtggggcgag gacttctgcg   2700
tccggacatg agtcaagtgc gctcggatgc gccgcaggca ttgaagcgct ggccgagga   2760
ttgcattaag tatacccca aggatcgacc gctctcttagg ccgctgctca atatgctgga   2820
gaacatgctg cgcactttgc ccaaaattca tcgcagtgcc agtgaaccaa acttgacgca   2880
atcgcagctg cagaacgatg agtttctgta tctgcccagc ccgaaaacgc cggtgaactt   2940
caacaacttt cagttcttcg gcagcgctgg gaatatctag acagcgacct gtacctgtac   3000
ttacatatat cctgcgtgat caacgtgatc ctacatctat atactttttg ttcttgtccc   3060
tctgtacata agcgattcgc gaaggggacg gctttggttg tccaccaaag tgaaagagag   3120
```

-continued

```
agagagagag agaaagagag agagatgggt tgcctgccga cccgggagcg aaacttgctt    3180
ctttccttgg aactgacaaa gtgcatttct gttaccacac acaaaacgac tacaaactgt    3240
aaactaaact gcaacgccca tgtgtacata actgcatcat aacttatata cgttaggcaa    3300
gactactgaa actaaactaa actaaactaa actagctgat cgcaattaca ttatacacat    3360
tatacttata ctacaagaga tggtgttgtt tctggagtcg agcacgatga agaacattta    3420

<210> SEQ ID NO 17
<211> LENGTH: 966
<212> TYPE: PRT
<213> ORGANISM: Drosophila melanogaster

<400> SEQUENCE: 17

Met Ser Ser Asn Asn Asn Ala Pro Ala Ser Ala Pro Asp Thr Gly Ser
1               5                   10                  15

Thr Asn Ala Asn Asp Pro Ile Ser Gly Ser Leu Ser Val Asp Ser Asn
                20                  25                  30

Leu Val Ile Ile Gln Asp Met Ile Asp Leu Ser Ala Asn His Leu Glu
            35                  40                  45

Gly Leu Arg Thr Gln Cys Ala Ile Ser Ser Thr Leu Thr Gln Gln Glu
        50                  55                  60

Ile Arg Cys Leu Glu Ser Lys Leu Val Arg Tyr Phe Ser Glu Leu Leu
65                  70                  75                  80

Leu Ala Lys Met Arg Leu Asn Glu Arg Ile Pro Ala Asn Gly Leu Val
                85                  90                  95

Pro His Thr Thr Gly Asn Glu Leu Arg Gln Trp Leu Arg Val Val Gly
            100                 105                 110

Leu Ser Gln Gly Thr Leu Thr Ala Cys Leu Ala Arg Leu Thr Thr Leu
        115                 120                 125

Glu Gln Ser Leu Arg Leu Ser Asp Glu Glu Ile Arg Gln Leu Leu Ala
    130                 135                 140

Asp Ser Pro Ser Gln Arg Glu Glu Glu Leu Arg Arg Leu Thr Arg
145                 150                 155                 160

Ala Met Gln Asn Leu Arg Lys Cys Met Glu Ser Leu Glu Ser Gly Thr
                165                 170                 175

Ala Ala Ser Asn Asn Asp Pro Glu Gln Trp His Trp Asp Ser Trp Asp
            180                 185                 190

Arg Pro Thr His Ile His Arg Gly Ser Val Gly Asn Ile Gly Leu Gly
        195                 200                 205

Asn Asn Ser Thr Ala Ser Pro Arg Thr His His Arg Gln His Gly Val
    210                 215                 220

Lys Gly Lys Asn Ser Ala Leu Ala Asn Ser Thr Asn Phe Lys Ser Gly
225                 230                 235                 240

Arg Gln Ser Pro Ser Ala Thr Glu Glu Leu Asn Ser Thr Gln Gly Ser
                245                 250                 255

Gln Leu Thr Leu Thr Leu Thr Pro Ser Pro Pro Asn Ser Pro Phe Thr
            260                 265                 270

Pro Ser Ser Gly Leu Ser Ser Ser Leu Asn Gly Thr Pro Gln Arg Ser
        275                 280                 285

Arg Gly Thr Pro Pro Ala Arg Lys His Gln Thr Leu Leu Ser Gln
    290                 295                 300

Ser His Val Gln Val Asp Gly Glu Gln Leu Ala Arg Asn Arg Leu Pro
305                 310                 315                 320
```

-continued

Thr Asp Pro Ser Pro Asp Ser His Ser Ser Thr Ser Ser Asp Ile Phe
                325                 330                 335

Val Asp Pro Asn Thr Asn Ala Ser Ser Gly Gly Ser Ser Ser Asn Val
            340                 345                 350

Leu Met Val Pro Cys Ser Pro Gly Val Gly His Val Gly Met Gly His
        355                 360                 365

Ala Ile Lys His Arg Phe Thr Lys Ala Leu Gly Phe Met Ala Thr Cys
370                 375                 380

Thr Leu Cys Gln Lys Gln Val Phe His Arg Trp Met Lys Cys Thr Asp
385                 390                 395                 400

Cys Lys Tyr Ile Cys His Lys Ser Cys Ala Pro His Val Pro Pro Ser
                405                 410                 415

Cys Gly Leu Pro Arg Glu Tyr Val Asp Glu Phe Arg His Ile Lys Glu
            420                 425                 430

Gln Gly Gly Tyr Ala Ser Leu Pro His Val His Gly Ala Ala Lys Gly
        435                 440                 445

Ser Pro Leu Val Lys Lys Ser Thr Leu Gly Lys Pro Leu His Gln Gln
    450                 455                 460

His Gly Asp Ser Ser Ser Pro Ser Ser Ser Cys Thr Ser Ser Thr Pro
465                 470                 475                 480

Ser Ser Pro Ala Leu Phe Gln Gln Arg Glu Arg Glu Leu Asp Gln Ala
                485                 490                 495

Gly Ser Ser Ser Ser Ala Asn Leu Leu Pro Thr Pro Ser Leu Gly Lys
            500                 505                 510

His Gln Pro Ser Gln Phe Asn Phe Pro Asn Val Thr Val Thr Ser Ser
        515                 520                 525

Gly Gly Ser Gly Gly Val Ser Leu Ile Ser Asn Glu Pro Val Pro Glu
    530                 535                 540

Gln Phe Pro Thr Ala Pro Ala Thr Ala Asn Gly Gly Leu Asp Ser Leu
545                 550                 555                 560

Val Ser Ser Ser Asn Gly His Met Ser Ser Leu Ile Gly Ser Gln Thr
                565                 570                 575

Ser Asn Ala Ser Thr Ala Ala Thr Leu Thr Gly Ser Leu Val Asn Ser
            580                 585                 590

Thr Thr Thr Thr Ser Thr Cys Ser Phe Phe Pro Arg Lys Leu Ser Thr
        595                 600                 605

Ala Gly Val Asp Lys Arg Thr Pro Phe Thr Ser Glu Tyr Thr Asp Thr
    610                 615                 620

His Lys Ser Asn Asp Ser Asp Lys Thr Val Ser Leu Ser Gly Ser Ala
625                 630                 635                 640

Ser Thr Asp Ser Asp Arg Thr Pro Val Arg Val Asp Ser Thr Glu Asp
                645                 650                 655

Gly Asp Ser Gly Gln Trp Arg Gln Asn Ser Ile Ser Leu Lys Glu Trp
            660                 665                 670

Asp Ile Pro Tyr Gly Asp Leu Leu Leu Glu Arg Ile Gly Gln Gly
        675                 680                 685

Arg Phe Gly Thr Val His Arg Ala Leu Trp His Gly Asp Val Ala Val
    690                 695                 700

Lys Leu Leu Asn Glu Asp Tyr Leu Gln Asp His Met Leu Glu Thr
705                 710                 715                 720

Phe Arg Ser Glu Val Ala Asn Phe Lys Asn Thr Arg His Glu Asn Leu
                725                 730                 735

Val Leu Phe Met Gly Ala Cys Met Asn Pro Pro Tyr Leu Ala Ile Val

```
                    740                 745                 750
Thr Ser Leu Cys Lys Gly Asn Thr Leu Tyr Thr Tyr Ile His Gln Arg
        755                 760                 765

Arg Glu Lys Phe Ala Met Asn Arg Thr Leu Leu Ile Ala Gln Gln Ile
        770                 775                 780

Ala Gln Gly Met Gly Tyr Leu His Ala Arg Glu Ile Ile His Lys Asp
785                 790                 795                 800

Leu Arg Thr Lys Asn Ile Phe Ile Glu Asn Gly Lys Val Ile Ile Thr
                805                 810                 815

Asp Phe Gly Leu Phe Ser Ser Thr Lys Leu Leu Tyr Cys Asp Met Gly
                820                 825                 830

Leu Gly Val Pro His Asn Trp Leu Cys Tyr Leu Ala Pro Glu Leu Ile
                835                 840                 845

Arg Ala Leu Gln Pro Glu Lys Pro Arg Gly Glu Cys Leu Glu Phe Thr
        850                 855                 860

Pro Tyr Ser Asp Val Tyr Ser Phe Gly Thr Val Trp Tyr Glu Leu Ile
865                 870                 875                 880

Cys Gly Glu Phe Thr Phe Lys Asp Gln Pro Ala Glu Ser Ile Ile Trp
                885                 890                 895

Gln Val Gly Arg Gly Met Lys Gln Ser Leu Ala Asn Leu Gln Ser Gly
                900                 905                 910

Arg Asp Val Lys Asp Leu Leu Met Leu Cys Trp Thr Tyr Glu Lys Glu
                915                 920                 925

His Arg Pro Gln Phe Ala Arg Leu Leu Ser Leu Leu Glu His Leu Pro
        930                 935                 940

Lys Lys Arg Leu Ala Arg Ser Pro Ser His Pro Val Asn Leu Ser Arg
945                 950                 955                 960

Ser Ala Glu Ser Val Phe
                965
```

<210> SEQ ID NO 18
<211> LENGTH: 3737
<212> TYPE: DNA
<213> ORGANISM: Drosophila melanogaster

<400> SEQUENCE: 18

```
cttgggtgta gagaaatttc aacaacagcc gaggaacttg tacaaattat tgcttttcg       60
cattgcctaa gccgtttaga gttgcgggcg ttagcgtgcg cgatagccgg agcaccgaac     120
gtcaaggtcg cttggcgagg ccacaatgc ggggcggagt cccagccatt ggtcccatcg      180
aatcgtcgag tccccgaggg ggcgtctgaa aaaatcaatc gggctccact ccgtcgcgaa     240
taagcaggat gagcagcaac aacaacgcac ccgcatcggc tccagacacg ggctccacca     300
atgccaacga tcccatctcc ggttcgctgt ccgtagacag caacctggtt atcattcagg     360
acatgattga tctctcggcc aaccatctgg agggcctgcg aacgcagtgc gcgatcagct     420
ccacgctgac gcagcaggag attcgttgcc tggagtcgaa gctggtgcga tacttctccg     480
agctgctgct ggcgaagatg cggctaaatg agcgcatccc ggccaacggg cttgtgcccc     540
acacaacggg caacgaactg aggcaatggc tgcgcgtagt gggccttagc cagggggactc    600
ttaccgcctg ccttgctcgc ctgaccactc tagagcaaag cctgcgtctc agcgacgagg     660
agatccgtca actcctggct gacagcccca gccagcgaga ggaggaggaa ctgcgacgcc     720
tgaccagggc catgcagaac ttaaggaagt gcatggagtc gctggagagc ggtactgcgg     780
ctagcaacaa cgatccagag cagtggcact gggactcctg ggacaggccc acccacattc     840
```

```
atcgcggcag tgtgggaaac attggactgg gtaacaattc aaccgcctcc ccgagaaccc    900
atcatcgcca gcatggtgtc aagggaaaga attccgctct ggccaactcc accaacttca    960
aaagtggccg ccaatcgccc tcagcgacag aagagctgaa cagcacacag ggttcccagc   1020
tgactttaac ccttacgccc tcgccaccca attcgccctt cacgccttcc agtgggctga   1080
gcagcagcct taatggaaca ccacagagga gtcgtggtac cccgccgcca gctagaaagc   1140
accagacctt gctgagccag agtcatgtgc aagtggacgg ggagcaatta gcccgcaacc   1200
gtttgcccac tgatcccagc cccgatagcc acagctccac cagctcggac atctttgtgg   1260
acccaaatac taatgccagc tccggaggaa gttcctcgaa cgtgcttatg gtgccatgct   1320
ctccgggcgt gggtcacgtg ggcatgggtc atgcaatcaa gcatcgtttc accaaggccc   1380
tgggcttcat ggccacctgt accctgtgcc agaagcaggt cttccaccgc tggatgaagt   1440
gcaccgactg caagtacatc tgccacaagt catgcgcacc gcacgtaccg ccctcctgtg   1500
gacttccacg agaatatgtg gacgagtttc ggcacataaa ggagcaggga ggatacgcca   1560
gtctgccgca tgtgcatggc gcggcgaaag gatcccctt ggtaaaaaag agcaccctgg   1620
gtaagccctt gcatcagcag cacggcgata gcagttcgcc gagttccagc tgcactagtt   1680
ccacgcccag cagtccggcg ctgttccagc aaagggagcg cgagctggat caggcgggca   1740
gcagctctag cgccaatctg ttacctacgc cttcgcttgg caagcaccag ccgagtcaat   1800
tcaactttcc caacgtgacg gtgacgagca gtggcggaag cggtggtgta tcgctcatct   1860
ccaatgaacc agtgccagag caattcccca cggcgcctgc aacagccaac ggaggacttg   1920
atagtctggt gagcagctcc aacgggcaca tgagctcgct catcggtagc caaacttcaa   1980
acgcttctac tgcggccacc ttgacgggca gtctggtcaa tagcacaacc accaccagca   2040
cctgcagttt ctttccgcga aaattgagca cagccggtgt ggataagagg acgccgttca   2100
ccagcgagta cacggatacc cacaagtcaa atgacagcga caagacagtc tccttgtctg   2160
gaagtgccag cacggactcg gaccggacac ccgttcgtgt ggattcaacg aaagacggag   2220
actcgggaca atggcgccag aactcgatct cactcaagga atgggacatc ccgtatggtg   2280
atctgcttct gctcgagcgg ataggcagg acgcttcgg caccgtgcat cgagcccttt   2340
ggcacggaga tgtggcggtt aagctgctca acgaggacta tctgcaagac gaacacatgc   2400
tggagacgtt tcgcagcgag gtagccaact tcaagaacac tcgacacgag aacctggtgc   2460
tgttcatggg agcctgcatg aacccaccat atttggccat tgtgacttca ttgtgcaagg   2520
gcaacacctt gtatacgtat attcaccagc gtcgggagaa gtttgccatg aaccggactc   2580
tcctcattgc ccagcagatc gcccagggca tgggctacct gcacgcaagg gagatcatcc   2640
acaaagatct gcgcaccaag aacatcttca tcgagaacgg caaggtgatt atcacggact   2700
ttgggctgtt cagctccacc aagctgctct actgtgatat gggcctagga gtgccccaca   2760
ctggttgtg ctacctggcg ccggagctaa tccgagcatt gcagcggag aagccgcgtg   2820
gagagtgtct ggagttcacc ccatactccg atgtctactc tttcggaacc gtttggtacg   2880
agctaatctg cggcgagttc acattcaagg atcagccggc ggaatcgatc atctggcagg   2940
ttggccgtgg gatgaagcag tcgctggcca acctgcagtc tggacgggat gtcaaggact   3000
tgctgatgct gtgctggacc tacgagaagg agcaccggcc gcagttcgca cgcctgctct   3060
ccctgctgga gcatcttccc aagaagcgtg tggcgcgcag tccctcccac cccgtcaacc   3120
tttcccgttc cgccgagtcc gtgttctgag ggaactgcag catggccact gtcactgtct   3180
```

```
agtacaattt cgatctacca actaagctag ctcgctttgt gccctcgtcc actctacaca    3240
aactctctcc caaggcgaag ttctatcgag ccgagcgaag attgtaaata cataaacgta    3300
actaccaaat tatagcaatc cattttaaaa actacataca tatgtgtagg catgtatcgg    3360
gagcactcca gttgcagttg ttagcaaacg aaacaaaggc aaatcaaatg ttaactcgaa    3420
aaagacaaaa cgcttaaatg tttaagagca gaggcaaaca gagaaggcat agacatacat    3480
atacaaacaa acaaacaagc actgtggcaa acataaatgt aaacgttaat caggtgagca    3540
atttctaaat tgttaattat gtgtaagaga actatatata tatatatata tatatatata    3600
tatatatata tatatataca tgtatataca gcagcaatgt attgtatatg acggactagt    3660
gttaaattaa atatatattg tgaattatgt atggtcaagt gtatatagta aatggacttt    3720
aaatgcgaaa tcgaaac                                                   3737
```

<210> SEQ ID NO 19
<211> LENGTH: 63
<212> TYPE: DNA
<213> ORGANISM: Homo sapiens

<400> SEQUENCE: 19

```
aagatgagca agatggtaa aaagaagaaa aagaagtcaa agacaaagtg tgtaattatg     60
taa                                                                  63
```

<210> SEQ ID NO 20
<211> LENGTH: 20
<212> TYPE: PRT
<213> ORGANISM: Homo sapiens

<400> SEQUENCE: 20

```
Lys Met Ser Lys Asp Gly Lys Lys Lys Lys Lys Ser Lys Thr Lys
1               5                   10                  15

Cys Val Ile Met
            20
```

<210> SEQ ID NO 21
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca cectgagcta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cccccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgttca cccagtccgc cctgagcaaa gaccccaacg agaagcgcga tcacatggtc    660
```

```
ctgctggagt cgtgaccgc cgccgggatc actctcggca tggacgagct gtacaaggga    720
tccgcctag                                                           729
```

<210> SEQ ID NO 22
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Val Ser Lys Gly Glu Glu Leu Phe Thr Gly Val Val Pro Ile Leu
1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Phe Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Ala
```

<210> SEQ ID NO 23
<211> LENGTH: 945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgaccagca aggtgtacga ccccgagcag aggaagagga tgatcaccgg cccccagtgg    60
tgggccaggt gcaagcagat gaacgtgctg gacagcttca tcaactacta cgacagcgag   120
aagcacgccg agaacgccgt gatcttcctg cacggcaacg ccactagcag ctacctgtgg   180
```

```
aggcacgtgg tgccccacat cgagcccgtg gccaggtgca tcatccccga tctgatcggc    240
atgggcaaga gcggcaagag cggcaacggc agctacaggc tgctggacca ctacaagtac    300
ctgaccgcct ggttcgagct cctgaacctg cccaagaaga tcatcttcgt gggccacgac    360
tggggcgccg cactggcctt ccactacagc tacgagcacc aggacaagat caaggccatc    420
gtgcacgccg agagcgtggt tgacgtgatc gagagctggg acgagtggcc agacatcgag    480
gaggacatcg ccctgatcaa gagcgaggag ggcgagaaga tggtgctgga gaacaacttc    540
ttcgtggaga ccgttctgcc cagcaagatc atgagaaagc tggagcccga ggagttcgcc    600
gcctacctgg agcccttcaa ggagaagggc gaggtgagaa gacccaccct gagctggccc    660
agagagatcc ccctggtgaa gggcggcaag cccgacgtgg tgcagatcgt gagaaactac    720
aacgcctacc tgagagccag cgacgacctg cccaagatgt tcatcgagag cgaccccggc    780
ttcttcagca acgccatcgt ggagggcgcc aagaagttcc ccaacaccga gttcgtgaag    840
gtgaagggcc tgcacttcag ccaggaggac gcccccgacg agatgggcaa gtacatcaag    900
agcttcgtgg agagagtgct gaagaacgag cagggatccg cctag                   945
```

<210> SEQ ID NO 24
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Met Phe Ile Glu
            245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln Gly Ser Ala
305                 310

<210> SEQ ID NO 25
<211> LENGTH: 960
<212> TYPE: DNA
<213> ORGANISM: Homo sapiens

<400> SEQUENCE: 25
atggatgatt gggagattcc tgatgggcag attacagtgg gacaaagaat tggatctgga      60
tcatttggaa cagtctacaa gggaaagtgg catggtgatg tggcagtgaa atgttgaat     120
gtgacagcac ctacacctca gcagttacaa gccttcaaaa atgaagtagg agtactcagg     180
aaaacacgac atgtgaatat cctactcttc atgggctatt ccacaaagcc acaactggct     240
attgttaccc agtggtgtga gggctccagc ttgtatcacc atctccatat cattgagacc     300
aaatttgaga tgatcaaact tatagatatt gcacgacaga ctgcacaggg catggattac     360
ttacacgcca gtcaatcat ccacagagac ctcaagagta ataatatatt tcttcatgaa     420
gacctcacag taaaaatagg tgattttggt ctagctacag tgaaatctcg atggagtggg     480
tcccatcagt ttgaacagtt gtctggatcc attttgtgga tggcaccaga agtcatcaga     540
atgcaagata aaaatccata cagctttcag tcagatgtat atgcatttgg aattgttctg     600
tatgaattga tgactggaca gttaccttat tcaaacatca caacaggga ccagataatt     660
tttatggtgg gacgaggata cctgtctcca gatctcagta aggtacggag taactgtcca     720
aaagccatga agagattaat ggcagagtgc ctcaaaaaga aagagatga gagaccactc     780
tttccccaaa ttctcgcctc tattgagctg ctggcccgct cattgccaaa aattcaccgc     840
agtgcatcag aaccctcctt gaatcgggct ggtttccaaa cagaggattt tagtctatat     900
gcttgtgctt ctccaaaaac acccatccag gcaggggat atggtgcgtt tcctgtccac     960

<210> SEQ ID NO 26
<211> LENGTH: 320
<212> TYPE: PRT
<213> ORGANISM: Homo sapiens

<400> SEQUENCE: 26

Met Asp Asp Trp Glu Ile Pro Asp Gly Gln Ile Thr Val Gly Gln Arg
1               5                   10                  15

Ile Gly Ser Gly Ser Phe Gly Thr Val Tyr Lys Gly Lys Trp His Gly
            20                  25                  30

Asp Val Ala Val Lys Met Leu Asn Val Thr Ala Pro Thr Pro Gln Gln
        35                  40                  45

Leu Gln Ala Phe Lys Asn Glu Val Gly Val Leu Arg Lys Thr Arg His
    50                  55                  60

Val Asn Ile Leu Leu Phe Met Gly Tyr Ser Thr Lys Pro Gln Leu Ala

|    |     |     |     | 65  |     |     |     | 70  |     |     |     | 75  |     |     |     | 80  |
|----|-----|-----|-----|-----|-----|-----|-----|-----|-----|-----|-----|-----|-----|-----|-----|-----|
| Ile | Val | Thr | Gln | Trp | Cys | Glu | Gly | Ser | Ser | Leu | Tyr | His | His | Leu | His |

Ile Val Thr Gln Trp Cys Glu Gly Ser Ser Leu Tyr His His Leu His
                    85                  90                  95
Ile Ile Glu Thr Lys Phe Glu Met Ile Lys Leu Ile Asp Ile Ala Arg
                100                 105                 110
Gln Thr Ala Gln Gly Met Asp Tyr Leu His Ala Lys Ser Ile Ile His
                115                 120                 125
Arg Asp Leu Lys Ser Asn Asn Ile Phe Leu His Glu Asp Leu Thr Val
130                 135                 140
Lys Ile Gly Asp Phe Gly Leu Ala Thr Val Lys Ser Arg Trp Ser Gly
145                 150                 155                 160
Ser His Gln Phe Glu Gln Leu Ser Gly Ser Ile Leu Trp Met Ala Pro
                    165                 170                 175
Glu Val Ile Arg Met Gln Asp Lys Asn Pro Tyr Ser Phe Gln Ser Asp
                180                 185                 190
Val Tyr Ala Phe Gly Ile Val Leu Tyr Glu Leu Met Thr Gly Gln Leu
                195                 200                 205
Pro Tyr Ser Asn Ile Asn Asn Arg Asp Gln Ile Ile Phe Met Val Gly
210                 215                 220
Arg Gly Tyr Leu Ser Pro Asp Leu Ser Lys Val Arg Ser Asn Cys Pro
225                 230                 235                 240
Lys Ala Met Lys Arg Leu Met Ala Glu Cys Leu Lys Lys Lys Arg Asp
                    245                 250                 255
Glu Arg Pro Leu Phe Pro Gln Ile Leu Ala Ser Ile Glu Leu Leu Ala
                260                 265                 270
Arg Ser Leu Pro Lys Ile His Arg Ser Ala Ser Glu Pro Ser Leu Asn
                275                 280                 285
Arg Ala Gly Phe Gln Thr Glu Asp Phe Ser Leu Tyr Ala Cys Ala Ser
                290                 295                 300
Pro Lys Thr Pro Ile Gln Ala Gly Gly Tyr Gly Ala Phe Pro Val His
305                 310                 315                 320

<210> SEQ ID NO 27
<211> LENGTH: 960
<212> TYPE: DNA
<213> ORGANISM: Homo sapiens

<400> SEQUENCE: 27

```
atggatgatt gggagattcc tgatgggcag attacagtgg acaaagaat tggatctgga      60
tcatttggaa cagtctacaa gggaaagtgg catggtgatg tggcagtgaa atgttgaat    120
gtgacagcac ctacacctca gcagttacaa gccttcaaaa atgaagtagg agtactcagg    180
aaaacacatc atgtgaatat cctactcttc atgggctatt ccacaaagcc acaactggct    240
attgttaccc agtggtgtga gggctccagc ttgtatcacc atctccatat cattgagacc    300
aaatttgaga tgatcaaact tatagatatt gcacgacaga ctgcacaggg catggattac    360
ttacacgcca agtcaatcat ccacagagac ctcaagagta ataatatatt tcttcatgaa    420
gacctcacag taaaaatagg tgattttggt ctagctacag tgaaatctcg atggagtggg    480
tcccatcagt ttgaacagtt gtctggatcc attttgtgga tggcaccaga agtcatcaga    540
atgcaagata aaaatccata cagctttcag tcagatgtat atgcatttgg aattgttctg    600
tatgaattga tgactggaca gttacccttat tcaaacatca acaacaggga ccagataatt    660
tttatggtgg gacgaggata cctgtctcca gatctcagta aggtacggag taactgtcca    720
```

```
aaagccatga agagattaat ggcagagtgc ctcaaaaaga aaagagatga gagaccactc    780 tttcccccaaa ttctcgcctc tattgagctg ctggcccgct cattgccaaa aattcaccgc    840
agtgcatcag aaccctcctt gaatcgggct ggtttccaaa cagaggattt tagtctatat    900
gcttgtgctt ctccaaaaac acccatccag gcaggggat atggtgcgtt cctgtccac    960
```

<210> SEQ ID NO 28
<211> LENGTH: 320
<212> TYPE: PRT
<213> ORGANISM: Homo sapiens

<400> SEQUENCE: 28

```
Met Asp Asp Trp Glu Ile Pro Asp Gly Gln Ile Thr Val Gly Gln Arg
1               5                   10                  15

Ile Gly Ser Gly Ser Phe Gly Thr Val Tyr Lys Gly Lys Trp His Gly
                20                  25                  30

Asp Val Ala Val Lys Met Leu Asn Val Thr Ala Pro Thr Pro Gln Gln
            35                  40                  45

Leu Gln Ala Phe Lys Asn Glu Val Gly Val Leu Arg Lys Thr His His
        50                  55                  60

Val Asn Ile Leu Leu Phe Met Gly Tyr Ser Thr Lys Pro Gln Leu Ala
65                  70                  75                  80

Ile Val Thr Gln Trp Cys Glu Gly Ser Ser Leu Tyr His His Leu His
                85                  90                  95

Ile Ile Glu Thr Lys Phe Glu Met Ile Lys Leu Ile Asp Ile Ala Arg
                100                 105                 110

Gln Thr Ala Gln Gly Met Asp Tyr Leu His Ala Lys Ser Ile Ile His
            115                 120                 125

Arg Asp Leu Lys Ser Asn Asn Ile Phe Leu His Glu Asp Leu Thr Val
        130                 135                 140

Lys Ile Gly Asp Phe Gly Leu Ala Thr Val Lys Ser Arg Trp Ser Gly
145                 150                 155                 160

Ser His Gln Phe Glu Gln Leu Ser Gly Ser Ile Leu Trp Met Ala Pro
                165                 170                 175

Glu Val Ile Arg Met Gln Asp Lys Asn Pro Tyr Ser Phe Gln Ser Asp
                180                 185                 190

Val Tyr Ala Phe Gly Ile Val Leu Tyr Glu Leu Met Thr Gly Gln Leu
            195                 200                 205

Pro Tyr Ser Asn Ile Asn Asn Arg Asp Gln Ile Ile Phe Met Val Gly
        210                 215                 220

Arg Gly Tyr Leu Ser Pro Asp Leu Ser Lys Val Arg Ser Asn Cys Pro
225                 230                 235                 240

Lys Ala Met Lys Arg Leu Met Ala Glu Cys Leu Lys Lys Lys Arg Asp
                245                 250                 255

Glu Arg Pro Leu Phe Pro Gln Ile Leu Ala Ser Ile Glu Leu Leu Ala
                260                 265                 270

Arg Ser Leu Pro Lys Ile His Arg Ser Ala Ser Glu Pro Ser Leu Asn
            275                 280                 285

Arg Ala Gly Phe Gln Thr Glu Asp Phe Ser Leu Tyr Ala Cys Ala Ser
        290                 295                 300

Pro Lys Thr Pro Ile Gln Ala Gly Gly Tyr Gly Ala Phe Pro Val His
305                 310                 315                 320
```

<210> SEQ ID NO 29
<211> LENGTH: 1755

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctacccga ccacatgaag      240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cccccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgttca cccagtccgc cctgagcaaa gaccccaacg agaagcgcga tcacatggtc     660
ctgctggagt tcgtgaccgc cgccgggatc actctcggca tggacgagct gtacaaggga     720
tccgccggta ccatggatga ttgggagatt cctgatgggc agattacagt gggacaaaga     780
attggatctg atcatttgg aacagtctac aagggaaagt ggcatggtga tgtggcagtg     840
aaaatgttga atgtgacagc acctacacct cagcagttac aagccttcaa aaatgaagta     900
ggagtactca ggaaaacacg acatgtgaat atcctactct tcatgggcta ttccacaaag     960
ccacaactgg ctattgttac ccagtggtgt gagggctcca gcttgtatca ccatctccat    1020
atcattgaga ccaaatttga gatgatcaaa cttatagata ttgcacgaca gactgcacag    1080
ggcatggatt acttacacgc caagtcaatc atccacagag acctcaagag taataatata    1140
tttcttcatg aagacctcac agtaaaaata ggtgattttg gtctagctac agtgaaatct    1200
cgatggagtg gtcccatca gtttgaacag ttgtctggat ccattttgtg gatggcacca    1260
gaagtcatca gaatgcaaga taaaaatcca tacagctttc agtcagatgt atatgcattt    1320
ggaattgttc tgtatgaatt gatgactgga cagttacctt attcaaacat caacaacagg    1380
gaccagataa ttttatggt gggacgagga tacctgtctc cagatctcag taaggtacgg    1440
agtaactgtc caaaagccat gaagagatta atggcagagt gcctcaaaaa gaaaagagat    1500
gagagaccac tctttcccca aattctcgcc tctattgagc tgctggcccg ctcattgcca    1560
aaaattcacc gcagtgcatc agaaccctcc ttgaatcggg ctggtttcca acagaggat    1620
tttagtctat atgcttgtgc ttctccaaaa acacccatcc aggcagggg atatggtgcg    1680
tttcctgtcc acaagatgag caaagatggt aaaagaaga aaaagaagtc aaagacaaag    1740
tgtgtaatta tgtaa                                                    1755
```

<210> SEQ ID NO 30
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Phe Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Ala Gly Thr Met Asp Asp Trp Glu Ile Pro Asp Gly Gln Ile Thr
                245                 250                 255

Val Gly Gln Arg Ile Gly Ser Gly Ser Phe Gly Thr Val Tyr Lys Gly
            260                 265                 270

Lys Trp His Gly Asp Val Ala Val Lys Met Leu Asn Val Thr Ala Pro
        275                 280                 285

Thr Pro Gln Gln Leu Gln Ala Phe Lys Asn Glu Val Gly Val Leu Arg
    290                 295                 300

Lys Thr Arg His Val Asn Ile Leu Leu Phe Met Gly Tyr Ser Thr Lys
305                 310                 315                 320

Pro Gln Leu Ala Ile Val Thr Gln Trp Cys Glu Gly Ser Ser Leu Tyr
                325                 330                 335

His His Leu His Ile Ile Glu Thr Lys Phe Glu Met Ile Lys Leu Ile
            340                 345                 350

Asp Ile Ala Arg Gln Thr Ala Gln Gly Met Asp Tyr Leu His Ala Lys
        355                 360                 365

Ser Ile Ile His Arg Asp Leu Lys Ser Asn Asn Ile Phe Leu His Glu
    370                 375                 380

Asp Leu Thr Val Lys Ile Gly Asp Phe Gly Leu Ala Thr Val Lys Ser
385                 390                 395                 400

Arg Trp Ser Gly Ser His Gln Phe Glu Gln Leu Ser Gly Ser Ile Leu
                405                 410                 415

Trp Met Ala Pro Glu Val Ile Arg Met Gln Asp Lys Asn Pro Tyr Ser
```

```
            420              425              430
Phe Gln Ser Asp Val Tyr Ala Phe Gly Ile Val Leu Tyr Glu Leu Met
            435                  440                  445

Thr Gly Gln Leu Pro Tyr Ser Asn Ile Asn Asn Arg Asp Gln Ile Ile
        450                  455                  460

Phe Met Val Gly Arg Gly Tyr Leu Ser Pro Asp Leu Ser Lys Val Arg
465                  470                  475                  480

Ser Asn Cys Pro Lys Ala Met Lys Arg Leu Met Ala Glu Cys Leu Lys
                485                  490                  495

Lys Lys Arg Asp Glu Arg Pro Leu Phe Pro Gln Ile Leu Ala Ser Ile
            500                  505                  510

Glu Leu Leu Ala Arg Ser Leu Pro Lys Ile His Arg Ser Ala Ser Glu
        515                  520                  525

Pro Ser Leu Asn Arg Ala Gly Phe Gln Thr Glu Asp Phe Ser Leu Tyr
    530                  535                  540

Ala Cys Ala Ser Pro Lys Thr Pro Ile Gln Ala Gly Gly Tyr Gly Ala
545                  550                  555                  560

Phe Pro Val His Lys Met Ser Lys Asp Gly Lys Lys Lys Lys Lys
                565                  570                  575

Ser Lys Thr Lys Cys Val Ile Met
            580

<210> SEQ ID NO 31
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cccccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgttca cccagtccgc cctgagcaaa gaccccaacg agaagcgcga tcacatggtc     660
ctgctggagt tcgtgaccgc cgccgggatc actctcggca tggacgagct gtacaaggga     720
tccgccggta ccatggatga ttgggagatt cctgatgggc agattacagt gggacaaaga     780
attggatctg atcatttgg  aacagtctac aagggaaagt ggcatggtga tgtggcagtg     840
aaaatgttga atgtgacagc acctacacct cagcagttac aagccttcaa aaatgaagta     900
ggagtactca ggaaaacaca tcatgtgaat atcctactct tcatgggcta ttccacaaag     960
ccacaactgg ctattgttac ccagtggtgt gagggctcca gcttgtatca ccatctccat    1020
atcattgaga ccaaatttga gatgatcaaa cttatagata ttgcacgaca gactgcacag    1080
```

-continued

```
ggcatggatt acttacacgc caagtcaatc atccacagag acctcaagag taataatata  1140
tttcttcatg aagacctcac agtaaaaata ggtgattttg gtctagctac agtgaaatct  1200
cgatggagtg ggtcccatca gtttgaacag ttgtctggat ccattttgtg gatggcacca  1260
gaagtcatca gaatgcaaga taaaaatcca tacagctttc agtcagatgt atatgcattt  1320
ggaattgttc tgtatgaatt gatgactgga cagttacctt attcaaacat caacaacagg  1380
gaccagataa tttttatggt gggacgagga tacctgtctc cagatctcag taaggtacgg  1440
agtaactgtc caaaagccat gaagagatta atggcagagt gcctcaaaaa gaaaagagat  1500
gagagaccac tctttcccca aattctcgcc tctattgagc tgctggcccg ctcattgcca  1560
aaaattcacc gcagtgcatc agaaccctcc ttgaatcggg ctggtttcca acagaggat  1620 tttagtctat atgcttgtgc ttctccaaaa acacccatcc aggcaggggg atatggtgcg  1680
tttcctgtcc acaagatgag caaagatggt aaaaagaaga aaagaagtc aaagacaaag  1740 tgtgtaatta tgtaa                                                   1755
```

<210> SEQ ID NO 32
<211> LENGTH: 584
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Phe Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240
```

Ser Ala Gly Thr Met Asp Asp Trp Glu Ile Pro Asp Gly Gln Ile Thr
            245                 250                 255

Val Gly Gln Arg Ile Gly Ser Gly Ser Phe Gly Thr Val Tyr Lys Gly
        260                 265                 270

Lys Trp His Gly Asp Val Ala Val Lys Met Leu Asn Val Thr Ala Pro
    275                 280                 285

Thr Pro Gln Gln Leu Gln Ala Phe Lys Asn Glu Val Gly Val Leu Arg
290                 295                 300

Lys Thr His His Val Asn Ile Leu Leu Phe Met Gly Tyr Ser Thr Lys
305                 310                 315                 320

Pro Gln Leu Ala Ile Val Thr Gln Trp Cys Glu Gly Ser Ser Leu Tyr
                325                 330                 335

His His Leu His Ile Ile Glu Thr Lys Phe Glu Met Ile Lys Leu Ile
            340                 345                 350

Asp Ile Ala Arg Gln Thr Ala Gln Gly Met Asp Tyr Leu His Ala Lys
        355                 360                 365

Ser Ile Ile His Arg Asp Leu Lys Ser Asn Asn Ile Phe Leu His Glu
370                 375                 380

Asp Leu Thr Val Lys Ile Gly Asp Phe Gly Leu Ala Thr Val Lys Ser
385                 390                 395                 400

Arg Trp Ser Gly Ser His Gln Phe Glu Gln Leu Ser Gly Ser Ile Leu
                405                 410                 415

Trp Met Ala Pro Glu Val Ile Arg Met Gln Asp Lys Asn Pro Tyr Ser
            420                 425                 430

Phe Gln Ser Asp Val Tyr Ala Phe Gly Ile Val Leu Tyr Glu Leu Met
        435                 440                 445

Thr Gly Gln Leu Pro Tyr Ser Asn Ile Asn Asn Arg Asp Gln Ile Ile
    450                 455                 460

Phe Met Val Gly Arg Gly Tyr Leu Ser Pro Asp Leu Ser Lys Val Arg
465                 470                 475                 480

Ser Asn Cys Pro Lys Ala Met Lys Arg Leu Met Ala Glu Cys Leu Lys
                485                 490                 495

Lys Lys Arg Asp Glu Arg Pro Leu Phe Pro Gln Ile Leu Ala Ser Ile
            500                 505                 510

Glu Leu Leu Ala Arg Ser Leu Pro Lys Ile His Arg Ser Ala Ser Glu
        515                 520                 525

Pro Ser Leu Asn Arg Ala Gly Phe Gln Thr Glu Asp Phe Ser Leu Tyr
    530                 535                 540

Ala Cys Ala Ser Pro Lys Thr Pro Ile Gln Ala Gly Gly Tyr Gly Ala
545                 550                 555                 560

Phe Pro Val His Lys Met Ser Lys Asp Gly Lys Lys Lys Lys Lys
                565                 570                 575

Ser Lys Thr Lys Cys Val Ile Met
            580

<210> SEQ ID NO 33
<211> LENGTH: 1971
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33
atgaccagca aggtgtacga ccccgagcag aggaagagga tgatcaccgg cccccagtgg      60

```
tgggccaggt gcaagcagat gaacgtgctg gacagcttca tcaactacta cgacagcgag    120
aagcacgccg agaacgccgt gatcttcctg cacggcaacg ccactagcag ctacctgtgg    180
aggcacgtgg tgccccacat cgagcccgtg ccaggtgca tcatccccga tctgatcggc    240
atgggcaaga gcggcaagag cggcaacggc agctacaggc tgctggacca ctacaagtac    300
ctgaccgcct ggttcgagct cctgaacctg cccaagaaga tcatcttcgt gggccacgac    360
tggggcgccg cactggcctt ccactacagc tacgagcacc aggacaagat caaggccatc    420
gtgcacgccg agagcgtggt tgacgtgatc gagagctggg acgagtggcc agacatcgag    480
gaggacatcg ccctgatcaa gagcgaggag ggcgagaaga tggtgctgga gaacaacttc    540
ttcgtggaga ccgttctgcc cagcaagatc atgagaaagc tggagcccga ggagttcgcc    600
gcctacctgg agcccttcaa ggagaagggc gaggtgagaa gacccacccct gagctggccc    660 agagagatcc ccctggtgaa gggcggcaag cccgacgtgg tgcagatcgt gagaaactac    720
aacgcctacc tgagagccag cgacgacctg cccaagatgt tcatcgagag cgaccccggc    780
ttcttcagca acgccatcgt ggagggcgcc aagaagttcc ccaacaccga gttcgtgaag    840
gtgaagggcc tgcacttcag ccaggaggac gcccccgacg agatgggcaa gtacatcaag    900
agcttcgtgg agagagtgct gaagaacgag cagggatccg ccggtaccat ggatgattgg    960
gagattcctg atgggcagat tacagtggga caaagaattg gatctggatc atttggaaca   1020
gtctacaagg gaaagtggca tggtgatgtg gcagtgaaaa tgttgaatgt gacagcacct   1080
acacctcagc agttacaagc cttcaaaaat gaagtaggag tactcaggaa aacacgacat   1140
gtgaatatcc tactcttcat gggctattcc acaaagccac aactggctat tgttacccag   1200
tggtgtgagg gctccagctt gtatcaccat ctccatatca ttgagaccaa atttgagatg   1260
atcaaactta tagatattgc acgacagact gcacagggca tggattactt acacgccaag   1320
tcaatcatcc acagagacct caagagtaat aatatatttc ttcatgaaga cctcacagta   1380
aaaataggtg attttggtct agctacagtg aaatctcgat ggagtgggtc ccatcagttt   1440
gaacagttgt ctggatccat tttgtggatg gcaccagaag tcatcagaat gcaagataaa   1500
aatccataca gctttcagtc agatgtatat gcatttggaa ttgttctgta tgaattgatg   1560
actggacagt taccttattc aaacatcaac aacagggacc agataatttt tatggtggga   1620
cgaggatacc tgtctccaga tctcagtaag gtacggagta actgtccaaa agccatgaag   1680
agattaatgg cagagtgcct caaaaagaaa agagatgaga gaccactctt tccccaaatt   1740
ctcgcctcta ttgagctgct ggcccgctca ttgccaaaaa ttcaccgcag tgcatcagaa   1800
ccctccttga atcgggctgg tttccaaaca gaggatttta gtctatatgc ttgtgcttct   1860
ccaaaaacac ccatccaggc aggggggatat ggtgcgtttc ctgtccacaa gatgagcaaa   1920
gatggtaaaa agaagaaaaa gaagtcaaag acaaagtgtg taattatgta a            1971
```

<210> SEQ ID NO 34
<211> LENGTH: 656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Met Thr Ser Lys Val Tyr Asp Pro Glu Gln Arg Lys Arg Met Ile Thr
1               5                   10                  15
```

```
Gly Pro Gln Trp Trp Ala Arg Cys Lys Gln Met Asn Val Leu Asp Ser
             20                  25                  30

Phe Ile Asn Tyr Tyr Asp Ser Glu Lys His Ala Glu Asn Ala Val Ile
         35                  40                  45

Phe Leu His Gly Asn Ala Thr Ser Ser Tyr Leu Trp Arg His Val Val
     50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln Gly Ser Ala Gly Thr Met Asp Asp Trp
305                 310                 315                 320

Glu Ile Pro Asp Gly Gln Ile Thr Val Gly Gln Arg Ile Gly Ser Gly
                325                 330                 335

Ser Phe Gly Thr Val Tyr Lys Gly Lys Trp His Gly Asp Val Ala Val
            340                 345                 350

Lys Met Leu Asn Val Thr Ala Pro Thr Pro Gln Gln Leu Gln Ala Phe
        355                 360                 365

Lys Asn Glu Val Gly Val Leu Arg Lys Thr Arg His Val Asn Ile Leu
    370                 375                 380

Leu Phe Met Gly Tyr Ser Thr Lys Pro Gln Leu Ala Ile Val Thr Gln
385                 390                 395                 400

Trp Cys Glu Gly Ser Ser Leu Tyr His His Leu His Ile Ile Glu Thr
                405                 410                 415

Lys Phe Glu Met Ile Lys Leu Ile Asp Ile Ala Arg Gln Thr Ala Gln
            420                 425                 430

Gly Met Asp Tyr Leu His Ala Lys Ser Ile Ile His Arg Asp Leu Lys
```

```
                        435                 440                 445

Ser Asn Asn Ile Phe Leu His Glu Asp Leu Thr Val Lys Ile Gly Asp
450                     455                 460

Phe Gly Leu Ala Thr Val Lys Ser Arg Trp Ser Gly Ser His Gln Phe
465                 470                  475                 480

Glu Gln Leu Ser Gly Ser Ile Leu Trp Met Ala Pro Glu Val Ile Arg
                485                 490                 495

Met Gln Asp Lys Asn Pro Tyr Ser Phe Gln Ser Asp Val Tyr Ala Phe
            500                 505                 510

Gly Ile Val Leu Tyr Glu Leu Met Thr Gly Gln Leu Pro Tyr Ser Asn
        515                 520                 525

Ile Asn Asn Arg Asp Gln Ile Ile Phe Met Val Gly Arg Gly Tyr Leu
    530                 535                 540

Ser Pro Asp Leu Ser Lys Val Arg Ser Asn Cys Pro Lys Ala Met Lys
545                 550                 555                 560

Arg Leu Met Ala Glu Cys Leu Lys Lys Lys Arg Asp Glu Arg Pro Leu
                565                 570                 575

Phe Pro Gln Ile Leu Ala Ser Ile Glu Leu Leu Ala Arg Ser Leu Pro
            580                 585                 590

Lys Ile His Arg Ser Ala Ser Glu Pro Ser Leu Asn Arg Ala Gly Phe
        595                 600                 605

Gln Thr Glu Asp Phe Ser Leu Tyr Ala Cys Ala Ser Pro Lys Thr Pro
    610                 615                 620

Ile Gln Ala Gly Gly Tyr Gly Ala Phe Pro Val His Lys Met Ser Lys
625                 630                 635                 640

Asp Gly Lys Lys Lys Lys Lys Ser Lys Thr Lys Cys Val Ile Met
                645                 650                 655

<210> SEQ ID NO 35
<211> LENGTH: 1971
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgaccagca aggtgtacga ccccgagcag aggaagagga tgatcaccgg cccccagtgg    60
tgggccaggt gcaagcagat gaacgtgctg gacagcttca tcaactacta cgacagcgag   120
aagcacgccg agaacgccgt gatcttcctg cacggcaacg ccactagcag ctacctgtgg   180
aggcacgtgg tgccccacat cgagcccgtg gccaggtgca tcatccccga tctgatcggc   240
atgggcaaga gcggcaagag cggcaacggc agctacaggc tgctggacca ctacaagtac   300
ctgaccgcct ggttcgagct cctgaacctg cccaagaaga tcatcttcgt gggccacgac   360
tggggcgccg cactggcctt ccactacagc tacgagcacc aggacaagat caaggccatc   420
gtgcacgccg agagcgtggt tgacgtgatc gagagctgga cgagtggcc agacatcgag   480 gaggacatcg ccctgatcaa gagcgaggag ggcgagaaga tggtgctgga gaacaacttc   540
ttcgtggaga ccgttctgcc cagcaagatc atgagaaagc tggagcccga ggagttcgcc   600
gcctacctgg agcccttcaa ggagaagggc gaggtgagaa gacccaccct gagctggccc   660
agagagatcc ccctggtgaa gggcggcaag cccgacgtgg tgcagatcgt gagaaactac   720
aacgcctacc tgagagccag cgacgacctg cccaagatgt catcgagag cgaccccggc   780 ttcttcagca acgccatcgt ggagggcgcc aagaagttcc ccaacaccga gttcgtgaag   840
```

```
gtgaagggcc tgcacttcag ccaggaggac gcccccgacg agatgggcaa gtacatcaag      900
agcttcgtgg agagagtgct gaagaacgag cagggatccg ccggtaccat ggatgattgg      960
gagattcctg atgggcagat tacagtggga caaagaattg gatctggatc atttggaaca     1020
gtctacaagg gaaagtggca tggtgatgtg gcagtgaaaa tgttgaatgt gacagcacct     1080
acacctcagc agttacaagc cttcaaaaat gaagtaggag tactcaggaa aacacatcat     1140
gtgaatatcc tactcttcat gggctattcc acaaagccac aactggctat tgttacccag     1200
tggtgtgagg gctccagctt gtatcaccat ctccatatca ttgagaccaa atttgagatg     1260
atcaaactta tagatattgc acgacagact gcacagggca tggattactt acacgccaag     1320
tcaatcatcc acagagacct caagagtaat aatatatttc ttcatgaaga cctcacagta     1380
aaaataggtg attttggtct agctacagtg aaatctcgat ggagtgggtc ccatcagttt     1440
gaacagttgt ctggatccat tttgtggatg gcaccagaag tcatcagaat gcaagataaa     1500
aatccataca gctttcagtc agatgtatat gcatttggaa ttgttctgta tgaattgatg     1560
actggacagt taccttattc aaacatcaac aacagggacc agataatttt tatggtggga     1620
cgaggatacc tgtctccaga tctcagtaag gtacggagta actgtccaaa agccatgaag     1680
agattaatgg cagagtgcct caaaaagaaa agagatgaga ccactctt tccccaaatt     1740 ctcgcctcta ttgagctgct ggcccgctca ttgccaaaaa ttcaccgcag tgcatcagaa     1800
ccctccttga atcgggctgg tttccaaaca gaggatttta gtctatatgc ttgtgcttct     1860
ccaaaaacac ccatccaggc aggggatat ggtgcgtttc ctgtccacaa gatgagcaaa      1920
gatggtaaaa agaagaaaaa gaagtcaaag acaaagtgtg taattatgta a              1971
```

<210> SEQ ID NO 36
<211> LENGTH: 656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160
```

```
Glu Asp Ile Ala Leu Ile Lys Ser Glu Glu Gly Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Met Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Ser Gln
                275                 280                 285

Glu Asp Ala Pro Asp Glu Met Gly Lys Tyr Ile Lys Ser Phe Val Glu
    290                 295                 300

Arg Val Leu Lys Asn Glu Gln Gly Ser Ala Gly Thr Met Asp Asp Trp
305                 310                 315                 320

Glu Ile Pro Asp Gly Gln Ile Thr Val Gly Gln Arg Ile Gly Ser Gly
                325                 330                 335

Ser Phe Gly Thr Val Tyr Lys Gly Lys Trp His Gly Asp Val Ala Val
                340                 345                 350

Lys Met Leu Asn Val Thr Ala Pro Thr Pro Gln Gln Leu Gln Ala Phe
                355                 360                 365

Lys Asn Glu Val Gly Val Leu Arg Lys Thr His His Val Asn Ile Leu
    370                 375                 380

Leu Phe Met Gly Tyr Ser Thr Lys Pro Gln Leu Ala Ile Val Thr Gln
385                 390                 395                 400

Trp Cys Glu Gly Ser Ser Leu Tyr His His Leu His Ile Ile Glu Thr
                405                 410                 415

Lys Phe Glu Met Ile Lys Leu Ile Asp Ile Ala Arg Gln Thr Ala Gln
                420                 425                 430

Gly Met Asp Tyr Leu His Ala Lys Ser Ile Ile His Arg Asp Leu Lys
                435                 440                 445

Ser Asn Asn Ile Phe Leu His Glu Asp Leu Thr Val Lys Ile Gly Asp
450                 455                 460

Phe Gly Leu Ala Thr Val Lys Ser Arg Trp Ser Gly Ser His Gln Phe
465                 470                 475                 480

Glu Gln Leu Ser Gly Ser Ile Leu Trp Met Ala Pro Glu Val Ile Arg
                485                 490                 495

Met Gln Asp Lys Asn Pro Tyr Ser Phe Gln Ser Asp Val Tyr Ala Phe
                500                 505                 510

Gly Ile Val Leu Tyr Glu Leu Met Thr Gly Gln Leu Pro Tyr Ser Asn
                515                 520                 525

Ile Asn Asn Arg Asp Gln Ile Ile Phe Met Val Gly Arg Gly Tyr Leu
    530                 535                 540

Ser Pro Asp Leu Ser Lys Val Arg Ser Asn Cys Pro Lys Ala Met Lys
545                 550                 555                 560

Arg Leu Met Ala Glu Cys Leu Lys Lys Lys Arg Asp Glu Arg Pro Leu
                565                 570                 575
```

```
Phe Pro Gln Ile Leu Ala Ser Ile Glu Leu Ala Arg Ser Leu Pro
            580                 585                 590

Lys Ile His Arg Ser Ala Ser Glu Pro Ser Leu Asn Arg Ala Gly Phe
            595                 600                 605

Gln Thr Glu Asp Phe Ser Leu Tyr Ala Cys Ala Ser Pro Lys Thr Pro
        610                 615                 620

Ile Gln Ala Gly Gly Tyr Gly Ala Phe Pro Val His Lys Met Ser Lys
625                 630                 635                 640

Asp Gly Lys Lys Lys Lys Lys Ser Lys Thr Lys Cys Val Ile Met
                645                 650                 655

<210> SEQ ID NO 37
<211> LENGTH: 933
<212> TYPE: DNA
<213> ORGANISM: Homo sapiens

<400> SEQUENCE: 37
```

| | | | | | |
|---|---|---|---|---|---|
| atgtattatt | gggaaataga | agccagtgaa | gtgatgctgt | ccactcggat | tgggtcaggc | 60 |
| tcttttggaa | ctgtttataa | gggtaaatgg | cacggagatg | ttgcagtaaa | gatcctaaag | 120 |
| gttgtcgacc | caaccccaga | gcaattccag | gccttcagga | atgaggtggc | tgttctgcgc | 180 |
| aaaacacggc | atgtgaacat | tctgcttttc | atggggtaca | tgacaaagga | caacctggca | 240 |
| attgtgaccc | agtggtgcga | gggcagcagc | ctctacaaac | acctgcatgt | ccaggagacc | 300 |
| aagtttcaga | tgttccagct | aattgacatt | gcccggcaga | cggctcaggg | aatggactat | 360 |
| ttgcatgcaa | agaacatcat | ccatagagac | atgaaatcca | acaatatatt | tctccatgaa | 420 |
| ggcttaacag | tgaaaattgg | agattttggt | ttggcaacag | taaagtcacg | ctggagtggt | 480 |
| tctcagcagg | ttgaacaacc | tactggctct | gtcctctgga | tggccccaga | ggtgatccga | 540 |
| atgcaggata | acaacccatt | cagtttccag | tcggatgtct | actcctatgg | catcgtattg | 600 |
| tatgaactga | tgacggggga | gcttccttat | tctcacatca | acaaccgaga | tcagatcatc | 660 |
| ttcatggtgg | gccgaggata | tgcctcccca | gatcttagta | agctatataa | gaactgcccc | 720 |
| aaagcaatga | agaggctggt | agctgactgt | gtgaagaaag | taaggaaga | gaggcctctt | 780 |
| tttccccaga | tcctgtcttc | cattgagctg | ctccaacact | ctctaccgaa | gatcaaccgg | 840 |
| agcgcttccg | agccatcctt | gcatcgggca | gcccacactg | aggatatcaa | tgcttgcacg | 900 |
| ctgaccacgt | ccccgaggct | gcctgtcttc | tag | | | 933 |

```
<210> SEQ ID NO 38
<211> LENGTH: 310
<212> TYPE: PRT
<213> ORGANISM: Homo sapiens

<400> SEQUENCE: 38

Met Tyr Tyr Trp Glu Ile Glu Ala Ser Glu Val Met Leu Ser Thr Arg
1               5                   10                  15

Ile Gly Ser Gly Ser Phe Gly Thr Val Tyr Lys Gly Lys Trp His Gly
            20                  25                  30

Asp Val Ala Val Lys Ile Leu Lys Val Val Asp Pro Thr Pro Glu Gln
        35                  40                  45

Phe Gln Ala Phe Arg Asn Glu Val Ala Val Leu Arg Lys Thr Arg His
    50                  55                  60

Val Asn Ile Leu Leu Phe Met Gly Tyr Met Thr Lys Asp Asn Leu Ala
65                  70                  75                  80

Ile Val Thr Gln Trp Cys Glu Gly Ser Ser Leu Tyr Lys His Leu His
```

```
                    85                  90                  95
Val Gln Glu Thr Lys Phe Gln Met Phe Gln Leu Ile Asp Ile Ala Arg
                100                 105                 110

Gln Thr Ala Gln Gly Met Asp Tyr Leu His Ala Lys Asn Ile Ile His
            115                 120                 125

Arg Asp Met Lys Ser Asn Asn Ile Phe Leu His Glu Gly Leu Thr Val
        130                 135                 140

Lys Ile Gly Asp Phe Gly Leu Ala Thr Val Lys Ser Arg Trp Ser Gly
145                 150                 155                 160

Ser Gln Gln Val Glu Gln Pro Thr Gly Ser Val Leu Trp Met Ala Pro
                165                 170                 175

Glu Val Ile Arg Met Gln Asp Asn Asn Pro Phe Ser Phe Gln Ser Asp
                180                 185                 190

Val Tyr Ser Tyr Gly Ile Val Leu Tyr Glu Leu Met Thr Gly Glu Leu
                195                 200                 205

Pro Tyr Ser His Ile Asn Asn Arg Asp Gln Ile Ile Phe Met Val Gly
            210                 215                 220

Arg Gly Tyr Ala Ser Pro Asp Leu Ser Lys Leu Tyr Lys Asn Cys Pro
225                 230                 235                 240

Lys Ala Met Lys Arg Leu Val Ala Asp Cys Val Lys Lys Val Lys Glu
                245                 250                 255

Glu Arg Pro Leu Phe Pro Gln Ile Leu Ser Ser Ile Glu Leu Leu Gln
                260                 265                 270

His Ser Leu Pro Lys Ile Asn Arg Ser Ala Ser Glu Pro Ser Leu His
            275                 280                 285

Arg Ala Ala His Thr Glu Asp Ile Asn Ala Cys Thr Leu Thr Thr Ser
        290                 295                 300

Pro Arg Leu Pro Val Phe
305                 310

<210> SEQ ID NO 39
<211> LENGTH: 1725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgagcta cggcgtgcag tgcttcagcc gctacccgga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cccccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgttca cccagtccgc cctgagcaaa gaccccaacg agaagcgcga tcacatggtc     660
ctgctggagt tcgtgaccgc cgccgggatc actctcggca tggacgagct gtacaaggga     720
```

```
tccgccggta ccatgtatta ttgggaaata gaagccagtg aagtgatgct gtccactcgg    780
attgggtcag gctctttttgg aactgtttat aagggtaaat ggcacggaga tgttgcagta   840
aagatcctaa aggttgtcga cccaaccccca gagcaattcc aggccttcag gaatgaggtg   900
gctgttctgc gcaaaacacg gcatgtgaac attctgcttt tcatgggta catgacaaag    960 gacaacctgg caattgtgac ccagtggtgc gagggcagca gcctctacaa acacctgcat  1020
gtccaggaga ccaagtttca gatgttccag ctaattgaca ttgcccggca gacggctcag  1080
ggaatggact atttgcatgc aaagaacatc atccatagag acatgaaatc aacaatata   1140 tttctccatg aaggcttaac agtgaaaatt ggagattttg gtttggcaac agtaaagtca  1200
cgctggagtg gttctcagca ggttgaacaa cctactggct ctgtcctctg gatggcccca  1260
gaggtgatcc gaatgcagga taacaaccca ttcagtttcc agtcggatgt ctactcctat  1320
ggcatcgtat tgtatgaact gatgacgggg gagcttcctt attctcacat caacaaccga  1380
gatcagatca tcttcatggt gggccgagga tatgcctccc cagatcttag taagctatat  1440
aagaactgcc ccaaagcaat gaagaggctg gtagctgact gtgtgaagaa agtaaaggaa  1500
gagaggcctc tttttccccca gatcctgtct tccattgagc tgctccaaca ctctctaccg  1560
aagatcaacc ggagcgcttc cgagccatcc ttgcatcggg cagcccacac tgaggatatc  1620
aatgcttgca cgctgaccac gtccccgagg ctgcctgtct tcaagatgag caaagatggt  1680
aaaaagaaga aaaagaagtc aaagacaaag tgtgtaatta tgtaa              1725
```

<210> SEQ ID NO 40
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
```

```
            180                 185                 190
Pro Val Leu Leu Pro Asp Asn His Tyr Leu Phe Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Ser Ala Gly Thr Met Tyr Tyr Trp Glu Ile Glu Ala Ser Glu Val Met
                245                 250                 255

Leu Ser Thr Arg Ile Gly Ser Gly Ser Phe Gly Thr Val Tyr Lys Gly
                260                 265                 270

Lys Trp His Gly Asp Val Ala Val Lys Ile Leu Lys Val Val Asp Pro
                275                 280                 285

Thr Pro Glu Gln Phe Gln Ala Phe Arg Asn Glu Val Ala Val Leu Arg
            290                 295                 300

Lys Thr Arg His Val Asn Ile Leu Leu Phe Met Gly Tyr Met Thr Lys
305                 310                 315                 320

Asp Asn Leu Ala Ile Val Thr Gln Trp Cys Glu Gly Ser Ser Leu Tyr
                325                 330                 335

Lys His Leu His Val Gln Glu Thr Lys Phe Gln Met Phe Gln Leu Ile
                340                 345                 350

Asp Ile Ala Arg Gln Thr Ala Gln Gly Met Asp Tyr Leu His Ala Lys
            355                 360                 365

Asn Ile Ile His Arg Asp Met Lys Ser Asn Asn Ile Phe Leu His Glu
370                 375                 380

Gly Leu Thr Val Lys Ile Gly Asp Phe Gly Leu Ala Thr Val Lys Ser
385                 390                 395                 400

Arg Trp Ser Gly Ser Gln Gln Val Glu Gln Pro Thr Gly Ser Val Leu
                405                 410                 415

Trp Met Ala Pro Glu Val Ile Arg Met Gln Asp Asn Asn Pro Phe Ser
                420                 425                 430

Phe Gln Ser Asp Val Tyr Ser Tyr Gly Ile Val Leu Tyr Glu Leu Met
            435                 440                 445

Thr Gly Glu Leu Pro Tyr Ser His Ile Asn Asn Arg Asp Gln Ile Ile
450                 455                 460

Phe Met Val Gly Arg Gly Tyr Ala Ser Pro Asp Leu Ser Lys Leu Tyr
465                 470                 475                 480

Lys Asn Cys Pro Lys Ala Met Lys Arg Leu Val Ala Asp Cys Val Lys
                485                 490                 495

Lys Val Lys Glu Glu Arg Pro Leu Phe Pro Gln Ile Leu Ser Ser Ile
                500                 505                 510

Glu Leu Leu Gln His Ser Leu Pro Lys Ile Asn Arg Ser Ala Ser Glu
            515                 520                 525

Pro Ser Leu His Arg Ala Ala His Thr Glu Asp Ile Asn Ala Cys Thr
530                 535                 540

Leu Thr Thr Ser Pro Arg Leu Pro Val Phe Lys Met Ser Lys Asp Gly
545                 550                 555                 560

Lys Lys Lys Lys Lys Ser Lys Thr Lys Cys Val Ile Met
                565                 570

<210> SEQ ID NO 41
<211> LENGTH: 1941
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 41

| | | | | | |
|---|---|---|---|---|---|
| atgaccagca | aggtgtacga | ccccgagcag | aggaagagga | tgatcaccgg | ccccccagtgg | 60 |
| tgggccaggt | gcaagcagat | gaacgtgctg | gacagcttca | tcaactacta | cgacagcgag | 120 |
| aagcacgccg | agaacgccgt | gatcttcctg | cacggcaacg | ccactagcag | ctacctgtgg | 180 |
| aggcacgtgg | tgccccacat | cgagcccgtg | gccaggtgca | tcatccccga | tctgatcggc | 240 |
| atgggcaaga | gcggcaagag | cggcaacggc | agctacaggc | tgctggacca | ctacaagtac | 300 |
| ctgaccgcct | ggttcgagct | cctgaacctg | cccaagaaga | tcatcttcgt | gggccacgac | 360 |
| tggggcgccg | cactggcctt | ccactacagc | tacgagcacc | aggacaagat | caaggccatc | 420 |
| gtgcacgccg | agagcgtggt | tgacgtgatc | gagagctggg | acgagtggcc | agacatcgag | 480 |
| gaggacatcg | ccctgatcaa | gagcgaggag | ggcgagaaga | tggtgctgga | gaacaacttc | 540 |
| ttcgtggaga | ccgttctgcc | cagcaagatc | atgagaaagc | tggagcccga | ggagttcgcc | 600 |
| gcctacctgg | agcccttcaa | ggagaagggc | gaggtgagaa | gacccaccct | gagctggccc | 660 |
| agagagatcc | ccctggtgaa | gggcggcaag | cccgacgtgg | tgcagatcgt | gagaaactac | 720 |
| aacgcctacc | tgagagccag | cgacgacctg | cccaagatgt | tcatcgagag | cgaccccggc | 780 |
| ttcttcagca | acgccatcgt | ggagggcgcc | aagaagttcc | ccaacaccga | gttcgtgaag | 840 |
| gtgaagggcc | tgcacttcag | ccaggaggac | gcccccgacg | agatgggcaa | gtacatcaag | 900 |
| agcttcgtgg | agagagtgct | gaagaacgag | cagggatccg | ccggtaccat | gtattattgg | 960 |
| gaaatagaag | ccagtgaagt | gatgctgtcc | actcggattg | ggtcaggctc | ttttggaact | 1020 |
| gtttataagg | gtaaatggca | cggagatgtt | gcagtaaaga | tcctaaaggt | tgtcgaccca | 1080 |
| accccagagc | aattccaggc | cttcaggaat | gaggtggctg | ttctgcgcaa | aacacggcat | 1140 |
| gtgaacattc | tgcttttcat | ggggtacatg | acaaaggaca | acctggcaat | gtgacccag | 1200 |
| tggtgcgagg | gcagcagcct | ctacaaacac | ctgcatgtcc | aggagaccaa | gtttcagatg | 1260 |
| ttccagctaa | ttgacattgc | ccggcagacg | gctcagggaa | tggactattt | gcatgcaaag | 1320 |
| aacatcatcc | atagagacat | gaaatccaac | aatatatttc | tccatgaagg | cttaacagtg | 1380 |
| aaaattggag | attttggttt | ggcaacagta | aagtcacgct | ggagtggttc | tcagcaggtt | 1440 |
| gaacaaccta | ctggctctgt | cctctggatg | gccccagagg | tgatccgaat | gcaggataac | 1500 |
| aacccattca | gttccagtc | ggatgtctac | tcctatggca | tcgtattgta | tgaactgatg | 1560 |
| acgggggagc | ttccttattc | tcacatcaac | aaccgagatc | agatcatctt | catggtgggc | 1620 |
| cgaggatatg | cctccccaga | tcttagtaag | ctatataaga | actgccccaa | agcaatgaag | 1680 |
| aggctggtag | ctgactgtgt | gaagaaagta | aaggaagaga | ggcctctttt | tccccagatc | 1740 |
| ctgtcttcca | ttgagctgct | ccaacactct | ctaccgaaga | tcaaccggag | cgcttccgag | 1800 |
| ccatccttgc | atcgggcagc | ccacactgag | gatatcaatg | cttgcacgct | gaccacgtcc | 1860 |
| ccgaggctgc | ctgtcttcaa | gatgagcaaa | gatggtaaaa | agaagaaaaa | gaagtcaaag | 1920 |
| acaaagtgtg | taattatgta | a | | | | 1941 |

<210> SEQ ID NO 42
<211> LENGTH: 646
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Met Thr Ser Lys Val Tyr Asp Pro Glu Gln Arg Lys Arg Met Ile Thr
 1               5                  10                  15
Gly Pro Gln Trp Trp Ala Arg Cys Lys Gln Met Asn Val Leu Asp Ser
            20                  25                  30
Phe Ile Asn Tyr Tyr Asp Ser Glu Lys His Ala Glu Asn Ala Val Ile
        35                  40                  45
Phe Leu His Gly Asn Ala Thr Ser Ser Tyr Leu Trp Arg His Val Val
    50                  55                  60
Pro His Ile Glu Pro Val Ala Arg Cys Ile Ile Pro Asp Leu Ile Gly
65                  70                  75                  80
Met Gly Lys Ser Gly Lys Ser Gly Asn Gly Ser Tyr Arg Leu Leu Asp
                85                  90                  95
His Tyr Lys Tyr Leu Thr Ala Trp Phe Glu Leu Leu Asn Leu Pro Lys
            100                 105                 110
Lys Ile Ile Phe Val Gly His Asp Trp Gly Ala Ala Leu Ala Phe His
        115                 120                 125
Tyr Ser Tyr Glu His Gln Asp Lys Ile Lys Ala Ile Val His Ala Glu
    130                 135                 140
Ser Val Val Asp Val Ile Glu Ser Trp Asp Glu Trp Pro Asp Ile Glu
145                 150                 155                 160
Glu Asp Ile Ala Leu Ile Lys Ser Glu Glu Gly Glu Lys Met Val Leu
                165                 170                 175
Glu Asn Asn Phe Phe Val Glu Thr Val Leu Pro Ser Lys Ile Met Arg
            180                 185                 190
Lys Leu Glu Pro Glu Glu Phe Ala Ala Tyr Leu Glu Pro Phe Lys Glu
        195                 200                 205
Lys Gly Glu Val Arg Arg Pro Thr Leu Ser Trp Pro Arg Glu Ile Pro
    210                 215                 220
Leu Val Lys Gly Gly Lys Pro Asp Val Val Gln Ile Val Arg Asn Tyr
225                 230                 235                 240
Asn Ala Tyr Leu Arg Ala Ser Asp Asp Leu Pro Lys Met Phe Ile Glu
                245                 250                 255
Ser Asp Pro Gly Phe Phe Ser Asn Ala Ile Val Glu Gly Ala Lys Lys
            260                 265                 270
Phe Pro Asn Thr Glu Phe Val Lys Val Lys Gly Leu His Phe Ser Gln
        275                 280                 285
Glu Asp Ala Pro Asp Glu Met Gly Lys Tyr Ile Lys Ser Phe Val Glu
    290                 295                 300
Arg Val Leu Lys Asn Glu Gln Gly Ser Ala Gly Thr Met Tyr Tyr Trp
305                 310                 315                 320
Glu Ile Glu Ala Ser Glu Val Met Leu Ser Thr Arg Ile Gly Ser Gly
                325                 330                 335
Ser Phe Gly Thr Val Tyr Lys Gly Lys Trp His Gly Asp Val Ala Val
            340                 345                 350
Lys Ile Leu Lys Val Val Asp Pro Thr Pro Glu Gln Phe Gln Ala Phe
        355                 360                 365
Arg Asn Glu Val Ala Val Leu Arg Lys Thr Arg His Val Asn Ile Leu
    370                 375                 380
Leu Phe Met Gly Tyr Met Thr Lys Asp Asn Leu Ala Ile Val Thr Gln
385                 390                 395                 400
```

Trp Cys Glu Gly Ser Ser Leu Tyr Lys His Leu His Val Gln Glu Thr
            405                 410                 415

Lys Phe Gln Met Phe Gln Leu Ile Asp Ile Ala Arg Gln Thr Ala Gln
        420                 425                 430

Gly Met Asp Tyr Leu His Ala Lys Asn Ile Ile His Arg Asp Met Lys
    435                 440                 445

Ser Asn Asn Ile Phe Leu His Glu Gly Leu Thr Val Lys Ile Gly Asp
450                 455                 460

Phe Gly Leu Ala Thr Val Lys Ser Arg Trp Ser Gly Ser Gln Gln Val
465                 470                 475                 480

Glu Gln Pro Thr Gly Ser Val Leu Trp Met Ala Pro Glu Val Ile Arg
                485                 490                 495

Met Gln Asp Asn Asn Pro Phe Ser Phe Gln Ser Asp Val Tyr Ser Tyr
            500                 505                 510

Gly Ile Val Leu Tyr Glu Leu Met Thr Gly Glu Leu Pro Tyr Ser His
        515                 520                 525

Ile Asn Asn Arg Asp Gln Ile Ile Phe Met Val Gly Arg Gly Tyr Ala
    530                 535                 540

Ser Pro Asp Leu Ser Lys Leu Tyr Lys Asn Cys Pro Lys Ala Met Lys
545                 550                 555                 560

Arg Leu Val Ala Asp Cys Val Lys Val Lys Glu Glu Arg Pro Leu
                565                 570                 575

Phe Pro Gln Ile Leu Ser Ser Ile Glu Leu Leu Gln His Ser Leu Pro
            580                 585                 590

Lys Ile Asn Arg Ser Ala Ser Glu Pro Ser Leu His Arg Ala Ala His
        595                 600                 605

Thr Glu Asp Ile Asn Ala Cys Thr Leu Thr Thr Ser Pro Arg Leu Pro
    610                 615                 620

Val Phe Lys Met Ser Lys Asp Gly Lys Lys Lys Lys Ser Lys
625                 630                 635                 640

Thr Lys Cys Val Ile Met
            645

<210> SEQ ID NO 43
<211> LENGTH: 930
<212> TYPE: DNA
<213> ORGANISM: Homo sapiens

<400> SEQUENCE: 43
cccatctctc gcaaggccag ccagaccagc gtgtacctgc aggagtggga catcccttc     60 gagcaggtag agctgggcga gcccatcggg cagggccgct ggggccgggt gcaccgcggc   120
cgctggcatg gcgaggtggc cattcgcctg ctggagatgg acggccacaa ccaggaccac   180
ctgaagctct tcaagaaaga ggtgatgaac taccggcaga cgcggcatga aacgtggtg    240 ctcttcatgg gggcctgcat gaacccgccc cacctggcca ttatcaccag cttctgcaag   300
gggcggacgt tgcactcgtt tgtgagggac cccaagacgt ctctggacat caacaagacg   360
aggcaaatcg ctcaggagat catcaagggc atgggatatc ttcatgccaa gggcatcgta   420
cacaaagatc tcaaatctaa gaacgtcttc tatgacaacg gcaaggtggt catcacagac   480
ttcgggctgt ttgggatctc aggcgtggtc cgagagggac ggcgtgagaa ccagctaaag   540
ctgtcccacg actggctgtg ctatctggcc cctgagattg tacgcgagat gaccccggg    600 aaggacgagg atcagctgcc attctccaaa gctgctgatg tctatgcatt tgggactgtt   660
tggtatgagc tgcaagcaag agactggccc ttgaagaacc aggctgcaga ggcatccatc   720

```
tggcagattg gaagcgggga aggaatgaag cgtgtcctga cttctgtcag cttggggaag        780
gaagtcagtg agatcctgtc ggcctgctgg gctttcgacc tgcaggagag acccagcttc        840
agcctgctga tggacatgct ggagaaactt cccaagctga accggcggct ctcccaccct        900
ggacacttct ggaagtcagc tgagttgtag                                         930
```

```
<210> SEQ ID NO 44
<211> LENGTH: 309
<212> TYPE: PRT
<213> ORGANISM: Homo sapiens

<400> SEQUENCE: 44
```

| | | | | | | | | | | | | | | |
|---|---|---|---|---|---|---|---|---|---|---|---|---|---|---|
| Pro | Ile | Ser | Arg | Lys | Ala | Ser | Gln | Thr | Ser | Val | Tyr | Leu | Gln | Glu | Trp |
| 1 | | | | 5 | | | | | 10 | | | | | 15 | |

Asp Ile Pro Phe Glu Gln Val Glu Leu Gly Glu Pro Ile Gly Gln Gly
            20                  25                  30

Arg Trp Gly Arg Val His Arg Gly Arg Trp His Gly Glu Val Ala Ile
        35                  40                  45

Arg Leu Leu Glu Met Asp Gly His Asn Gln Asp His Leu Lys Leu Phe
    50                  55                  60

Lys Lys Glu Val Met Asn Tyr Arg Gln Thr Arg His Glu Asn Val Val
65                  70                  75                  80

Leu Phe Met Gly Ala Cys Met Asn Pro Pro His Leu Ala Ile Ile Thr
                85                  90                  95

Ser Phe Cys Lys Gly Arg Thr Leu His Ser Phe Val Arg Asp Pro Lys
            100                 105                 110

Thr Ser Leu Asp Ile Asn Lys Thr Arg Gln Ile Ala Gln Glu Ile Ile
        115                 120                 125

Lys Gly Met Gly Tyr Leu His Ala Lys Gly Ile Val His Lys Asp Leu
    130                 135                 140

Lys Ser Lys Asn Val Phe Tyr Asp Asn Gly Lys Val Val Ile Thr Asp
145                 150                 155                 160

Phe Gly Leu Phe Gly Ile Ser Gly Val Val Arg Glu Gly Arg Arg Glu
                165                 170                 175

Asn Gln Leu Lys Leu Ser His Asp Trp Leu Cys Tyr Leu Ala Pro Glu
            180                 185                 190

Ile Val Arg Glu Met Thr Pro Gly Lys Asp Glu Asp Gln Leu Pro Phe
        195                 200                 205

Ser Lys Ala Ala Asp Val Tyr Ala Phe Gly Thr Val Trp Tyr Glu Leu
    210                 215                 220

Gln Ala Arg Asp Trp Pro Leu Lys Asn Gln Ala Ala Glu Ala Ser Ile
225                 230                 235                 240

Trp Gln Ile Gly Ser Gly Glu Gly Met Lys Arg Val Leu Thr Ser Val
                245                 250                 255

Ser Leu Gly Lys Glu Val Ser Glu Ile Leu Ser Ala Cys Trp Ala Phe
            260                 265                 270

Asp Leu Gln Glu Arg Pro Ser Phe Ser Leu Leu Met Asp Met Leu Glu
        275                 280                 285

Lys Leu Pro Lys Leu Asn Arg Arg Leu Ser His Pro Gly His Phe Trp
    290                 295                 300

Lys Ser Ala Glu Leu
305

```
<210> SEQ ID NO 45
```

```
<211> LENGTH: 933
<212> TYPE: DNA
<213> ORGANISM: Homo sapiens

<400> SEQUENCE: 45
atgcccatct ctcgcaaggc cagccagacc agcgtgtacc tgcaggagtg ggacatcccc      60
ttcgagcagg tagagctggg cgagcccatc gggcagggcc gctggggccg ggtgcaccgc     120
ggccgctggc atggcgaggt ggccattcgc ctgctggaga tggacggcca caaccaggac     180
cacctgaagc tcttcaagaa agaggtgatg aactaccggc agacgcggca tgagaacgtg     240
gtgctcttca tggggccctg catgaacccg ccccacctgg ccattatcac cagcttctgc     300
aaggggcgga cgttgcactc gtttgtgagg acccccaaga cgtctctgga catcaacaag     360
acgaggcaaa tcgctcagga gatcatcaag ggcatgggat atcttcatgc caagggcatc     420
gtacacaaag atctcaaatc taagaacgtc ttctatgaca acggcaaggt ggtcatcaca     480
gacttcgggc tgtttgggat ctcaggcgtg gtccgagagg gacggcgtga gaaccagcta     540
aagctgtccc acgactggct gtgctatctg gcccctgaga ttgtacgcga gatgaccccc     600
gggaaggacg aggatcagct gccattctcc aaagctgctg atgtctatgc atttgggact     660
gtttggtatg agctgcaagc aagagactgg cccttgaaga accaggctgc agaggcatcc     720
atctggcaga ttggaagcgg ggaaggaatg aagcgtgtcc tgacttctgt cagcttgggg     780
aaggaagtca gtgagatcct gtcggcctat tgggctttcg acctgcagga gagacccagc     840
ttcagcctgc tgatggacat gctggagaaa cttcccaagc tgaaccggcg gctctcccac     900
cctggacact tctggaagtc agctgagttg tag                                  933

<210> SEQ ID NO 46
<211> LENGTH: 310
<212> TYPE: PRT
<213> ORGANISM: Homo sapiens

<400> SEQUENCE: 46

Met Pro Ile Ser Arg Lys Ala Ser Gln Thr Ser Val Tyr Leu Gln Glu
1               5                   10                  15

Trp Asp Ile Pro Phe Glu Gln Val Glu Leu Gly Glu Pro Ile Gly Gln
            20                  25                  30

Gly Arg Trp Gly Arg Val His Arg Gly Arg Trp His Gly Glu Val Ala
        35                  40                  45

Ile Arg Leu Leu Glu Met Asp Gly His Asn Gln Asp His Leu Lys Leu
    50                  55                  60

Phe Lys Lys Glu Val Met Asn Tyr Arg Gln Thr Arg His Glu Asn Val
65                  70                  75                  80

Val Leu Phe Met Gly Ala Cys Met Asn Pro Pro His Leu Ala Ile Ile
                85                  90                  95

Thr Ser Phe Cys Lys Gly Arg Thr Leu His Ser Phe Val Arg Asp Pro
            100                 105                 110

Lys Thr Ser Leu Asp Ile Asn Lys Thr Arg Gln Ile Ala Gln Glu Ile
        115                 120                 125

Ile Lys Gly Met Gly Tyr Leu His Ala Lys Gly Ile Val His Lys Asp
    130                 135                 140

Leu Lys Ser Lys Asn Val Phe Tyr Asp Asn Gly Lys Val Val Ile Thr
145                 150                 155                 160

Asp Phe Gly Leu Phe Gly Ile Ser Gly Val Val Arg Glu Gly Arg Arg
                165                 170                 175
```

| | | | | | | | | | | | | |
|---|---|---|---|---|---|---|---|---|---|---|---|---|
|Glu|Asn|Gln|Leu|Lys|Leu|Ser|His|Asp|Trp|Leu|Cys|Tyr|Leu|Ala|Pro|
| | | |180| | | |185| | | | |190| | | |

Glu Ile Val Arg Glu Met Thr Pro Gly Lys Asp Glu Asp Gln Leu Pro
                195                 200                 205

Phe Ser Lys Ala Ala Asp Val Tyr Ala Phe Gly Thr Val Trp Tyr Glu
        210                 215                 220

Leu Gln Ala Arg Asp Trp Pro Leu Lys Asn Gln Ala Ala Glu Ala Ser
225                 230                 235                 240

Ile Trp Gln Ile Gly Ser Gly Glu Gly Met Lys Arg Val Leu Thr Ser
                245                 250                 255

Val Ser Leu Gly Lys Glu Val Ser Glu Ile Leu Ser Ala Tyr Trp Ala
            260                 265                 270

Phe Asp Leu Gln Glu Arg Pro Ser Phe Ser Leu Leu Met Asp Met Leu
        275                 280                 285

Glu Lys Leu Pro Lys Leu Asn Arg Arg Leu Ser His Pro Gly His Phe
    290                 295                 300

Trp Lys Ser Ala Glu Leu
305                 310

<210> SEQ ID NO 47
<211> LENGTH: 1881
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgcccatct ctcgcaaggc cagccagacc agcgtgtacc tgcaggagtg ggacatcccc      60
ttcgagcagg tagagctggg cgagcccatc gggcagggcc gctggggccg ggtgcaccgc     120
ggccgctggc atggcgaggt ggccattcgc ctgctggaga tggacggcca caaccaggac     180
cacctgaagc tcttcaagaa agaggtgatg aactaccggc agacgcggca tgagaacgtg     240
gtgctcttca tgggggcctg catgaacccg ccccacctgg ccattatcac cagcttctgc     300
aaggggcgga cgttgcactc gtttgtgagg accccaaga cgtctctgga catcaacaag     360
acgaggcaaa tcgctcagga gatcatcaag gcatgggat atcttcatgc caagggcatc     420
gtacacaaag atctcaaatc taagaacgtc ttctatgaca cggcaaggt ggtcatcaca     480 gacttcgggc tgtttgggat ctcaggcgtg gtccgagagg gacggcgtga gaaccagcta     540
aagctgtccc acgactggct gtgctatctg gcccctgaga ttgtacgcga gatgacccc     600 gggaaggacg aggatcagct gccattctcc aaagctgctg atgtctatgc atttgggact     660
gtttggtatg agctgcaagc aagagactgg cccttgaaga accaggctgc agaggcatcc     720
atctggcaga ttggaagcgg ggaaggaatg aagcgtgtcc tgacttctgt cagcttgggg     780
aaggaagtca gtgagatcct gtcggcctgc tgggctttcg acctgcagga gagacccagc     840
ttcagcctgc tgatggacat gctggagaaa cttcccaagc tgaaccggcg gctctcccac     900
cctggacact ctggaagtc agctgagttg tctagaggag ggggatgac agcaaggtg       960 tacgaccccg agcagaggaa gaggatgatc accggccccc agtggtgggc caggtgcaag    1020
cagatgaacg tgctggacag cttcatcaac tactacgaca gcgagaagca cgccgagaac    1080
gccgtgatct tcctgcacgg caacgccact agcagctacc tgtggaggca cgtggtgccc    1140
cacatcgagc ccgtgccag gtgcatcatc ccgatctga tcggcatggg caagagcggc    1200
aagagcggca acggcagcta caggctgctg gaccactaca gtacctgac cgcctggttc    1260
```

```
gagctcctga acctgcccaa gaagatcatc ttcgtgggcc acgactgggg cgccgcactg   1320
gccttccact acagctacga gcaccaggac aagatcaagg ccatcgtgca cgccgagagc   1380
gtggttgacg tgatcgagag ctgggacgag tggccagaca tcgaggagga catcgccctg   1440
atcaagagcg aggagggcga gaagatggtg ctggagaaca acttcttcgt ggagaccgtt   1500
ctgcccagca agatcatgag aaagctggag cccgaggagt cgccgcccta cctggagccc   1560
ttcaaggaga agggcgaggt gagaagaccc accctgagct ggcccagaga gatccccctg   1620
gtgaagggcg gcaagcccga cgtggtgcag atcgtgagaa actacaacgc ctacctgaga   1680
gccagcgacg acctgcccaa gatgttcatc gagagcgacc ccggcttctt cagcaacgcc   1740
atcgtggagg gcgccaagaa gttccccaac accgagttcg tgaaggtgaa gggcctgcac   1800
ttcagccagg aggacgcccc cgacgagatg ggcaagtaca tcaagagctt cgtggagaga   1860
gtgctgaaga acgagcagta g                                              1881
```

<210> SEQ ID NO 48
<211> LENGTH: 626
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Met Pro Ile Ser Arg Lys Ala Ser Gln Thr Ser Val Tyr Leu Gln Glu
1               5                   10                  15

Trp Asp Ile Pro Phe Glu Gln Val Glu Leu Gly Glu Pro Ile Gly Gln
            20                  25                  30

Gly Arg Trp Gly Arg Val His Arg Gly Arg Trp His Gly Glu Val Ala
        35                  40                  45

Ile Arg Leu Leu Glu Met Asp Gly His Asn Gln Asp His Leu Lys Leu
    50                  55                  60

Phe Lys Lys Glu Val Met Asn Tyr Arg Gln Thr Arg His Glu Asn Val
65                  70                  75                  80

Val Leu Phe Met Gly Ala Cys Met Asn Pro Pro His Leu Ala Ile Ile
                85                  90                  95

Thr Ser Phe Cys Lys Gly Arg Thr Leu His Ser Phe Val Arg Asp Pro
            100                 105                 110

Lys Thr Ser Leu Asp Ile Asn Lys Thr Arg Gln Ile Ala Gln Glu Ile
        115                 120                 125

Ile Lys Gly Met Gly Tyr Leu His Ala Lys Gly Ile Val His Lys Asp
    130                 135                 140

Leu Lys Ser Lys Asn Val Phe Tyr Asp Asn Gly Lys Val Val Ile Thr
145                 150                 155                 160

Asp Phe Gly Leu Phe Gly Ile Ser Gly Val Val Arg Glu Gly Arg Arg
                165                 170                 175

Glu Asn Gln Leu Lys Leu Ser His Asp Trp Leu Cys Tyr Leu Ala Pro
            180                 185                 190

Glu Ile Val Arg Glu Met Thr Pro Gly Lys Asp Glu Asp Gln Leu Pro
        195                 200                 205

Phe Ser Lys Ala Ala Asp Val Tyr Ala Phe Gly Thr Val Trp Tyr Glu
    210                 215                 220

Leu Gln Ala Arg Asp Trp Pro Leu Lys Asn Gln Ala Ala Glu Ala Ser
225                 230                 235                 240
```

```
Ile Trp Gln Ile Gly Ser Gly Glu Gly Met Lys Arg Val Leu Thr Ser
            245                 250                 255
Val Ser Leu Gly Lys Glu Val Ser Glu Ile Leu Ser Ala Cys Trp Ala
        260                 265                 270
Phe Asp Leu Gln Glu Arg Pro Ser Phe Ser Leu Leu Met Asp Met Leu
    275                 280                 285
Glu Lys Leu Pro Lys Leu Asn Arg Arg Leu Ser His Pro Gly His Phe
290                 295                 300
Trp Lys Ser Ala Glu Leu Ser Arg Gly Gly Met Thr Ser Lys Val
305                 310                 315                 320
Tyr Asp Pro Glu Gln Arg Lys Arg Met Ile Thr Gly Pro Gln Trp Trp
                325                 330                 335
Ala Arg Cys Lys Gln Met Asn Val Leu Asp Ser Phe Ile Asn Tyr Tyr
            340                 345                 350
Asp Ser Glu Lys His Ala Glu Asn Ala Val Ile Phe Leu His Gly Asn
        355                 360                 365
Ala Thr Ser Ser Tyr Leu Trp Arg His Val Val Pro His Ile Glu Pro
    370                 375                 380
Val Ala Arg Cys Ile Ile Pro Asp Leu Ile Gly Met Gly Lys Ser Gly
385                 390                 395                 400
Lys Ser Gly Asn Gly Ser Tyr Arg Leu Leu Asp His Tyr Lys Tyr Leu
                405                 410                 415
Thr Ala Trp Phe Glu Leu Leu Asn Leu Pro Lys Lys Ile Ile Phe Val
            420                 425                 430
Gly His Asp Trp Gly Ala Ala Leu Ala Phe His Tyr Ser Tyr Glu His
        435                 440                 445
Gln Asp Lys Ile Lys Ala Ile Val His Ala Glu Ser Val Val Asp Val
    450                 455                 460
Ile Glu Ser Trp Asp Glu Trp Pro Asp Ile Glu Glu Asp Ile Ala Leu
465                 470                 475                 480
Ile Lys Ser Glu Glu Gly Glu Lys Met Val Leu Glu Asn Asn Phe Phe
                485                 490                 495
Val Glu Thr Val Leu Pro Ser Lys Ile Met Arg Lys Leu Glu Pro Glu
            500                 505                 510
Glu Phe Ala Ala Tyr Leu Glu Pro Phe Lys Glu Lys Gly Glu Val Arg
        515                 520                 525
Arg Pro Thr Leu Ser Trp Pro Arg Glu Ile Pro Leu Val Lys Gly Gly
    530                 535                 540
Lys Pro Asp Val Val Gln Ile Val Arg Asn Tyr Asn Ala Tyr Leu Arg
545                 550                 555                 560
Ala Ser Asp Asp Leu Pro Lys Met Phe Ile Glu Ser Asp Pro Gly Phe
                565                 570                 575
Phe Ser Asn Ala Ile Val Glu Gly Ala Lys Lys Phe Pro Asn Thr Glu
            580                 585                 590
Phe Val Lys Val Lys Gly Leu His Phe Ser Gln Glu Asp Ala Pro Asp
        595                 600                 605
Glu Met Gly Lys Tyr Ile Lys Ser Phe Val Glu Arg Val Leu Lys Asn
    610                 615                 620
Glu Gln
625

<210> SEQ ID NO 49
<211> LENGTH: 1881
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 49

```
atgcccatct ctcgcaaggc cagccagacc agcgtgtacc tgcaggagtg ggacatcccc      60
ttcgagcagg tagagctggg cgagcccatc gggcagggcc gctggggccg ggtgcaccgc     120
ggccgctggc atggcgaggt ggccattcgc ctgctggaga tggacggcca caaccaggac     180
cacctgaagc tcttcaagaa agaggtgatg aactaccggc agacgcggca tgagaacgtg     240
gtgctcttca tggggcctg catgaacccg ccccacctgg ccattatcac cagcttctgc     300
aaggggcgga cgttgcactc gtttgtgagg acccccaaga cgtctctgga catcaacaag     360
acgaggcaaa tcgctcagga gatcatcaag ggcatgggat atcttcatgc caagggcatc     420
gtacacaaag atctcaaatc taagaacgtc ttctatgaca cggcaaggt ggtcatcaca      480
gacttcgggc tgtttggat ctcaggcgtg tccgagagg gacggcgtga gaaccagcta      540
aagctgtccc acgactggct gtgctatctg gccctgaga ttgtacgcga tgacccc        600
gggaaggacg aggatcagct gccattctcc aaagctgctg atgtctatgc atttgggact     660
gtttggtatg agctgcaagc aagagactgg cccttgaaga accaggctgc agaggcatcc     720
atctggcaga ttggaagcgg ggaaggaatg aagcgtgtcc tgacttctgt cagcttgggg     780
aaggaagtca gtgagatcct gtcggcctat gggctttcg acctgcagga gagacccagc     840
ttcagcctgc tgatggacat gctggagaaa cttcccaagc tgaaccggcg gctctcccac     900
cctggacact tctggaagtc agctgagttg tctagaggag gggggatgac cagcaaggtg     960
tacgaccccg agcagaggaa gaggatgatc accggccccc agtggtgggc caggtgcaag    1020
cagatgaacg tgctggacag cttcatcaac tactacgaca gcgagaagca cgccgagaac    1080
gccgtgatct tcctgcacgg caacgccact agcagctacc tgtggagggca cgtggtgccc    1140
cacatcgagc ccgtggccag gtgcatcatc cccgatctga tcggcatggg caagagcggc    1200
aagagcggca acggcagcta caggctgctg gaccactaca gtacctgac cgcctggttc    1260
gagctcctga acctgcccaa gaagatcatc ttcgtgggcc acgactgggg cgccgcactg    1320
gccttccact acagctacga gcaccaggac aagatcaagg ccatcgtgca cgccgagagc    1380
gtggttgacg tgatcgagag ctgggacgag tggccagaca tcgaggagga catcgccctg    1440
atcaagagcg aggagggcga gaagatggtg ctggagaaca acttcttcgt ggagaccgtt    1500
ctgcccagca agatcatgag aaagctggag cccgaggagt cgccgcctca cctggagccc    1560
ttcaaggaga agggcgaggt gagaagaccc accctgagct ggcccagaga gatcccctg    1620
gtgaagggcg gcaagcccga cgtggtgcag atcgtgagaa actacaacgc ctacctgaga    1680
gccagcgacg acctgcccaa gatgttcatc gagagcgacc ccggcttctt cagcaacgcc    1740
atcgtggagg gcgccaagaa gttccccaac accgagttcg tgaaggtgaa gggcctgcac    1800
ttcagccagg aggacgcccc cgacgagatg ggcaagtaca tcaagagctt cgtggagaga    1860
gtgctgaaga acgagcagta g                                              1881
```

<210> SEQ ID NO 50
<211> LENGTH: 626
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 50

Met Pro Ile Ser Arg Lys Ala Ser Gln Thr Ser Val Tyr Leu Gln Glu
1               5                   10                  15

Trp Asp Ile Pro Phe Glu Gln Val Glu Leu Gly Glu Pro Ile Gly Gln
            20                  25                  30

Gly Arg Trp Gly Arg Val His Arg Gly Arg Trp His Gly Glu Val Ala
        35                  40                  45

Ile Arg Leu Leu Glu Met Asp Gly His Asn Gln Asp His Leu Lys Leu
    50                  55                  60

Phe Lys Lys Glu Val Met Asn Tyr Arg Gln Thr Arg His Glu Asn Val
65                  70                  75                  80

Val Leu Phe Met Gly Ala Cys Met Asn Pro Pro His Leu Ala Ile Ile
                85                  90                  95

Thr Ser Phe Cys Lys Gly Arg Thr Leu His Ser Phe Val Arg Asp Pro
                100                 105                 110

Lys Thr Ser Leu Asp Ile Asn Lys Thr Arg Gln Ile Ala Gln Glu Ile
            115                 120                 125

Ile Lys Gly Met Gly Tyr Leu His Ala Lys Gly Ile Val His Lys Asp
    130                 135                 140

Leu Lys Ser Lys Asn Val Phe Tyr Asp Asn Gly Lys Val Val Ile Thr
145                 150                 155                 160

Asp Phe Gly Leu Phe Gly Ile Ser Gly Val Val Arg Glu Gly Arg Arg
                165                 170                 175

Glu Asn Gln Leu Lys Leu Ser His Asp Trp Leu Cys Tyr Leu Ala Pro
            180                 185                 190

Glu Ile Val Arg Glu Met Thr Pro Gly Lys Asp Glu Asp Gln Leu Pro
    195                 200                 205

Phe Ser Lys Ala Ala Asp Val Tyr Ala Phe Gly Thr Val Trp Tyr Glu
210                 215                 220

Leu Gln Ala Arg Asp Trp Pro Leu Lys Asn Gln Ala Ala Glu Ala Ser
225                 230                 235                 240

Ile Trp Gln Ile Gly Ser Gly Glu Gly Met Lys Arg Val Leu Thr Ser
                245                 250                 255

Val Ser Leu Gly Lys Glu Val Ser Glu Ile Leu Ser Ala Tyr Trp Ala
            260                 265                 270

Phe Asp Leu Gln Glu Arg Pro Ser Phe Ser Leu Leu Met Asp Met Leu
        275                 280                 285

Glu Lys Leu Pro Lys Leu Asn Arg Arg Leu Ser His Pro Gly His Phe
290                 295                 300

Trp Lys Ser Ala Glu Leu Ser Arg Gly Gly Met Thr Ser Lys Val
305                 310                 315                 320

Tyr Asp Pro Glu Gln Arg Lys Arg Met Ile Thr Gly Pro Gln Trp Trp
                325                 330                 335

Ala Arg Cys Lys Gln Met Asn Val Leu Asp Ser Phe Ile Asn Tyr Tyr
            340                 345                 350

Asp Ser Glu Lys His Ala Glu Asn Ala Val Ile Phe Leu His Gly Asn
        355                 360                 365

Ala Thr Ser Ser Tyr Leu Trp Arg His Val Val Pro His Ile Glu Pro
    370                 375                 380

Val Ala Arg Cys Ile Ile Pro Asp Leu Ile Gly Met Gly Lys Ser Gly
385                 390                 395                 400

Lys Ser Gly Asn Gly Ser Tyr Arg Leu Leu Asp His Tyr Lys Tyr Leu
```

```
                405                 410                 415
Thr Ala Trp Phe Glu Leu Leu Asn Leu Pro Lys Lys Ile Ile Phe Val
            420                 425                 430
Gly His Asp Trp Gly Ala Ala Leu Ala Phe His Tyr Ser Tyr Glu His
            435                 440                 445
Gln Asp Lys Ile Lys Ala Ile Val His Ala Glu Ser Val Val Asp Val
450                 455                 460
Ile Glu Ser Trp Asp Glu Trp Pro Asp Ile Glu Glu Asp Ile Ala Leu
465                 470                 475                 480
Ile Lys Ser Glu Glu Gly Glu Lys Met Val Leu Glu Asn Asn Phe Phe
            485                 490                 495
Val Glu Thr Val Leu Pro Ser Lys Ile Met Arg Lys Leu Glu Pro Glu
            500                 505                 510
Glu Phe Ala Ala Tyr Leu Glu Pro Phe Lys Glu Lys Gly Glu Val Arg
            515                 520                 525
Arg Pro Thr Leu Ser Trp Pro Arg Glu Ile Pro Leu Val Lys Gly Gly
            530                 535                 540
Lys Pro Asp Val Val Gln Ile Val Arg Asn Tyr Asn Ala Tyr Leu Arg
545                 550                 555                 560
Ala Ser Asp Asp Leu Pro Lys Met Phe Ile Glu Ser Asp Pro Gly Phe
            565                 570                 575
Phe Ser Asn Ala Ile Val Glu Gly Ala Lys Lys Phe Pro Asn Thr Glu
            580                 585                 590
Phe Val Lys Val Lys Gly Leu His Phe Ser Gln Glu Asp Ala Pro Asp
            595                 600                 605
Glu Met Gly Lys Tyr Ile Lys Ser Phe Val Glu Arg Val Leu Lys Asn
            610                 615                 620
Glu Gln
625

<210> SEQ ID NO 51
<211> LENGTH: 1182
<212> TYPE: DNA
<213> ORGANISM: Homo sapiens

<400> SEQUENCE: 51
atgcccaaga agaagccgac gcccatccag ctgaacccgg cccccgacgg ctctgcagtt      60
aacgggacca gctctgcgga gaccaacttg gaggccttgc agaagaagct ggaggagcta     120
gagcttgatg agcagcagcg aaagcgcctt gaggcctttc ttacccagaa gcagaaggtg     180
ggagaactga aggatgacga ctttgagaag atcagtgagc tggggctgg caatggcggt     240 gtggtgttca aggtctccca caagccttct ggcctggtca tggccagaaa gctaattcat     300
ctggagatca aacccgcaat ccggaaccag atcataaggg agctgcaggt tctgcatgag     360
tgcaactctc cgtacatcgt gggcttctat ggtgcgttct acagcgatgg cgagatcagt     420
atctgcatgg agcacatgga tggaggttct ctggatcaag tcctgaagaa gctggaaga     480 attcctgaac aaattttagg aaaagttagc attgctgtaa taaaggcct gacatatctg     540 agggagaagc acaagatcat gcacagagat gtcaagccct ccaacatcct agtcaactcc     600 cgtgggggaga tcaagctctg tgactttggg gtcagcgggc agctcatcga ctccatggcc     660
aactccttcg tgggcacaag gtcctacatg tcgccagaaa gactccaggg gactcattac     720
tctgtgcagt cagacatctg gagcatggga ctgtctctgg tagagatggc ggttgggagg     780
tatcccatcc ctcctccaga tgccaaggag ctggagctga tgtttgggtg ccaggtggaa     840
```

```
ggagatgcgg ctgagacccc acccaggcca aggaccccg ggaggcccct tagctcatac    900
ggaatggaca gccgacctcc catggcaatt tttgagttgt tggattacat agtcaacgag    960
cctcctccaa aactgcccag tggagtgttc agtctggaat tcaagatttt tgtgaataaa   1020
tgcttaataa aaaaccccgc agagagagca gatttgaagc aactcatggt tcatgctttt   1080
atcaagagat ctgatgctga ggaagtggat tttgcaggtt ggctctgctc caccatcggc   1140
cttaaccagc ccagcacacc aacccatgct gctggcgtct aa                      1182

<210> SEQ ID NO 52
<211> LENGTH: 393
<212> TYPE: PRT
<213> ORGANISM: Homo sapiens

<400> SEQUENCE: 52

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
```

```
                305                 310                 315                 320
Pro Pro Pro Lys Leu Pro Ser Gly Val Phe Ser Leu Glu Phe Gln Asp
                    325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

<210> SEQ ID NO 53
<211> LENGTH: 1915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caccatggtg agcaagggcg aggagctgtt caccggggtg gtgcccatcc tggtcgagct     60
ggacggcgac gtaaacggcc acaagttcag cgtgtccggc gagggcgagg gcgatgccac    120
ctacggcaag ctgaccctga gttcatctg caccaccggc aagctgcccg tgccctggcc    180
caccctcgtg accaccctga gctacggcgt gcagtgcttc agccgctacc ccgaccacat    240
gaagcagcac gacttcttca gtccgccat gcccgaaggc tacgtccagg agcgcaccat    300
cttcttcaag gacgacggca actacaagac ccgcgccgag gtgaagttcg agggcgacac    360
cctggtgaac cgcatcgagc tgaagggcat cgacttcaag gaggacggca acatcctggg    420
gcacaagctg gagtacaact acaaccccca caacgtctat atcatggccg acaagcagaa    480
gaacggcatc aaggtgaact tcaagatccg ccacaacatc gaggacggca gcgtgcagct    540
cgccgaccac taccagcaga cacccccat cggcgacggc cccgtgctgc tgcccgacaa    600
ccactacctg ttcacccagt ccgccctgag caaagacccc aacgagaagc gcgatcacat    660
ggtcctgctg gagttcgtga ccgccgccgg gatcactctc ggcatggacg agctgtacaa    720
gggatccgcc ggtaccccca agaagaagcc gacgcccatc cagctgaacc cggcccccga    780
cggctctgca gttaacggga ccagctctgc ggagaccaac ttggaggcct tgcagaagaa    840
gctggaggag ctagagcttg atgagcagca gcgaaagcgc cttgaggcct ttcttaccca    900
gaagcagaag gtgggagaac tgaaggatga cgactttgag aagatcagtg agctgggggc    960 tgcaatggc ggtgtggtgt tcaaggtctc ccacaagcct tctggcctgg tcatggccag   1020
aaagctaatt catctggaga tcaaacccgc aatccggaac cagatcataa gggagctgca   1080
ggttctgcat gagtgcaact ctccgtacat cgtgggcttc tatggtgcgt tctacagcga   1140
tggcgagatc agtatctgca tggagcacat ggatggaggt tctctggatc aagtcctgaa   1200
gaaagctgga agaattcctg aacaaatttt aggaaaagtt agcattgctg taataaaagg   1260
cctgacatat ctgagggaga agcacaagat catgcacaga gatgtcaagc ctccaacat   1320 cctagtcaac tcccgtgggg agatcaagct ctgtgacttt ggggtcagcg gcagctcat   1380 cgactccatg gccaactcct tcgtgggcac aaggtcctac atgtcgccag aaagactcca   1440
ggggactcat tactctgtgc agtcagacat ctggagcatg ggactgtctc tggtagagat   1500
ggcggttggg aggtatcccg tccctcctcc agatgccaag gagctggagc tgatgtttgg   1560
```

```
gtgccaggtg gaaggagatg cggctgagac cccacccagg ccaaggaccc ccggggaggcc      1620 ccttagctca tacggaatgg acagccgacc tcccatggca atttttgagt tgttggatta      1680
catagtcaac gagcctcctc caaaactgcc cagtggagtg ttcagtctgg aatttcaaga      1740
ttttgtgaat aaatgcttaa taaaaaaccc cgcagagaga gcagatttga agcaactcat      1800
ggttcatgct tttatcaaga gatctgatgc tgaggaagtg gattttgcag gttggctctg      1860
ctccaccatc ggccttaacc agcccagcac accaacccat gctgctggcg tctaa           1915

<210> SEQ ID NO 54
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Phe Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Ala Gly Thr Pro Lys Lys Pro Thr Pro Ile Gln Leu Asn Pro
                245                 250                 255

Ala Pro Asp Gly Ser Ala Val Asn Gly Thr Ser Ser Ala Glu Thr Asn
            260                 265                 270

Leu Glu Ala Leu Gln Lys Lys Leu Glu Glu Leu Glu Leu Asp Glu Gln
        275                 280                 285

Gln Arg Lys Arg Leu Glu Ala Phe Leu Thr Gln Lys Gln Lys Val Gly

```
                290             295             300
Glu Leu Lys Asp Asp Phe Glu Lys Ile Ser Glu Leu Gly Ala Gly
305                 310                 315                 320

Asn Gly Gly Val Val Phe Lys Val Ser His Lys Pro Ser Gly Leu Val
                325                 330                 335

Met Ala Arg Lys Leu Ile His Leu Glu Ile Lys Pro Ala Ile Arg Asn
                340                 345                 350

Gln Ile Ile Arg Glu Leu Gln Val Leu His Glu Cys Asn Ser Pro Tyr
            355                 360                 365

Ile Val Gly Phe Tyr Gly Ala Phe Tyr Ser Asp Gly Glu Ile Ser Ile
            370                 375                 380

Cys Met Glu His Met Asp Gly Gly Ser Leu Asp Gln Val Leu Lys Lys
385                 390                 395                 400

Ala Gly Arg Ile Pro Glu Gln Ile Leu Gly Lys Val Ser Ile Ala Val
                405                 410                 415

Ile Lys Gly Leu Thr Tyr Leu Arg Glu Lys His Lys Ile Met His Arg
            420                 425                 430

Asp Val Lys Pro Ser Asn Ile Leu Val Asn Ser Arg Gly Glu Ile Lys
            435                 440                 445

Leu Cys Asp Phe Gly Val Ser Gly Gln Leu Ile Asp Ser Met Ala Asn
450                 455                 460

Ser Phe Val Gly Thr Arg Ser Tyr Met Ser Pro Glu Arg Leu Gln Gly
465                 470                 475                 480

Thr His Tyr Ser Val Gln Ser Asp Ile Trp Ser Met Gly Leu Ser Leu
                485                 490                 495

Val Glu Met Ala Val Gly Arg Tyr Pro Ile Pro Pro Pro Asp Ala Lys
            500                 505                 510

Glu Leu Glu Leu Met Phe Gly Cys Gln Val Glu Gly Asp Ala Ala Glu
            515                 520                 525

Thr Pro Pro Arg Pro Arg Thr Pro Gly Arg Pro Leu Ser Ser Tyr Gly
            530                 535                 540

Met Asp Ser Arg Pro Pro Met Ala Ile Phe Glu Leu Leu Asp Tyr Ile
545                 550                 555                 560

Val Asn Glu Pro Pro Pro Lys Leu Pro Ser Gly Val Phe Ser Leu Glu
                565                 570                 575

Phe Gln Asp Phe Val Asn Lys Cys Leu Ile Lys Asn Pro Ala Glu Arg
            580                 585                 590

Ala Asp Leu Lys Gln Leu Met Val His Ala Phe Ile Lys Arg Ser Asp
            595                 600                 605

Ala Glu Glu Val Asp Phe Ala Gly Trp Leu Cys Ser Thr Ile Gly Leu
610                 615                 620

Asn Gln Pro Ser Thr Pro Thr His Ala Ala Gly Val
625                 630                 635
```

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggggtaccat ggatgattgg gagattcctg atgggc                                 36

```
<210> SEQ ID NO 56
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gctctagatt acataattac acactttgtc tttgacttct ttttcttctt tttaccatct      60
ttgctcatct tgtggacagg aaacgcacca ta                                   92

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggggtaccat gtattattgg gaaatagaag cc                                   32

<210> SEQ ID NO 58
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gctctagatt acataattac acactttgtc tttgacttct ttttcttctt tttaccatct      60
ttgctcatct tgaagacagg cagcctcggg ga                                   92

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggggtacccc catctctcgc aaggccagcc ag                                   32

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctctagact acaactcagc tgacttccag aag                                  33

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
```

```
ggggtacccc caagaagaag ccgacgccca tc                                32
```

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
gctctagatt agacgccagc agcatgggtt gg                                32
```

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
gggtttccgc tgtcaaacat gtgg                                         24
```

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
tattgttacc cagtggtgtg aggg                                         24
```

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

```
acacctaatg tccacatggt cagc                                         24
```

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

```
tttccagtcg gatgtctact ccta                                         24
```

<210> SEQ ID NO 67
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
aatgaagtag gagtactcag gaaaacacat catgtgaata tcctactctt catgggc     57
```

<210> SEQ ID NO 68
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcccatgaag agtaggatat tcacatgatg tgttttcctg agtactccta cttcatt        57

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gaagtcagtg agatcctgtc ggcctattgg gctttcgacc tgcaggagag a              51

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tctctcctgc aggtcgaaag cccaataggc cgacaggatc tcactgactt c              51

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgtaaacggc cacaagttca g                                               21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acgaactcca gcaggaccat g                                               21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aatacaaact ggtcgtcgtt g                                               21

```
<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aatctacgat tcggcttgtt c                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tttggacaga tctatatgca g                                              21

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tcggttcaaa ggtctccag                                                 19

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccgattgtgt caccccctaat                                               20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccacttgagc acatcgctaa                                                20

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gacacttcct agtgcggctc gcgtg                                          25
```

```
<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtaatcatac atctggtaat ctacc                                           25

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgactgagcg cgagaacaat g                                               21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tcttctgcct gcatatcgga c                                               21

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gacagtcgat aaggaagagc tgg                                             23

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcgttcagtg tgtccagctc                                                 20

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 85

His His His His His His
1               5
```

```
<210> SEQ ID NO 86
<211> LENGTH: 276
<212> TYPE: PRT
<213> ORGANISM: Homo sapiens

<400> SEQUENCE: 86

Asp Asp Trp Glu Ile Pro Asp Gly Gln Ile Thr Val Gly Gln Arg Ile
1               5                   10                  15

Gly Ser Gly Ser Phe Gly Thr Val Tyr Lys Gly Lys Trp His Gly Asp
            20                  25                  30

Val Ala Val Lys Met Leu Asn Val Thr Ala Pro Thr Pro Gln Gln Leu
        35                  40                  45

Gln Ala Phe Lys Asn Glu Val Gly Val Leu Arg Lys Thr Arg His Val
    50                  55                  60

Asn Ile Leu Leu Phe Met Gly Tyr Ser Thr Lys Pro Gln Leu Ala Ile
65                  70                  75                  80

Val Thr Gln Trp Cys Glu Gly Ser Ser Leu Tyr His His Leu His Ile
                85                  90                  95

Ile Glu Thr Lys Phe Glu Met Ile Lys Leu Ile Asp Ile Ala Arg Gln
            100                 105                 110

Thr Ala Gln Gly Met Asp Tyr Leu His Ala Lys Ser Ile Ile His Arg
        115                 120                 125

Asp Leu Lys Ser Asn Asn Ile Phe Leu His Glu Asp Leu Thr Val Lys
    130                 135                 140

Ile Gly Asp Phe Gly Leu Ala Thr Val Lys Ser Arg Trp Ser Gly Ser
145                 150                 155                 160

His Gln Phe Glu Gln Leu Ser Gly Ser Ile Leu Trp Met Ala Pro Glu
                165                 170                 175

Val Ile Arg Met Gln Asp Lys Asn Pro Tyr Ser Phe Gln Ser Asp Val
            180                 185                 190

Tyr Ala Phe Gly Ile Val Leu Tyr Glu Leu Met Thr Gly Gln Leu Pro
        195                 200                 205

Tyr Ser Asn Ile Asn Asn Arg Asp Gln Ile Ile Phe Met Val Gly Arg
    210                 215                 220

Gly Tyr Leu Ser Pro Asp Leu Ser Lys Val Arg Ser Asn Cys Pro Lys
225                 230                 235                 240

Ala Met Lys Arg Leu Met Ala Glu Cys Leu Lys Lys Arg Asp Glu
                245                 250                 255

Arg Pro Leu Phe Pro Gln Ile Leu Ala Ser Ile Glu Leu Leu Ala Arg
            260                 265                 270

Ser Leu Pro Lys
        275

<210> SEQ ID NO 87
<211> LENGTH: 276
<212> TYPE: PRT
<213> ORGANISM: Mus musculus

<400> SEQUENCE: 87

Asp Asp Trp Glu Ile Pro Asp Gly Gln Ile Thr Val Gly Gln Arg Ile
1               5                   10                  15

Gly Ser Gly Ser Phe Gly Thr Val Tyr Lys Gly Lys Trp His Gly Asp
            20                  25                  30

Val Ala Val Lys Met Leu Asn Val Thr Ala Pro Thr Pro Gln Gln Leu
        35                  40                  45

Gln Ala Phe Lys Asn Glu Val Gly Val Leu Arg Lys Thr Arg His Val
```

```
                  50                  55                  60

Asn Ile Leu Leu Phe Met Gly Tyr Ser Thr Lys Pro Gln Leu Ala Ile
 65                  70                  75                  80

Val Thr Gln Trp Cys Glu Gly Ser Ser Leu Tyr His His Leu His Ile
                     85                  90                  95

Ile Glu Thr Lys Phe Glu Met Ile Lys Leu Ile Asp Ile Ala Arg Gln
                    100                 105                 110

Thr Ala Gln Gly Met Asp Tyr Leu His Ala Lys Ser Ile Ile His Arg
                    115                 120                 125

Asp Leu Lys Ser Asn Asn Ile Phe Leu His Glu Asp Leu Thr Val Lys
            130                 135                 140

Ile Gly Asp Phe Gly Leu Ala Thr Val Lys Ser Arg Trp Ser Gly Ser
145                 150                 155                 160

His Gln Phe Glu Gln Leu Ser Gly Ser Ile Leu Trp Met Ala Pro Glu
                    165                 170                 175

Val Ile Arg Met Gln Asp Lys Asn Pro Tyr Ser Phe Gln Ser Asp Val
                    180                 185                 190

Tyr Ala Phe Gly Ile Val Leu Tyr Glu Leu Met Thr Gly Gln Leu Pro
                    195                 200                 205

Tyr Ser Asn Ile Asn Asn Arg Asp Gln Ile Ile Phe Met Val Gly Arg
            210                 215                 220

Gly Tyr Leu Ser Pro Asp Leu Ser Lys Val Arg Ser Asn Cys Pro Lys
225                 230                 235                 240

Ala Met Lys Arg Leu Met Ala Glu Cys Leu Lys Lys Arg Asp Glu
                    245                 250                 255

Arg Pro Leu Phe Pro Gln Ile Leu Ala Ser Ile Glu Leu Leu Ala Arg
            260                 265                 270

Ser Leu Pro Lys
        275

<210> SEQ ID NO 88
<211> LENGTH: 276
<212> TYPE: PRT
<213> ORGANISM: Gallus sp.

<400> SEQUENCE: 88

Asp Asp Trp Glu Ile Pro Asp Gly Gln Ile Thr Val Gly Gln Arg Ile
 1               5                  10                  15

Gly Ser Gly Ser Phe Gly Thr Val Tyr Lys Gly Lys Trp His Gly Asp
                     20                  25                  30

Val Ala Val Lys Met Leu Asn Val Thr Ala Pro Thr Pro Gln Gln Leu
                     35                  40                  45

Gln Ala Phe Lys Asn Glu Val Gly Val Leu Arg Lys Thr Arg His Val
             50                  55                  60

Asn Ile Leu Leu Phe Met Gly Tyr Ser Thr Lys Pro Gln Leu Ala Ile
 65                  70                  75                  80

Val Thr Gln Trp Cys Glu Gly Ser Ser Leu Tyr His His Leu His Ile
                     85                  90                  95

Ile Glu Thr Lys Phe Glu Met Ile Lys Leu Ile Asp Ile Ala Arg Gln
                    100                 105                 110

Thr Ala Gln Gly Met Asp Tyr Leu His Ala Lys Ser Ile Ile His Arg
                    115                 120                 125

Asp Leu Lys Ser Asn Asn Ile Phe Leu His Glu Asp Leu Thr Val Lys
            130                 135                 140
```

```
Ile Gly Asp Phe Gly Leu Ala Thr Val Lys Ser Arg Trp Ser Gly Ser
145                 150                 155                 160

His Gln Phe Glu Gln Leu Ser Gly Ser Ile Leu Trp Met Ala Pro Glu
                165                 170                 175

Val Ile Arg Met Gln Asp Lys Asn Pro Tyr Ser Phe Gln Ser Asp Val
            180                 185                 190

Tyr Ala Phe Gly Ile Val Leu Tyr Glu Leu Met Thr Gly Gln Leu Pro
        195                 200                 205

Tyr Ser Asn Ile Asn Asn Arg Asp Gln Ile Ile Phe Met Val Gly Arg
    210                 215                 220

Gly Tyr Leu Ser Pro Asp Leu Ser Lys Val Arg Ser Asn Cys Pro Lys
225                 230                 235                 240

Ala Met Lys Arg Leu Met Ala Glu Cys Leu Lys Lys Lys Arg Asp Glu
                245                 250                 255

Arg Pro Leu Phe Pro Gln Ile Leu Ala Ser Ile Glu Leu Leu Ala Arg
            260                 265                 270

Ser Leu Pro Lys
        275

<210> SEQ ID NO 89
<211> LENGTH: 276
<212> TYPE: PRT
<213> ORGANISM: Danio sp.

<400> SEQUENCE: 89

Asp Asp Trp Glu Ile Pro Glu Gly Gln Ile Thr Leu Gly Gln Arg Ile
1               5                   10                  15

Gly Ser Gly Ser Phe Gly Thr Val Tyr Lys Gly Lys Trp His Gly Asp
                20                  25                  30

Val Ala Val Lys Met Leu Asn Val Thr Ala Pro Thr Pro Gln Gln Leu
            35                  40                  45

Gln Ala Phe Lys Asn Glu Val Gly Val Leu Arg Lys Thr Arg His Val
        50                  55                  60

Asn Ile Leu Leu Phe Met Gly Tyr Thr Thr Lys Pro Gln Leu Ala Ile
65                  70                  75                  80

Val Thr Gln Trp Cys Glu Gly Ser Ser Leu Tyr His His Leu His Ile
                85                  90                  95

Ile Glu Thr Lys Phe Glu Met Ile Lys Leu Ile Asp Ile Ala Arg Gln
            100                 105                 110

Thr Ala Gln Gly Met Asp Tyr Leu His Ala Lys Ser Ile Ile His Arg
        115                 120                 125

Asp Leu Lys Ser Asn Asn Ile Phe Leu His Glu Asp Leu Thr Val Lys
    130                 135                 140

Ile Gly Asp Phe Gly Leu Ala Thr Val Lys Ser Arg Trp Ser Gly Ser
145                 150                 155                 160

His Gln Phe Glu Gln Leu Ser Gly Ser Ile Leu Trp Met Ala Pro Glu
                165                 170                 175

Val Ile Arg Leu Gln Asp Lys Asn Pro Tyr Ser Phe Gln Ser Asp Val
            180                 185                 190

Tyr Ala Phe Gly Ile Val Leu Tyr Glu Leu Met Ser Gly Ala Leu Pro
        195                 200                 205

Tyr Ser Asn Ile Asn Asn Arg Asp Gln Ile Ile Phe Met Val Gly Arg
    210                 215                 220

Gly Tyr Leu Ser Pro Asp Leu Ser Lys Val Arg Ser Asn Cys Pro Lys
225                 230                 235                 240
```

```
Ala Met Lys Arg Leu Met Ala Asp Cys Leu Lys Lys Arg Glu Glu
            245                 250                 255

Arg Pro Leu Phe Pro Gln Ile Leu Ala Ser Ile Glu Leu Leu Ala Arg
        260                 265                 270

Ser Leu Pro Lys
        275

<210> SEQ ID NO 90
<211> LENGTH: 276
<212> TYPE: PRT
<213> ORGANISM: Drosophila melanogaster

<400> SEQUENCE: 90

Glu Asn Trp Asn Ile Leu Ala Glu Glu Ile Leu Ile Gly Pro Arg Ile
1               5                   10                  15

Gly Ser Gly Ser Phe Gly Thr Val Tyr Arg Ala His Trp His Gly Pro
            20                  25                  30

Val Ala Val Lys Thr Leu Asn Val Lys Thr Pro Ser Pro Ala Gln Leu
        35                  40                  45

Gln Ala Phe Lys Asn Glu Val Ala Met Leu Lys Lys Thr Arg His Cys
    50                  55                  60

Asn Ile Leu Leu Phe Met Gly Cys Val Ser Lys Pro Ser Leu Ala Ile
65                  70                  75                  80

Val Thr Gln Trp Cys Glu Gly Ser Ser Leu Tyr Lys His Val His Val
                85                  90                  95

Ser Glu Thr Lys Phe Lys Leu Asn Thr Leu Ile Asp Ile Gly Arg Gln
            100                 105                 110

Val Ala Gln Gly Met Asp Tyr Leu His Ala Lys Asn Ile Ile His Arg
        115                 120                 125

Asp Leu Lys Ser Asn Asn Ile Phe Leu His Glu Asp Leu Ser Val Lys
    130                 135                 140

Ile Gly Asp Phe Gly Leu Ala Thr Ala Lys Thr Arg Trp Ser Gly Glu
145                 150                 155                 160

Lys Gln Ala Asn Gln Pro Thr Gly Ser Ile Leu Trp Met Ala Pro Glu
                165                 170                 175

Val Ile Arg Met Gln Glu Leu Asn Pro Tyr Ser Phe Gln Ser Asp Val
            180                 185                 190

Tyr Ala Phe Gly Ile Val Met Tyr Glu Leu Leu Ala Glu Cys Leu Pro
        195                 200                 205

Tyr Gly His Ile Ser Asn Lys Asp Gln Ile Leu Phe Met Val Gly Arg
    210                 215                 220

Gly Leu Leu Arg Pro Asp Met Ser Gln Val Arg Ser Asp Ala Pro Gln
225                 230                 235                 240

Ala Leu Lys Arg Leu Ala Glu Asp Cys Ile Lys Tyr Thr Pro Lys Asp
                245                 250                 255

Arg Pro Leu Phe Arg Pro Leu Leu Asn Met Leu Glu Asn Met Leu Arg
            260                 265                 270

Thr Leu Pro Lys
        275

<210> SEQ ID NO 91
<211> LENGTH: 279
<212> TYPE: PRT
<213> ORGANISM: Homo sapiens

<400> SEQUENCE: 91
```

Gln Glu Trp Asp Ile Pro Phe Glu Gln Val Glu Leu Gly Glu Pro Ile
1               5                   10                  15

Gly Gln Gly Arg Trp Gly Arg Val His Arg Gly Arg Trp His Gly Glu
            20                  25                  30

Val Ala Ile Arg Leu Leu Glu Met Asp Gly His Asn Gln Asp His Leu
        35                  40                  45

Lys Leu Phe Lys Lys Glu Val Met Asn Tyr Arg Gln Thr Arg His Glu
    50                  55                  60

Asn Val Val Leu Phe Met Gly Ala Cys Met Asn Pro Pro His Leu Ala
65                  70                  75                  80

Ile Ile Thr Ser Phe Cys Lys Gly Arg Thr Leu His Ser Phe Val Arg
                85                  90                  95

Asp Pro Lys Thr Ser Leu Asp Ile Asn Lys Thr Arg Gln Ile Ala Gln
            100                 105                 110

Glu Ile Ile Lys Gly Met Gly Tyr Leu His Ala Lys Gly Ile Val His
            115                 120                 125

Lys Asp Leu Lys Ser Lys Asn Val Phe Tyr Asp Asn Gly Lys Val Val
    130                 135                 140

Ile Thr Asp Phe Gly Leu Phe Gly Ile Ser Gly Val Val Arg Glu Gly
145                 150                 155                 160

Arg Arg Glu Asn Gln Leu Lys Leu Ser His Asp Trp Leu Cys Tyr Leu
            165                 170                 175

Ala Pro Glu Ile Val Arg Glu Met Thr Pro Gly Lys Asp Glu Asp Gln
            180                 185                 190

Leu Pro Phe Ser Lys Ala Ala Asp Val Tyr Ala Phe Gly Thr Val Trp
    195                 200                 205

Tyr Glu Leu Gln Ala Arg Asp Trp Pro Leu Lys Asn Gln Ala Ala Glu
    210                 215                 220

Ala Ser Ile Trp Gln Ile Gly Ser Gly Glu Gly Met Lys Arg Val Leu
225                 230                 235                 240

Thr Ser Val Ser Leu Gly Lys Glu Val Ser Glu Ile Leu Ser Ala Cys
            245                 250                 255

Trp Ala Phe Asp Leu Gln Glu Arg Pro Ser Phe Ser Leu Leu Met Asp
            260                 265                 270

Met Leu Glu Lys Leu Pro Lys
        275

<210> SEQ ID NO 92
<211> LENGTH: 279
<212> TYPE: PRT
<213> ORGANISM: Mus musculus

<400> SEQUENCE: 92

Gln Glu Trp Asp Ile Pro Phe Glu Gln Val Glu Leu Gly Glu Pro Ile
1               5                   10                  15

Gly Gln Gly Arg Trp Gly Arg Val His Arg Gly Arg Trp His Gly Glu
            20                  25                  30

Val Ala Ile Arg Leu Leu Glu Met Asp Gly His Asn Gln Asp His Leu
        35                  40                  45

Lys Leu Phe Lys Lys Glu Val Met Asn Tyr Arg Gln Thr Arg His Glu
    50                  55                  60

Asn Val Val Leu Phe Met Gly Ala Cys Met Asn Pro Pro His Leu Ala
65                  70                  75                  80

Ile Ile Thr Ser Phe Cys Lys Gly Arg Thr Leu His Ser Phe Val Arg

|   |   | 85 |   |   |   | 90 |   |   |   | 95 |   |
|---|---|---|---|---|---|---|---|---|---|---|---|

Asp Pro Lys Thr Ser Leu Asp Ile Asn Lys Thr Arg Gln Ile Ala Gln
            100                 105                 110

Glu Ile Ile Lys Gly Met Gly Tyr Leu His Ala Lys Gly Ile Val His
            115                 120                 125

Lys Asp Leu Lys Ser Lys Asn Val Phe Tyr Asp Asn Gly Lys Val Val
130                 135                 140

Ile Thr Asp Phe Gly Leu Phe Gly Ile Ser Gly Val Val Arg Glu Glu
145                 150                 155                 160

Arg Arg Glu Asn Gln Leu Lys Leu Ser His Asp Trp Leu Cys Tyr Leu
            165                 170                 175

Ala Pro Glu Ile Val Arg Glu Met Ile Pro Gly Arg Asp Glu Asp Gln
            180                 185                 190

Leu Pro Phe Ser Lys Ala Ala Asp Val Tyr Ala Phe Gly Thr Val Trp
            195                 200                 205

Tyr Glu Leu Gln Ala Arg Asp Trp Pro Phe Lys His Gln Pro Ala Glu
            210                 215                 220

Ala Leu Ile Trp Gln Ile Gly Ser Gly Glu Gly Val Arg Arg Val Leu
225                 230                 235                 240

Ala Ser Val Ser Leu Gly Lys Glu Val Gly Glu Ile Leu Ser Ala Cys
            245                 250                 255

Trp Ala Phe Asp Leu Gln Glu Arg Pro Ser Phe Ser Leu Leu Met Asp
            260                 265                 270

Met Leu Glu Arg Leu Pro Lys
            275

<210> SEQ ID NO 93
<211> LENGTH: 279
<212> TYPE: PRT
<213> ORGANISM: Gallus sp.

<400> SEQUENCE: 93

Gln Glu Trp Asp Ile Pro Phe Glu Gln Ile Glu Leu Gly Asp Pro Ile
1               5                   10                  15

Gly Gln Gly Arg Trp Gly Lys Val His Lys Gly Lys Trp His Gly Glu
            20                  25                  30

Val Ala Ile Arg Leu Leu Glu Ile Asp Gly Asn Asn Gln Asp His Leu
        35                  40                  45

Lys Leu Phe Lys Lys Glu Val Met Asn Tyr Arg Gln Thr Arg His Glu
    50                  55                  60

Asn Val Val Leu Phe Met Gly Ala Cys Met Asn Pro Pro His Leu Ala
65                  70                  75                  80

Ile Ile Thr Ser Phe Cys Lys Gly Arg Thr Leu Tyr Ser Phe Val Arg
                85                  90                  95

Asp Pro Lys Ile Ser Leu Asp Ile Asn Lys Thr Arg Gln Ile Ala Gln
            100                 105                 110

Glu Ile Ile Lys Gly Met Gly Tyr Leu His Ala Lys Gly Ile Val His
            115                 120                 125

Lys Asp Leu Lys Ser Lys Asn Val Phe Tyr Asp Asn Gly Lys Val Val
130                 135                 140

Ile Thr Asp Phe Gly Leu Phe Gly Ile Ser Gly Val Val Gln Glu Gly
145                 150                 155                 160

Arg Arg Glu Asn Glu Leu Lys Leu Pro His Asp Trp Leu Cys Tyr Leu
            165                 170                 175

```
Ala Pro Glu Ile Val Arg Glu Met Ala Pro Gly Lys Asp Glu Asp Lys
            180                 185                 190

Leu Pro Phe Ser Lys Ala Ala Asp Ile Tyr Ala Phe Gly Thr Val Trp
        195                 200                 205

Tyr Glu Leu Gln Ala Arg Glu Trp Pro Phe Lys Asn Gln Pro Ala Glu
    210                 215                 220

Ala Leu Ile Trp Gln Ile Gly Ser Gly Glu Gly Val Lys Gln Ile Leu
225                 230                 235                 240

Ala Thr Ile Ser Leu Gly Lys Glu Ile Asn Glu Ile Leu Ser Ala Cys
                245                 250                 255

Trp Ser Phe Asp Leu Ser Glu Arg Pro Ser Phe Thr Val Leu Met Asp
            260                 265                 270

Met Leu Glu Lys Leu Pro Lys
        275

<210> SEQ ID NO 94
<211> LENGTH: 276
<212> TYPE: PRT
<213> ORGANISM: Danio sp.

<400> SEQUENCE: 94

Gly His Arg Glu Asp Val Leu Glu Leu Gly Glu Leu Ile Gly Lys Gly
1               5                   10                  15

Arg Trp Gly Lys Val Cys Arg Gly Arg Trp His Gly Glu Val Ala Val
            20                  25                  30

Arg Leu Leu Glu Ile Asp Gly Asn Asn Gln Glu His Leu Lys Leu Phe
        35                  40                  45

Lys Lys Glu Val Met Asn Tyr Arg Gln Thr Arg His Glu Asn Val Val
    50                  55                  60

Leu Phe Met Gly Ala Cys Met His Pro Pro His Leu Ala Ile Ile Thr
65                  70                  75                  80

Ser Phe Cys Lys Gly Arg Thr Leu Tyr Ser Val Val Arg Asp Ser Lys
                85                  90                  95

Leu Asp Ile Asn Lys Ile Arg Gln Ile Ala Gln Glu Ile Val Lys Gly
            100                 105                 110

Met Gly Tyr Leu His Ala Lys Gly Ile Val His Lys Asp Leu Lys Ser
        115                 120                 125

Lys Asn Val Phe Tyr Asp Ser Asn Lys Val Val Ile Thr Asp Phe Gly
    130                 135                 140

Leu Phe Gly Met Ser Gly Val Val Gln Glu Asp Arg Arg Glu Asn Glu
145                 150                 155                 160

Leu Lys Leu Pro Arg Gly Trp Ile Tyr Tyr Leu Ala Pro Glu Ile Val
                165                 170                 175

Arg Lys Ile Gly Pro Gly Asn Gln Glu Asp Cys Leu Pro Phe Ser Lys
            180                 185                 190

Ala Ala Asp Val Tyr Ala Phe Gly Thr Ile Trp Tyr Glu Leu Gln Ala
        195                 200                 205

Lys Ala Trp Pro Ile Ile Asn Gln Pro Thr Gln Val Leu Ile Tyr Gln
    210                 215                 220

Leu Gly Ser Gly Glu Gly Ile Arg Ser Leu Leu Thr Lys Gly Thr
225                 230                 235                 240

Ser Leu Gly Lys Glu Val Thr Glu Ile Leu Ser Ala Cys Trp Cys Phe
                245                 250                 255

Lys Ala Glu Asp Arg Pro Thr Phe Thr Gln Leu Ser Asp Leu Leu Glu
            260                 265                 270
```

-continued

Lys Leu Pro Lys
        275

<210> SEQ ID NO 95
<211> LENGTH: 276
<212> TYPE: PRT
<213> ORGANISM: Drosophila melanogaster

<400> SEQUENCE: 95

Lys Glu Trp Asp Ile Pro Tyr Gly Asp Leu Leu Leu Glu Arg Ile
1               5                   10                  15

Gly Gln Gly Arg Phe Gly Thr Val His Arg Ala Leu Trp His Gly Asp
            20                  25                  30

Val Ala Val Lys Leu Leu Asn Glu Asp Tyr Leu Gln Asp Glu His Met
        35                  40                  45

Leu Glu Thr Phe Arg Ser Glu Val Ala Asn Phe Lys Asn Thr Arg His
    50                  55                  60

Glu Asn Leu Val Leu Phe Met Gly Ala Cys Met Asn Pro Pro Tyr Leu
65                  70                  75                  80

Ala Ile Val Thr Ser Leu Cys Lys Gly Asn Thr Leu Tyr Thr Tyr Ile
                85                  90                  95

His Gln Arg Arg Glu Lys Phe Ala Met Asn Arg Thr Leu Leu Ile Ala
            100                 105                 110

Gln Gln Ile Ala Gln Gly Met Gly Tyr Leu His Ala Arg Glu Ile Ile
        115                 120                 125

His Lys Asp Leu Arg Thr Lys Asn Ile Phe Ile Glu Asn Gly Lys Val
    130                 135                 140

Ile Ile Thr Asp Phe Gly Leu Phe Ser Ser Thr Lys Leu Leu Tyr Cys
145                 150                 155                 160

Asp Met Gly Leu Gly Val Pro His Asn Trp Leu Cys Tyr Leu Ala Pro
                165                 170                 175

Glu Leu Ile Arg Ala Leu Gln Pro Glu Lys Pro Arg Gly Glu Cys Leu
            180                 185                 190

Glu Phe Thr Pro Tyr Ser Asp Val Tyr Ser Phe Gly Thr Val Trp Tyr
        195                 200                 205

Glu Leu Ile Cys Gly Glu Phe Thr Phe Lys Asp Gln Pro Ala Glu Ser
    210                 215                 220

Ile Ile Trp Gln Val Gly Arg Gly Met Lys Gln Ser Leu Ala Asn Leu
225                 230                 235                 240

Gln Ser Gly Arg Asp Val Lys Asp Leu Leu Met Leu Cys Trp Thr Tyr
                245                 250                 255

Glu Lys Glu His Arg Pro Gln Phe Ala Arg Leu Leu Ser Leu Leu Glu
            260                 265                 270

His Leu Pro Lys
        275

<210> SEQ ID NO 96
<211> LENGTH: 268
<212> TYPE: PRT
<213> ORGANISM: Homo sapiens

<400> SEQUENCE: 96

Asp Glu Trp Glu Val Pro Arg Glu Thr Leu Lys Leu Val Glu Arg Leu
1               5                   10                  15

Gly Ala Gly Gln Phe Gly Glu Val Trp Met Gly Tyr Tyr Asn Gly His
            20                  25                  30

```
Thr Lys Val Ala Val Lys Ser Leu Lys Gln Gly Ser Met Ser Pro Asp
             35                  40                  45

Ala Phe Leu Ala Glu Ala Asn Leu Met Lys Gln Leu Gln His Gln Arg
 50                  55                  60

Leu Val Arg Leu Tyr Ala Val Val Thr Gln Glu Pro Ile Tyr Ile Ile
 65                  70                  75                  80

Thr Glu Tyr Met Glu Asn Gly Ser Leu Val Asp Phe Leu Lys Thr Pro
                 85                  90                  95

Ser Gly Ile Lys Leu Thr Ile Asn Lys Leu Leu Asp Met Ala Ala Gln
                100                 105                 110

Ile Ala Glu Gly Met Ala Phe Ile Glu Arg Asn Tyr Ile His Arg
            115                 120                 125

Asp Leu Arg Ala Ala Asn Ile Leu Val Ser Asp Thr Leu Ser Cys Lys
            130                 135                 140

Ile Ala Asp Phe Gly Leu Ala Arg Leu Ile Glu Asp Asn Glu Tyr Thr
145                 150                 155                 160

Ala Arg Glu Gly Ala Lys Phe Pro Ile Lys Trp Thr Ala Pro Glu Ala
                165                 170                 175

Ile Asn Tyr Gly Thr Phe Thr Ile Lys Ser Asp Val Trp Ser Phe Gly
            180                 185                 190

Ile Leu Leu Thr Glu Ile Val Thr His Gly Arg Ile Pro Tyr Pro Gly
            195                 200                 205

Met Thr Asn Pro Glu Val Ile Gln Asn Leu Glu Arg Gly Tyr Arg Met
    210                 215                 220

Val Arg Pro Asp Asn Cys Pro Glu Glu Leu Tyr Gln Leu Met Arg Leu
225                 230                 235                 240

Cys Trp Lys Glu Arg Pro Glu Asp Arg Pro Thr Phe Asp Tyr Leu Arg
                245                 250                 255

Ser Val Leu Glu Asp Phe Phe Thr Ala Thr Glu Gly
                260                 265

<210> SEQ ID NO 97
<211> LENGTH: 269
<212> TYPE: PRT
<213> ORGANISM: Mus musculus

<400> SEQUENCE: 97

Thr Ala Gln Leu Asp Gln Phe Asp Arg Ile Lys Thr Leu Gly Thr Gly
 1               5                  10                  15

Ser Phe Gly Arg Val Met Leu Val Lys His Lys Glu Ser Gly Asn His
                20                  25                  30

Tyr Ala Met Lys Ile Leu Asp Lys Gln Lys Val Val Lys Leu Lys Gln
             35                  40                  45

Ile Glu His Thr Leu Asn Glu Lys Arg Ile Leu Gln Ala Val Asn Phe
 50                  55                  60

Pro Phe Leu Val Lys Leu Glu Phe Ser Phe Lys Asp Asn Ser Asn Leu
 65                  70                  75                  80

Tyr Met Val Met Glu Tyr Val Ala Gly Gly Glu Met Phe Ser His Leu
                 85                  90                  95

Arg Arg Ile Gly Arg Phe Ser Glu Pro His Ala Arg Phe Tyr Ala Ala
                100                 105                 110

Gln Ile Val Leu Thr Phe Glu Tyr Leu His Ser Leu Asp Leu Ile Tyr
            115                 120                 125

Arg Asp Leu Lys Pro Glu Asn Leu Leu Ile Asp Gln Gln Gly Tyr Ile
```

-continued

```
                130                 135                 140
Gln Val Thr Asp Phe Gly Phe Ala Lys Arg Val Lys Gly Arg Thr Trp
145                 150                 155                 160

Thr Leu Cys Gly Thr Pro Glu Tyr Leu Ala Pro Glu Ile Ile Leu Ser
                165                 170                 175

Lys Gly Tyr Asn Lys Ala Val Asp Trp Trp Ala Leu Gly Val Leu Ile
                180                 185                 190

Tyr Glu Met Ala Ala Gly Tyr Pro Pro Phe Phe Ala Asp Gln Pro Ile
            195                 200                 205

Gln Ile Tyr Glu Lys Ile Val Ser Gly Lys Val Arg Phe Pro Ser His
            210                 215                 220

Phe Ser Ser Asp Leu Lys Asp Leu Leu Arg Asn Leu Leu Gln Val Asp
225                 230                 235                 240

Leu Thr Lys Arg Phe Gly Asn Leu Lys Asn Gly Val Asn Asp Ile Lys
                245                 250                 255

Asn His Lys Trp Phe Ala Thr Thr Asp Trp Ile Ala Ile
            260                 265
```